(12) United States Patent
Lynch et al.

(10) Patent No.: US 11,142,761 B2
(45) Date of Patent: *Oct. 12, 2021

(54) COMPOSITIONS AND METHODS FOR RAPID AND DYNAMIC FLUX CONTROL USING SYNTHETIC METABOLIC VALVES

(71) Applicant: DUKE UNIVERSITY, Durham, NC (US)

(72) Inventors: Michael David Lynch, Durham, NC (US); Ashley Trahan, Hillsborough, NC (US); Daniel Rodriguez, Durham, NC (US); Zhixia Ye, Raleigh, NC (US); Charles Cooper, Durham, NC (US); Ahmet Bozdag, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/849,441

(22) Filed: Apr. 15, 2020

(65) Prior Publication Data

US 2020/0299687 A1 Sep. 24, 2020

Related U.S. Application Data

(63) Continuation of application No. 15/317,768, filed as application No. PCT/US2015/035306 on Jun. 11, 2015, now Pat. No. 10,662,426.

(60) Provisional application No. 62/010,574, filed on Jun. 11, 2014.

(51) Int. Cl.
| | |
|---|---|
| C12N 15/63 | (2006.01) |
| C12N 15/70 | (2006.01) |
| C12N 15/11 | (2006.01) |
| C12N 15/113 | (2010.01) |

(52) U.S. Cl.
CPC ........ *C12N 15/111* (2013.01); *C12N 15/1137* (2013.01); *C12N 15/63* (2013.01); *C12N 15/70* (2013.01); *C12N 2310/14* (2013.01); *C12N 2320/50* (2013.01)

(58) Field of Classification Search
None
See application file for complete search history.

(56) References Cited

U.S. PATENT DOCUMENTS

| | | | |
|---|---|---|---|
| 8,916,358 B2 | 12/2014 | Swartz | |
| 10,036,001 B2 | 7/2018 | Swartz | |
| 10,662,426 B2* | 5/2020 | Lynch | C12N 15/63 |
| 2010/0297736 A1 | 11/2010 | Duhring et al. | |
| 2011/0125118 A1 | 5/2011 | Lynch | |
| 2011/0244575 A1 | 10/2011 | Lipscomb | |
| 2012/0052547 A1 | 3/2012 | Swartz | |
| 2012/0107892 A1 | 5/2012 | Agbogbo et al. | |
| 2012/0214170 A1 | 8/2012 | Moore | |
| 2015/0072399 A1 | 3/2015 | Lynch et al. | |
| 2019/0390232 A1* | 12/2019 | Lynch | C12Y 106/03001 |
| 2020/0056211 A1* | 2/2020 | Lynch | C12N 9/0008 |

FOREIGN PATENT DOCUMENTS

| | | |
|---|---|---|
| EP | 2562249 A1 | 2/2013 |
| EP | 2842542 A1 | 3/2015 |
| WO | 2001068883 A1 | 9/2001 |
| WO | 2003054140 | 2/2004 |
| WO | 2008141174 A2 | 11/2008 |
| WO | 2010141468 A1 | 12/2010 |
| WO | 2012129450 A1 | 9/2012 |
| WO | 2013176772 A1 | 11/2013 |
| WO | 2014160025 A2 | 10/2014 |
| WO | 2015191638 A1 | 12/2015 |
| WO | 2018156646 A1 | 8/2018 |

OTHER PUBLICATIONS

Ziemann et al. Gene name errors are widespread in the scientific literature. 2016. Genome Biology. vol. 17, No. 177, 3 pages. (Year: 2016).*
Lynch et al., "Slenderized two-stage bioprocess development using synthetic metabolic valves and dynamic metabolic control", Abstracts of Papers ; ACS National Meeting & Exposition; 249th National Meeting and Exposition of the American-Chemical-Society (ACS), vol. 249, p. BIOT418.
Brockman et al., "Dynamic knockdown of E. coli central metabolism for redirecting fluxes of primary metabolites", Metabolic Engineering, vol. 28., pp. 104-113.
Qi et al, "Repurposing CRISPR as an RNA-guided platform for sequence-specific control of gene expression," Cell (2013); vol. 152, pp. 1173-1183.
Office Action issued in European patent application No. 15845669.9, dated Dec. 3, 2018, 6 pages.
Extended European search report issued in patent application No. 15845669.9, dated Jan. 3, 2018, 10 pages.
Yuki Soma et al: "Metabolic flux redirection from a central metabolic pathway toward a synthetic pathway using a metabolic toggle switch", Metabolic Engineering, vol. 23, May 1, 2014, pp. 175-184.
Kathleen E. McGinness et al: "Engineering Controllable Protein Degradation", Molecular Cell., vol. 22, No. 5, Jun. 1, 2006, pp. 701-707.

(Continued)

*Primary Examiner* — Channing S Mahatan
(74) *Attorney, Agent, or Firm* — Benesch, Friedlander, Coplan & Aronoff LLP

(57) ABSTRACT

This invention relates to metabolically engineered microorganisms, such as bacterial and or fungal strains, and bioprocesses utilizing such strains. These strains enable the dynamic control of metabolic pathways, which can be used to optimize production. Dynamic control over metabolism is accomplished via a combination of methodologies including but not limited to transcriptional silencing and controlled enzyme proteolysis. These microbial strains are utilized in a multi-stage bioprocess encompassing at least two stages, the first stage in which microorganisms are grown and metabolism can be optimized for microbial growth and at least one other stage in which growth can be slowed or stopped, and dynamic changes can be made to metabolism to improve the production of desired product, such as a chemical or fuel.

19 Claims, 15 Drawing Sheets

Specification includes a Sequence Listing.

(56) References Cited

OTHER PUBLICATIONS

Levchenko Igor et al: " a specificity-enhancing factor for the ClpXP degradation machine", Science, vol. 289, No. 5488, Sep. 29, 2000, pp. 2354-2356.

UK Examination Report dated Apr. 1, 2019 from related UK Application No. GB1511937.3.

English Translation of Mar. 12, 2019 Office Action related to Japanese application JP2016-572578.

Kim et al., "A genetic strategy to identify targets for the development of drugs that prevent bacterial persistence", Proc. Natl. Acad. Sci. USA (2013); vol. 110, pp. 19095-19100.

Examination Report issued in European patent application No. 15845669.9 dated Sep. 26, 2019.

Torella, et al. Tailored fatty acid synthesis via dynamic control of fatty acid elongation. Proc Natl Acad Sci U S A. Jul. 9, 2013; 110(28): 11290-5. doi: 101073/pnas. 1307129110. Epub 2013.

International Preliminary Report on Patentability dated Dec. 15, 2016 from related International App. No. PCT/US2015035306.

UK Combined Examination and Search Report dated Dec. 8, 2016, from related UK Application No. GB1511937.3.

International Search Report and Written Opinion dated Apr. 27, 2016 from related International Application No. PCT/US2015/035306.

Fang, Shi-Ming et al., "A Practical Strategy to Discover New Antitumor Compounds by Activating Silent Metabolite Production in Fungi by Diethyl Sulphate Mutagenesis," Marine Drugs, vol. 12, pp. 1788-1814, 2014.

Imaizumi, A. et al, Improved production of L-lysine by disruption of stationary phase-specific rmf gene in *Escherchia coli*, Journal of Biotechnology, 117 (2005) 111-118.

Office Action issued in JP Application No. JP 2020-033434, dated Mar. 30, 2021.

* cited by examiner

COMPOSITIONS AND METHODS FOR RAPID AND DYNAMIC FLUX CONTROL USING SYNTHETIC METABOLIC VALVES

CROSS-REFERENCE TO RELATED APPLICATIONS

This application is a continuation of U.S. application Ser. No. 15/317,768 which is a § 371 U.S. National Stage of International Application PCT/US2015/035306, filed Jun. 11, 2015, which claims the benefit of U.S. Provisional Application No. 62/010,574, filed Jun. 11, 2014, the entire content of which are incorporated by reference herein in their entirety.

FEDERALLY SPONSORED RESEARCH OR DEVELOPMENT

This invention was made with government support under Federal Grant No. MCB-1445726 awarded by the National Science Foundation and Federal Contract No. HR0011-14-C-0075 awarded by the Defense Advanced Research Projects Agency of the United States Department of Defense. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "OLG Ref 210-44 ST25.txt". The sequence listing is 184,352 bytes in size, and was created on Jun. 11, 2015. It is hereby incorporated by reference in its entirety.

FIELD OF THE INVENTION

This invention relates to metabolically engineered microorganisms, such as bacterial and or fungal strains, and bioprocesses utilizing such strains. These strains enable the dynamic control of metabolic pathways.

BACKGROUND OF THE INVENTION

Petroleum is the primary feedstock, not only for the fuels we use, but the majority of the chemicals we consume as well. The chemical industry is heavily reliant on this non-renewable resource. Replacement of petroleum with renewable feedstocks ensures longer-term viability and environmental sustainability. Novel fermentation based processes to make chemicals have been a contributing technology, enabling the change to renewable feedstocks (Werpy &Peterson, Top Value Added Chemicals from Biomass. Volume I—Results of Screening for Potential Candidates from Sugars and Synthesis Gas., Yixiang et al. "Green" Chemicals from Renewable Agricultural Biomass—A Mini Review. The Open Agriculture Journal, 2008). These fermentation processes have made rapid advancements in recent years due to technology developments in the fields of fermentation science, synthetic biology, as well as metabolic and enzyme engineering (Jarboe, L. R., et al., Metabolic engineering for production of biorenewable fuels and chemicals: contributions of synthetic biology. J Biomed Biotechnol, 2010, Lee, J. W., et al., Systems metabolic engineering of microorganisms for natural and non-natural chemicals. Nat Chem Biol, 2012). Despite these substantial advances, most successful examples of rationale directed engineering approaches have also greatly relied on numerous cycles of trial and error. The field of metabolic engineering has historically been limited in predicting the behavior of complex biological systems in-vivo, from simplified models and basic in-vitro biochemical principles. Such rational approaches have required significant a priori knowledge of microbial physiology that in many cases is incomplete. This is particularly true for complex phenotypes that require an intricate balance between the activities of many seemingly unrelated gene products. In many cases it has proven much more difficult than expected to integrate a possibly well characterized production pathway into a living host and balance the complex requirements of both biomass growth and production.

One solution is the development of platform microbial strains that utilize synthetic metabolic valves (SMVs) that can decouple growth from product formation. These strains enable the dynamic control of metabolic pathways, including those that when altered have negative effects on microorganism growth. Dynamic control over metabolism is accomplished via a combination of methodologies including but not limited to transcriptional silencing and controlled enzyme proteolysis. These microbial strains are utilized in a multi-stage bioprocess encompassing as least two stages, the first stage in which microorganisms are grown and metabolism can be optimized for microbial growth and at least one other stage in which growth can be slowed or stopped, and dynamic changes can be made to metabolism to improve production of desired product, such as a chemical or fuel. The transition of growing cultures between stages and the manipulation of metabolic fluxes can be controlled by artificial chemical inducers or preferably by controlling the level of key limiting nutrients. In addition, genetic modifications may be made to provide metabolic pathways for the biosynthesis of one or more chemical or fuel products. Also, genetic modifications may be made to enable the utilization of a variety of carbon feedstocks including but not limited sugars such as glucose, sucrose, xylose, arabinose, mannose, and lactose, oils, carbon dioxide, carbon monoxide, methane, methanol and formaldehyde.

This approach allows for simpler models of metabolic fluxes and physiological demands during a production phase, turning a growing cell into a stationary phase biocatalyst. These synthetic metabolic valves can be used to turn off essential genes and redirect carbon, electrons and energy flux to product formation in a multi-stage fermentation process. One or more of the following enables these synthetic valves: 1) transcriptional gene silencing or repression technologies in combination with 2) inducible enzyme degradation and 3) nutrient limitation to induce a stationary or non-dividing cellular state. SMVs are generalizable to any pathway and microbial host. These synthetic metabolic valves allow for novel rapid metabolic engineering strategies useful for the production of renewable chemicals and fuels and any product that can be produced via whole cell catalysis.

A simplified two-stage bioprocess using synthetic metabolic valves is depicted in FIG. 1, strains are grown in a minimal media with a single limiting nutrient such as inorganic phosphate. During this growth phase cells are not producing any product other than biomass and as a result are not subject to any possible toxic or unwanted side effects of product formation. Biomass growth and yield can be optimized. As the limiting nutrient is depleted, cell growth is stopped. Simultaneously, these strains will be engineered to contain synthetic metabolic valves, which silence genes and enzymes essential for growth and redirect carbon, electrons and energy to any molecule of interest. This process utilizes a novel combination of a two-stage production and concurrent metabolic engineering strategy.

There is significant precedent in the biotechnology industry for using and scaling two stage processes similar to that described in FIG. 1. Many similar processes are routinely used for the heterologous expression of proteins. In these standard processes cells are grown to a productive or "primed" state for protein synthesis (such as mid-exponential phase in E. coli) and then induced to express a heterologous protein. In many cases, the diversion of cellular amino acids and energy to the heterologous protein has a significant effect on, if not halting, cellular growth. It is not surprising that these types of processes have not been developed for the biological production of small molecules as historically most successful efforts to metabolically engineer the production of small molecules have leveraged the power of anaerobic metabolism to couple product formation with growth.

Anaerobic growth-coupled product formation enables the use of powerful growth based selections to identify better producers. The faster the cells grow the more product they make. This has allowed for the classical selection of industrial strains for many natural products such as ethanol and isobutanol. However, the requirement for anaerobic production greatly limits the number and variety of different molecules or products that can be made using synthetic biology. Numerous products would require aerobic metabolism to supply the needed energy and cofactors to allow for a thermodynamically feasible metabolic pathway. In these cases a generic and robust aerobic production platform would greatly simplify the optimization and scale up of a diverse number of products. A controlled multi-stage process, enabled by synthetic metabolic valves, supplies such a platform.

Synthetic metabolic valves enable synthetic biologists and metabolic engineers the ability to decouple the complex metabolic and thermodynamic needs of growth from those of product formation. This decoupling also enables the removal of growth based regulatory mechanisms that may inhibit product formation and allows for the silencing of essential metabolic pathways that may detract from or interfere with production. These essential interfering metabolic pathways could include amino acid biosynthesis or the citric acid cycle as well as the biosynthesis of many secondary metabolites, and those pathways involved in maintaining intracellular redox and energy balances. These pathways have traditionally been off limits to many metabolic engineering strategies, as attempts at manipulation have led to growth defects.

SUMMARY OF THE INVENTION

According to one embodiment, the invention is directed to methods to construct controllable synthetic metabolic valves. In certain of these embodiments synthetic metabolic valves are used to controllably reduce or eliminate flux through one more metabolic pathways. In further embodiments, flux is reduced or eliminated through one or more metabolic pathways whose enzymes are essential for microbial growth in a given environment. In other embodiments, the invention is related to genetically modified microorganisms that utilize one or more synthetic metabolic valves thereby enabling dynamic control over metabolic pathways. Other embodiments of the invention are directed to multi-stage bioprocesses that utilize genetically modified microorganism that in turn utilize one or more synthetic metabolic valves that enable dynamic flux control. Still in other embodiments of the invention, the transitions between stages in multistage bioprocesses using genetically modified microorganisms are controlled by the addition of chemical inducers or by the control of key nutrient levels. Additional genetic modifications may be added to a microorganism to enable the conversion of carbon feedstocks to chemical or fuel products. In certain embodiments, carbon feedstocks can include, but are not limited to the sugars: glucose, sucrose xylose, arabinose, mannose, lactose, or alternatively carbon dioxide, carbon monoxide, methane, methanol, formaldehyde, or oils. In addition, genetic modifications to produce chemical or fuel products from various carbon feedstocks can include metabolic pathways utilizing, but not limited to, the central metabolites acetyl-CoA, malonyl-CoA, pyruvate, oxaloacetate, erthyrose-4-phosphate, xylulose-5-phosphate, alpha-ketoglutarate and citrate. Products that can be derived from these central metabolites include but are not limited to acetate, alcohols (ethanol, butanol, hexanol, and longer n-alcohols), organic acids (3-hydroxy-prpionic acid, lactic acid, itaconic acid), amino acids (alanine, serine, valine), fatty acids and their derivatives (fatty acid methyl esters (FAMEs), fatty aldehydes, alkenes, alkanes) and isoprenoids.

In various embodiments, the increased production of acetate from acetyl-phosphate may occur via the increased expression of an acetate kinase. A non-limiting example is the acetate kinase from E. coli encoded by the ackA gene. Increased expression of an acetate kinase may optionally be combined with genetic modifications that result decreased activity phosphoacetyltransferase such as that encoded by the pta gene of E. coli.

In various embodiments, the increased production of ethanol from acetyl-CoA may occur via the increased expression of an oxygen tolerant ethanol dehydrogenase, such as the enzyme from E. coli encoded by the adhE gene with a mutation Glu568Lys as taught by Dellomonaco et al, AEM. August 2010, Vol. 76, No. 15, p 5067. and Holland-Staley et al. JBACs. November 2000, Vol. 182, No. 21, p 6049.

In various embodiments, the increased production of butyrate from acetyl-CoA may occur via the increased expression of butyrate pathway enzymes including an acetoacetyl-CoA thiolase, crotonase, crotonyl-CoA reductase, butyrate phospho-transferase and butyrate kinase as taught by Fischer et al, Appl Microbiol Biotechnol. 2010, September, Vol. 88, No. 1, p. 265-275. Alternatively, increased butyrate may be accomplished via the increased expression of butyrate pathway enzymes including an acetoacetyl-CoA synthase, crotonase, crotonyl-CoA reductase and butyryl-CoA thioesterase as taught by PCT/US2012/030209.

In various embodiments, the increased production of n-butanol from acetyl-CoA may occur via the increased expression of n-butanol pathway enzymes including an acetoacetyl-CoA thiolase, crotonase, crotonyl-CoA reductase, butyryl-CoA reductase and butyraldehyde reductase as taught by Atsumi et al, Metabolic Engineering. 2008. November, Vol. 10, No. 6, p. 305).

In various embodiments, the increased production of fatty acids of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, and a acyl-CoA thioesterase as taught by PCT/US2012/030209.

In various embodiments, the increased production of fatty acid methyl esters from acetyl-CoA may occur via the increased expression of fatty acid methyl ester synthesis pathway enzymes including an ketoacetyl-CoA synthase, 3-hydroxyacyl-CoA dehydratase, an enoyl-CoA reductase, and a acyl-CoA wax ester synthase as taught by: PCT/US2012/030209 and US 20110146142 A1.

In various embodiments, the increased production of n-hexanol from acetyl-CoA may occur via the increased expression of a fatty acid synthesis pathway enzymes including an ketoacetyl-CoA thiolases, 3-hydroxyacyl-CoA dehydratase, an enoyl-CoA reductase, and a acyl-CoA thioesterase as taught by Dekishima et al. J Am Chem Soc. 2011. August. Vol. 133, No. 30, p. 1139.

In various embodiments, the increased production of n-alcohols of chain length greater than 4, from acetyl-CoA may occur via the increased expression of a fatty acid synthesis pathway enzymes including an ketoacetyl-CoA synthase, 3-hydroxyacyl-CoA dehydratase, an enoyl-CoA reductase, as taught by PCT/US2012/030209 and a fatty acyl-CoA reductase and fatty aldehyde reductase as taught by Yan-Ning Zheng et al. Microbial Cell Factories. 2012.

In various embodiments, the increased production of n-alkenes can be accomplished by first producing n-alcohols as described elsewhere followed by the chemical dehydration of the n-alcohol to an n-alkene by catalytic methods well known in the art.

In various embodiments, the increased production of n-alkanes can be accomplished by first producing fatty acids as described elsewhere followed by the chemical decarboxylation of the n-alcohol to an alkane by catalytic methods well known in the art.

In various embodiments, the increased production of isoprene from acetyl-CoA may occur via the increased expression of pathway enzymes including an acetoacetyl-CoA thiolase, hydroxymethylglutaryl-CoA synthase, hydroxymethylglutaryl-CoA reductase, mevalonate kinase, phosphomevalonate kinase, mevalonte diphosphate decarboxylase, isopentenyl-diphosphate isomerase and isoprene synthase as taught by US 20120276603 A1.

In various embodiments, the increased production of a product from acetyl-CoA may occur via both the increased expression of an acetyl-CoA carboxylase enzyme which can convert acetyl-CoA into malonyl-CoA and the increased expression of a production pathway comprising multiple pathway enzymes which can convert malonyl-CoA further to a product.

In various embodiments, the increased production of a product from malonyl-CoA may occur via both the increased activity of an acetyl-CoA carboxylase enzyme which can caused by mutation of one or more fatty acid synthesis enzymes such as is taught by PCT/US2012/030209, PCT/US2011/0222790 and 3. UK Patent GB2473755 and the increased expression of a production pathway comprising multiple pathway enzymes which can convert malonyl-CoA further to a product.

Within the scope of the invention are genetically modified microorganism, wherein the microorganism is capable of producing an acetyl-CoA derived product at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

Within the scope of the invention are genetically modified microorganism, wherein the microorganism is capable of producing a product derived from any key metabolic intermediate including but not limited to malonyl-CoA, pyruvate, oxaloacetate, erthyrose-4-phosphate, xylulose-5-phosphate, alpha-ketoglutarate and citrate at a specific rate selected from the rates of greater than 0.05 g/gDCW-hr, 0.08 g/gDCW-hr, greater than 0.1 g/gDCW-hr, greater than 0.13 g/gDCW-hr, greater than 0.15 g/gDCW-hr, greater than 0.175 g/gDCW-hr, greater than 0.2 g/gDCW-hr, greater than 0.25 g/gDCW-hr, greater than 0.3 g/gDCW-hr, greater than 0.35 g/gDCW-hr, greater than 0.4 g/gDCW-hr, greater than 0.45 g/gDCW-hr, or greater than 0.5 g/gDCW-hr.

In various embodiments, the invention includes a culture system comprising a carbon source in an aqueous medium and a genetically modified microorganism according to any one of claims herein, wherein said genetically modified organism is present in an amount selected from greater than 0.05 gDCW/L, 0.1 gDCW/L, greater than 1 gDCW/L, greater than 5 gDCW/L, greater than 10 gDCW/L, greater than 15 gDCW/L or greater than 20 gDCW/L, such as when the volume of the aqueous medium is selected from greater than 5 mL, greater than 100 mL, greater than 0.5 L, greater than 1 L, greater than 2 L, greater than 10 L, greater than 250 L, greater than 1000 L, greater than 10,000 L, greater than 50,000 L, greater than 100,000 L or greater than 200,000 L, and such as when the volume of the aqueous medium is greater than 250 L and contained within a steel vessel.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the claims. A better understanding of the features and advantages of the present invention will be obtained by reference to the following detailed description that sets forth illustrative embodiments, in which the principles of the invention are utilized, and the accompanying drawings of which:

Expression can be controlled such as by the controlled ptet promoter induced by aTc. The constructs produce dCas9 and sspB proteins in addition to a targeting sgRNA. Bottom Panel: (LEFT) The target gene/protein contains a C-terminal DAS4 tag for binding to sspB. (RIGHT) When expression is induced, dCas9 is targeted to the gene of interest by the targeting sgRNA thereby silencing transcription. Concurrently, the expression of sspB results in the binding of sspB to the DAS4 C-terminal tag of protein that has already been translated. The sspB/DAS4 complex is then targeted for degradation by the clpXP protease.

Figure 3:
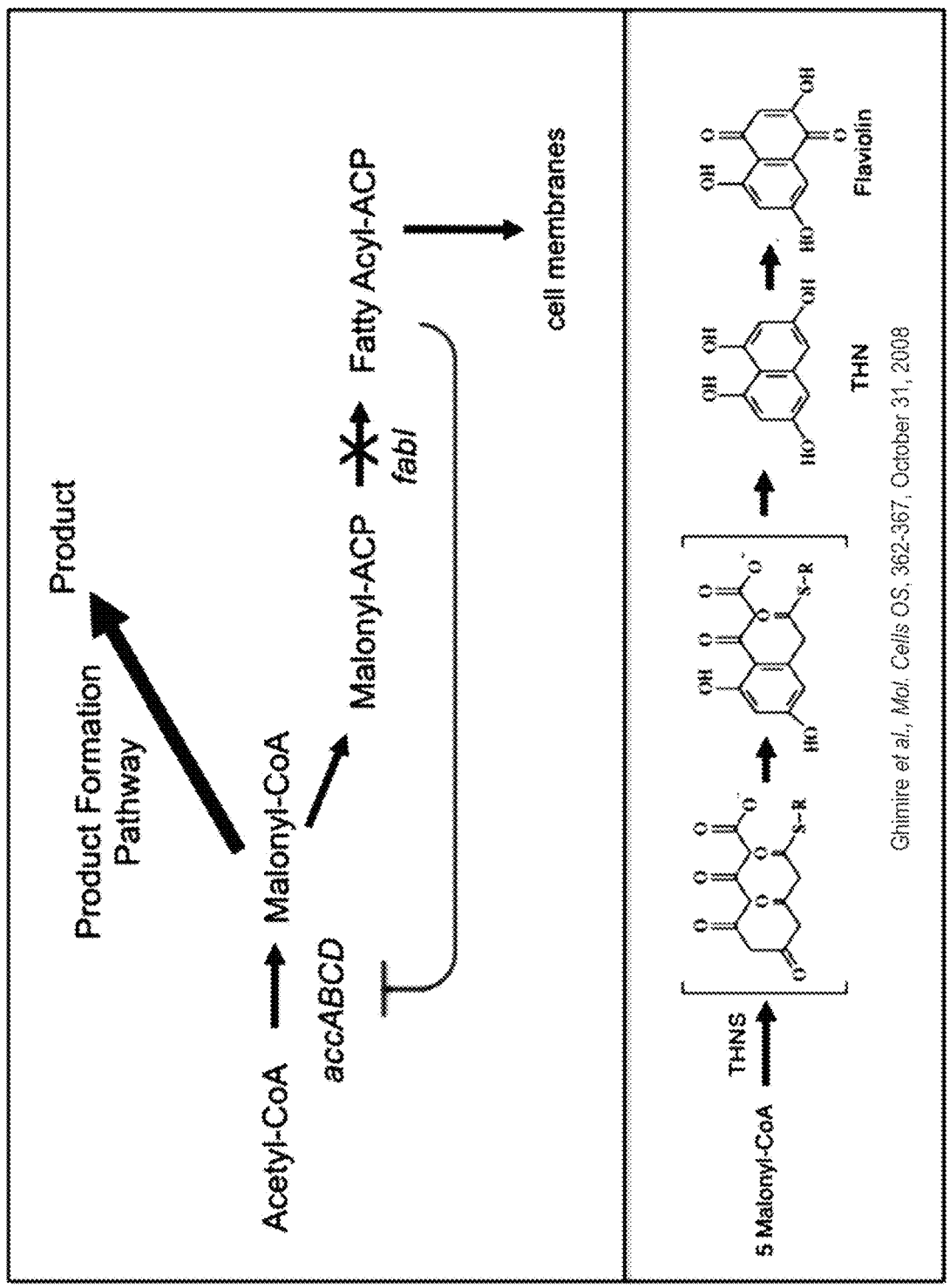

FIG. 3 depicts the production of tetrahydroxynapthalene (THN) by redirecting flux from malonyl-CoA. Upper Panel: An overview of redirecting flux from growth to product by controlling fabI (enoyl-coA reductase levels) in E. coli. In E. coli, the primary fate of the intermediate malonyl-CoA is to provide precursors for fatty acid synthesis. The key enzyme controlling the rate of lipid synthesis, acetyl-CoA carboxylase, encoded by the accABCD genes, is strongly inhibited by the fatty acid production intermediates, fatty acyl-ACPs. Removal of fabI leads to a decrease in acyl-ACP pools and a reduction in inhibition of acetyl-CoA carboxylase allowing malonyl-CoA levels to accumulate and be used for product synthesis. The removal of fabI limits lipid production and halts growth. Lowe Panel: One potential product from malonyl-CoA is tetrahydroxynapthalene (THN). THN is produced from 5 molecules of malonyl-CoA via the polyketide synthase, THN synthase encoded by the rppA gene of S. coelicolor.

Figure 4:
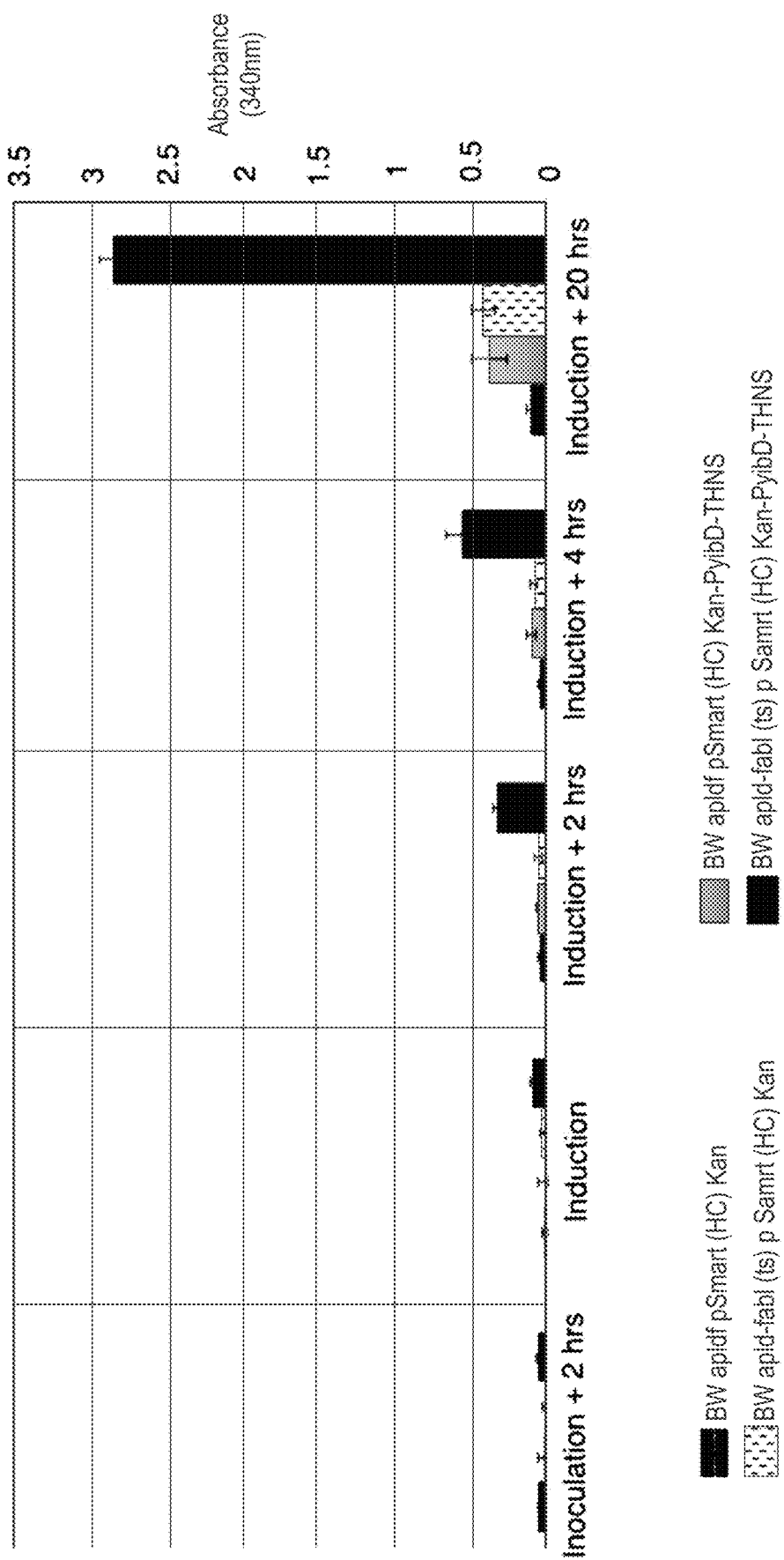

FIG. 4 depicts increased production of tetrahydroxynapthalene from malonyl-CoA in a two stage process as a result of the controlled inactivation of a temperature sensitive fabI allele. Improved production of THN by redirecting malonyl-CoA flux, using a temperature controlled process to inactivate a temperature sensitive allele of fabI. Strains as listed BWalpdf (BW25113: ΔldhA, ΔpflB, ΔpoxB, ΔackA-pta, ΔadhE), BWalpdf-fabI(ts) (BW25113: ΔldhA, ΔpflB, ΔpoxB, ΔackA-pta, ΔadhE, fabI(F241 S), gentR). Plasmids are i) pSMART-HC-Kan-yibD-THNS and ii) pSMART-HC-Kan (control).

Figure 5:
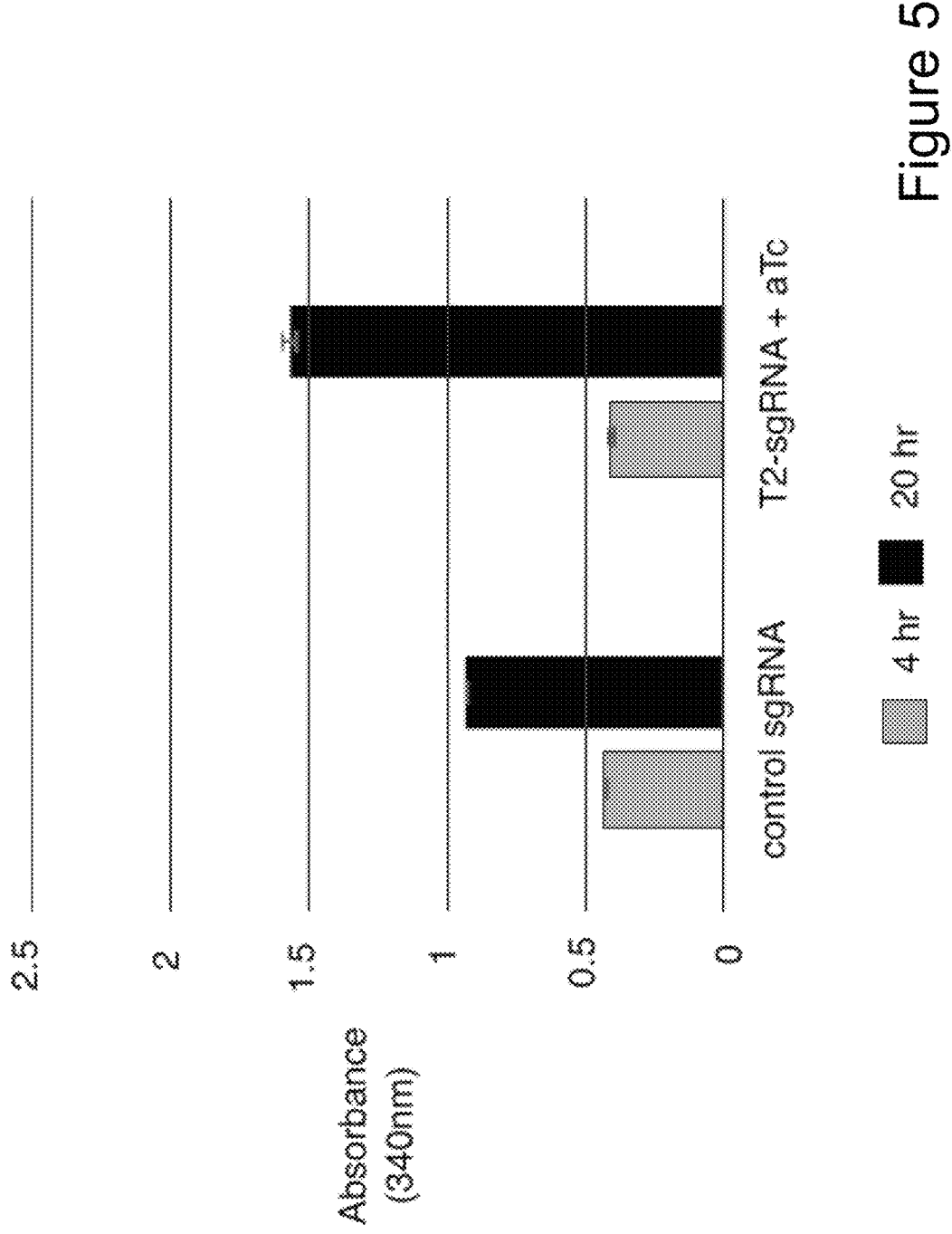

FIG. 5 depicts increased production of tetrahydroxynapthalene from malonyl-CoA in a two stage process as a result of a combination of controlled protein degradation and gene silencing. Improved production of THN by redirecting malonyl-CoA flux, using a synthetic metabolic vlae comprising a combination of CRISPR interference gene silencing and controlled proteolysis as outlined in FIG. 2. THN production at 4 hrs and 20 hrs is compared for two strains. LEFT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-control lacking a targeting sgRNA. RIGHT: Strain BW25113: ΔldhA, ΔpflB, ΔpoxB, ΔackA-pta, ΔadhE, ΔsspB, fabI::DAS4, gentR containing plasmids i) pSMART-HC-Kan-yibD-THNS ii) pdCas9-ptet-sspB and iii) pCDF-T2-fabIsgRNA expressing a sgRNA targeting fabI.

Figure 6:
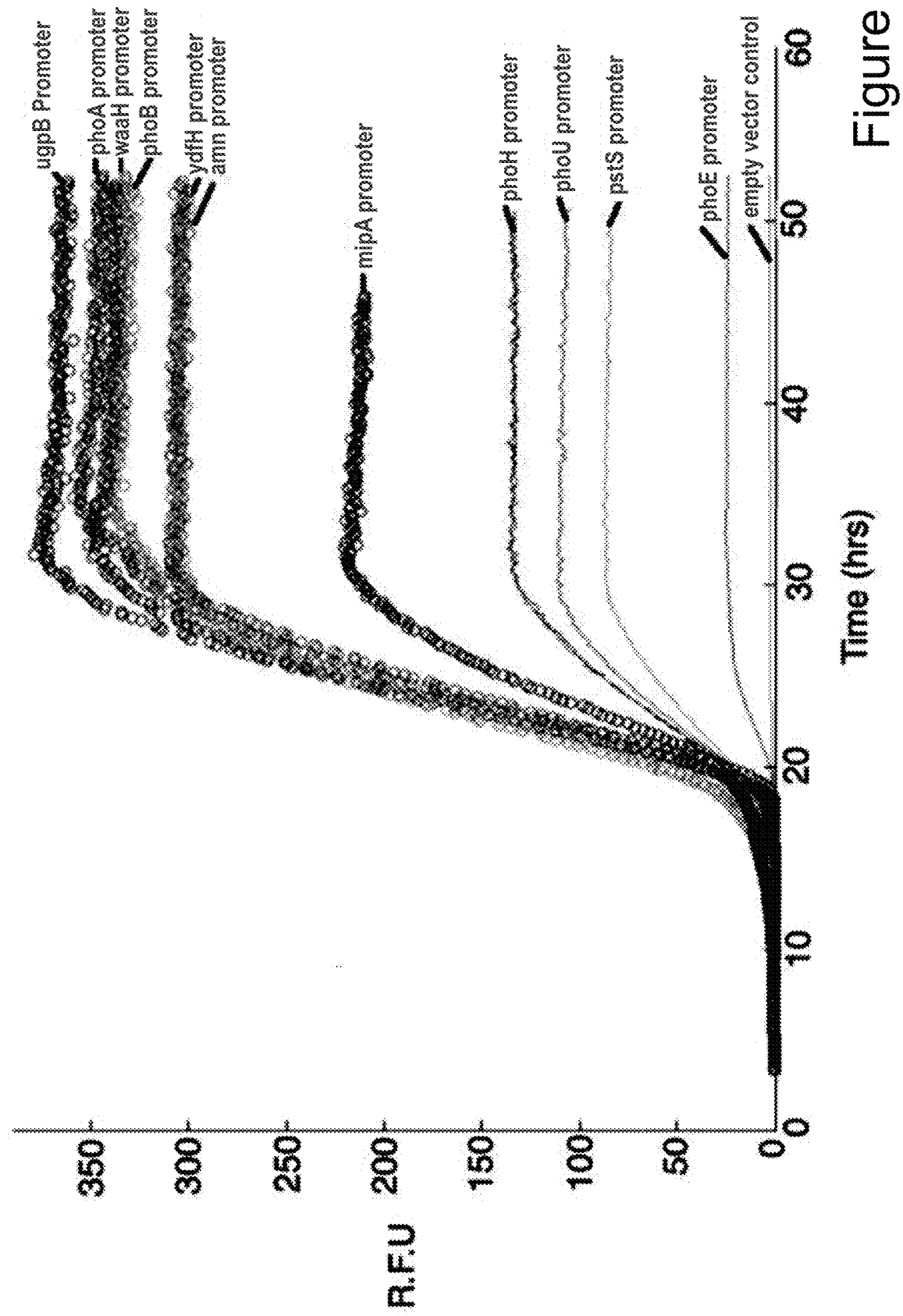

FIG. 6 depicts the low phosphate induction of a GFP reporter with various low phosphate inducible promoters. A comparison of the low phosphate inducible expression for the following gene promoters: amn, phoA, phoB, phoE, phoH, phoU, mipA, pstS, ugpB, waaH and ydfH, is shown. An ultraviolet excitable, green fluorescent protein (GFPuv) reporter gene was used and relative fluorescent units (RFU) are plotted as a function of time. Growth stops and phosphate depletion begins at about 15-20 hrs.

Figure 7:
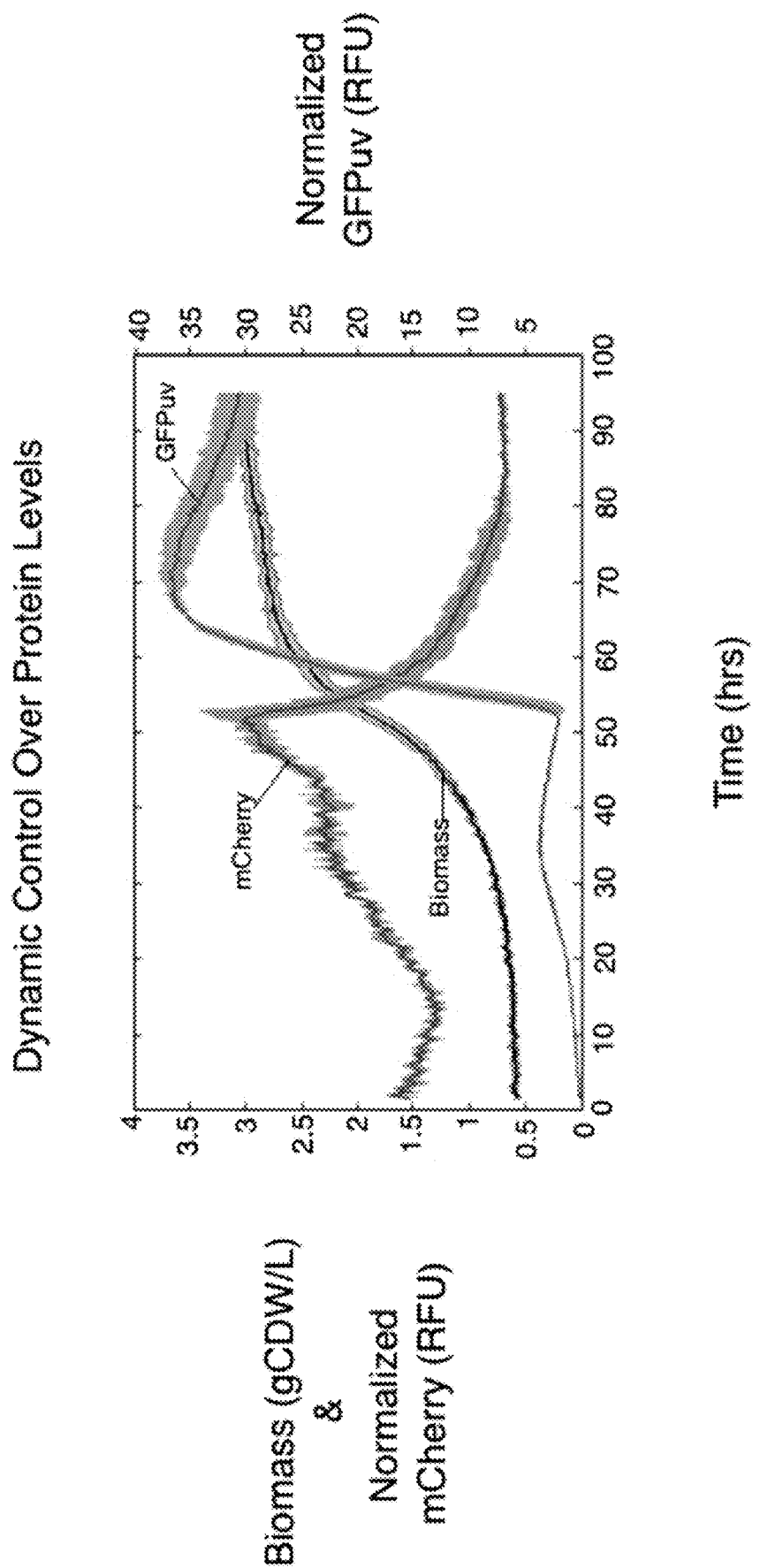

FIG. 7 depicts the dynamic control over protein levels in E. coli using the CASCADE System and controlled proteolysis. Strain DLF_0025 (enabling low phosphate DAS+4 degradation) has been modified to constitutively express a mCherry protein with a C-terminal DAS+4 degradation tag. In addition the strain has been modified for the low phosphate induction of GFPuv as well as a guide RNA repressing mCherry expression. As cells grow phosphate is depleted, and cells "turn off" mCherry and "turn on" GFPuv. Biomass is plotted as grams cell dry weight per liter, GFPuv and mCherry are plotted as relative fluorescence units (RFU) which are normalized to biomass levels.

Figure 8:
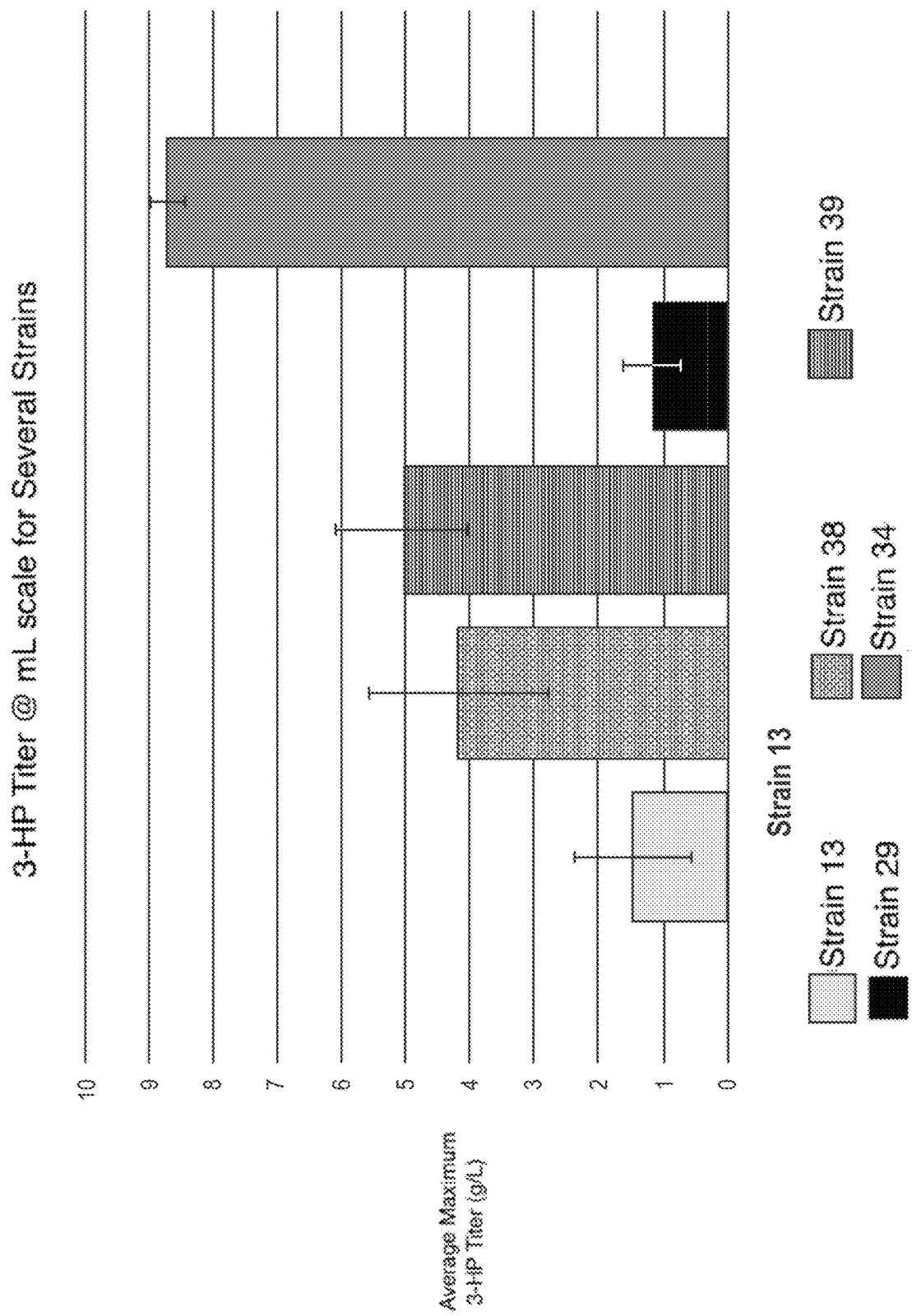

FIG. 8 depicts the production of 3-HP from malonyl-CoA and NADPH at mL scale. Average Maximal 3-HP titers are plotted for several production strains.

Figure 9:
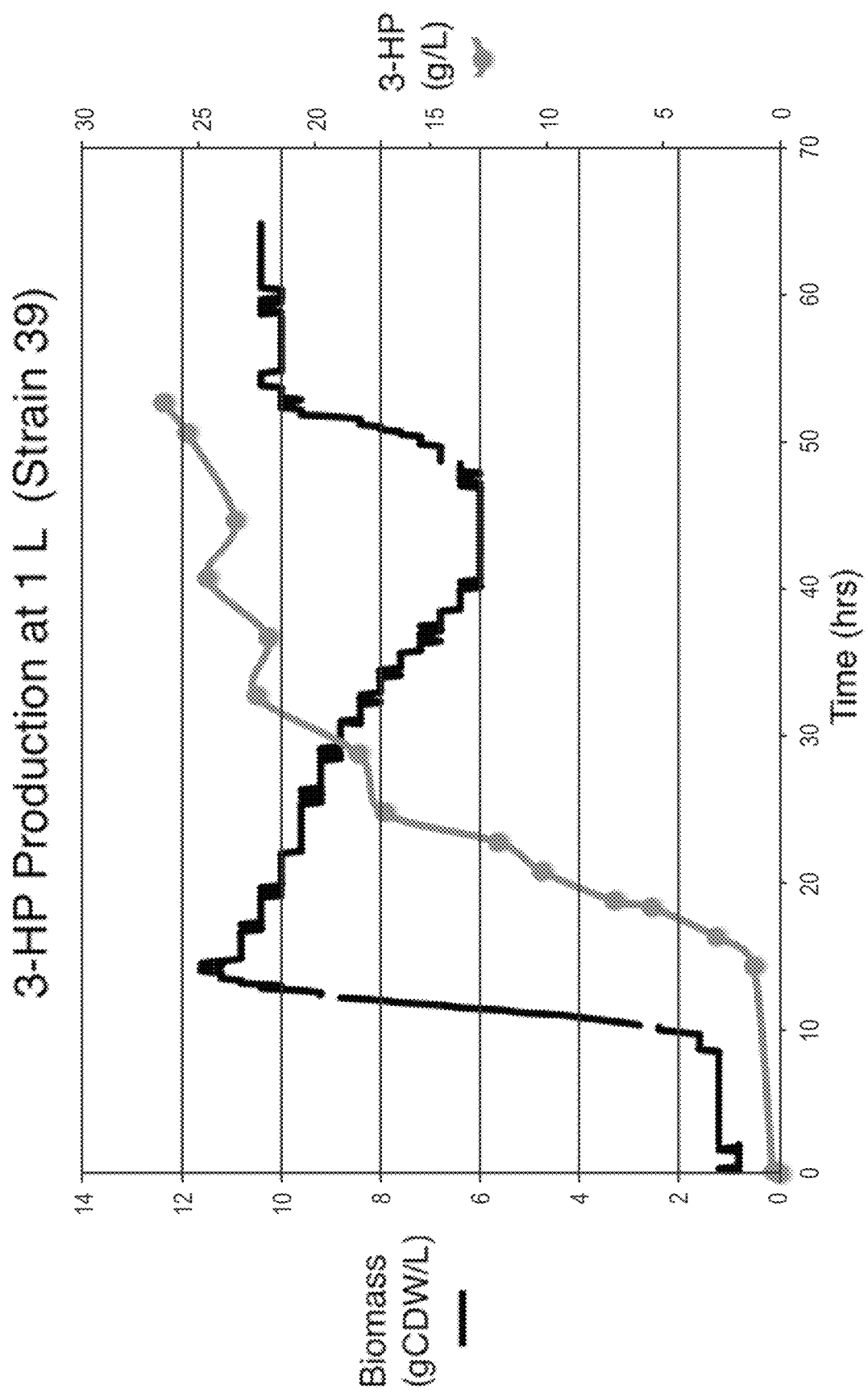

FIG. 9 depicts the production of 3-HP from malonyl-CoA and NADPH at L scale. Biomass and 3-HP titers are plotted as a function of time.

Figure 10:
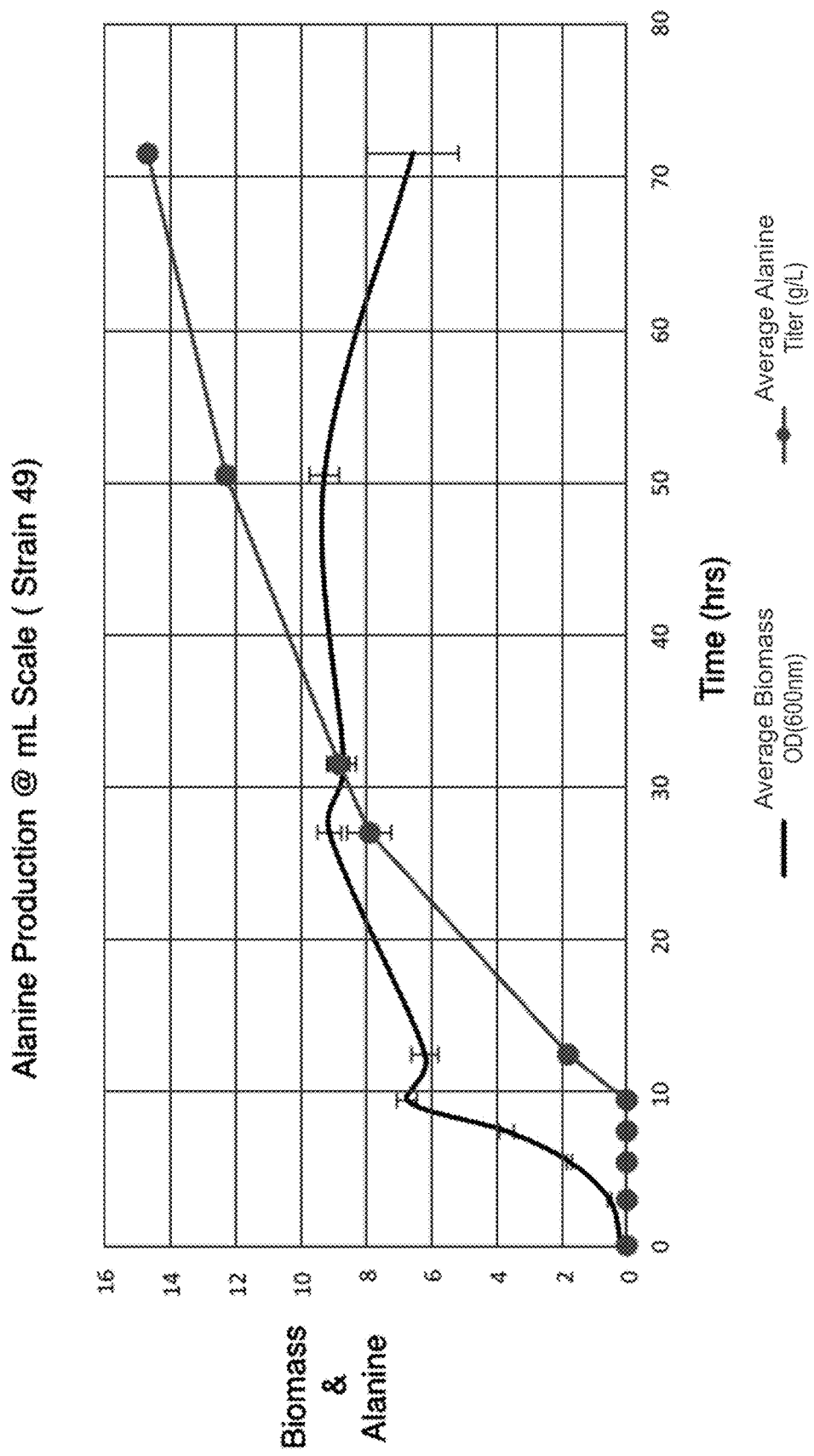

FIG. 10 depicts the production of alanine from pyruvate and NADPH at mL scale. Biomass and alanine titers are plotted as a function of time.

Figure 11:
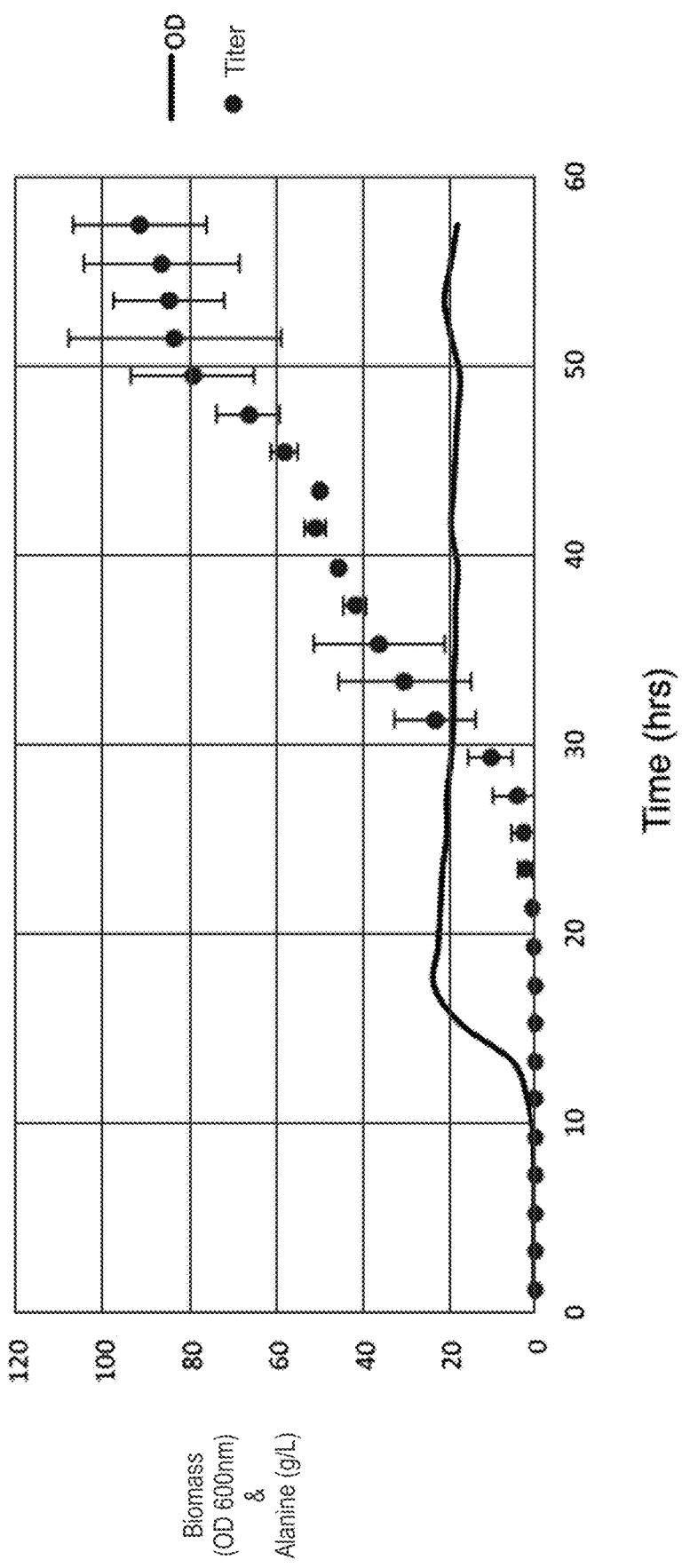

FIG. 11 depicts the production of alanine from pyruvate and NADPH at the L scale. Biomass and alanine titers are plotted as a function of time.

Figure 12:
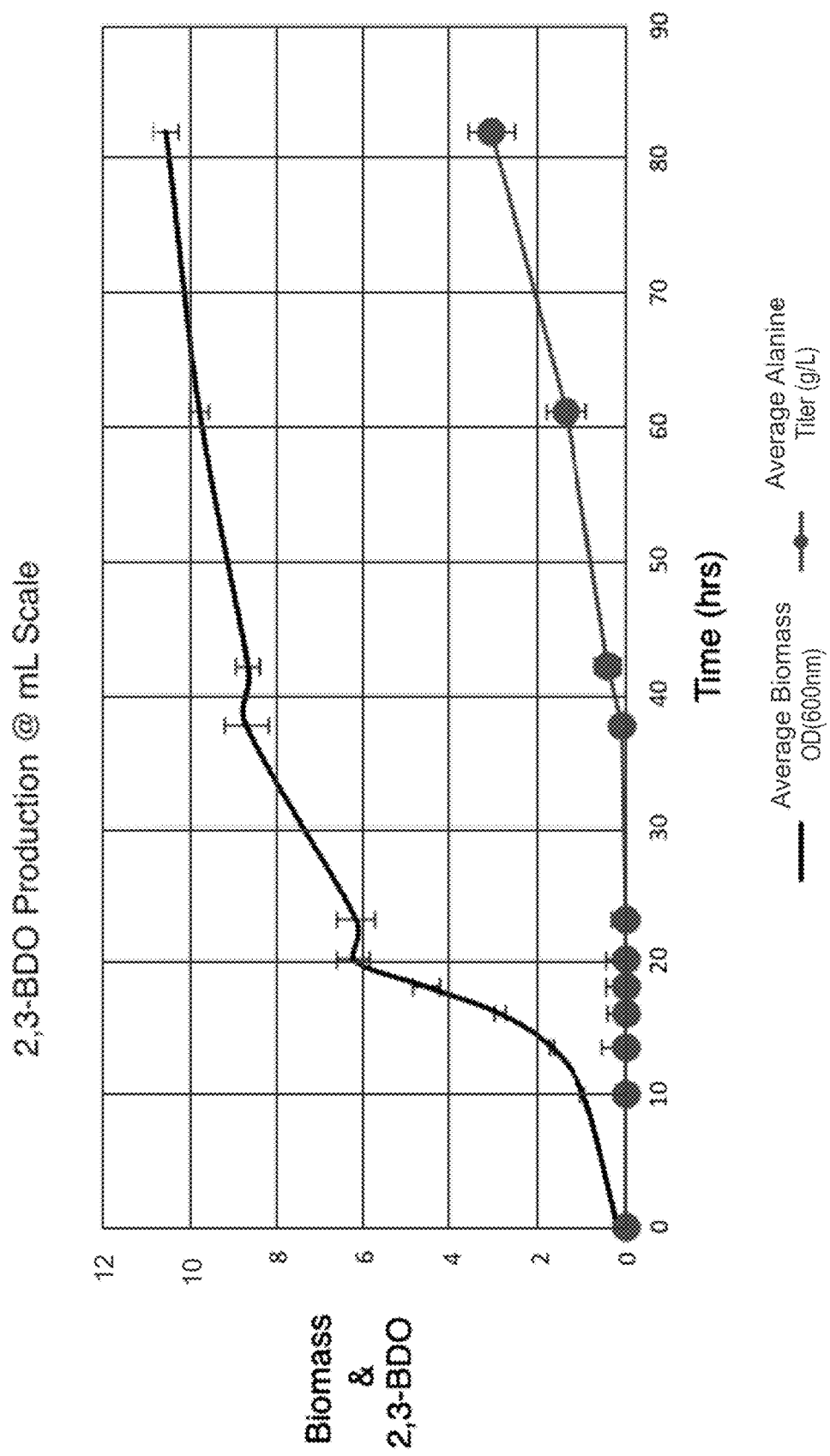

FIG. 12 depicts the production of 2,3-butanediol from pyruvate and NADH at mL scale. Biomass and 2,3-butanediol titers are plotted as a function of time.

Figure 13:
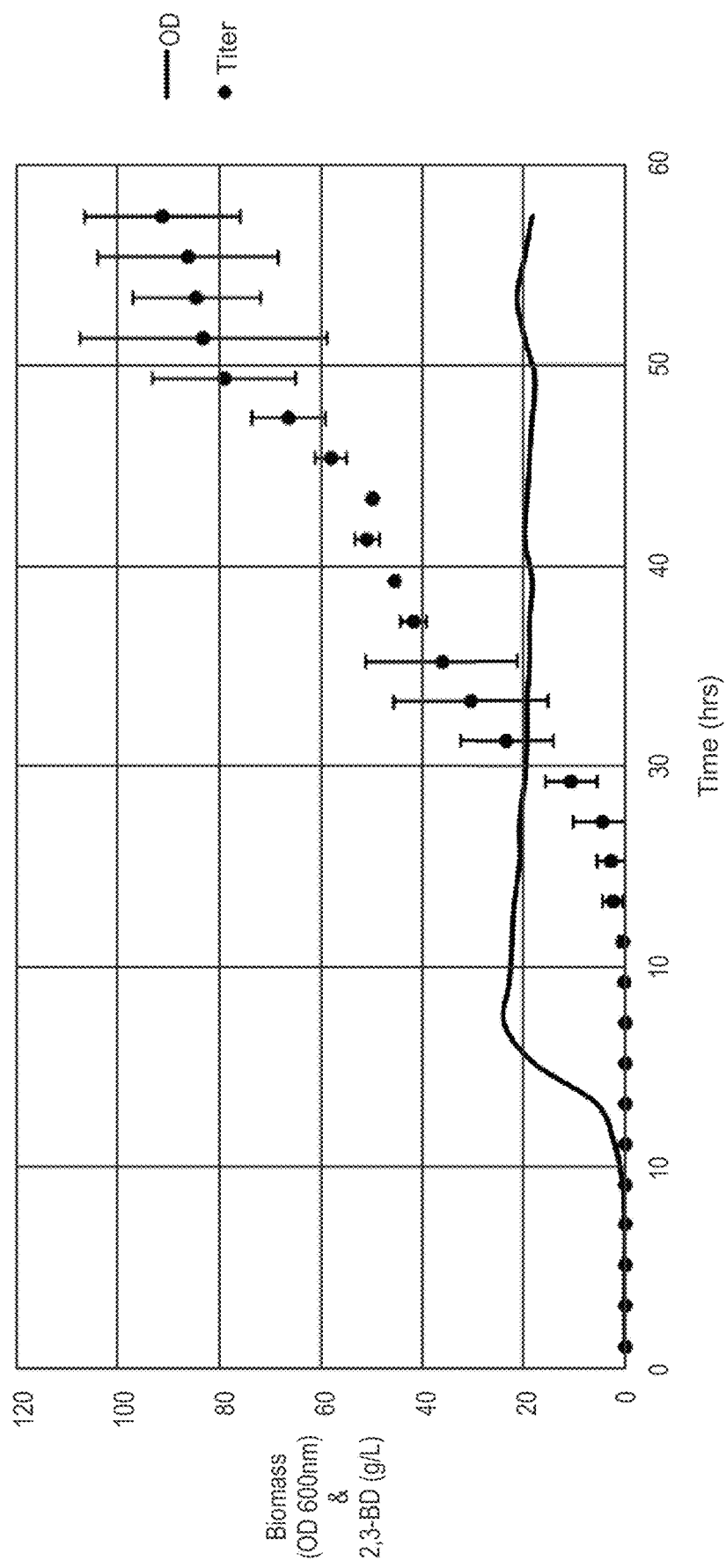

FIG. 13 depicts the production of 2,3-butanediol from pyruvate and NADH at L scale. Biomass and 2,3-butanediol titers are plotted as a function of time.

Figure 14:
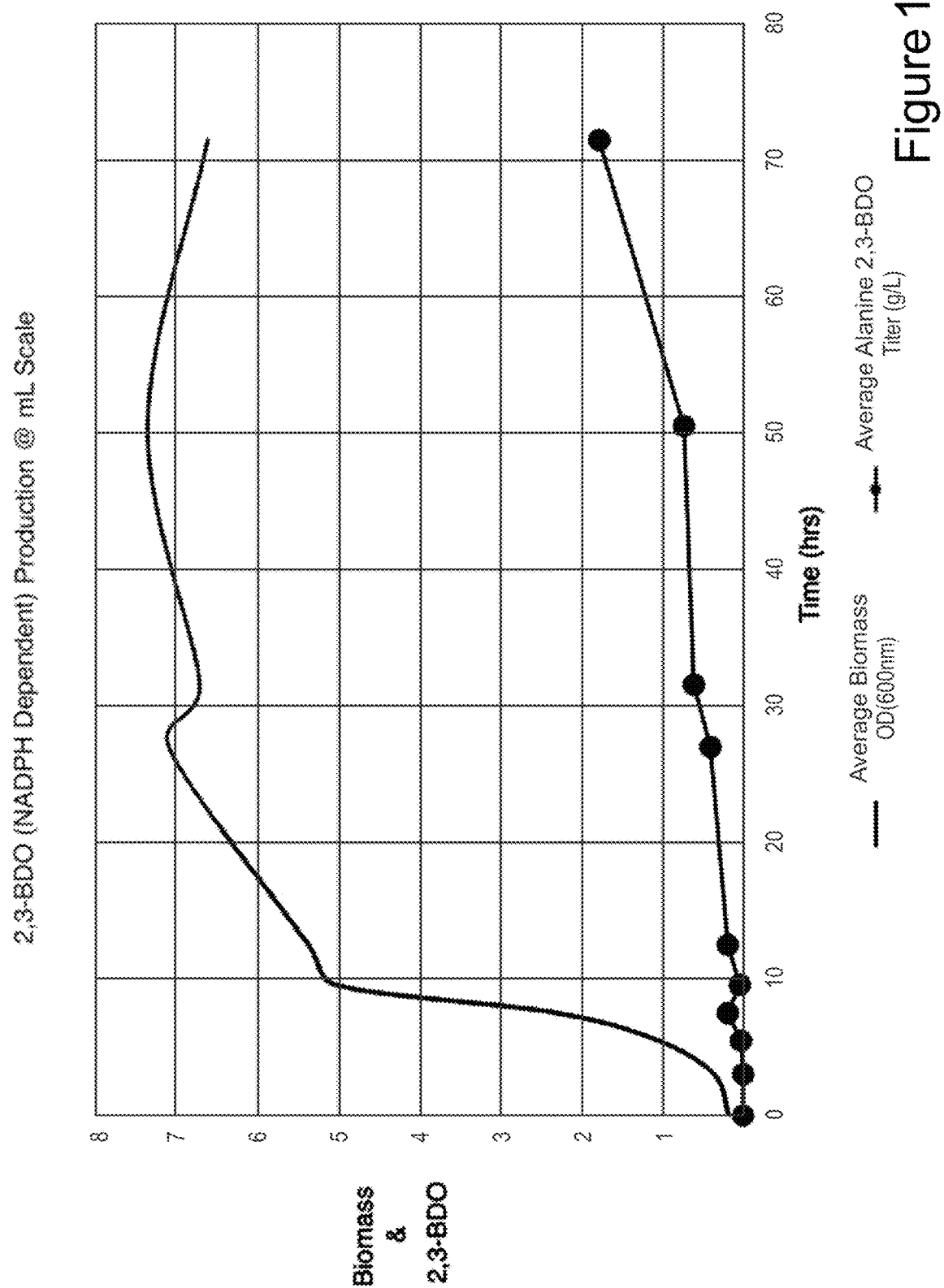

FIG. 14 depicts the production of 2,3-butanediol from pyruvate and NADPH at mL scale. Biomass and 2,3-butanediol titers are plotted as a function of time.

Figure 15:
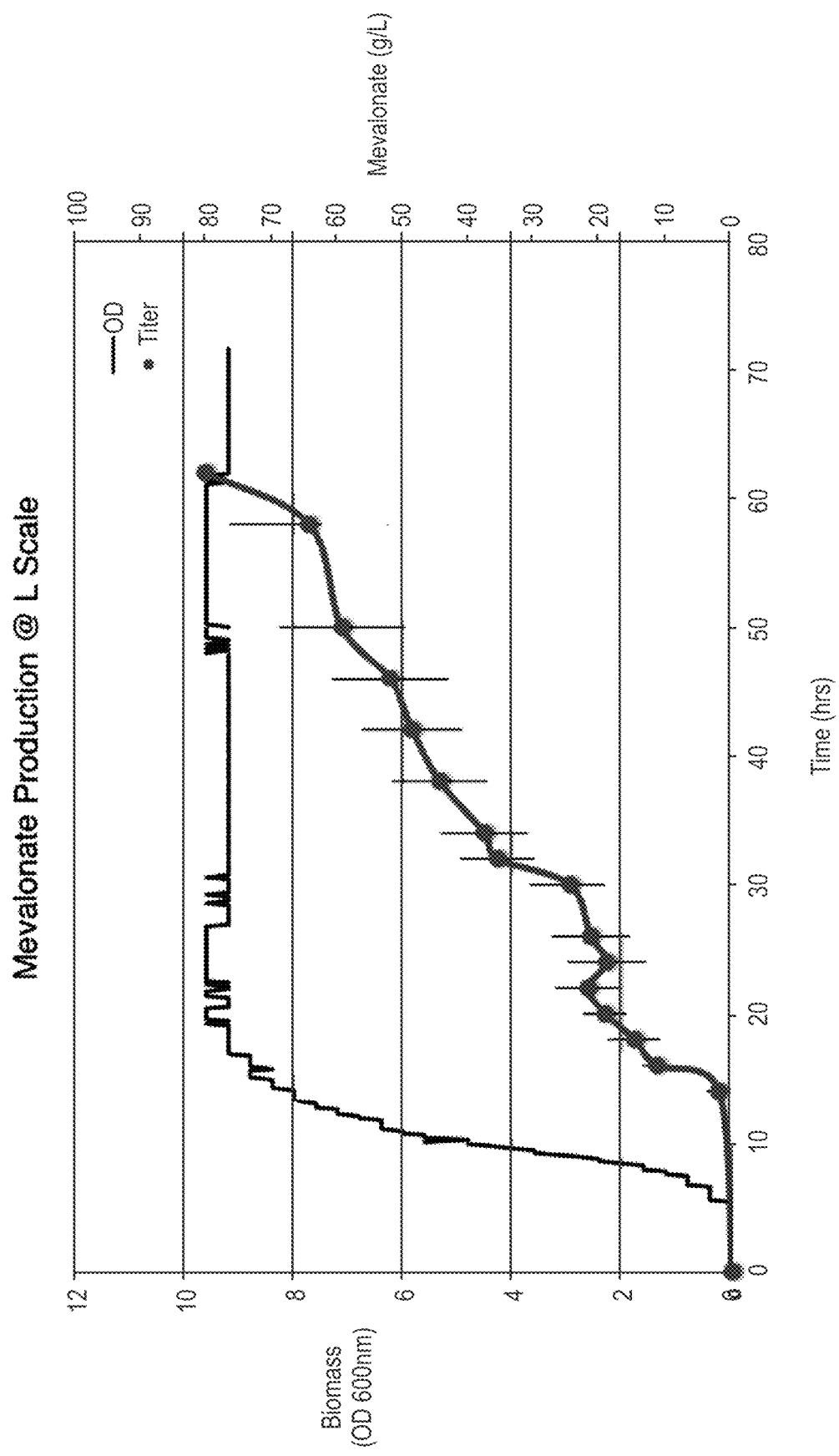

FIG. 15 depicts the production of mevalonic acid from acetyl-CoA and NADPH at L scale. Biomass and mevalonic acid titers are plotted as a function of time.

DETAILED DESCRIPTION OF THE INVENTION

The present invention is related to various production methods and/or genetically modified microorganisms that have utility for fermentative production of various chemical products, to methods of making such chemical products that utilize populations of these microorganisms in vessels, and to systems for chemical production that employ these microorganisms and methods. Among the benefits of the present invention is the increased ability to reduce or eliminate metabolic pathways required for microbial growth that may interfere with production.

Definitions

As used in the specification and the claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

As used herein, "reduced enzymatic activity," "reducing enzymatic activity," and the like is meant to indicate that a microorganism cell's, or an isolated enzyme, exhibits a lower level of activity than that measured in a comparable cell of the same species or its native enzyme. That is, enzymatic conversion of the indicated substrate(s) to indicated product(s) under known standard conditions for that enzyme is at least 10, at least 20, at least 30, at least 40, at least 50, at least 60, at least 70, at least 80, or at least 90 percent less than the enzymatic activity for the same biochemical conversion by a native (non-modified) enzyme under a standard specified condition. This term also can include elimination of that enzymatic activity. A cell having reduced enzymatic activity of an enzyme can be identified using any method known in the art. For example, enzyme activity assays can be used to identify cells having reduced enzyme activity. See, for example, *Enzyme Nomenclature*, Academic Press, Inc., New York 2007.

The term "heterologous DNA," "heterologous nucleic acid sequence," and the like as used herein refers to a nucleic acid sequence wherein at least one of the following is true: (a) the sequence of nucleic acids foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid, such as an nonnative promoter driving gene expression.

The term "synthetic metabolic valve," and the like as used herein refers to either the use of controlled proteolysis, gene silencing or the combination of both proteolysis and gene silencing to alter metabolic fluxes.

The term "heterologous" is intended to include the term "exogenous" as the latter term is generally used in the art. With reference to the host microorganism's genome prior to the introduction of a heterologous nucleic acid sequence, the nucleic acid sequence that codes for the enzyme is heterologous (whether or not the heterologous nucleic acid sequence is introduced into that genome).

As used herein, the term "gene disruption," or grammatical equivalents thereof (and including "to disrupt enzymatic function," "disruption of enzymatic function," and the like), is intended to mean a genetic modification to a microorganism that renders the encoded gene product as having a reduced polypeptide activity compared with polypeptide activity in or from a microorganism cell not so modified. The genetic modification can be, for example, deletion of the entire gene, deletion or other modification of a regulatory sequence required for transcription or translation, deletion of a portion of the gene which results in a truncated gene product (e.g., enzyme) or by any of various mutation strategies that reduces activity (including to no detectable activity level) the encoded gene product. A disruption may broadly include a deletion of all or part of the nucleic acid sequence encoding the enzyme, and also includes, but is not limited to other types of genetic modifications, e.g., introduction of stop codons, frame shift mutations, introduction or removal of portions of the gene, and introduction of a degradation signal, those genetic modifications affecting mRNA transcription levels and/or stability, and altering the promoter or repressor upstream of the gene encoding the enzyme.

Bio-production or Fermentation, as used herein, may be aerobic, microaerobic, or anaerobic.

When the genetic modification of a gene product, i.e., an enzyme, is referred to herein, including the claims, it is understood that the genetic modification is of a nucleic acid sequence, such as or including the gene, that normally encodes the stated gene product, i.e., the enzyme.

As used herein, the term "metabolic flux" and the like refers to changes in metabolism that lead to changes in product and/or byproduct formation, including production rates, production titers and production yields from a given substrate.

Species and other phylogenic identifications are according to the classification known to a person skilled in the art of microbiology.

Enzymes are listed here within, with reference to a Universal Protein Resource (Uniprot) identification number, which would be well known to one skilled in the art (Uniprot is maintained by and available through the UniProt Consortium).

Where methods and steps described herein indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Prophetic examples provided herein are meant to be broadly exemplary and not limiting in any way.

The meaning of abbreviations is as follows: "C" means Celsius or degrees Celsius, as is clear from its usage, DCW means dry cell weight, "s" means second(s), "min" means minute(s), "h," "hr," or "hrs" means hour(s), "psi" means pounds per square inch, "nm" means nanometers, "d" means day(s), "4" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "PCR" means polymerase chain reaction, "OD" means optical density, "OD$_{600}$" means the optical density measured at a photon wavelength of 600 nm, "kDa" means kilodaltons, "g" means the gravitation constant, "bp" means base pair(s), "kbp" means kilobase pair(s), "% w/v" means weight/volume percent, "% v/v" means volume/volume percent, "IPTG" means isopropyl-µ-D-thiogalactopyranoiside, "aTc" means anhydrotetracycline, "RBS" means ribosome binding site, "rpm" means revolutions per minute, "HPLC" means high performance liquid chromatography, and "GC" means gas chromatography.

I. Carbon Sources

Bio-production media, which is used in the present invention with recombinant microorganisms must contain suitable carbon sources or substrates for both growth and production stages. Suitable substrates may include, but are not limited to glucose, sucrose, xylose, mannose, arabinose, oils, carbon dioxide, carbon monoxide, methane, methanol, formaldehyde and glycerol. It is contemplated that all of the above mentioned carbon substrates and mixtures thereof are suitable in the present invention as a carbon source(s).

II. Microorganisms

Features as described and claimed herein may be provided in a microorganism selected from the listing herein, or another suitable microorganism, that also comprises one or more natural, introduced, or enhanced product bio-production pathways. Thus, in some embodiments the microorganism(s) comprise an endogenous product production pathway (which may, in some such embodiments, be enhanced), whereas in other embodiments the microorganism does not comprise an endogenous product production pathway.

The examples describe specific modifications and evaluations to certain bacterial and fungal microorganisms. The scope of the invention is not meant to be limited to such species, but to be generally applicable to a wide range of suitable microorganisms.

More particularly, based on the various criteria described herein, suitable microbial hosts for the bio-production of a chemical product generally may include, but are not limited to the organisms described in the Common Methods Section III. Media and Culture Conditions In addition to an appropriate carbon source, such as selected from one of the herein-disclosed types, bio-production media must contain suitable minerals, salts, cofactors, buffers and other components, known to those skilled in the art, suitable for the growth of the cultures and promotion of the enzymatic pathway necessary for chemical product bio-production under the present invention.

Another aspect of the invention regards media and culture conditions that comprise genetically modified microorganisms of the invention and optionally supplements.

Typically cells are grown at a temperature in the range of about 25° C. to about 40° C. in an appropriate medium, as well as up to 70° C. for thermophilic microorganisms. Suitable growth media are well characterized and known in the art.

Suitable pH ranges for the bio-production are between pH 2.0 to pH 10.0, where pH 6.0 to pH 8.0 is a typical pH range for the initial condition. However, the actual culture conditions for a particular embodiment are not meant to be limited by these pH ranges.

Bio-productions may be performed under aerobic, microaerobic or anaerobic conditions with or without agitation.

IV. Bio-Production Reactors and Systems

Fermentation systems utilizing methods and/or compositions according to the invention are also within the scope of the invention.

Any of the recombinant microorganisms as described and/or referred to herein may be introduced into an industrial bio-production system where the microorganisms convert a carbon source into a product in a commercially viable operation. The bio-production system includes the introduction of such a recombinant microorganism into a bioreactor vessel, with a carbon source substrate and bio-production media suitable for growing the recombinant microorganism, and maintaining the bio-production system within a suitable temperature range (and dissolved oxygen concentration range if the reaction is aerobic or microaerobic) for a suitable time to obtain a desired conversion of a portion of the substrate molecules to a selected chemical product. Bio-productions may be performed under aerobic, microaerobic, or anaerobic conditions, with or without agitation. Industrial bio-production systems and their operation are well-known to those skilled in the arts of chemical engineering and bioprocess engineering.

The following published resources are incorporated by reference herein for their respective teachings to indicate the level of skill in these relevant arts, and as needed to support a disclosure that teaches how to make and use methods of industrial bio-production of chemical product(s) produced under the invention, from sugar sources, and also industrial systems that may be used to achieve such conversion with any of the recombinant microorganisms of the present invention (Biochemical Engineering Fundamentals, 2nd Ed. J. E. Bailey and D. F. Ollis, McGraw Hill, New York, 1986, entire book for purposes indicated and Chapter 9, pages 533-657 in particular for biological reactor design; Unit Operations of Chemical Engineering, 5th Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

The amount of a product produced in a bio-production media generally can be determined using a number of methods known in the art, for example, high performance liquid chromatography (HPLC), gas chromatography (GC), or GC/Mass Spectroscopy (MS).

V. Genetic Modifications, Nucleotide Sequences, and Amino Acid Sequences

Embodiments of the present invention may result from introduction of an expression vector into a host microorganism, wherein the expression vector contains a nucleic acid sequence coding for an enzyme that is, or is not, normally found in a host microorganism.

The ability to genetically modify a host cell is essential for the production of any genetically modified (recombinant) microorganism. The mode of gene transfer technology may be by electroporation, conjugation, transduction, or natural transformation. A broad range of host conjugative plasmids and drug resistance markers are available. The cloning vectors are tailored to the host organisms based on the nature of antibiotic resistance markers that can function in that host. Also, as disclosed herein, a genetically modified (recombinant) microorganism may comprise modifications other than via plasmid introduction, including modifications to its genomic DNA.

More generally, nucleic acid constructs can be prepared comprising an isolated polynucleotide encoding a polypeptide having enzyme activity operably linked to one or more (several) control sequences that direct the expression of the coding sequence in a microorganism, such as *E. coli*, under conditions compatible with the control sequences. The isolated polynucleotide may be manipulated to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well established in the art.

The control sequence may be an appropriate promoter sequence, a nucleotide sequence that is recognized by a host cell for expression of a polynucleotide encoding a polypeptide of the present invention. The promoter sequence may contain transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell. The techniques for modifying and utilizing recombinant DNA promoter sequences are well established in the art.

For various embodiments of the invention the genetic manipulations may be described to include various genetic manipulations, including those directed to change regulation of, and therefore ultimate activity of, an enzyme or enzymatic activity of an enzyme identified in any of the respective pathways. Such genetic modifications may be directed to transcriptional, translational, and post-translational modifications that result in a change of enzyme activity and/or selectivity under selected and/or identified culture conditions and/or to provision of additional nucleic acid sequences such as to increase copy number and/or mutants of an enzyme related to product production. Specific methodologies and approaches to achieve such genetic modification are well known to one skilled in the art.

In various embodiments, to function more efficiently, a microorganism may comprise one or more gene deletions. For example, in *E. coli*, the genes encoding the lactate dehydrogenase (ldhA), phosphate acetyltransferase (pta), pyruvate oxidase (poxB), pyruvate-formate lyase (pflB), methylglyoxal synthase (mgsA), acetate kinase (ackA), alcohol dehydrogenase (adhE), the clpXP protease specificity enhancing factor (sspB), the ATP-dependent Lon protease (lon), the outer membrane protease (ompT), the arcA transcriptional dual regulator (arcA), and the iclR transcriptional regulator (iclR) may be disrupted, including deleted. Such gene disruptions, including deletions, are not meant to be limiting, and may be implemented in various combinations in various embodiments. Gene deletions may be accomplished by numerous strategies well known in the art, as are methods to incorporate foreign DNA into a host chromosome.

In various embodiments, to function more efficiently, a microorganism may comprise one or more synthetic metabolic valves, composed of enzymes targeted for controlled proteolysis, expression silencing or a combination of both controlled proteolysis and expression silencing. For example, one enzyme encoded by one gene or a combination of numerous enzymes encoded by numerous genes in *E. coli* may be designed as synthetic metabolic valves to alter metabolism and improve product formation. Representative genes in *E. coli* may include but are not limited to the following: fabI, zwf, gltA, ppc, udhA, lpd, sucD, aceA, pfkA, lon, rpoS, tktA or tktB. It is appreciated that it is well known to one skilled in the art how to identify homologues of these genes and or other genes in additional microbial species.

For all nucleic acid and amino acid sequences provided herein, it is appreciated that conservatively modified variants of these sequences are included, and are within the scope of the invention in its various embodiments. Functionally equivalent nucleic acid and amino acid sequences (functional variants), which may include conservatively modified variants as well as more extensively varied sequences, which are well within the skill of the person of ordinary skill in the art, and microorganisms comprising these, also are within the scope of various embodiments of the invention, as are methods and systems comprising such sequences and/or microorganisms.

Accordingly, as described in various sections above, some compositions, methods and systems of the present invention comprise providing a genetically modified microorganism that comprises both a production pathway to make a desired product from a central intermediate in combination with synthetic metabolic valves to redistribute flux.

Aspects of the invention also regard provision of multiple genetic modifications to improve microorganism overall effectiveness in converting a selected carbon source into a selected product. Particular combinations are shown, such as in the Examples, to increase specific productivity, volumetric productivity, titer and yield substantially over more basic combinations of genetic modifications.

In addition to the above-described genetic modifications, in various embodiments genetic modifications, including synthetic metabolic valves also are provided to increase the pool and availability of the cofactor NADPH and/or NADH which may be consumed in the production of a product.

More generally, and depending on the particular metabolic pathways of a microorganism selected for genetic modification, any subgroup of genetic modifications may be made to decrease cellular production of fermentation product(s) other than the desired fermentation product, selected from the group consisting of acetate, acetoin, acetone, acrylic, malate, fatty acid ethyl esters, isoprenoids, glycerol, ethylene glycol, ethylene, propylene, butylene, isobutylene, ethyl acetate, vinyl acetate, other acetates, 1,4-butanediol, 2,3-butanediol, butanol, isobutanol, sec-butanol, butyrate, isobutyrate, 2-OH-isobutryate, 3-OH-butyrate, ethanol, isopropanol, D-lactate, L-lactate, pyruvate, itaconate, levulinate, glucarate, glutarate, caprolactam, adipic acid, propanol, isopropanol, fused alcohols, and 1,2-propanediol, 1,3-propanediol, formate, fumaric acid, propionic acid, succinic acid, valeric acid, maleic acid and poly-hydroxybutyrate. Gene deletions may be made as disclosed generally herein, and other approaches may also be used to achieve a desired decreased cellular production of selected fermentation products other than the desired products.

VI. Synthetic Metabolic Valves

Figure 1:
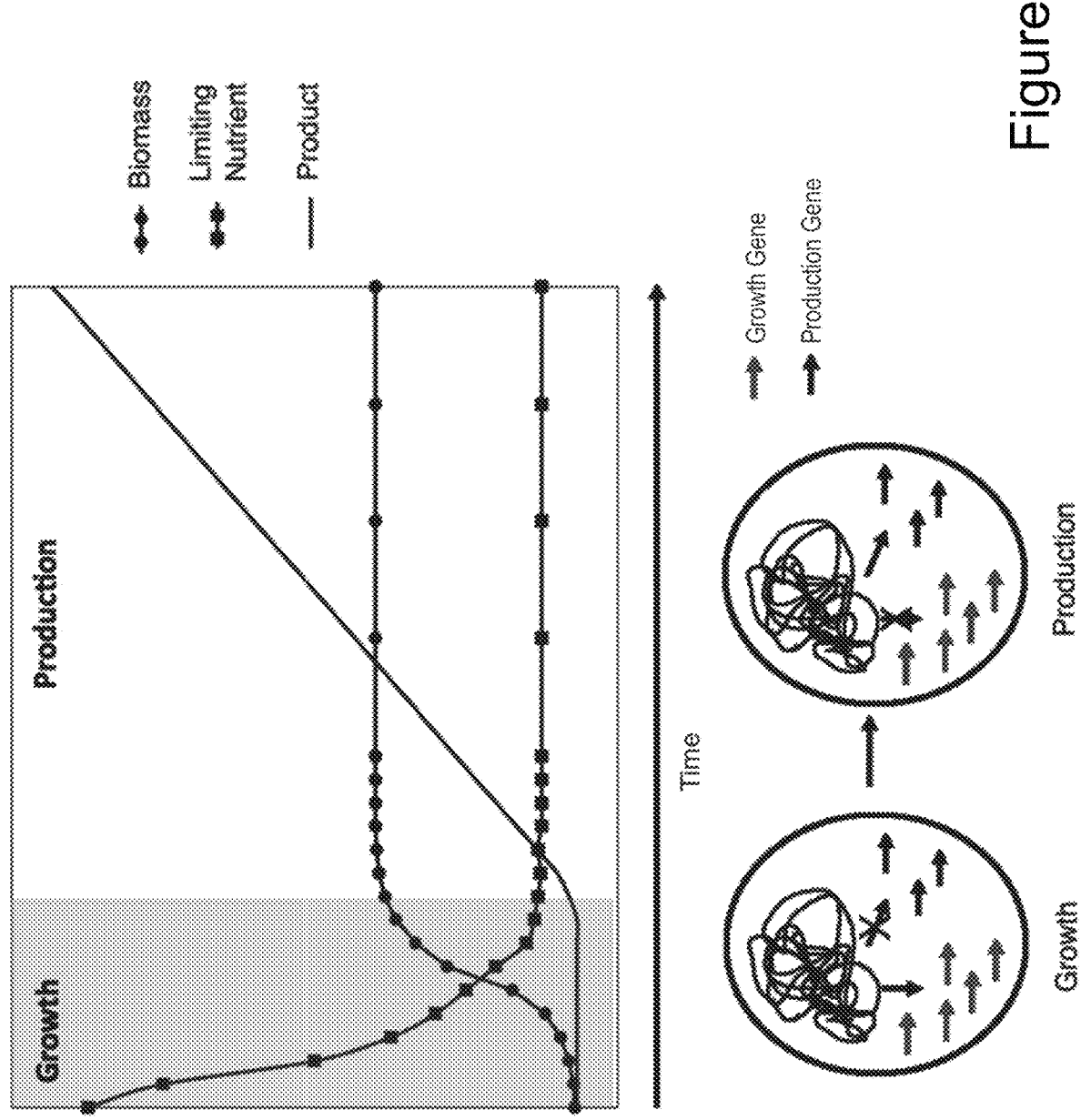
FIG. 1 depicts an overview of a two-phase fermentation processes utilizing a microbe with synthetic metabolic valves. Top Panel: Overview of the fermentation process. Biomass is grown in minimal media with a single limiting macronutrient, such as inorganic phosphate. As the biomass level (black line) or number of cells increases the limiting nutrient (red line) is depleted. When the limiting nutrient is completely consumed, biomass growth is halted. Simultaneously the limitation induces metabolic changes to initiate product biosynthesis through engineered synthetic valves. Lower Panel: Metabolic Changes in the Two Phase Process. In correlation with the system level changes, metabolic changes are induced upon depletion of the limiting nutrient. Specifically, genes encoding metabolic pathways essential for cellular growth "growth genes" are active in the growth phase while genes encoding product biosynthesis "product genes" are silenced. Upon entry into the production phase triggered by nutrient depletion, "growth genes" are silenced and "product genes" are activated.
Figure 2:
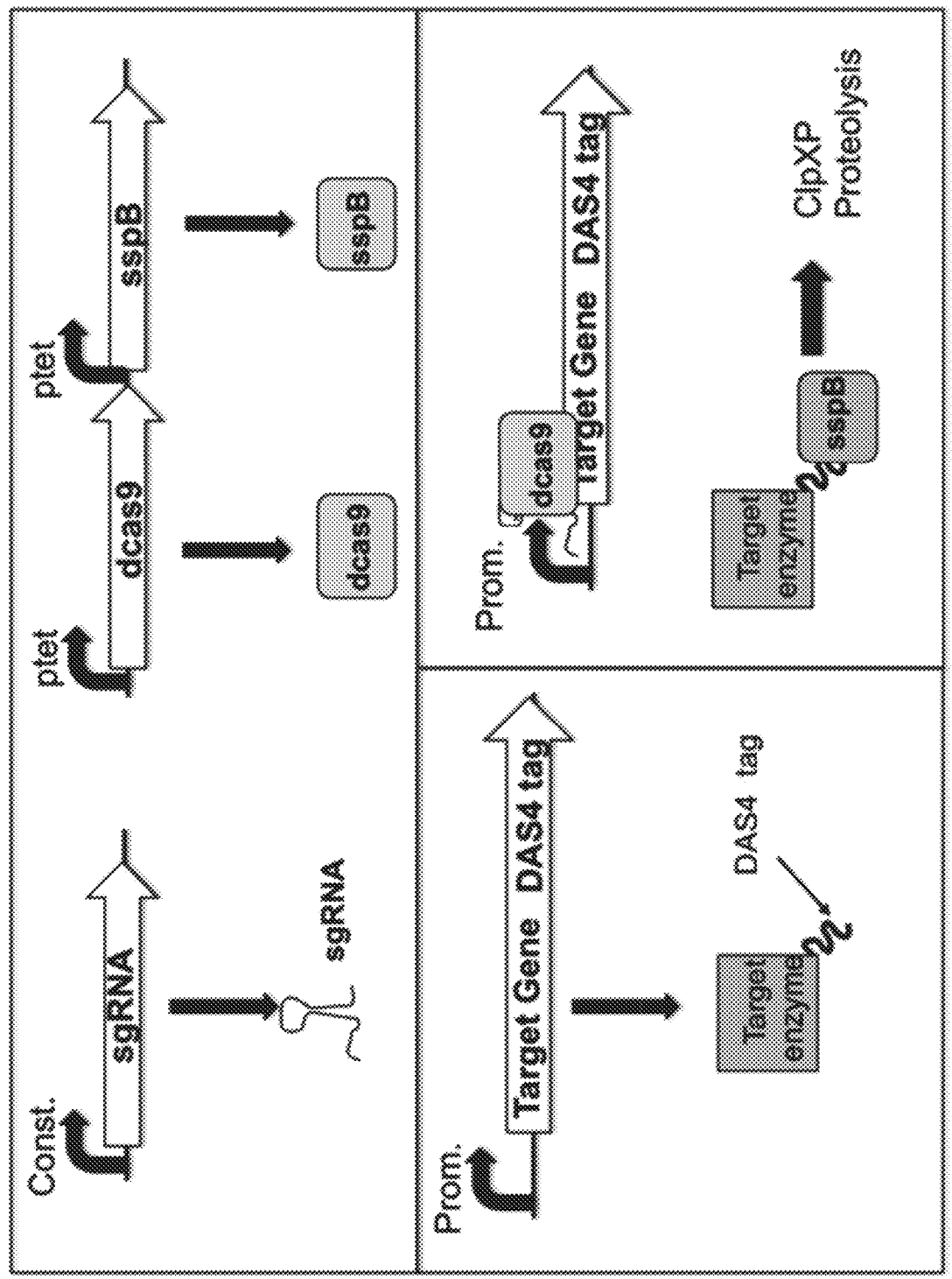
FIG. 2 depicts an overview of a synthetic metabolic valve in *E. coli* using a combination of CRISPR interference gene silencing and controlled protein degradation. Upper Panel: (LEFT) Constructs are made to express small guide RNAs to target a gene of interest in addition to (RIGHT) the controlled induction of a cascade protein complex such as catalytically inactive Cas9 or dCas9 as well as the controlled induction of the chaperone (clpXP enhancing factor) sspB.

In particular the invention describes the construction of synthetic metabolic valves comprising one or more or a combination of the following: controlled gene silencing and controlled proteolysis. It is appreciated that one well skilled in the art is aware of several methodologies for gene silencing and controlled proteolysis. An example of the combination of CRISPR interference based gene silencing and controlled proteolysis is illustrated in FIG. 2.

VI.A Gene Silencing

In particular the invention describes the use of controlled gene silencing to help enable the control over metabolic fluxes in controlled multi-stage fermentation processes. There are several methodologies known in the art for controlled gene silencing, including but not limited to mRNA silencing or RNA interference, silencing via transcriptional repressors and CRISPR interference. Methodologies and mechanisms for RNA interference are taught by Agrawal et al. "RNA Interference: Biology, Mechanism, and Applications" Microbiology and Molecular Biology Reviews, December 2003; 67(4) p 657-685. DOI: 10.1128/MMBR.67.657-685.2003. Methodologies and mechanisms for CRISRPR interference are taught by Qi et al. "Repurposing CRISPR as an RNA-guided platform for sequence-specific control of gene expression" Cell February 2013; 152(5) p 1173-1183. DOI: 10.1016/j.cell.2013.02.022. In addition, methodologies and mechanisms for CRISRPR interference using the native *E. coli* CASCADE system are taught by Luo et al. "Repurposing endogenous type I CRISPR-Cas systems for programmable gene repression" NAR. October 2014; DOI: 10.1093. In additional numerous transcriptional repressor systems are well known in the art and can be used to turn off gene expression.

VI.B Controlled Proteolysis

In particular the invention describes the use of controlled protein degradation or proteolysis to help enable the control over metabolic fluxes in controlled multi-stage fermentation processes. There are several methodologies known in the art for controlled protein degradation, including but not limited to targeted protein cleavage by a specific protease and controlled targeting of proteins for degradation by specific peptide tags. Systems for the use of the *E. coli* clpXP protease for controlled protein degradation are taught by McGinness et al, "Engineering controllable protein degradation", Mol Cell. June 2006; 22(5) p 701-707. This methodology relies upon adding a specific C-terminal peptide tag such as a DAS4 (or DAS+4) tag. Proteins with this tag are not degraded by the clpXP protease until the specificity enhancing chaperone sspB is expressed. sspB induces degradation of DAS4 tagged proteins by the clpXP protease. In additional numerous site specific protease systems are well known in the art. Proteins can be engineered to contain a specific target site of a given protease and then cleaved after the controlled expression of the protease. In some embodiments the cleavage can be expected lead to protein inactivation or degradation. For example Schmidt et al, "ClpS is the recognition component for *Escherichia coli* substrates of the N-end rule degradation pathway" Molecular Microbiology March 2009. 72(2), 506-517. doi:10.1111, teaches that an N-terminal sequence can be added to a protein of interest in enable clpS dependent clpAP degradation. In addition, this sequence can further be masked by an additional N-terminal sequence, which can be controllable cleaved such as by a ULP hydrolase. This allows for controlled N-rule degradation dependent on hydrolase expression. It is therefore possible to tag proteins for controlled proteolysis either at the N-terminus or C-terminus. The preference of using an N-terminal vs. C-terminal tag will largely depend on whether either tag affects protein function prior to the controlled onset of degradation.

The invention describes the use of controlled protein degradation or proteolysis to help enable the control over metabolic fluxes in controlled multi-stage fermentation processes, in *E. coli*. There are several methodologies known in the art for controlled protein degradation in other microbial hosts, including a wide range of gram-negative as well as gram-positive bacteria, yeast and even archaea. In particular, systems for controlled proteolysis can be transferred from a native microbial host and used in a non-native host. For example Grilly et al, "A synthetic gene network for tuning protein degradation in *Saccharomyces cerevisiae*" Molecular Systems Biology 3, Article 127. doi:10.1038, teaches the expression and use of the *E. coli* clpXP protease in the yeast *Saccharomyces cerevisiae*. Such approaches can be used to transfer the methodology for synthetic metabolic valves to any genetically tractable host.

VI.C Synthetic Metabolic Valve Control

In particular the invention describes the use of synthetic metabolic valves to control metabolic fluxes in multi-stage fermentation processes. There are numerous methodologies known in the art to induce expression that can be used at the transition between stages in multi-stage fermentations. These include but are not limited to artificial chemical inducers including: tetracycline, anhydrotetracycline, lactose, IPTG (isopropyl-beta-D-1-thiogalactopyranoside), arabinose, raffinose, tryptophan and numerous others. Systems linking the use of these well known inducers to the control of gene expression silencing and/or controlled proteolysis can be integrated into genetically modified microbial systems to control the transition between growth and production phases in multi-stage fermentation processes.

In addition, it may be desirable to control the transition between growth and production in multi-stage fermentations by the depletion of one or more limiting nutrients that are consumed during growth. Limiting nutrients can include but are not limited to: phosphate, nitrogen, sulfur and magnesium. Natural gene expression systems that respond to these nutrient limitations can be used to operably link the control of gene expression silencing and/or controlled proteolysis to the transition between growth and production phases in multi-stage fermentation processes.

VII. Disclosed Embodiments are Non-Limiting

While various embodiments of the present invention have been shown and described herein, it is emphasized that such embodiments are provided by way of example only. Numerous variations, changes and substitutions may be made without departing from the invention herein in its various embodiments. Specifically, and for whatever reason, for any grouping of compounds, nucleic acid sequences, polypeptides including specific proteins including functional enzymes, metabolic pathway enzymes or intermediates, elements, or other compositions, or concentrations stated or otherwise presented herein in a list, table, or other grouping (such as metabolic pathway enzymes shown in a figure), unless clearly stated otherwise, it is intended that each such grouping provides the basis for and serves to identify various subset embodiments, the subset embodiments in their broadest scope comprising every subset of such grouping by exclusion of one or more members (or subsets) of the respective stated grouping. Moreover, when any range is described herein, unless clearly stated otherwise, that range includes all values therein and all sub-ranges therein.

Also, and more generally, in accordance with disclosures, discussions, examples and embodiments herein, there may be employed conventional molecular biology, cellular biology, microbiology, and recombinant DNA techniques within the skill of the art. Such techniques are explained fully in the literature. (See, e.g., Sambrook and Russell, "Molecular Cloning: A Laboratory Manual," Third Edition 2001 (volumes 1-3), Cold Spring Harbor Laboratory Press, Cold Spring Harbor, N.Y.; Animal Cell Culture, R. I. Freshney, ed., 1986.) These published resources are incorporated by reference herein for their respective teachings of standard laboratory methods found therein. Such incorporation, at a minimum, is for the specific teaching and/or other purpose that may be noted when citing the reference herein. If a specific teaching and/or other purpose is not so noted, then the published resource is specifically incorporated for the teaching(s) indicated by one or more of the title, abstract, and/or summary of the reference. If no such specifically identified teaching and/or other purpose may be so relevant, then the published resource is incorporated in order to more fully describe the state of the art to which the present invention pertains, and/or to provide such teachings as are generally known to those skilled in the art, as may be applicable. However, it is specifically stated that a citation of a published resource herein shall not be construed as an admission that such is prior art to the present invention. Also, in the event that one or more of the incorporated published resources differs from or contradicts this application, including but not limited to defined terms, term usage, described techniques, or the like, this application controls. Subject matter in the Examples is incorporated into this section to the extent not already present.

EXAMPLES

The examples herein provide some examples, not meant to be limiting. All reagents, unless otherwise indicated, are obtained commercially. Species and other phylogenic identifications are according to the classification known to a person skilled in the art of microbiology, molecular biology and biochemistry.

The names and city addresses of major suppliers are provided herein.

Example 1: Dynamic Flux Control Using Temperature Sensitive Enzymes to Improve Malonyl-CoA Flux in *E. coli*

This example describes the increased production of tetrahydroxynaphtalene (THN) in *E. coli* from the intermediate malonyl-CoA using the controlled inactivation of fabI via a temperature sensitive allele. Briefly, strain BWapldf (BW25113:ΔldhA, ΔpflB, ΔpoxB, ΔackA-pta, ΔadhE) was further genetically modified so that the fabI gene was mutated to contain both a temperature sensitive (ts) mutation (F241 S) as well as to incorporate gentamicin resistance cassette a the C-terminus of the fabI gene. This was accomplished using standard recombineering protocols. The strain was further modified to express the tetrahydroxynapthalene (THN) synthase gene (rppA from Steptomyces coelicolor) under phosphate limiting conditions by transformation with the plasmid pSMART-HC-Kan-yibD-THNS (SEQ ID NO:1). Control strains were made with a control empty vector pSMART-HC-Kan (Genbank Accession #AF532107.1), obtained from Lucigen. This high copy plasmid conferring kanamycin resistance was constructed using routine molecular biology methods utilizing the pSMART-HC-Kan kit obtained from Lucigen. The rppA gene under the control of the promoter of low phosphate induced yibD(waaH) gene of E. coli. This strain, as well as controls, were evaluated for THN production using the two-stage protocol as outline in the Common Methods section "Shake Flask Protocol-1". Relative THN production was quantified by measuring the absorbance of the supernatant at 340 nm. FIG. 4 summarizes the results.

Example 2: A Synthetic Metabolic Valve to Improve Malonyl-CoA Flux in E. coli

This example describes the increased production of tetrahydroxynaphtalene (THN) in E. coli from the intermediate malonyl-CoA using the controlled repression of fabI using synthetic metabolic valve technology. In this example a combination of CRISPR interference gene silencing technology and controlled protein degradation was used in a two-stage process. Briefly, strain BWapldf (BW25113: ΔldhA, 4pflB, ΔpoxB, ΔackA-pta, ΔadhE) was further genetically modified so that the fabI gene was tagged to contain a C-terminal DAS4 tag as well as to incorporate gentamicin resistance cassette a the C-terminus of the fabI gene. The C-terminal nucleotide sequence encoding the DAS4 tag was integrated as the following sequence: 5'-GCGGCCAACGATGAAAACTATTCTGAAAAC-TATGCGGATGCGTCT-34 (SEQ ID NO: 48). This was accomplished using standard recombineering protocols. In addition, the strain was further modified so as to delete the sspB gene. This was also performed with standard recombineering methods. In addition, these strains were still further modified to contain three plasmids, the first plasmid expresses the tetrahydroxynapthalene (THN) synthase gene, pSMART-HC-Kan-yibD-THNS (SEQ ID NO:1), as described above. The second plasmid was constructed to express a small guide RNA targeting the fabI gene from a high copy spectinomycin resistance plasmid derived from pCDF-1b, which was obtained from EMD Millipore Biosciences. The plasmid, pCDF-T2-fabIsgRNA (SEQ ID NO:2), expresses a small guide RNA to use with S. pyogenes dCas9. The specific fabI T2 targeting sequence is given by 5'-CAGCCTGCTCCGGTCGGACCG-3' (SEQ ID NO.47). A control plasmid was also made missing any targeting sequence as described by Qi et al. Cell February 2013; 152(5) p 1173-1183. DOI: 10.1016/j.cell.2013.02.022. The last plasmid, pdCas9-ptet-sspB (SEQ ID NO:3), was derived from the plasmid pdCas9-bacteria, from Qi et al, which was obtained from Addgene (Cambridge, Mass. 02139; Plasmid ID 44249). Briefly, pdCas9-bacteria was linearized and the sspB gene was introduced under the control of an additional ptet promoter at the 3' of the catalytically inactive dcas9 gene. The addition of anhydrotetracycline (aTc) will induce expression of both dCas9 as well as sspB from this Chloramphenicol resistance conferring plasmid. All plasmids were constructed using standard molecular biology methods and sequences confirmed by DNA sequencing. These strains, as well as controls, were evaluated for THN production using the two-stage protocol as outline in the Common Methods section "Shake Flask Protocol-2". Relative THN production was quantified by measuring the absorbance of the supernatant at 340 nm. FIG. 5 summarizes the results.

Example 3: General Example

Numerous microbial strains, such as any of the strains listed in the Common Methods Section, may be genetically modified to express enzymes for the biosynthesis of a product. In addition these modified microbial strains can be further modified to contain a controllable synthetic metabolic valve for the dynamic reduction in enzyme activity of one or more metabolic pathways including those required for growth. These valves may utilize one or a combination of methods including gene silencing and controlled proteolysis. Further these modified strains may be used in a multistage fermentation process wherein transition between stages is concurrent with controlled activation of these valves. Specifically, any of these microbial strains may also be further engineered to express a heterologous production pathway enabling the product formation.

Example 4: E. coli Host Strain Construction

Briefly, strain BWapldf (BW25113:ΔldhA, ΔpflB, ΔpoxB, ΔackA-pta, ΔadhE) was further genetically modified for the deletion of the following genes: arcA, iclR and sspB, to construct strain DLF_0002. This was also performed with standard scarless recombineering methods. To construct a strain capable of both crispr based gene silencing using the native CASCADE system in E. coli as well as controlled proteolysis, the cas3 gene of E. coli was first deleted. This gene was replaced with a sequence to enable both constitutive expression of the casABCDE-cas1,2 operon enabling CASCADE based gene silencing, as well as a construct allowing for the low phosphate induction of the sspB chaperone. The DNA sequence integrated was ordered as a single synthetic construct: SEQ ID NO:4, and integrated using standard recombineering methodologies. In the place of the cas3 gene, this construct integrates a transcriptional terminator, followed by the low phosphate inducible E. coli ugpB gene promoter and the sspB gene. The sspB gene is followed by another transcriptional terminator and a subsequent constitutive proB promoter adapted from (Davis, J H., Rubin, A J., and Sauer, R T. NAR. February 2011; 39(3) p 1131-1141. DOI: 10.1093) to drive constant expression of the CASCADE operon. The resulting strain is termed DLF_0025.

A derivative of E. coli strain DLF_0025 was constructed to utilize a non-PTS dependent glucose uptake system. PTS (phosphotransferase system) based sugar uptake is well known in the art and links the phosphorylation of glucose to the production of pyruvate. Alternative uptake has been previously described in E. coli, (Hernandez-Montalvo, V., et al., Biotechnol Bioeng. September 2003; 83(6) p 687-694), and relies on the overexpression of the E. coli galP permease and glucokinase (glk gene) along with the deletion of the E. coli ptsG gene. The ptsG gene was deleted and replaced with a constitutively expressed glucokinase construct, this construct was ordered as a single synthetic linear DNA construct (SEQ ID NO:5) and integrated according to standard methodologies. In addition, the galP promoter was also replaced via chromosomal replacement using another single synthetic linear DNA construct (SEQ ID NO:6), the resulting strain was called DLF_0286. In both cases the proC promoter was used to drive constitutive expression (Davis, J H., Rubin, A J., and Sauer, R T. NAR. February 2011; 39(3) p 1131-1141. DOI: 10.1093).

E. coli strains DLF_0025 and DLF_0286 were further modified for the controlled proteolysis of key enzymes in central metabolism including: 1) enoyl-ACP reductase encoded by the fabI gene, involved in fatty acid biosynthesis, 2) citrate synthase encoded by the gltA gene, involved in citric acid cycle, 3) soluble transhydrogenase encoded by the udhA gene, involved in NADPH metabolism, 4) glucose-6-phosphate-1-dehydrogenase encoded by the zwf gene, involved in the pentose phosphate pathway and 5) the lipoamide dehydrogenase or E3 component of the pyruvate dehydrogenase complex encoded by lpd gene. C-terminal DAS+4 tags enabling sspB controlled proteolysis were integrated at the 3' end of each of the above genes as the following sequence: 5'-GCGGCCAACGATGAAAACTAT-TCTGAAAACTATGCGGATGCGTCT-3' (SEQ ID NO:48). This was accomplished by the insertion of single DNA cassettes containing the DAS4 tags, targeting sequences as well as a downstream antibiotic resistance cassette. The fabI-DAS4 tag and lpd-DAS4 tag were followed by a gentamicin resistance cassette, the gltA-DAS4 tag was followed by a zeocin resistance cassette, and the udhA-DAS4 and zwf-DAS4 tags were both followed by a blasticidin resistance cassette. The integrated sequences used for the C-terminal tagging fabI, lpd, gltA, udhA and zwf are SEQ ID NO:7, SEQ ID NO:8, SEQ ID NO:9 SEQ ID NO:10 and SEQ ID NO:11 respectively. Strains with single and combinations of DAS4 tagged enzymes were constructed. Host strain genotypes are listed in Table 1.

TABLE 1

E. coli Host Strains

| Strain ID | Genotype |
| --- | --- |
| BW25113 | F-, λ-, Δ(araD-araB)567, ΔlacZ4787(::rrnB-3), rph-1, Δ(rhaD-rhaB)568, hsdR514 |
| BWapldf | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt |
| DLF_0002 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB |
| DLF_0025 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB |
| DLF_0286 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP |
| DLF_0043 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS + 4:zeoR |
| DLF_0028 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR |
| DLF_0031 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS + 4:gentR |
| DLF_0038 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR, udhA-DAS + 4:bsdR |
| DLF_0040 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR, zwf-DAS + 4:bsdR |
| DLF_0039 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR, gltA-DAS + 4:zeoR |
| DLF_0047 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR, gltA-DAS + 4:zeoR, udhA-DAS + 4:bsdR |
| DLF_0167 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, fabI-DAS + 4:gentR, gltA-DAS + 4:zeoR, zwf-DAS + 4:bsdR |
| DLF_0041 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS + 4:gentR, gltA-DAS + 4:zeoR, |
| DLF_0165 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, |

TABLE 1-continued

E. coli Host Strains

| Strain ID | Genotype |
|---|---|
| | ΔadhE::frt, ΔiclR, ΔarcA, ΔsspB, Δcas3::ugpBp-sspB-proB, lpd-DAS + 4:gentR, zwf-DAS + 4:bsdR |
| DLF_0042 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS + 4:gentR, udhA-DAS + 4:bsdR |
| DLF_0049 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS + 4:gentR, gltA-DAS + 4:zeoR, udhA-DAS + 4:bsdR |
| DLF_0048 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, lpd-DAS + 4:gentR, gltA-DAS + 4:zeoR, zwf-DAS + 4:bsdR |
| DLF_0045 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS + 4: zeoR, udhA-DAS + 4:bsdR |
| DLF_0044 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-proB, gltA-DAS + 4: zeoR, zwf-DAS + 4:bsdR |
| DLF_0287 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS + 4:zeoR |
| DLF_0288 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS + 4:zeoR, zwf-DAS + 4:bsdR |
| DLF_0289 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS + 4:zeoR, udhA-DAS + 4:bsdR |
| DLF_0290 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS + 4:zeoR, zwf-DAS + 4:bsdR, fabI-DAS + 4:gentR |
| DLF_0291 | F-, λ-, Δ(araD-araB)567, ΔlacZ4787(::rrnB-3), rph-1, Δ(rhaD-rhaB)568, hsdR514, ΔldhA::frt, ΔpoxB::frt, ΔpflB::frt, ΔackA-pta::frt, ΔadhE::frt, ΔiclR, ΔarcA, ΔsspB, Δcas3::ugpBp-sspB-pro, ΔptsG::proC-glk, proC-galP, gltA-DAS + 4:zeoR, udhA-DAS + 4:bsdR, fabI-DAS + 4:gentR |

Example 5: Low Phosphate Gene Expression in *E. coli*

In order to evaluate different low phosphate induction schemes to control synthetic metabolic valves, several known low phosphate inducible promoters form *E. coli* were evaluated with a ultraviolet excitable, green fluorescent protein (GFPuv) reporter gene. These gene promoters included those for the following genes: amn, phoA, phoB, phoE, phoH, phoU, mipA, pstS, ugpB, waaH and ydfH, were evaluated for low phosphate induction. Reporter plasmids linking each promoter to a GFPuv gene reporter were constructed and sequences are as follows: pSMART-amnp-GFPuv (SEQ ID NO:36), pSMART-phoAp-GFPuv (SEQ ID NO:37), pSMART-phoBp-GFPuv (SEQ ID NO:38), pSMART-phoEp-GFPuv (SEQ ID NO:38), pSMART-phoHp-GFPuv (SEQ ID NO:40), pSMART-phoUp-GFPuv (SEQ ID NO:41), pSMART-mipAp-GFPuv (SEQ ID NO:42), pSMART-pstSp-GFPuv (SEQ ID NO:43), pSMART-ugpBp-GFPuv (SEQ ID NO:12), pSMART-waaHp-GFPuv (SEQ ID NO:44), and pSMART-ydfHp-GFPuv (SEQ ID NO:45). Briefly, plasmids were transformed into *E. coli* strain BWapldf (Refer to Example 4). Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 μL of normalized culture was used to inoculate 760 μL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence. Cells were incubated in the Microreactor at 37 degrees Celsius and a shaking speed of 1200 rpm for 60 hrs. Growth stopped and phosphate depletion begins at about 15-20 hrs (data not shown for clarity). Fluorescence results for each reporter construct as well as an empty vector control are reported as relative fluorescence units (R.F.U) in FIG. 6. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*.

Example 6: pCASCADE Plasmid Cloning pCASCADE-control (SEQ ID NO:13) was prepared by swapping the tetracycline inducible promoter in perRNA plasmid (Luo et al. "Repurposing endogenous type I CRISPR-Cas systems for programmable gene repression" NAR. October 2014; DOI: 10.1093.) with an insulated ugpB promoter. The plasmid was constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations.

Additional pCASCADE plasmids with single RNA guides were prepared via Q5 site-directed mutagenesis (New England Biolabs, Ipswich, Mass., USA),) following manufacturer's protocol, except that 5% v/v DMSO was added to the Q5 PCR reaction. For example pCASCADE-gltA2 (SEQ ID NO:14) was prepared using pCASCADE-control as template and the following primers: gltA2-FOR 5'-GGGACAGTTATTAGTTCGAGTTCCCCGCGCCA GCGGGGATAAACCGAAAAAAAAACCCC-3' (SEQ ID NO:49) and gltA2-REV 5'-GAATGAATTGGT-CAATACGGTTTATCCCCGCTGGCGCGGG-GAACTCGAGGTGGTACCAGATCT-3' (SEQ ID NO:50). Additional pCASCADE plasmids including pCASCADE-fabI (SEQ ID NO:15), pCASCADE-udhA, (SEQ ID NO:16), pCASCADE-zwf (SEQ ID NO:17) and pCASCADE-gltA1 (SEQ ID NO:18) were prepared in a similar manner by exchanging the guide RNA targeting sequence using Q5 mutagenesis.

Additional pCASCADE plasmids with multiple RNA guides were prepared as follows. For example pCASCADE-gltA2-udhA (SEQ ID NO:19) plasmid was prepared by amplifying gltA2 guide half and udhA guide half from pCASCADE-gltA2 and pCASCADE-udhA respectively using Q5 High-Fidelity 2× Master Mix (NEB, MA). The primers used: G2U-FOR1: 5'-CCGGATGAGCATT-CATCAGGCGGGCAAG-3' (SEQ ID NO:51), REV1: 5'-CGGTTTATCCCCGCTGGCGCGGG-GAACTCGAACTTCATAACTTTTAC-3' (SEQ ID NO:52) and FOR2: 5'-GCGCCAGCGGGGATAAACCGTTAC-CATTCTGTTG-3' (SEQ ID NO:53) and REV2: 5'-CTTGCCCGCCTGATGAATGCTCATCCGG-3' (SEQ ID NO:54).

PCR products were purified by gel-extraction and were then used for Gibson Assembly (NEB, MA). pCASCADE-fabI-udhA (SEQ ID NO:20), pCASCADE-fabI-gltA1 (SEQ ID NO:21), pCASCADE-fabI-gltA2 (SEQ ID NO:22), pCASCADE-fabI-zwf (SEQ ID NO:23), pCASCADE-gltA1-udhA (SEQ ID NO:24), pCASCADE-gltA2-udhA (SEQ ID NO:25), pCASCADE-gltA1-zwf (SEQ ID NO:26), pCASCADE-gltA2-zwf (SEQ ID NO:27), were all prepared in a similar way by amplification of each guide and part of the vector backbone followed by Gibson Assembly. All plasmid sequences were confirmed by DNA sequencing (Eton Bioscience, Research Triangle Park, NC, USA).

Example 7: Dynamic Control Over Protein Levels in *E. coli* Using the CASCADE System and Controlled Proteolysis All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*. First a plasmid expressing a low phosphate inducible (utilizing the low phosphate inducible waaH gene promoter from *E. coli*), ultraviolet excitable, green fluorescent protein (GFPuv) was constructed using standard cloning techniques and called pSMART-waaHp-GFPuv (SEQ ID NO:12). Secondly, a compatible vector with the constitutive expression of a red fluorescent protein (mCherry), tagged with a DAS+4 tag enabling controlled proteolysis was constructed pBT1-mCherry-DAS+4 (SEQ ID NO:28). Constitutive expression was achieved using a proD promoter (Davis, J H., Rubin, A J., and Sauer, R T. NAR. February 2011; 39(3) p 1131-1141. DOI: 10.1093). Lastly, another compatible vector enabling the low phosphate expression (utilizing the low phosphate inducible ugpB gene promoter from *E. coli*) expression of a gene silencing guide RNA targeting the proD promoter was constructed (Refer to Example 6 for methods) and called pCASCADE-proD (SEQ ID NO:29). These plasmids were transformed into several host strains as described in Example 4, including strain DLF_0025 to create several strains. Colonies were used to inoculate 4 mL of SM3 media with kanamycin (Refer to Common Methods Section) and incubated overnight at 37 degrees Celsius and a shaking speed of 225 rpm. After overnight growth, cells were normalized to an optical density at 600 nm of 5, and 40 µL of normalized culture was used to inoculate 760 µL of fresh FGM3 (Refer to Common Methods Section) medium with kanamycin in wells of a 48 well FlowerPlate™ B which was transferred into a BioLector Microbioreactor both obtained from M2P Labs (Baesweiler, Germany). The BioLector Microbioreactor can continuously measure fluorescence and biomass levels. Cells were incubated in the Microreactor at 37 degrees Celsius and a shaking speed of 1200 rpm for 60 hrs. Fluorescence results for each reporter construct as well as an empty vector control are reported as relative fluorescence units (R.F.U) normalized to biomass levels are depicted in FIG. 7. All plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*.

Example 8: *E. coli* Pathway Plasmid Cloning

All production plasmids were constructed using standard Gibson Assembly methodology (Gibson Assembly Master Mix, obtained from New England Biolabs, Ipswich, Mass., USA), and synthetic linear double stranded DNA provided as Gblocks™ (Integrated DNA Technology, Coralville, Iowa, USA). Eton Bioscience (Research Triangle Park, NC, USA) was used for plasmid DNA sequence confirmations. Standard codon optimization was performed to optimize constructs for expression in *E. coli*.

A plasmid expressing an NADPH dependent 3-hydroxy-propionic acid (3-HP) production pathway was constructed as an operon of two genes. The mcr gene from *Chloroflexus auranticus* (CaMCR), encoding a malonyl-CoA reductase (Uniprot #A9WIU3), and the ydfG gene from *E. coli*, encoding an NADPH dependent 3-HP dehydrogenase (Uniprot #P39831) were used. Only the C-terminal end (residues 550-1219) of the mcr enzyme encoding the malonyl-CoA reductase domain was utilized (Liu, C., Wang, Q., Ding., Y and Zhao, Gu., PLOS One. September 2013. DOI: 10.1371). The operon was assembled into the pSMART-HC-Kan vector, resulting in plasmid pSMART-3HP1, (SEQ ID NO:30).

A plasmid expressing a malonic acid production pathway was constructed from a single gene encoding a triple mutant (E95N/Q384A/F304R) *Pseudomonas fulva* (strain 12-X) isobutyryl-CoA thioesterase (Uniprot #F6AA82), with altered specificity (Steen, E., Patent Application PCT/US2014/047645). This gene was cloned behind the phosphate dependent waaH gene promoter from *E. coli*. The gene was then assembled into the pSMART-HC-Kan vector (Lucigen, Middleton Wis.), resulting in plasmid pSMART-F6AA82M, (SEQ ID NO:31).

A plasmid expressing an NADPH dependent L-alanine production pathway was constructed from a single gene encoding a double mutant (Leu197Arg Asp196Ala) *Bacillus subtilis* alanine dehydrogenase (AlaDH) (Uniprot #Q08352), with NADPH cofactor specificity (Haas, T., et al. Patent Application PCT/EP2013/057855). This gene was cloned behind the phosphate dependent waaH gene promoter from *E. coli*. The gene was then assembled into the pSMART-HC-Kan vector (Lucigen, Middleton Wis.), resulting in plasmid pSMART-Ala1, (SEQ ID NO:32). A additional plasmid expressing the same NADPH dependent L-alanine production pathway was constructed using the phosphate dependent ugpB gene promoter from *E. coli*. The gene was then assembled into the pSMART-HC-Kan vector (Lucigen, Middleton Wis.), resulting in plasmid pSMART-Ala2, (SEQ ID NO:46).

A plasmid expressing a mevalonate production pathway was constructed from two genes assembled into two transcriptional units. First, the mvaE gene from *Enterococcus faecalis* encoding a bifunctional acetoacetyl-CoA thiolase, and NADPH dependent HMG-CoA reductase (Uniprot #Q9FD70) was cloned behind an insulated version of the phosphate dependent waaH gene promoter from *E. coli*. Additionally, the mvaS gene, also from *E. faecalis*, encoding a hydroxymethylglutaryl-CoA synthase (Uniprot #Q9FD71) was cloned behind an insulated version of the phosphate dependent mipA gene promoter from *E. coli*. The mvaS expression construct was cloned behind the mvaE construct and both assembled into the pSMART-HC-Kan vector, resulting in plasmid pSMART-Mev1, (SEQ ID NO:33).

A plasmid expressing an NADH dependent 2,3-butanediol production pathway was constructed as an operon of three genes. The budA, budB and budC genes from *Enterobacter cloacae* subsp. *dissolvens* SDM, encoding an α-acetolactate decarboxylase, an acetolactate synthase and acetoin reductase, respectively, were cloned behind the phosphate dependent waaH gene promoter from *E. coli*. The operon was assembled into the pSMART-HC-Kan vector, resulting in plasmid pSMART-2,3-BDO1, (SEQ ID NO:34).

A plasmid expressing an NADPH dependent 2,3-butanediol production pathway was constructed as an operon of three genes. The budA, budB genes from *Enterobacter cloacae* subsp. *dissolvens* SDM, encoding an α-acetolactate decarboxylase, an acetolactate synthase, and a Glu221Ser/Ile222Arg/Ala223Ser triple mutant bdh1 gene from *S. cerevisiae*, encoding an NADPH dependent acetoin reductase (Ehsani, M., Fernandez, M R., Biosca J A and Dequin, S. Biotechnol Bioeng. 2009 Oct. 1; 104(2):381-9. doi: 10.1002) respectively, were cloned behind the phosphate dependent waaH gene promoter from *E. coli*. The operon was assembled into the pSMART-HC-Kan vector, resulting in plasmid pSMART-2,3-BDO2 (SEQ ID NO:35).

Example 9: Production of 3-Hydroxypropionic Acid (3-HP) in *E. coli*, from Malonyl-CoA and NADPH in 96 Well Plates Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 2.

TABLE 2

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |
| 11 | DLF_0286 | | Empty vector | 0 | 0 |
| 12 | DLF_0039 | | pSMART-3HP1 | 0 | 0 |
| 13 | DLF_0028 | pCASCADE-fabI | pSMART-3HP1 | 0 | 0 |
| 14 | DLF_0028 | pCASCADE-fabI-zwf | pSMART-3HP1 | 0 | 0 |
| 15 | DLF_0043 | pCASCADE-fabI | pSMART-3HP1 | 0 | 0 |
| 16 | DLF_0025 | pCASCADE-fabI | pSMART-3HP1 | 0.02 | 0.03 |
| 17 | DLF_0045 | pCASCADE-udhA-gltA2 | pSMART-3HP1 | 0.11 | 0.06 |
| 18 | DLF_0025 | | pSMART-3HP1 | 0.16 | 0.14 |
| 19 | DLF_0043 | pCASCADE-gltA2 | pSMART-3HP1 | 0.19 | 0.06 |
| 20 | DLF_0025 | pCASCADE-fabI-udhA | pSMART-3HP1 | 0.36 | 0.18 |
| 21 | DLF_0046 | | pSMART-3HP1 | 0.41 | 0.14 |
| 22 | DLF_0039 | pCASCADE-fabI-gltA2 | pSMART-3HP1 | 0.45 | 0.29 |
| 23 | DLF_0028 | | pSMART-3HP1 | 0.55 | 0.24 |
| 24 | DLF_0025 | pCASCADE-udhA | pSMART-3HP1 | 0.57 | 0.14 |
| 25 | DLF_0046 | pCASCADE-fabI-udhA | pSMART-3HP1 | 0.58 | 0.09 |
| 26 | DLF_0025 | pCASCADE-fabI-zwf | pSMART-3HP1 | 0.66 | 0.26 |
| 27 | DLF_0046 | pCASCADE-fabI-zwf | pSMART-3HP1 | 0.89 | 0.11 |
| 28 | DLF_0047 | pCASCADE-fabI-gltA1 | pSMART-3HP1 | 1.00 | 1.74 |
| 29 | DLF_0038 | pCASCADE-fabI-udhA | pSMART-3HP1 | 1.58 | 0.32 |
| 30 | DLF_0039 | pCASCADE- | pSMART- | 1.66 | 0.34 |

TABLE 2-continued

3-HP Production from malonyl-CoA and NADPH in 96 well plates

| Strain | Host Strain | pCASCADE plasmid | Production Plasmid | Final 3-HP Titer (g/L) | Final 3-HP Std Deviation |
|---|---|---|---|---|---|
| 31 | DLF_0047 | pCASCADE-fabI gltAl | pSMART-3HP1 3HP1 | 1.82 | 0.41 |
| 32 | DLF_0047 | pCASCADE-fabI-zwf | pSMART-3HP1 | 2.05 | 0.16 |
| 33 | DLF_0038 | | pSMART-3HP1 | 2.09 | 0.34 |
| 34 | DLF_0047 | pCASCADE-fabI-udhA | pSMART-3HP1 | 2.28 | 0.39 |
| 35 | DLF_0047 | pCASCADE-udhA | pSMART-3HP1 | 2.33 | 1.30 |
| 36 | DLF_0291 | pCASCADE-gltA2 | pSMART-3HP1 | 3.17 | 0.93 |
| 37 | DLF_0291 | pCASCADE-udhA-gltA2 | pSMART-3HP1 | 4.95 | 2.18 |

Example 10: Production of 3-Hydroxypropionic Acid (3-HP) in *E. coli*, from Malonyl-CoA and NADPH at mL Scale Several *E. coli* strains were constructed utilizing a combination of host strains as described in Example 5, production pathway plasmids as described in Example 6 and CASCADE based gene silencing constructs such as those described in Example 7. Strains were then evaluated for product formation using the standard mL scale evaluation protocol "Micro24 Protocol—1" as described in the Common Methods Section. Products levels were then measured using the analytical methods as described in the Common Methods Section. Summary metrics are listed in Table 3 and shown in FIG. 8.

TABLE 3

3-HP Summary Production metrics for 3-HP produced from malonyl-CoA and NADPH at mL scale.

| Strain | Host Strain | pCASCADE plasmid | Production Plasmid | Final 3-HP Titer (g/L) |
|---|---|---|---|---|
| 18 | DLF_0025 | | pSMART-3HP1 | Below Detection |
| 13 | DLF_0028 | pCASCADE-fabI | pSMART-3HP1 | 1.48 ± 0.91 |
| 38 | DLF_0038 | pCASCADE-fabI | pSMART-3HP1 | 4.19 ± 1.39 |
| 39 | DLF_0038 | pCASCADE-udhA | pSMART-3HP1 | 5.07 ± 1.03 |
| 29 | DLF_0038 | pCASCADE-fabI-udhA | pSMART-3HP1 | 1.17 ± 0.44 |
| 34 | DLF_0047 | pCASCADE-fabI-udhA | pSMART-3HP1 | 8.71 ± 0.28 |

Example 11: Production of 3-Hydroxypropionic Acid (3-HP) in *E. coli*, from Malonyl-CoA and NADPH L Scale

*E. coli* strain 39 from Example 10, was evaluated at 1 L scale using the standard evaluation protocol "1 L Fermentation Protocol—1" as described in the Common Methods Section. Products levels were then measured using the analytical methods as described in the Common Methods Section. Biomass growth and 3-HP production are shown in FIG. 9.

Example 12: Production of Malonic Acid in *E. coli*, from Malonyl-CoA in 96 Well Plates Several *E. coli* strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 4.

TABLE 4

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 10 | DLF_0286 | | | 0 | 0 |
| 11 | DLF_0286 | | Empty vector | 0 | 0 |
| 40 | DLF_0025 | pCASCADE-control | Empty vector | 0 | 0 |
| 41 | DLF_0025 | pCASCADE-control | pSMART-F6AA82M | 0 | 0 |
| 42 | DLF_0028 | pCASCADE-control | pSMART-F6AA82M | 0.19 | 0.095 |
| 43 | DLF_0039 | pCASCADE-control | pSMART-F6AA82M | 0 | 0 |
| 44 | DLF_0039 | pCASCADE-gltA1 | pSMART-F6AA82M | 0 | 0 |
| 45 | DLF_0039 | pCASCADE-gltA2 | pSMART-F6AA82M | 0 | 0 |

TABLE 4-continued

Malonic Acid Production from malonyl-CoA in 96 well plates

| Strain | Host Strain | pCASCADE plasmid | Production Plasmid | Final Malonic Acid Titer (g/L) | Final Malonic Acid Std Deviation |
|---|---|---|---|---|---|
| 46 | DLF_0039 | pCASCADE-zwf | pSMART-F6AA82M | 0 | 0 |
| 47 | DLF_0290 | pCASCADE-control | pSMART-F6AA82M | 0.017 | 0.029 |
| 48 | DLF_0167 | pCASCADE-control | pSMART-F6AA82M | 0.45 | 0.04 |

Example 13: Production of Alanine in E. coli, from Pyruvate in 96 Well Plates Several E. coli strains were constructed utilizing a combination of host strains as described in Example 5, production pathway plasmids as described in Example 8 and CASCADE based gene silencing constructs such as those described in Example 6. Strains were then evaluated for product formation using the standard 96 well plate evaluation protocol "96 Well Plate Protocol—1" as described in the Common Methods Section. Products levels were then measured using the analytical methods as described in the Common Methods Section. These strains and the associated production data are given in Table 5.

TABLE 5

Alanine Production from pyruvate and NADPH in 96 well plates

| Strain | Host Strain | pCASCADE plasmid | Production Plasmid | Final Alanine Titer (g/L) | Final Alanine Std Deviation |
|---|---|---|---|---|---|
| 1 | DLF_0028 | | | 0 | 0 |
| 2 | DLF_0043 | | | 0 | 0 |
| 3 | DLF_0038 | | | 0 | 0 |
| 4 | DLF_0040 | | | 0 | 0 |
| 5 | DLF_0049 | | | 0 | 0 |
| 6 | DLF_0045 | | | 0 | 0 |
| 7 | DLF_0039 | | | 0 | 0 |
| 8 | DLF_0167 | | | 0 | 0 |
| 9 | DLF_0047 | | | 0 | 0 |
| 49 | DLF_0042 | | pSMART-Ala1 | 2.62 | 0.069 |
| 50 | DLF_0043 | pCASCADE-udhA-gltAl | pSMART-Ala2 | 0 | 0 |
| 51 | DLF_0041 | pCASCADE-udhA-gltAl | pSMART-Ala2 | 0.23 | 0.075 |
| 52 | DLF_0041 | | pSMART-Ala1 | 0.71 | 0.256 |
| 53 | DLF_0049 | pCASCADE-udhA-gltA2 | pSMART-Ala2 | 1.26 | 0.737 |
| 54 | DLF_0025 | | pSMART-Ala1 | 1.39 | 0.338 |
| 55 | DLF_0049 | | pSMART-Ala1 | 1.48 | 0.136 |
| 56 | DLF_0031 | | pSMART-Ala1 | 1.62 | 0.245 |
| 57 | DLF_0042 | pCASCADE-udhA | pSMART-Ala2 | 1.63 | 0.190 |
| 58 | DLF_0043 | | pSMART-Ala1 | 1.64 | 0.104 |
| 59 | DLF_0043 | pCASCADE-gltA2 | pSMART-Ala2 | 1.72 | 0.355 |
| 60 | DLF_0049 | pCASCADE-udhA | pSMART-Ala2 | 2.42 | 0.105 |
| 61 | DLF_0045 | pCASCADE-udhA-gltA2 | pSMART-Ala2 | 2.44 | 0.125 |
| 62 | DLF_0049 | pCASCADE-gltA2 | pSMART-Ala2 | 2.74 | 0.551 |
| 63 | DLF_0041 | pCASCADE-gltA2 | pSMART-Ala2 | 3.32 | 1.501 |
| 64 | DLF_0045 | | pSMART-Ala1 | 3.65 | 0.441 |
| 65 | DLF_0043 | pCASCADE-udhA-gltA2 | pSMART-Ala2 | 4.03 | 0.202 |

Example 14: Production of Alanine in E. coli, from Pyruvate at mL Scale

E. coli strain 49 from Example 13, was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 10.

Example 15: Production of Alanine in E. coli, from Pyruvate at L Scale

E. coli strain 60 from Example 13, was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 11.

Example 16: Production of 2,3-Butanediol in E. coli, from Pyruvate and NADH at mL Scale An E. coli strain was made by transforming host strain DLF_00165 with both plasmid pSMART-2,3-BDO1 and pCASCADE-zwf (Refer to Examples 4, 6 and 8). This strain was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 12.

Example 17: Production of 2,3-Butanediol in E. coli, from Pyruvate and NADH at L Scale An E. coli strain was made by transforming host strain DLF_00165 with both plasmid pSMART-2,3-BDO1 and pCASCADE-zwf (Refer to Examples 4, 6 and 8). This strain was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 13.

Example 18: Production of 2,3-Butanediol in *E. coli*, from Pyruvate and NADPH at mL Scale An *E. coli* strain was made by transforming host strain DLF_00049 with both plasmid pSMART-2,3-BDO2 and pCASCADE-udhA (Refer to Examples 4, 6 and 8). This strain was evaluated at mL scale using the standard evaluation protocol "Micro24 Protocol—1" as described in the Common Methods Section. Products levels were then measured using the analytical methods as described in the Common Methods Section. Biomass growth and alanine production are shown in FIG. 14.

Example 19: Production of Mevalonic Acid in *E. coli*, from Acetyl-CoA and NADPH at L Scale An *E. coli* strain was made by transforming host strain DLF_0004 with plasmid pSMART-Mev1 (Refer to Examples 4 and 8). This strain was evaluated at 1 L scale using the standard evaluation protocol "1 L Fermentation Protocol—1" as described in the Common Methods Section. Products levels were then measured using the analytical methods as described in the Common Methods Section. Biomass growth and alanine production are shown in FIG. 15.

Common Methods Section

All methods in this Section are provided for incorporation into the Examples where so referenced.

Subsection I. Microorganism Species and Strains, Cultures, and Growth Media

Microbial species, that may be utilized as needed, are as follows:

*Acinetobacter calcoaceticus* (DSMZ #1139) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of theresuspended *A. calcoaceticus* culture are made into BHI and are allowed to grow for aerobically for 48 hours at 37° C. at 250 rpm until saturated.

*Bacillus subtilis* is a gift from the Gill lab (University of Colorado at Boulder) and is obtained as an actively growing culture. Serial dilutions of the actively growing *B. subtilis* culture are made into Luria Broth (RPI Corp, Mt. Prospect, Ill., USA) and are allowed to grow for aerobically for 24 hours at 37° C. at 250 rpm until saturated.

*Chlorobium limicola* (DSMZ #245) is obtained from the German Collection of Microorganisms and Cell Cultures (Braunschweig, Germany) as a vacuum dried culture. Cultures are then resuspended using Pfennig's Medium I and II (#28 and 29) as described per DSMZ instructions. *C. limicola* is grown at 25° C. under constant vortexing.

*Citrobacter braakii* (DSMZ #30040) is obtained from the German Collection of Microorganisms and Cell Cultures (Braunschweig, Germany) as a vacuum dried culture. Cultures are then resuspended in Brain Heart Infusion(BHI) Broth (RPI Corp, Mt. Prospect, Ill., USA). Serial dilutions of the resuspended *C. braakii* culture are made into BHI and are allowed to grow for aerobically for 48 hours at 30° C. at 250 rpm until saturated.

*Clostridium acetobutylicum* (DSMZ #792) is obtained from the German Collection of Microorganisms and Cell Cultures (Braunschweig, Germany) as a vacuum dried culture. Cultures are then resuspended in *Clostridium acetobutylicum* medium (#411) as described per DSMZ instructions. *C. acetobutylicum* is grown anaerobically at 37° C. at 250 rpm until saturated.

*Clostridium aminobutyricum* (DSMZ #2634) is obtained from the German Collection of Microorganisms and Cell Cultures (Braunschweig, Germany) as a vacuum dried culture. Cultures are then resuspended in *Clostridium aminobutyricum* medium (#286) as described per DSMZ instructions. *C. aminobutyricum* is grown anaerobically at 37° C. at 250 rpm until saturated.

*Clostridium kluyveri* (DSMZ #555) is obtained from the German Collection of Microorganisms and Cell Cultures (Braunschweig, Germany) as an actively growing culture. Serial dilutions of *C. kluyveri* culture are made into *Clostridium kluyveri* medium (#286) as described per DSMZ instructions. *C. kluyveri* is grown anaerobically at 37° C. at 250 rpm until saturated.

*Cornyebacterium glutamicum* (DSMZ #1412) is obtained from the German Collection of Microorganisms and Cell Cultures (Braunschweig, Germany) as an actively growing culture. Serial dilutions of *C. glutamicum* culture are made into *C. glutamicum* medium (#1) as described per DSMZ instructions. *C. glutamicum* is grown aerobically or anaerobically at 37° C. at 250 rpm until saturated.

*Cupriavidus metallidurans* (DMSZ #2839) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. metallidurans* culture are made into BHI and are allowed to grow for aerobically for 48 hours at 30° C. at 250 rpm until saturated.

*Cupriavidus necator* (DSMZ #428) is obtained from the German Collection of Microorganisms and Cell Cultures (Braunschweig, Germany) as a vacuum dried culture. Cultures are then resuspended in Brain Heart Infusion (BHI) Broth (RPI Corp, Mt. Prospect, Ill., USA). Serial dilutions of the resuspended *C. necator* culture are made into BHI and are allowed to grow for aerobically for 48 hours at 30° C. at 250 rpm until saturated. As noted elsewhere, previous names for this species are *Alcaligenes eutrophus* and *Ralstonia eutrophus*.

*Desulfovibrio fructosovorans* (DSMZ #3604) is obtained from the German Collection of Microorganisms and Cell Cultures (Braunschweig, Germany) as a vacuum dried culture. Cultures are thenresuspended in *Desulfovibrio fructosovorans* medium (#63) as described per DSMZ instructions. *D. fructosovorans* is grown anaerobically at 37° C. at 250 rpm until saturated.

*Escherichia coli* strain BW25113 is obtained from the Yale Genetic Stock Center (New Haven, Conn. 06520) and is obtained as an actively growing culture. Serial dilutions of the actively growing *E. coli* K12 culture are made into Luria Broth (RPI Corp, Mt. Prospect, Ill., USA) and are allowed to grow for aerobically for 24 hours at 37° C. at 250 rpm until saturated.

*Escherichia coli* strain BWapldf is a generous gift from George Chen from Tsinghua University in China. Serial dilutions of the actively growing *E. coli* BWapldf is culture are made into Luria Broth (RPI Corp, Mt. Prospect, Ill., USA) and are allowed to grow for aerobically for 24 hours at 37° C. at 250 rpm until saturated.

*Halobacterium salinarum* (DSMZ #1576) is obtained from the German Collection of Microorganisms and Cell Cultures (Braunschweig, Germany) as a vacuum dried culture. Cultures are then resuspended in *Halobacterium* medium (#97) as described per DSMZ instructions. *H. salinarum* is grown aerobically at 37° C. at 250 rpm until saturated.

*Lactobacillus delbrueckii* (#4335) is obtained from WYEAST USA (Odell, Oreg., USA) as an actively growing culture. Serial dilutions of the actively growing *L. delbrueckii* culture are made into Brain Heart Infusion (BHI) broth (RPI Corp, Mt. Prospect, Ill., USA) and are allowed to grow for aerobically for 24 hours at 30° C. at 250 rpm until saturated.

*Metallosphaera sedula* (DSMZ #5348) is obtained from the German Collection of Microorganisms and Cell Cultures (Braunschweig, Germany) as an actively growing culture. Serial dilutions of *M. sedula* culture are made into *Metallosphaera* medium (#485) as described per DSMZ instructions. *M. sedula* is grown aerobically at 65° C. at 250 rpm until saturated.

*Methylococcus capsulatus* Bath (ATCC #33009) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 45° C.

*Methylococcus thermophilus* IMV 2 Yu T is obtained. Cultures are then resuspended in ATCC® Medium 1306: Nitrate mineral salts medium (NMS) under a 50% air 50% methane atmosphere (ATCC, Manassas, Va. 20108 USA) and are allowed to grow at 50° C.

*Methylosinus tsporium* (ATCC #35069) is obtained from the American Type Culture Collection (ATCC) (Manassas, Va. 20108 USA) as a vacuum dried culture. Cultures are then resuspended in ATCC® Medium 1306: Nitrate mineral salts medium (NMS) under a 50% air 50% methane atmosphere (ATCC, Manassas, Va. 20108 USA) and are allowed to grow at 30° C.

*Pichia pastoris* (*Komagataella pastoris*) (DSMZ #70382) is obtained from the German Collection of Microorganisms and Cell Cultures (Braunschweig, Germany) as a vacuum dried culture. Cultures are then resuspended in YPD-medium (#393) as described per DSMZ instructions. *Pichia pastoris* is grown aerobically at 30° C. at 250 rpm until saturated.

*Propionibacterium freudenreichii* subsp. *shermanii* (DSMZ #4902) is obtained from the German Collection of Microorganisms and Cell Cultures (Braunschweig, Germany) as a vacuum dried culture. Cultures are then resuspended in PYG-medium (#104) as described per DSMZ instructions. *P. freudenreichii* subsp. *shermanii* is grown anaerobically at 30° C. at 250 rpm until saturated.

*Pseudomonas putida* is a gift from the Gill lab (University of Colorado at Boulder) and is obtained as an actively growing culture. Serial dilutions of the actively growing *P. putida* culture are made into Luria Broth (RPI Corp, Mt. Prospect, Ill., USA) and are allowed to grow for aerobically for 24 hours at 37° C. at 250 rpm until saturated.

*Saccharomyces cerevisiae* strains can be obtained from the American Type Culture Collection (ATCC) (Manassas, Va. 20108 USA) as a vacuum dried culture. Cultures are then resuspended in YPD Media and allowed to grow at 30° C.

*Streptococcus mutans* (DSMZ #6178) is obtained from the German Collection of Microorganisms and Cell Cultures (Braunschweig, Germany) as a vacuum dried culture. Cultures are then resuspended in Luria Broth (RPI Corp, Mt. Prospect, Ill., USA). *S. mutans* is grown aerobically at 37° C. at 250 rpm until saturated.

*Yarrowia lipolytica* (DSMZ #1345) is obtained from the German Collection of Microorganisms and Cell Cultures (Braunschweig, Germany) as a vacuum dried culture. Cultures are then resuspended in YPD-medium (#393) as described per DSMZ instructions *Yarrowia lipolytica* is grown aerobically at 37° C. at 250 rpm until saturated.

Subsection II. Molecular Biology Techniques—DNA Cloning

In addition to the above or below specific examples, this example is meant to describe a non-limiting approach to genetic modification of a selected microorganism to introduce, remove or alter a nucleic acid sequence of interest. Alternatives and variations are provided within this general example. The methods of this example are conducted to achieve a combination of desired genetic modifications in a selected microorganism species, such as a combination of genetic modifications as described in sections herein, and their functional equivalents, such as in other bacterial and other microorganism species.

A gene or other nucleic acid sequence segment of interest is identified in a particular species (such as *E. coli* as described herein) and a nucleic acid sequence comprising that gene or segment is obtained.

Based on the nucleic acid sequences at the ends of or adjacent the ends of the segment of interest, 5' and 3' nucleic acid primers are prepared. Each primer is designed to have a sufficient overlap section that hybridizes with such ends or adjacent regions. Such primers may include enzyme recognition sites for restriction digest of transposase insertion that could be used for subsequent vector incorporation or genomic insertion. These sites are typically designed to be outward of the hybridizing overlap sections. Numerous contract services are known that prepare primer sequences to order (e.g., Integrated DNA Technologies, Coralville, Iowa USA).

Once primers are designed and prepared, polymerase chain reaction (PCR) is conducted to specifically amplify the desired segment of interest. This method results in multiple copies of the region of interest separated from the microorganism's genome. The microorganism's DNA, the primers, and a thermophilic polymerase are combined in a buffer solution with potassium and divalent cations (e.g., Mg or Mn) and with sufficient quantities of deoxynucleoside triphosphate molecules. This mixture is exposed to a standard regimen of temperature increases and decreases. However, temperatures, components, concentrations, and cycle times may vary according to the reaction according to length of the sequence to be copied, annealing temperature approximations and other factors known or readily learned through routine experimentation by one skilled in the art.

In an alternative embodiment the segment of interest may be synthesized, such as by a commercial vendor, and prepared via PCR, rather than obtaining from a microorganism or other natural source of DNA.

The nucleic acid sequences then are purified and separated, such as on an agarose gel via electrophoresis. Optionally, once the region is purified it can be validated by standard DNA sequencing methodology and may be introduced into a vector. Any of a number of vectors may be used, which generally comprise markers known to those skilled in the art, and standard methodologies are routinely employed for such introduction. Commonly used vector systems are well known in the art. Similarly, the vector then is introduced into any of a number of host cells. Commonly used host cells are *E. coli* strains. Some of these vectors possess promoters, such as inducible promoters, adjacent the region into which the sequence of interest is inserted (such as into a multiple cloning site). The culturing of such plasmid-laden cells permits plasmid replication and thus replication of the segment of interest, which often corresponds to expression of the segment of interest.

Various vector systems comprise a selectable marker, such as an expressible gene encoding a protein needed for growth or survival under defined conditions. Common selectable markers contained on backbone vector sequences include genes that encode for one or more proteins required for antibiotic resistance as well as genes required to complement auxotrophic deficiencies or supply critical nutrients not present or available in a particular culture media. Vectors also comprise a replication system suitable for a host cell of interest.

The plasmids containing the segment of interest can then be isolated by routine methods and are available for introduction into other microorganism host cells of interest. Various methods of introduction are known in the art and can include vector introduction or genomic integration. In various alternative embodiments the DNA segment of interest may be separated from other plasmid DNA if the former will be introduced into a host cell of interest by means other than such plasmid.

While steps of the general prophetic example involve use of plasmids, other vectors known in the art may be used instead. These include cosmids, viruses (e.g., bacteriophage, animal viruses, plant viruses), and artificial chromosomes (e.g., yeast artificial chromosomes (YAC) and bacteria artificial chromosomes (BAC)).

Host cells into which the segment of interest is introduced may be evaluated for performance as to a particular enzymatic step, and/or tolerance or bio-production of a chemical compound of interest. Selections of better performing genetically modified host cells may be made, selecting for overall performance, tolerance, or production or accumulation of the chemical of interest.

It is noted that this procedure may incorporate a nucleic acid sequence for a single gene (or other nucleic acid sequence segment of interest), or multiple genes (under control of separate promoters or a single promoter), and the procedure may be repeated to create the desired heterologous nucleic acid sequences in expression vectors, which are then supplied to a selected microorganism so as to have, for example, a desired complement of enzymatic conversion step functionality for any of the herein-disclosed metabolic pathways. However, it is noted that although many approaches rely on expression via transcription of all or part of the sequence of interest, and then translation of the transcribed mRNA to yield a polypeptide such as an enzyme, certain sequences of interest may exert an effect by means other than such expression.

The specific laboratory methods used for these approaches are well-known in the art and may be found in various references known to those skilled in the art, such as Sambrook and Russell, Molecular Cloning: A Laboratory Manual, Third Edition 2001 (volumes 1-3), Cold Spring Harbor Laboratory Press, Cold Spring Harbor, N.Y. (hereinafter, Sambrook and Russell, 2001).

As an alternative to the above, other genetic modifications may also be practiced, such as a deletion of a nucleic acid sequence of the host cell's genome. One non-limiting method to achieve this is by use of Red/ET recombination, known to those of ordinary skill in the art and described in U.S. Pat. Nos. 6,355,412 and 6,509,156, issued to Stewart et al. and incorporated by reference herein for its teachings of this method. Material and kits for such method are available from Gene Bridges (Gene Bridges GmbH, Dresden, Germany), and the method may proceed by following the manufacturer's instructions. Targeted deletion of genomic DNA may be practiced to alter a host cell's metabolism so as to reduce or eliminate production of undesired metabolic products. This may be used in combination with other genetic modifications such as described herein in this general example.

In addition to the above, longer purified double stranded DNA fragments can now be specified and ordered from a variety of vendors. These DNA pieces can easily be assembled together into plasmid vectors as well as longer synthetic DNA constructs using Gibson Assembly methodologies as taught by Gibson, D. G., et al. "Enzymatic assembly of DNA molecules up to several hundred kilobases" Nature Methods. May 2009. Vol(6) p. 343-345. doi:10.1038.

In addition to the above, once synthetic genetic parts such as open reading frames, promoters and terminators have been synthesized, it is well known in the art, that these parts can easily be shuffled into numerous different combinations using numerous variant assembly technologies, such as Golden Gate Assembly taught by Engler, C., Kandzia, R., and Marillonnet, S., "A one pot, one step, precision cloning method with high throughput capability". PLoS ONE 2008; 3(11):e3647. doi: 10.1371.

Subsection III. Molecular Biology Techniques—Chromosomal Modifications in *E. coli*

Chromosomal modifications can be made to *E. coli* using one of many methods including phage transduction and recombineering. It is appreciated that one skilled in the art is well versed in these methods. Of particular use are scarless recombineering methods, which allow for the precise deletion or addition of sequences to the chromosome without any unneeded sequences remaining such as that taught by Li, X., et al. "Positive and negative selection using the tetA-sacB cassette: recombineering and P1 transduction in *Escherichia coli*". Nucleic Acids Res. December 2013. 41(22) doi: 10.1093.

Subsection IV. Molecular Biology Techniques—Chromosomal Modifications in *Saccharomyces cerevisiae*.

Chromosomal modifications can be made to many yeast strains including *Saccharomyces cerevisiae*. using methods well known in the art for homologous recombination. It is appreciated that one skilled in the art is well versed in these methods.

Subsection V: Media for *E. coli*

GM25 media: GM25 minimal growth media for *E. coli* contained per liter: 736 mL sterile distilled, deionized water, 2.0 mL of 100× Trace Metals Stock, 100 mL of 10× GM phosphate salts, 2.0 mL of 2M $MgSO_4$, 50 mL of 500 g/L glucose, 100 mL of 1 M MOPS buffer, pH 7.4, and 10.0 mL of 100 g/L Yeast Extract. The 100× Trace Metal Stock was prepared in 1.0 L of distilled, deionized water with 10.0 mL of concentrated HCl with 5.0 g $CaCl_2*2H_2O$, 1.00 g $FeCl_3*6H_2O$, 0.05 g $CoCl_2*6H_2O$, 0.3 g $CuCl_2*2H_2O$, 0.02 g $ZnCl_2$, 0.02 g $Na_2MoO_4*2H_2O$, 0.01 g $H_3BO_3$, and 0.04 g $MnCl_2*4H_2O$ and 0.2 μm sterile-filtered. The 10× GM Phosphate Salts were prepared in 1.0 L of distilled, deionized water with 3 g $K_2HPO_4$, 2 g $KH_2PO_4$, 30 g $(NH_4)_2SO_4$, and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered.

PM25 media: PM25 minimal production media for E. coli contained per liter: 636 mL sterile distilled, deionized water, 2.0 mL of 100× Trace Metals Stock, 100 mL of 10× PM phosphate-free salts, 2.0 mL of 2M $MgSO_4$, 50 mL of 500 g/L glucose, 200 mL of 1 M MOPS buffer, pH 7.4, and 10 mL of 1 mg/mL Thiamine. The 100× Trace Metal Stock was prepared in 1.0 L of distilled, deionized water with 10.0 mL of concentrated HCl with 5.0 g $CaCl_2*2H_2O$, 1.00 g $FeCl_3*6H_2O$, 0.05 g $CoCl_2*6H_2O$, 0.3 g $CuCl_2*2H_2O$, 0.02 g $ZnCl_2$, 0.02 g $Na_2MoO_4*2H_2O$, 0.01 g $H_3BO_3$, and 0.04 g $MnCl_2*4H_2O$ and 0.2 μm sterile-filtered. The 10× PM Phosphate-Free Salts were prepared in 1.0 L of distilled, deionized water with 30 g $(NH_4)_2SO_4$ and 1.5 g Citric Acid (anhydrous) and autoclaved. The 2M $MgSO_4$ was prepared in 1.0 L of distilled, deionized water with 240.0 g of anhydrous $MgSO_4$ and 0.2 μm sterile-filtered. The 500 g/L Glucose solution was prepared in 1.0 L of heated distilled, deionized water and 500 g of anhydrous dextrose and 0.2 μm sterile-filtered. The 1 M 4-Morpholinopropanesulfonic acid (MOPS) buffer was prepared in 700.0 mL of distilled, deionized water with 210.0 g MOPS and 30.0 mL 50% KOH solution. The pH was measured with stirring and final adjustments made to pH 7.4 by slowly adding 50% KOH and Q.S. to a final volume of 1.0 L. The final pH 7.4 solution was 0.2 μm sterile-filtered.

SM3 Media: SM3 minimal media for E. coli contained per liter: 596.2 mL sterile distilled, deionized water, 2.0 mL of 100× Trace Metals Stock, 100 mL of 10× Ammonium Citrate 30 Salts, 3.6 mL of Phosphate Buffer, pH=6.8, 2 mL of 40 mM Fe(II) sulfate, 1.0 mL of 2M $MgSO_4$, 5.0 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare a 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10 Media: SM10 minimal media for E. coli contained per liter: 574.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

SM10++ Media: SM10 minimal media for E. coli contained per liter: 549.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM $CaSO_4$, 90 mL of 500 g/L glucose, 200 mL of 1 M MOPS buffer, pH 7.4, and 0.2 mL of 1 mg/mL Thiamine and 25.0 mL of 100 g/L Yeast Extract and 25.0 mL of 100 g/L Casamino acids. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare a 1 M Potassium 3-(N-morpholino)propanesulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM3 Media: FGM3 media for E. coli contained per liter: 636.2 mL sterile distilled, deionized water, 2.0 mL of 100× Trace Metals Stock, 100 mL of 10× Ammonium Citrate 20 Salts, 3.6 mL of Phosphate Buffer, pH=6.8, 2 mL of 40 mM Fe(II) sulfate, 1.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine. Prepare 1 liter of 10× concentrated Ammonium-Citrate 20 salts by mixing 20 g of $(NH_4)_2SO_4$ and 1.5 g Citric Acid in water with stirring. Autoclave and store at room temperature. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

FGM10 Media: FGM10 media for *E. coli* contained per liter: 824.3 mL sterile distilled, deionized water, 4.0 mL of 100× Trace Metals Stock, 100 mL of 10× Ammonium Citrate 90 Salts, 10.0 mL of Phosphate Buffer, pH=6.8, 4 mL of 40 mM Fe(II) sulfate, 1.25 mL of 2M $MgSO_4$, 6.25 mL of 10 mM 2M $CaSO_4$, 50 mL of 500 g/L glucose, and 0.2 mL of 1 mg/mL Thiamine. Prepare 1 liter of 10× concentrated Ammonium-Citrate 90 salts by mixing 90 g of $(NH_4)_2SO_4$ and 2.5 g Citric Acid Autoclave and store at room temperature. Prepare 1 liter of 10× concentrated Ammonium-Citrate 90 salts by mixing 90 g of $(NH_4)_2SO_4$ and 2.5 g Citric Acid Autoclave and store at room temperature. 0.1 M potassium phosphate buffer, pH 6.8 by mixing 49.7 mL of 1.0 M $K_2HPO_4$ and 50.3 mL of 1.0 M $KH_2PO_4$ and adjust to a final volume of 1000 mL with ultrapure water. Filter sterilize (0.2 um) and store at room temperature. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

96WPM Media: 96WPM media for *E. coli* contained per liter: 638.8 mL sterile distilled, deionized water, 2.0 mL of 100× Trace Metals Stock, 100 mL of 10× Ammonium Citrate 30 Salts, 2 mL of 40 mM Fe(II) sulfate, 2.0 mL of 2M $MgSO_4$, 5.0 mL of 10 mM 2M $CaSO_4$, 50 mL of 500 g/L glucose, 200 mL of 1 M MOPS buffer, pH 7.4, and 0.2 mL of 1 mg/mL Thiamine and 10.0 mL of 100 g/L Yeast Extract. Prepare 1 liter of 10× concentrated Ammonium-Citrate 30 salts by mixing 30 g of $(NH_4)_2SO_4$ and 1.5 g Citric Acid in water with stirring. Autoclave and store at room temperature. Prepare a 1 M Potassium 3-(N-morpholino)propane-sulfonic Acid (MOPS) and adjust to pH 7.4 with KOH (~40 mL). Filter sterilize (0.2 um) and store at room temperature in the dark. Prepare 2 M $MgSO_4$ and 10 mM $CaSO_4$ solutions. Filter sterilize (0.2 um) and store at room temperature. Prepare a solution of 100× Trace metals in 1000 mL of water containing 10 mL of concentrated $H_2SO_4$: 0.6 g $CoSO_4*7H_2O$, 5.0 g $CuSO_4*5H_2O$, 0.6 g $ZnSO_4*7H_2O$, 0.2 g $Na_2MoO_4*2H_2O$, 0.1 g $H_3BO_3$, and 0.3 g $MnSO_4*H_2O$. Filter sterilize (0.2 um) and store at room temperature in the dark. Prepare a fresh solution of 40 mM ferrous sulfate heptahydrate in water. Filter sterilize (0.2 um) and discard after 1 day. Prepare a 50 g/L solution of thiamine-HCl. Filter sterilize (0.2 um) and store at 4 degrees Celsius. Prepare a 500 g/L solution of glucose by stirring with heat. Cool, filter sterilize (0.2 um), and store at room temperature.

Antibiotic concentrations: Unless other wise stated standard final concentrations of antibiotic in media are kanamycin (35 ug/mL), ampicillin (100 ug/ml), spectinomycin (100 ug/ml), chloramphenicol (20 ug/ml), anhydrotetracycline (50 ng/ml), gentamicin (10 ug/ml), zeocin (50 ug/ml), blasticidin (50 ug/ml). Low salt medium such as low salt LB medium is used when using blasticidin or zeocin as selective antibiotics.

Subsection VI: Protocols for Production in *E. coli*

Shake Flask Protocol—1

Bioproduction is demonstrated at a 50-mL scale using GM25 minimal defined media without phosphate. Cultures are started from single colonies by standard practice into 50 mL of GM25 media containing 3.2 mM phosphate plus appropriate antibiotics and grown to stationary phase overnight at 30° C. with rotation at 200 rpm. The optical density ($OD_{600}$, 1 cm pathlength) of each stationary phase culture is measured and the entire culture is transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus appropriate antibiotic in triplicate 250-ml non-baffled flasks and incubated at 30° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by changing the temperature of the shaking incubator to 37° C. at 4 hours post-inoculation. A sample is collected at this time point as well as 6-, 8-, and 24-hours post-inoculation for optical density and product measurement.

Shake Flask Protocol—2

Bioproduction is demonstrated at a 50-mL scale in GM25 minimal defined media without phosphate. Cultures are started from single colonies by standard practice into 50 mL of GM25 media containing 3.2 mM phosphate plus appropriate antibiotic(s) and grown to stationary phase overnight at 37° C. with rotation at 200 rpm. The optical density ($OD_{600}$, 1 cm pathlength) of each stationary phase culture is measured and the entire culture was transferred to 50 mL conical tubes and centrifuged at 4,000 rpm for 15 minutes. A 20 optical density resuspension is generated for each culture by calculating the volume of GM25 media to add to the pellet. Two and a half mL of this resuspension is added to 50 mL of PM25 media plus antibiotics in triplicate 250-ml non-baffled flasks and incubated at 37° C., 200 rpm. To monitor cell growth and production by these cultures, samples (2 ml) are withdrawn at designated time points for optical density measurements at 600 nm ($OD_{600}$, 1 cm pathlength). Samples are centrifuged at 14,000 rpm for 5 minutes and the supernatant retained at −20° C. for analyte measurements. Cultures are shifted to production by inducing the cultures using 50 ng/mL of anhydrotetracycline (aTc) at inoculation. A sample was collected at this time point as well as 4 and 20-hours post-inoculation for optical density and product measurement.

96 Well Plate Protocol—1

Bioproduction is demonstrated at μL in minimal medium. Colonies were used to inoculate individual wells in standard 96 well plates, filled with 150 μL of SM10++ medium with the appropriate antibiotics as needed. Plates were covered with sandwich covers (Model #CR1596 obtained from EnzyScreen, Haarlam, The Netherlands). These covers ensure minimal evaporative loss during incubation. To ensure adequate aeration, the inoculated 96 well plates and sandwich covers were clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model #CR1600, EnzyScreen, Haarlam, The Netherlands). Importantly, the shaker used had an orbit of 0.125 inches or 3 mm. This combination of orbit and minimal shaking speed is required to obtain needed mass transfer coefficient and enable adequate culture oxygenation. Cultures were grown for 16 hours.

After 16 hours of growth, 10 μL samples were taken to measure the optical density at 600 nm (OD(600 nm)). This was done using a plate spectrophotometer. Overnight cell densities at this point often range from 5-15 OD(600 nm). Cells from 100 μL of overnight growth in each well were pelleted by centrifugation, excess media was removed and cells were resuspended in 150 μL of 96WPM, which contains no phosphate. Subsequently cells were once again pelleted and again excess media was removed. Using the overnight measured optical densities, enough fresh 96WPM was added to each well, so upon re-suspension a final OD(600 nm) of 20 was obtained. 7.5 μL of the normalized and washed cultures of OD(600 nm)=20, was used to inoculate 150 μL of fresh 96WPM, plus appropriate antibiotics, in wells of a new standard 96 well plate. Plates were covered with sandwich covers (Model #CR1596 obtained from EnzyScreen, Haarlam, The Netherlands) and clamped into place into a Mini Shaking Incubator (VWR Catalog #12620-942, VWR International LLC., Radnor, Pa., USA.) at a temperature set to 37 degrees Celsius and a shaking speed of 1100 rpm. The plate clamps used were obtained from Enzyscreen (Model #CR1600, EnzyScreen, Haarlam, The Netherlands). Cultures were incubated for 24 hours. After 16-24 hours of production, 100 μL samples from each well were pelleted by centrifugation and the supernatant collected for subsequent analytical analyes.

Micro24 Protocol—1

Bioproduction is demonstrated at mL scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 500 μL of washed and normalized cells was added to 500 μL of 30% sterile glycerol in water, mixed and frozen in cryovial (seed vials) at minus 80 degrees Celsius in a ultralow temperature freezer.

The Micro24™ Microreactor system (Pall Corporation, Exton, Pa., USA) was used to evaluate strains at the mL scale. Pall 24-well PERC cassettes (Catalogue #MRT-PRC) were used for cell growth and production along with stainless steel check valve caps (Catalogue #MRT-CAP-E24). The experimental protocol was set up with an initial volume of 3 mL of FGM3 medium, with appropriate antibiotics as needed, and an agitation of 1000 rpm. pH control was initially turned off. The temperature was controlled at 37 degrees Celsius, with an environmental temperature of 35 degrees Celsius. Oxygen control was initially turned off with monitoring enabled. Frozen seed vials were thawed on ice and 150 μL was used to inoculate each 3 mL culture in each Micro24 cassette well. Samples were collected at inoculation and at regular intervals. Optical density of samples was measured at 600 nm, glucose using a YSI biochemistry analyzer was measured as described below. In addition, supernatants were collected for subsequent analytical analyses. pH control was turned on for each well at the point at which the culture's optical densities as measured at 600 nm was greater than 1.0. pH control was achieved with pressured ammonium hydroxide gas. In addition, oxygen control was turned on for each well when the dissolved oxygen reached below 60%. Glucose boluses of 10 g/L were added both 24 and 48 hours post inoculation using a sterile 500 g/L stock solution.

1 L Fermentation Protocol—1

Bioproduction is demonstrated at L scale in minimal medium. Seeds were prepared as follows. Colonies were used to inoculate 4 mL of SM10 medium, with appropriate antibiotics as needed, into a sterile 14 mL culture tube. Culture tubes were incubated overnight at 37 degrees Celsius in a standard floor model shaking incubator at 225 rpm. After overnight growth, 2.5 mL of these cultures were used to inoculate 50 mL of fresh SM10 medium, plus appropriate antibiotics as needed, in a 250 mL volume disposable and sterile rectangular cell culture flask, such as a Cellstar™ Cell Culture Flask (VWR Catalog #82050-856, VWR International LLC., Radnor, Pa., USA.). These seed cultures were incubated at 37 degrees Celsius in a standard floor model shaking incubator at 225 rpm. Samples were taken every few hours to measure the growth by optical density (OD(600 nm)), until they reached at an OD(600 nm) in the range of 4-10. At this point, cells were harvested by centrifugation, excess media removed and resuspended in fresh SM10 media to obtain a final OD(600 nm) of 10. 3.5 mL of washed and normalized cells was added to 3.5 mL of 30% sterile glycerol in water, mixed and frozen in cryovial (seed vials) at minus 80 degrees Celsius in a ultralow temperature freezer.

An Infors-HT Multifors (Laurel, Md., USA) parallel bioreactor system was used to perform 1 L fermentations, including three gas connection mass flow controllers configured for air, oxygen and nitrogen gases. Vessels used had a total volume of 1400 mL and a working volume of up to 1 L. Online pH and $pO_2$ monitoring and control were accomplished with Hamilton probes. Offgas analysis was accomplished with a multiplexed Blue-in-One BlueSens gas analyzer (BlueSens. Northbrook, Ill., USA). Culture densities were continually monitored using Optek 225 mm OD probes, (Optek, Germantown, Wis., USA). The system used was running IrisV6.0 command and control software and integrated with a Seg-flow automated sampling system (Flownamics, Rodeo, Calif. USA), including FISP cell free sampling probes, a Segmod 4800 and FlowFraction 96 well plate fraction collector.

Tanks were filled with 800 mL of FGM10 Medium, with enough phosphate to target a final *E. coli* biomass concentration close to 10 g dry cell weight per liter. Antibiotics were added as appropriate. Frozen seed vials were thawed on ice and 7 mL of seed culture was used to inoculate the tanks. After inoculation, tanks were controlled at 37 degrees Celsius and pH 6.8 using a 10M solution of sodium hydroxide solution as a titrant. The following oxygen control scheme was used to maintain a dissolved oxygen set point of 25%. First gas flow rate was increased from a minimum of 0.3 L/min of air to 0.8 L/min of air, subsequently, if more aeration was needed, agitation was increased from a minimum of 300 rpm to a maximum of 1000 rpm. Finally if more oxygen was required to achieve a 25% set point, oxygen supplementation was included using the integrated mass flow controllers. A constant concentrated sterile filtered glucose feed (500 g/L) was added to the tanks at a rate of 2 mL/hr, once agitation reached 800 rpm. Fermentation runs were extended for up to 70 hrs and samples automatically withdrawn every 2-4 hrs. Samples were saved for subsequent analytical analysis.

Subsection VII: Analytical Methods

Analytical Methods have been developed for all anticipated metabolites and products.

Quantification of Organic and Amino Acids

A reverse phase UPLC-MS/MS method was developed for the simultaneous quantification of organic and amino acids. Chromatographic separation was performed using an Acquity CSH $C_{18}$ column (100 mm×2.1 i.d., 1.7 μm; Waters Corp., Milford, Mass., USA) at 45 degrees C. The following eluents were used: solvent A: $H_2O$, 0.2% formic acid and 0.05% ammonium (v/v); solvent B: MeOH, 0.1% formic acid and 0.05% ammonium (v/v). The gradient elution was as follows: 0-0.2 min isocratic 5% B, 0.2-1.0 min linear from 5% to 90% B, 1.0-1.5 min isocratic 90% B, and 1.5-1.8 min linear from 90% to 5% B, with 1.8-3.0 min for initial conditions of 5% B for column equilibration. The flow rate remained constant at 0.4 ml/min. A 5 μl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). MS/MS parameters including MRM transitions were tuned for each analyte and are listed in Table 6 below. Adipic acid at a concentration of 36 mg/L was used as an internal standard for normalization in all samples. Peak integration and further analysis was performed using Mass Lynx v4.1 software. The linear range for all metabolites was 2-50 mg/L. Samples were diluted as needed to be within the accurate linear range.

TABLE 6

| | | | | | |
|---|---|---|---|---|---|
| | MS/MS parameters | | | | |
| Analyte | Retention Time (min) | ESI Mode | MRM Transition(s) | Cone Voltage | Collision Energy |
| 3-hydroxypropionic Acid | 1.04 | − | 88.94→ 59.09 | 22 | 8 |
| Alanine | 0.63 | + | 89.95→ 44.08 | 15 | 9 |
| α-ketoglutaric Acid | 1.97 | − | 144.80→ 56.90 | 13 | 11 |
| Citric Acid | 1.76 | − | 190.87→ 110.92 | 25 | 11 |
| Fumaric Acid | 1.91 | − | 114.72→ 70.94 | 21 | 7 |
| Glutamic Acid | 0.67 | − | 145.89→ 102.02 | 29 | 11 |
| Glyoxylic Acid | 0.83 | − | 72.84→ 44.98 | 33 | 7 |
| Lactic Acid | 1.18 | − | 88.94→ 43.08 | 26 | 8 |
| Malic Acid | 1.06 | − | 132.80→ 70.98 | 27 | 13 |
| Malonic Acid | 1.45 | − | 102.85→ 59.09 | 15 | 9 |
| Mevalonic Acid | 1.85 | − | 146.91→ 59.03 | 23 | 11 |
| Pyruvic Acid | 1.81 | − | 87.00→ 43.05 | 20 | 7 |
| Succinic Acid | 1.72 | − | 116.74→ 72.96 | 25 | 11 |
| Itaconic Acid | 1.86 | + | 130.87→ 84.98 | 20 | 12 |
| Adipic Acid | 2.0 | + | 144.77→ 82.96 | 32 | 12 |

Quantification of 2,3 Butanediol Using Mass Spectrometry

A rapid UPLC-MS/MS method was developed for the quantification of 2,3 butanediol (2,3-BDO). Chromatographic separation was performed using an Acquity UPLC BEH $C_{18}$ column (50 mm×2.1 i.d., 1.7 μm; Waters Corp., Milford, Mass., USA) at 45 degrees C. Isopropanol with 0.1% formic acid and 0.05% ammonium (v/v) was used in an isocratic separation. A 5 μl sample injection volume was used. UPLC method development was carried out using standard aqueous stock solutions of analytes. Separations were performed using an Acquity H-Class UPLC integrated with a Xevo™ TQD Mass spectrometer (Waters Corp., Milford, Mass. USA). An MRM transition for 2,3-BDO of 90.972-55.074 was used along with a cone voltage of 16V and Collision Energy of 10V, operating in ESI+ mode. Adipic acid at a concentration of 36 mg/L was used as an internal standard for normalization in all samples. The Adipic acid was measured in ESI—mode with an MRM transition of 144.77-82.96, a cone voltage of 32V and collision energy of 12 V. Both 2,3-BDO and adipic acid eluted at 0.38 minutes. Peak integration and further analysis was performed using Mass Lynx v4.1 software.

Quantification of Diols Using Refractive Index

A confirmatory HPLC method was developed for the quantification of 2,3 butanediol stereoisomers. Chromatographic separation was performed using a Biorad Aminex HPX-87H column (300×7.8 mm, 1.7 μm; Biorad, Hercules, Calif. USA). The isocratic separation was run at room temperature with 5 mM sulfuric acid as the mobile phase. The flow rate remained constant at 0.4 ml/min for 40 minutes after an injection. A 10 µl sample injection volume was used. Method development was carried out using standard aqueous stock solutions of analytes. Separations were performed using an Acquity H-Class UPLC integrated with an ESAT/IN refractive index (RI) detector. (Waters Corp., Milford, Mass. USA). Meso-2,3-butanediol eluted at 24.9 minutes, while (R,R)-2,3-butanediol eluted at 26.3 minutes. Peaks were integrated using Masslynx Software v4.1.

Quantification of Glucose

A YSI biochemistry analyzer, model 2950M (YSI Incorporated, Yellow Springs Ohio, USA) was used to routinely measure glucose concentrations as well as ethanol. The instrument was used according to manufacturer's instructions, using all reagents as supplied from YSI.

What is claimed:

1. A bioprocess for production of a product from a genetically modified microorganism, the bioprocess comprising:

providing a genetically modified microorganism that conditionally expressing a heterologous enzyme of a product production pathway and also comprises a synthetic metabolic valve, wherein the synthetic metabolic valve is characterized by: (i) controlled transcriptional gene silencing of a gene encoding a first enzyme, or (ii) controlled proteolysis of a second enzyme;

in a first stage, growing the genetically modified microorganism in a media and in a second stage, reducing the genetically modified microorganism growth of the first stage and expressing a heterologous enzyme of the product production pathway, wherein, a transition from the first stage to the second stage is at least partially controlled by depletion of a level of a limiting nutrient from the media and, as the limiting nutrient is depleted from the media growth of the genetically modified microorganism is stopped, and the transition comprising silencing the gene of the first enzyme or proteolysis of the second enzyme, wherein at least one of the first enzymes is one of: enoyl-ACP reductase (fabI), citrate synthase (gltA), soluble transhydrogenase (udhA), glucose-6-phosphate-1-dehydrogenase (zwf), lipoamide dehydrogenase (lpd), or combinations thereof; and wherein at least one of the second enzymes is one of: enoyl- ACP reductase (fabI), citrate synthase (gltA), soluble transhydrogenase (udhA), glucose-6-phosphate-1-dehydrogenase (zwf), lipoamide dehydrogenase (lpd), or combinations thereof.

2. The bioprocess of claim 1, wherein the product is one of an alcohol, a diol, a polyol, an organic acid, an amino acid, a fatty acid, a fatty acid derivative, an ester, an alkane, or an alkene.

3. The bioprocess of claim 1, wherein the limiting nutrient comprises inorganic phosphate.

4. The bioprocess of claim 1, wherein the genetically modified microorganism is characterized by disruption or deletion of a gene naturally occurring in the genetically modified microorganism, the naturally occurring gene one of a gene encoding lactate dehydrogenase (ldhA), phosphate acetyltransferase (pta), pyruvate oxidase (poxB), pyruvate-formate lyase (pflB), the methylglyoxal synthase (mgsA), acetate kinase (ackA), alcohol dehydrogenase (adhE), ATP-dependent Lon protease (lon), outer membrane protease (ompT), arcA transcriptional dual regulator (arcA), iclR transcriptional regulator (iclR), or combinations thereof.

5. The bioprocess of claim 1, further comprising a second synthetic metabolic valve controlling at least one enzyme essential for growth of the genetically modified microorganism that is one of: sucD, aceA, pfkA, lon, rpoS, tktA or tktB.

6. The bioprocess of claim 1, wherein the product is acetate, and the heterologous enzyme is encoded by the *E. coli* ackA gene.

7. The bioprocess of claim 1, wherein the product is ethanol from acetyl-CoA and the heterologous enzyme is an oxygen tolerant ethanol dehydrogenase is an *E. coli* adhE gene with a mutation Glu568Lys.

8. The bioprocess of claim 1, wherein the product is butyrate derived from acetyl-CoA and the heterologous enzyme is one of: acetoacetyl-CoA thiolase, crotonase, crotonyl-CoA reductase, butyrate phospho-transferase, butyrate kinase, or a combination thereof.

9. The bioprocess of claim 1, wherein the product is a fatty acid and the heterologous enzyme is one of: ketoacetyl-CoA synthase, 3-hydroxyacyl-CoA dehydratase, an enoyl-CoA reductase, an acyl-CoA thioesterase, or combinations thereof.

10. The bioprocess of claim 1, wherein the product is fatty acid methyl ester and the heterologous enzyme is one of: an ketoacetyl-CoA synthase, 3-hydroxyacyl-CoA dehydratase, an enoyl-CoA reductase, an acyl-CoA wax ester synthase, or combinations thereof.

11. The bioprocess of claim 1, wherein the product is n-hexanol and the heterologous enzyme is one of: an ketoacetyl-CoA thiolases, 3-hydroxyacyl-CoA dehydratase, an enoyl-CoA reductase, a acyl-CoA thioesterase, or combinations thereof.

12. The bioprocess of claim 1, wherein the product is an n-alcohol and the heterologous enzyme is one of: a ketoacetyl-CoA thiolases, 3-hydroxyacyl-CoA dehydratase, an enoyl-CoA reductase, a fatty acyl-CoA reductase, a fatty aldehyde reductase or combinations thereof.

13. The bioprocess of claim 1, wherein the production pathway further comprising increased expression of an acetyl-CoA carboxylase enzyme.

14. The bioprocess of claim 1, wherein the heterologous enzyme is rppA of *S. coelicolor*.

15. The bioprocess of claim 1, wherein the heterologous enzymes comprise the mcr gene of *C. auranticus* and ydfG gene of *E. coli*.

16. The bioprocess of claim 1, wherein the heterologous enzyme comprises aisobutyryl-CoAthioesterase of *P. fulva*.

17. The bioprocess of claim 1, wherein, the heterologous enzyme is AlaDH of *B. subtilis*.

18. The bioprocess of claim 1, wherein the heterologous enzymes are budA, budB and budC genes from *Enterobacter cloacae* subsp. *Dissolvens*.

19. A genetically modified microorganism comprising:
a production pathway comprising at least one enzyme for the production of a product, and
at least one synthetic metabolic valve characterized by (i) controlled transcriptional gene silencing of a gene encoding a first enzyme, or (ii) controlled proteolysis of a second enzyme;
wherein depletion of the limiting nutrient from a growth media in which the genetically modified microorganism is growing will inducing a stationary or non-dividing cellular state;
wherein the synthetic metabolic valve of the microorganism may be conditionally operated;
wherein at least one of the first enzymes is one of: enoyl-ACP reductase (fabI), citrate synthase (gltA), soluble transhydrogenase (udhA), glucose-6-phosphate-1-dehydrogenase (zwf), or lipoamide dehydrogenase (lpd), or combinations thereof; and
wherein at least one of the second enzymes is one of: enoyl-ACP reductase (fabI), citrate synthase (gltA), soluble transhydrogenase (udhA), glucose-6-phosphate-1-dehydrogenase (zwf), or lipoamide dehydrogenase (lpd), or combinations thereof.

* * * * *

SEQUENCE LISTING

<160> NUMBER OF SEQ ID NOS: 54

<210> SEQ ID NO 1
<211> LENGTH: 3111
<212> TYPE: DNA
<213> ORGANISM: Artificial Sequence
<220> FEATURE:
<223> OTHER INFORMATION: Plasmid pSMART-HC-Kan-yibD-THNS

<400> SEQUENCE: 1

```
gtgcgtaatt gtgctgatct cttatatagc tgctctcatt atctctctac cctgaagtga      60
ctctctcacc tgtaaaaata atatctcaca ggcttaatag tttcttaata caaagcctgt     120
aaaacgtcag gataacttct gtgtaggagg ataatctatg gcaactctct gccgtccgtc     180
cgtgagtgtg ccggagcatg ttatcacgat ggaagaaacc cttgaactgg cccgtcgtcg     240
tcatacggat catccacagc tgcccctggc gctgcgctta attgaaaaca ccggtgttcg     300
cacgcgtcat attgttcaac cgatcgagga taccctggag catccagggt ttgaagatcg     360
caataaagta tacgagcgcg aggccaaatc gcgtgtgccg gcggtaatcc aacgcgccct     420
ggacgacgcg gagcttctgg cgacggacat tgacgttatt atctatgtct catgcacggg     480
ttttatgatg cctagtctta ctgcttggtt aatcaacgaa atgggcttcg acagcacgac     540
ccgccaaatt cctatcgcac agcttggctg tgcggccggt ggtgccgcga ttaaccgcgc     600
tcacgatttt tgcacggcat atcctgaagc aaatgcgctg atcgttgcct gcgaattctg     660
cagcctgtgt tatcagccca cagatctcgg tgtaggttct ctcctgtgca acggtctgtt     720
cggtgatgga attgctgcgg ctgtggtgcg cggacgtggt ggtacggggg ttcgcttgga     780
gcgtaacggc agctacttaa ttccaaaaac cgaagattgg atcatgtatg atgtgaaagc     840
aaccggtttc cacttcttac tggataagcg cgtcccggcc accatggaac ccttggcgcc     900
ggctctgaaa gaactcgcgg gcgagcatgg ttgggacgcc agtgatctgg attttatat     960 tgttcacgcc ggtggtccgc gtattttaga cgacttgagt actttccttg aggtggatcc    1020
gcatgcgttt cgttttcccc gtgctaccct gaccgagtat ggtaacattg cgtcagcagt    1080
cgtgctggat gcgttacgcc gcttgttcga tgaaggcggt gtggaggaag gtgcgcgcgg    1140
tctgctggcg gggttcgggc caggtattac agccgaaatg tcactgggct gctggcaaac    1200
cgcgtagtaa ccggcttatc ggtcagtttc acctgattta cgtaaaaacc cgcttcggcg    1260 ggttttgct tttggagggg cagaaagatg aatgactgtc cacgacgcta tacccaaaag    1320
aaagacgaat tctctagata tcgctcaata ctgaccattt aaatcatacc tgacctccat    1380
agcagaaagt caaaagcctc cgaccggagg cttttgactt gatcggcacg taagaggttc    1440
caactttcac cataatgaaa taagatcact accgggcgta ttttttgagt tatcgagatt    1500
ttcaggagct aaggaagcta aaatgagcca tattcaacgg gaaacgtctt gctcgaggcc    1560
gcgattaaat tccaacatgg atgctgattt atatgggtat aaatgggctc gcgataatgt    1620
cgggcaatca ggtgcgacaa tctatcgatt gtatgggaag cccgatgcgc cagagttgtt    1680
```

```
tctgaaacat ggcaaaggta gcgttgccaa tgatgttaca gatgagatgg tcaggctaaa    1740
ctggctgacg gaatttatgc ctcttccgac catcaagcat tttatccgta ctcctgatga    1800
tgcatggtta ctcaccactg cgatcccagg gaaaacagca ttccaggtat tagaagaata    1860
tcctgattca ggtgaaaata ttgttgatgc gctggcagtg ttcctgcgcc ggttgcattc    1920
gattcctgtt tgtaattgtc cttttaacgg cgatcgcgta tttcgtctcg ctcaggcgca    1980
atcacgaatg aataacggtt tggttggtgc gagtgatttt gatgacgagc gtaatggctg    2040
gcctgttgaa caagtctgga agaaatgcat aagcttttg ccattctcac cggattcagt    2100
cgtcactcat ggtgatttct cacttgataa ccttattttt gacgagggga aattaatagg    2160
ttgtattgat gttggacgag tcggaatcgc agaccgatac caggatcttg ccatcctatg    2220
gaactgcctc ggtgagtttt ctccttcatt acagaaacgg cttttttcaaa aatatggtat    2280 tgataatcct gatatgaata aattgcagtt tcacttgatg ctcgatgagt ttttctaatg    2340
agggcccaaa tgtaatcacc tggctcacct tcggtgggc cttttctgcgt tgctggcgtt    2400 tttccatagg ctccgcccc ctgacgagca tcacaaaaat cgatgctcaa gtcagaggtg    2460
gcgaaacccg acaggactat aaagatacca ggcgtttccc cctggaagct ccctcgtgcg    2520
ctctcctgtt ccgaccctgc cgcttaccgg atacctgtcc gcctttctcc cttcgggaag    2580
cgtggcgctt tctcatagct cacgctgtag gtatctcagt tcggtgtagg tcgttcgctc    2640
caagctgggc tgtgtgcacg aaccccccgt tcagcccgac cgctgcgcct tatccggtaa    2700
ctatcgtctt gagtccaacc cggtaagaca cgacttatcg ccactggcag cagccactgg    2760
taacaggatt agcagagcga ggtatgtagg cggtgctaca gagttcttga agtggtggcc    2820
taactacggc tacactagaa gaacagtatt tggtatctgc gctctgctga gccagttac    2880 ctcggaaaaa gagttggtag ctcttgatcc ggcaaacaaa ccaccgctgg tagcggtggt    2940
ttttttgttt gcaagcagca gattacgcgc agaaaaaaag gatctcaaga agatcctttg    3000 atttttctacc gaagaaaggc ccacccgtga aggtgagcca gtgagttgat tgcagtccag    3060
ttacgctgga gtctgaggct cgtcctgaat gatatcaagc ttgaattcgt t             3111
```

<210> SEQ ID NO 2
<211> LENGTH: 2386
<212> TYPE: DNA
<213> ORGANISM: Artificial Sequence
<220> FEATURE:
<223> OTHER INFORMATION: Plasmid pCDF-T2-fabIsgRNA

<400> SEQUENCE: 2

```
gcactgaaat ctagagcggt tcagtagaaa agatcaaagg atcttcttga atccttttt      60 ttctgcgcgt aatctttttgc cctgtaaacg aaaaaaccac ctggggaggt ggtttgatcg    120
aaggttaagt cagttgggga actgcttaac cgtggtaact ggctttcgca gagcacagca    180
accaaatctg tccttccagt gtagccggac tttggcgcac acttcaagag caaccgcgtg    240
tttagctaaa caaatcctct gcgaactccc agttaccaat ggctgctgcc agtggcgttt    300
taccgtgctt ttccgggttg gactcaagtg aacagttacc ggataaggcg cagcagtcgg    360
gctgaacggg gagttcttgc ttacagccca gcttggagcg aacgacctac accgagccga    420
gataccagtg tgtgagctat gagaaagcgc cacacttccc gtaagggaga aaggcggaac    480
aggtatccgg taaacggcag ggtcggaaca ggagagcgca agagggagcg acccgccgga    540
aacggtgggg atctttaagt cctgtcgggt ttcgcccgta ctgtcagatt catggttgag    600
```

```
cctcacggct cccacagatg caccggaaaa gcgtctgttt atgtgaactc tggcaggagg      660
gcggagccta tggaaaaacg ccaccggcgc ggccctgctg ttttgcctca catgttagtc      720
ccctgcttat ccacggaatc tgtgggtaac tttgtatgtg tccgcagcgc ccgccgcagt      780
ctcacgcccg gagcgtagcg accgagtgag ctagctattt gtttattttt ctaaatacat      840
tcaaatatgt atccgctcat gagacaataa ccctgataaa tgcttcaata atattgaaaa      900
aggaagagta tgagggaagc ggtgatcgcc gaagtatcga ctcaactatc agaggtagtt      960
ggcgtcatcg agcgccatct cgaaccgacg ttgctggccg tacatttgta cggctccgca     1020
gtggatggcg gcctgaagcc acacagtgat attgatttgc tggttacggt gaccgtaagg     1080
cttgatgaaa caacgcggcg agctttgatc aacgaccttt ggaaacttc ggcttcccct      1140 ggagagagcg agattctccg cgctgtagaa gtcaccattg ttgtgcacga cgacatcatt     1200
ccgtggcgtt atccagctaa gcgcgaactg caatttggag aatggcagcg caatgacatt     1260
cttgcaggta tcttcgagcc agccacgatc gacattgatc tggctatctt gctgacaaaa     1320
gcaagagaac atagcgttgc cttggtaggt ccagcggcgg aggaactctt tgatccggtt     1380
cctgaacagg atctatttga ggcgctaaat gaaaccttaa cgctatggaa ctcgccgccc     1440
gactgggctg gcgatgagcg aaatgtagtg cttacgttgt cccgcatttg gtacagcgca     1500
gtaaccggca aaatcgcgcc gaaggatgtc gctgccgact gggcaatgga gcgcctgccg     1560
gcccagtatc agcccgtcat acttgaagct agacaggctt atcttggaca agaagaagat     1620
cgcttggcct cgcgcgcaga tcagttggaa gaatttgtcc actacgtgaa aggcgagatc     1680
accaaggtag tcgcaaata atgtctaaca attcgttcaa cactataggg cgaattgaag     1740
gaaggccgtc aaggccgcat tgaggctcgt cctgaatgat atcaagcttg aattcgttga     1800
attctaaaga tctttgacag ctagctcagt cctaggtata atactagtca gcctgctccg     1860
gtcggaccgt tttagagcta gaaatagcaa gttaaaataa ggctagtccg ttatcaactt     1920
gaaaaagtgg caccgagtcg gtgctttttt tgaagcttgg gcccgaacaa aaactcatct     1980
cagaagagga tctgaatagc gccgtcgacc atcatcatca tcatcattga gtttaaacgg     2040
tctccagctt ggctgttttg gcggatgaga agattttc agcctgatac agattaaatc     2100
agaacgcaga agcggtctga taaaacagaa tttgcctggc ggcagtagcg cggtggtccc     2160
acctgacccc atgccgaact cagaagtgaa acgccgtagc gccgatggta gtgtggggtc     2220
tccccatgcg agagtaggga actgccaggc atcaaataaa acgaaaggct cagtcgaaag     2280
actgggcctt tcgttttatc tgttgtttgt cggtgaactg gatccttact cgagtctaga     2340
ctgcagctgg gcctcatggg ccttcctttc actgcccgct ttccag                    2386
```

<210> SEQ ID NO 3
<211> LENGTH: 7413
<212> TYPE: DNA
<213> ORGANISM: Artificial Sequence
<220> FEATURE:
<223> OTHER INFORMATION: Plasmid pdCas9-ptet-sspB

<400> SEQUENCE: 3

```
gacgtcttaa gacccacttt cacatttaag ttgttttct aatccgcata tgatcaattc       60
aaggccgaat aagaaggctg ctctgcacc ttggtgatca ataattcga tagcttgtcg       120 taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaaggct aattgatttt cgagagtttc     300
```

```
atactgtttt tctgtaggcc gtgtacctaa atgtactttt gctccatcgc gatgacttag    360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa    480
agcccgctta tttttacat gccaatacaa tgtaggctgc tctacaccta gcttctgggc     540
gagtttacgg gttgttaaac cttcgattcc gacctcatta agcagctcta atgcgctgtt    600
aatcacttta cttttatcta atctagacat cattaattcc taattttgt tgacactcta    660 tcgttgatag agttatttta ccactcccta tcagtgatag agaaaagaat caaaagatc     720 taaagaggag aaaggatcta tggataagaa atactcaata ggcttagcta tcggcacaaa    780
tagcgtcgga tgggcggtga tcactgatga atataaggtt ccgtctaaaa agttcaaggt    840
tctgggaaat acagaccgcc acagtatcaa aaaaaatctt atagggggctc ttttatttga   900 cagtggagag acagcggaag cgactcgtct caaacggaca gctcgtagaa ggtatacacg    960
tcggaagaat cgtatttgtt atctacagga gattttttca aatgagatgg cgaaagtaga   1020
tgatagtttc tttcatcgac ttgaagagtc ttttttggtg gaagaagaca agaagcatga   1080
acgtcatcct attttggaa atatagtaga tgaagttgct tatcatgaga atatccaac     1140 tatctatcat ctgcgaaaaa aattggtaga ttctactgat aaagcggatt gcgcttaat    1200 ctatttggcc ttagcgcata tgattaagtt tcgtggtcat ttttttgattg agggagattt  1260 aaatcctgat aatagtgatg tggacaaact atttatccag ttggtacaaa cctacaatca   1320
attatttgaa gaaacccta ttaacgcaag tggagtagag gctaaagcga ttctttctgc    1380
acgattgagt aaatcaagac gattagaaaa tctcattgct cagctccccg gtgagaagaa   1440
aaatggctta tttgggaatc tcattgcttt gtcattgggt ttgacccta attttaaatc    1500 aaattttgat ttggcagaag atgctaaatt acagctttca aaagatactt acgatgatga   1560
tttagataat ttattggcgc aaattggaga tcaatatgct gatttgtttt tggcagctaa   1620
gaatttatca gatgctatt tactttcaga tatcctaaga gtaaatactg aaataactaa    1680
ggctccccta tcagcttcaa tgattaaacg ctacgatgaa catcatcaag acttgactct   1740
tttaaaagct ttagttcgac aacaacttcc agaaaagtat aaagaaatct tttttgatca   1800
atcaaaaaac ggatatgcag gttatattga tgggggagct agccaagaag aattttataa   1860
atttatcaaa ccaattttag aaaaaatgga tggtactgag gaattattgg tgaaactaaa   1920
tcgtgaagat ttgctgcgca agcaacggac ctttgacaac ggctctattc cccatcaaat   1980
tcacttgggt gagctgcatg ctattttgag aagacaagaa gactttatc cattttaaa    2040 agacaatcgt gagaagattg aaaaatctt gacttttcga attccttatt atgttggtcc    2100
attggcgcgt ggcaatagtc gttttgcatg gatgactcgg aagtctgaag aaacaattac   2160
cccatggaat tttgaagaag ttgtcgataa aggtgcttca gctcaatcat ttattgaacg   2220
catgacaaac tttgataaaa atcttccaaa tgaaaaagta ctaccaaaac atagtttgct   2280
ttatgagtat tttacggttt ataacgaatt gacaaaggtc aaatatgtta ctgaaggaat   2340
gcgaaaacca gcatttcttt caggtgaaca gaagaaagcc attgttgatt tactcttcaa   2400
aacaaatcga aaagtaaccg ttaagcaatt aaaagagaat tatttcaaaa aaatagaatg   2460
ttttgatagt gttgaaattt caggagttga agatagattt aatgcttcat taggtaccta   2520
ccatgatttg ctaaaaatta ttaaagataa agatttttg gataatgaag aaaatgaaga   2580
tatcttagag gatattgttt taacattgac cttatttgaa gatagggaga tgattgagga   2640
```

-continued

```
aagacttaaa acatatgctc acctctttga tgataaggtg atgaaacagc ttaaacgtcg    2700
ccgttatact ggttggggac gtttgtctcg aaaattgatt aatggtatta gggataagca    2760
atctggcaaa acaatattag attttttgaa atcagatggt tttgccaatc gcaattttat    2820
gcagctgatc catgatgata gtttgacatt taaagaagac attcaaaaag cacaagtgtc    2880
tggacaaggc gatagtttac atgaacatat tgcaaattta gctggtagcc ctgctattaa    2940
aaaaggtatt ttacagactg taaaagttgt tgatgaattg gtcaaagtaa tggggcggca    3000
taagccagaa aatatcgtta ttgaaatggc acgtgaaaat cagacaactc aaaagggcca    3060
gaaaaattcg cgagagcgta tgaaacgaat cgaagaaggt atcaaagaat taggaagtca    3120
gattcttaaa gagcatcctg ttgaaaatac tcaattgcaa aatgaaaagc tctatctcta    3180
ttatctccaa aatggaagag acatgtatgt ggaccaagaa ttagatatta atcgtttaag    3240
tgattatgat gtcgatgcca ttgttccaca aagtttcctt aaagacgatt caatagacaa    3300
taaggtctta acgcgttctg ataaaaatcg tggtaaatcg gataacgttc caagtgaaga    3360
agtagtcaaa aagatgaaaa actattggag acaacttcta aacgccaagt taatcactca    3420
acgtaagttt gataatttaa cgaaagctga acgtggaggt ttgagtgaac ttgataaagc    3480
tggttttatc aaacgccaat tggttgaaac tcgccaaatc actaagcatg tggcacaaat    3540
tttggatagt cgcatgaata ctaaatacga tgaaaatgat aaacttattc gagaggttaa    3600
agtgattacc ttaaaatcta aattagtttc tgacttccga aaagatttcc aattctataa    3660
agtacgtgag attaacaatt accatcatgc ccatgatgcg tatctaaatg ccgtcgttgg    3720
aactgctttg attaagaaat atccaaaact tgaatcggag tttgtctatg gtgattataa    3780
agtttatgat gttcgtaaaa tgattgctaa gtctgagcaa gaaataggca agcaaccgc    3840 aaaatatttc ttttactcta atatcatgaa cttcttcaaa acagaaatta cacttgcaaa    3900
tggagagatt cgcaaacgcc ctctaatcga aactaatggg gaaactggag aaattgtctg    3960
ggataaaggg cgagattttg ccacagtgcg caaagtattg tccatgcccc aagtcaatat    4020
tgtcaagaaa acagaagtac agacaggcgg attctccaag gagtcaattt taccaaaaag    4080
aaattcggac aagcttattg ctcgtaaaaa agactgggat ccaaaaaaat atggtggttt    4140
tgatagtcca acggtagctt attcagtcct agtggttgct aaggtggaaa agggaaatc    4200 gaagaagtta aaatccgtta aagagttact agggatcaca attatggaaa gaagttcctt    4260
tgaaaaaaat ccgattgact ttttagaagc taaaggatat aaggaagtta aaaaagactt    4320
aatcattaaa ctacctaaat atagtctttt tgagttagaa aacggtcgta acggatgct    4380 ggctagtgcc ggagaattac aaaaaggaaa tgagctggct ctgccaagca aatatgtgaa    4440 tttttttatat ttagctagtc attatgaaaa gttgaagggt agtccagaag ataacgaaca    4500
aaaacaattg tttgtggagc agcataagca ttatttagat gagattattg agcaaatcag    4560
tgaattttct aagcgtgtta ttttagcaga tgccaattta gataaagttc ttagtgcata    4620
taacaaacat agagacaaac caatacgtga acaagcagaa aatattattc atttatttac    4680
gttgacgaat cttggagctc ccgctgcttt taaatatttt gatacaacaa ttgatcgtaa    4740
acgatatacg tctacaaaag aagttttaga tgccactctt atccatcaat ccatcactgg    4800
tctttatgaa acacgcattg atttgagtca gctaggaggt gactaactcg agccggctta    4860
tcggtcagtt tcacctgatt tacgtaaaaa cccgcttcgg cgggttttg cttttggagg    4920 ggcagaaaga tgaatgactg tccacgacgc tatacccaaa agaaatccct atcagtgata    4980
gagattgaca tccctatcag tgatagagat actgagcaca tcagcaggac gcactgacca    5040
```

```
agaggagaaa ggatctatgg atttgtcaca gctaacacca cgtcgtccct atctgctgcg   5100
tgcattctat gagtggttgc tggataacca gctcacgccg cacctggtgg tggatgtgac   5160
gctccctggc gtgcaggttc ctatggaata tgcgcgtgac gggcaaatcg tactcaacat   5220
tgcgccgcgt gctgtcggca atctggaact ggcgaatgat gaggtgcgct ttaacgcgcg   5280
ctttggtggc attccgcgtc aggtttctgt gccgctggct gccgtgctgg ctatctacgc   5340
ccgtgaaaat ggcgcaggca cgatgtttga gcctgaagct gcctacgatg aagataccag   5400
catcatgaat gatgaagagg catcggcaga caacgaaacc gttatgtcgg ttattgatgg   5460
cgacaagcca gatcacgatg atgacactca tcctgacgat gaacctccgc agccaccacg   5520
cggtggtcga ccggcattac gcgttgtgaa gtaactcgag taaggatctc caggcatcaa   5580
ataaaacgaa aggctcagtc gaaagactgg gcctttcgtt ttatctgttg tttgtcggtg   5640
aacgctctct actagagtca cactggctca ccttcgggtg ggcctttctg cgtttatacc   5700
tagggatata ttccgcttcc tcgctcactg actcgctacg ctcggtcgtt cgactgcggc   5760
gagcggaaat ggcttacgaa cggggcggag atttcctgga agatgccagg aagatactta   5820
acagggaagt gagagggccg cggcaaagcc gttttttccat aggctccgcc cccctgacaa   5880
gcatcacgaa atctgacgct caaatcagtg gtggcgaaac ccgacaggac tataaagata   5940
ccaggcgttt cccctggcg ctccctcgt gcgctctcct gttcctgcct ttcggtttac   6000
cggtgtcatt ccgctgttat ggccgcgttt gtctcattcc acgcctgaca ctcagttccg   6060
ggtaggcagt tcgctccaag ctggactgta tgcacgaacc ccccgttcag tccgaccgct   6120
gcgccttatc cggtaactat cgtcttgagt ccaacccgga agacatgca aaagcaccac   6180 tggcagcagc cactggtaat tgatttagag gagttagtct tgaagtcatg cgccggttaa   6240
ggctaaactg aaaggacaag ttttggtgac tgcgctcctc caagccagtt acctcggttc   6300
aaagagttgg tagctcagag aaccttcgaa aaaccgccct gcaaggcggt ttttcgttt   6360 tcagagcaag agattacgcg cagaccaaaa cgatctcaag aagatcatct tattaatcag   6420
ataaaatatt tctagatttc agtgcaattt atctcttcaa atgtagcacc tgaagtcagc   6480
cccatacgat ataagttgtt actagtgctt ggattctcac caataaaaaa cgcccggcgg   6540
caaccgagcg ttctgaacaa atccagatgg agttctgagg tcattactgg atctatcaac   6600
aggagtccaa gcgagctcga tatcaaatta cgccccgccc tgccactcat cgcagtactg   6660
ttgtaattca ttaagcattc tgccgacatg gaagccatca caaacggcat gatgaacctg   6720
aatcgccagc ggcatcagca ccttgtcgcc ttgcgtataa tatttgccca tggtgaaaac   6780
gggggcgaag aagttgtcca tattggccac gtttaaatca aaactggtga actcaccca    6840 gggattggct gagacgaaaa acatattctc aataaaccct ttagggaaat aggccaggtt   6900
ttcaccgtaa cacgccacat cttgcgaata tatgtgtaga actgccgga atcgtcgtg     6960 gtattcactc cagagcgatg aaaacgtttc agtttgctca tggaaaacgg tgtaacaagg   7020
gtgaacacta tcccatatca ccagctcacc gtctttcatt gccatacgaa attccggatg   7080
agcattcatc aggcgggcaa gaatgtgaat aaaggccgga taaaacttgt gcttattttt   7140
ctttacggtc tttaaaaagg ccgtaatatc cagctgaacg gtctggttat aggtacattg   7200
agcaactgac tgaaatgcct caaaatgttc tttacgatgc cattgggata tatcaacggt   7260
ggtatatcca gtgatttttt tctccatttt agcttcctta gctcctgaaa atctcgataa   7320
ctcaaaaaat acgcccggta gtgatcttat ttcattatgg tgaaagttgg aacctcttac   7380
```

```
gtgccgatca acgtctcatt ttcgccagat atc                                  7413
```

<210> SEQ ID NO 4
<211> LENGTH: 974
<212> TYPE: DNA
<213> ORGANISM: Artificial Sequence
<220> FEATURE:
<223> OTHER INFORMATION: Synthetic Construct Delta-cas3::ugpBp-sspB-proB

<400> SEQUENCE: 4

```
caagacatgt gtatatcact gtaattcgat atttatgagc agcatcgaaa aatagcccgc      60
tgatatcatc gataatacta aaaaaacagg gaggctatta ccaggcatca aataaaacga     120
aaggctcagt cgaaagactg ggcctttcgt tttatctgtt gtttgtcggt gaacgctctc     180
tactagagtc acactggctc accttcgggt gggcctttct gcgtttatat ctttctgaca     240
ccttactatc ttacaaatgt aacaaaaaag ttattttttct gtaattcgag catgtcatgt    300
taccccgcga gcataaaacg cgtgtgtagg aggataatct atggatttgt cacagctaac     360
accacgtcgt ccctatctgc tgcgtgcatt ctatgagtgg ttgctggata accagctcac     420
gccgcacctg gtggtggatg tgacgctccc tggcgtgcag gttcctatgg aatatgcgcg     480
tgacgggcaa atcgtactca acattgcgcc gcgtgctgtc ggcaatctgg aactggcgaa     540
tgatgaggtg cgctttaacg cgcgctttgg tggcattccg cgtcaggttt ctgtgccgct     600
ggctgccgtg ctggctatct acgcccgtga aaatggcgca ggcacgatgt ttgagcctga     660
agctgcctac gatgaagata ccagcatcat gaatgatgaa gaggcatcgg cagacaacga     720
aaccgttatg tcggttattg atggcgacaa gccagatcac gatgatgaca ctcatcctga     780
cgatgaacct ccgcagccac cacgcggtgg tcgaccggca ttacgcgttg tgaagtaatt     840
gacggctagc tcagtcctag gtacagtgct agccatatga aggagaacaa atgaatttgc     900
ttattgataa ctggatccct gtacgcccgc gaaacggggg gaaagtccaa atcataaatc     960
tgcaatcgct atac                                                      974
```

<210> SEQ ID NO 5
<211> LENGTH: 1500
<212> TYPE: DNA
<213> ORGANISM: Artificial Sequence
<220> FEATURE:
<223> OTHER INFORMATION: Linear DNA Construct Delta-ptsG::proC-glk

<400> SEQUENCE: 5

```
ggctgtgttg aaaggtgttg ccgttgaaga actggcgcag gtaaccaccg ataacttcgc      60
ccgtctgttt cacatcgacg cttcccgcct tcaatccatc cgttgaatga gttttttttaa    120
agctcgtaat taatacttcg ctcttcatgc cgccgcaaac cccgcccctg acagggcggg     180
gtttcgccgc acgtctccat cgcttgccca agttgtgaag cacagctaac accacgtcgt     240
ccctatctgc tgccctaggt ctatgagtgg ttgctggata actttacggg catgcataag     300
gctcgtatga tatattcagg gagaccacaa cggtttccct ctacaaataa ttttgtttaa     360
ctttcgtaga agagcacttc cacacttctg gaaaaggag atataccatg accaagtatg     420
ccctggtcgg tgacgtaggt ggtaccaatg cacgtctcgc tctctgtgat atcgcaagcg     480
gggaaattttc tcaggccaaa acatattccg ggttggatta ccccagctta gaagccgtga    540
ttcgtgtcta tttagaagaa cataaagtag aagtcaaaga cggttgtatt gctattgcgt     600
gccccatcac tggggattgg gtagcaatga ccaaccatac ctgggcgttt tctattgccg     660
agatgaaaaa aaatctgggt ttctcacacc tggagatcat caacgatttt accgcggtga     720
```

```
gcatggcgat cccaatgtta aaaaaggaac acttaattca gttcggcggg gcagaacctg    780
tggagggcaa gccgatcgcg gtttatggtg caggcacagg cttaggtgtc gcgcacttgg    840
tacatgttga caagcgctgg gtgagtttgc cgggcgaagg cggccacgtg gattttgccc    900
ccaattctga agaggaggcg attattctgg aaatcttgcg tgcagaaatc ggtcatgtgt    960
ctgccgaacg tgtgctgagt ggtccaggtc tggtgaatct gtaccgcgct attgtcaaag   1020
cggataaccg cctgccagaa aaccttaaac cgaaagatat caccgaacgt gccttggccg   1080
actcctgtac cgattgccgc cgcgcactta gtctgttttg cgttatcatg ggtcgttttg   1140
gcggcaacct cgcgctgaac ctggggacct tggcggtgt ttttattgcg ggaggtattg   1200
ttccacgctt tttagaattt tcaaagcca gtggctttcg cgcggccttc gaagacaagg   1260
gacgttttaa agaatacgta catgatatcc cagtctattt aattgttcac gataacccag   1320
gactgttagg ctctggtgcc catctgcgtc agacattggg ccatattctg taatccgtaa   1380
gacgttgggg agactaaggc agccagatgg ctgccttttt tacaggtgtt attcagaatt   1440
gatacgtgcc ggtaatgctg aaattacgcg gtgtgccgta gacgatagaa ccttccacgt   1500
```

<210> SEQ ID NO 6
<211> LENGTH: 1332
<212> TYPE: DNA
<213> ORGANISM: Artificial Sequence
<220> FEATURE:
<223> OTHER INFORMATION: Linear DNA Construct proC-galP

<400> SEQUENCE: 6

```
tatgtcgcga aaacatcgt tgctgctggc ctggccgatc gttgtgaaat tcaggtttcc     60
tacgcaatcg gcgtggctga accgacctcc atcatggtag aaactttcgg tactgagaaa    120
gtgccttctg aacaactgac cctgctggta cgtgagttct tcgacctgcg cccatacggt    180
ctgattcaga tgctggatct gctgcacccg atctacaaag aaaccgcagc atacggtcac    240
tttggtcgtg aacatttccc gtgggaaaaa accgacaaag cgcagctgct gcgcgatgct    300
gccggtctga gtaatctttt cttcacctgc gttcaaagga cttcgctctt catgccgccg    360
caaaccccgc ccctgacagg gcggggtttc gccgcacgtc tccatcgctt gcccaagttg    420
tgaagcacag ctaacaccac gtcgtcccta tctgctgccc taggtctatg agtggttgct    480
ggataacttt acgggcatgc ataaggctcg tatgatatat tcaggagac acaacggtt    540 tccctctaca aataattttg tttaactttc gtagaagagc acttccacac ttctggaaaa    600
aggagatata ccatgccaga tgccaaaaag caaggccgtt ctaacaaggc aatgacattc    660
ttcgtgtgct tccttgcggc gcttgccggc ctcttgttcg gcttggacat cggcgtcatt    720
gccggtgctt taccatttat cgctgacgaa ttccagatca cctcgcacac gcaagaatgg    780
gtcgtaagct ccatgatgtt cggtgcggca gtcggtgcgg tgggcagcgg ctggctctcc    840
tttaaactcg ggcgcaaaaa gagcctgatg atcggcgcaa tttttgtttgt tgccggttcg    900 ctgttctctg cggctgcgcc aaacgttgaa gtactgattc tttcccgcgt tctactgggg    960
ctggcggtgg gtgtggcctc ttataccgca ccgctgtacc tctctgaaat tgcgccggaa   1020
aaaattcgtg gcagtatgat ctcgatgtat cagttgatga tcactatcgg gatcctcggt   1080
gcttatcttt ctgataccgc cttcagctac accggtgcat ggcgctggat gctgggtgtg   1140
attatcatcc cggcaatttt gctgctgatt ggtgtcttct tcctgccaga cagcccacgt   1200
tggtttgccg ccaaacgccg ttttgttgat gccgaacgcg tgctgctacg cctgcgtgac   1260
```

| | |
|---|---:|
| accagcgcgg aagcgaaacg cgaactggat gaaatccgtg aaagtttgca ggttaaacag | 1320 |
| agtggctggg cg | 1332 |

<210> SEQ ID NO 7
<211> LENGTH: 970
<212> TYPE: DNA
<213> ORGANISM: Artificial Sequence
<220> FEATURE:
<223> OTHER INFORMATION: fabI-DAS+4:gentR

<400> SEQUENCE: 7

| | |
|---|---:|
| ctattgaaga tgtgggtaac tctgcggcat tcctgtgctc cgatctctct gccggtatct | 60 |
| ccggtgaagt ggtccacgtt gacggcggtt tcagcattgc tgcaatgaac gaactcgaac | 120 |
| tgaaagcggc caacgatgaa aactattctg aaaactatgc ggatgcgtct aataggaag | 180 |
| ttcctattct ctagaaagta taggaacttc cgaatccatg tgggagttta ttcttgacac | 240 |
| agatatttat gatataataa ctgagtaagc ttaacataag gaggaaaaac atatgttacg | 300 |
| cagcagcaac gatgttacgc agcagggcag tcgccctaaa acaaagttag gtggctcaag | 360 |
| tatgggcatc attcgcacat gtaggctcgg ccctgaccaa gtcaaatcca tgcgggctgc | 420 |
| tcttgatctt ttcggtcgtg agttcggaga cgtagccacc tactcccaac atcagccgga | 480 |
| ctccgattac ctcgggaact tgctccgtag taagacattc atcgcgcttg ctgccttcga | 540 |
| ccaagaagcg gttgttggcg ctctcgcggc ttacgttctg cccaagtttg agcagccgcg | 600 |
| tagtgagatc tatatctatg atctcgcagt ctccggcgag caccggaggc agggcattgc | 660 |
| caccgcgctc atcaatctcc tcaagcatga ggccaacgcg cttggtgctt atgtgatcta | 720 |
| cgtgcaagca gattacggtg acgatcccgc agtggctctc tatacaaagt tgggcatacg | 780 |
| ggaagaagtg atgcactttg tatcgaccc aagtaccgcc acctaagaag ttcctattct | 840 |
| ctagaaagta taggaacttc cgttctgttg gtaaagatgg cggcgttct gccgcccgtt | 900 |
| atctctgtta tacctttctg atatttgtta tcgccgatcc gtctttctcc ccttcccgcc | 960 |
| ttgcgtcagg | 970 |

<210> SEQ ID NO 8
<211> LENGTH: 1026
<212> TYPE: DNA
<213> ORGANISM: Artificial Sequence
<220> FEATURE:
<223> OTHER INFORMATION: lpd-DAS+4:gentR

<400> SEQUENCE: 8

| | |
|---|---:|
| ggtactaacg gcggcgagct gctgggtgaa atcggcctgg caatcgaaat gggttgtgat | 60 |
| gctgaagaca tcgcactgac catccacgcg caccgactc tgcacgagtc tgtgggcctg | 120 |
| gcggcagaag tgttcgaagg tagcattacc gacctgccga acccgaaagc gaagaagaag | 180 |
| gcggccaacg atgaaaacta ttctgaaaac tatgcggatg cgtcttaata gcgaatccat | 240 |
| gtgggagttt attcttgaca cagatattta tgatataata actgagtaag cttaacataa | 300 |
| ggaggaaaaa catatgttac gcagcagcaa cgatgttacg cagcagggca gtcgccctaa | 360 |
| aacaaagtta ggtggctcaa gtatgggcat cattcgcaca tgtaggctcg gccctgacca | 420 |
| agtcaaatcc atgcgggctg ctcttgatct tttcggtcgt gagttcggag acgtagccac | 480 |
| ctactcccaa catcagccgg actccgatta cctcgggaac ttgctccgta gtaagacatt | 540 |
| catcgcgctt gctgccttcg accaagaagc ggttgttggc gctctcgcgg cttacgttct | 600 |
| gcccaagttt gagcagccgc gtagtgagat ctatatctat gatctcgcag tctccggcga | 660 |

```
gcaccggagg cagggcattg ccaccgcgct catcaatctc ctcaagcatg aggccaacgc     720
gcttggtgct tatgtgatct acgtgcaagc agattacggt gacgatcccg cagtggctct     780
ctatacaaag ttgggcatac gggaagaagt gatgcacttt gatatcgacc caagtaccgc     840
cacctaattt ttcgtttgcc ggaacatccg gcaattaaaa aagcggctaa ccacgccgct     900
ttttttacgt ctgcaattta cctttccagt cttcttgctc cacgttcaga gagacgttcg     960
catactgctg accgttgctc gttattcagc ctgacagtat ggttactgtc gtttagacgt    1020
tgtggg                                                               1026
```

<210> SEQ ID NO 9
<211> LENGTH: 869
<212> TYPE: DNA
<213> ORGANISM: Artificial Sequence
<220> FEATURE:
<223> OTHER INFORMATION: gltA-DAS+4:zeoR

<400> SEQUENCE: 9

```
gtattccgtc ttccatgttc accgtcattt tcgcaatggc acgtaccgtt ggctggatcg      60
cccactggag cgaaatgcac agtgacggta tgaagattgc ccgtccgcgt cagctgtata     120
caggatatga aaacgcgac tttaaaagcg atatcaagcg tgcggccaac gatgaaaact     180
attctgaaaa ctatgcggat gcgtcttaat agttgacaat taatcatcgg catagtatat     240
cggcatagta taatacgact cactatagga gggccatcat ggccaagttg accagtgccg     300
ttccggtgct caccgcgcgc gacgtcgccg gagcggtcga gttctggacc gaccggctcg     360
ggttctcccg ggacttcgtg gaggacgact cgccggtgt ggtccgggac gacgtgaccc     420
tgttcatcag cgcggtccag gaccaggtgg tgccggacaa caccctggcc tgggtgtggg     480
tgcgcggcct ggacgagctg tacgccgagt ggtcggaggt cgtgtccacg aacttccggg     540
acgcctccgg gccggccatg accgagatcg cgagcagcc gtggggcgg gagttcgccc     600 tgcgcgaccc ggccggcaac tgcgtgcact tgtggcaga ggagcaggac tgaggataag     660
taatggttga ttgctaagtt gtaaatattt taacccgccg ttcatatggc gggttgattt     720
ttatatgcct aaacacaaaa aattgtaaaa ataaaatcca ttaacagacc tatatagata     780
tttaaaaaga atagaacagc tcaaattatc agcaacccaa tactttcaat taaaaacttc     840
atggtagtcg catttataac cctatgaaa                                       869
```

<210> SEQ ID NO 10
<211> LENGTH: 852
<212> TYPE: DNA
<213> ORGANISM: Artificial Sequence
<220> FEATURE:
<223> OTHER INFORMATION: udhA-DAS+4:bsdR

<400> SEQUENCE: 10

```
tctgggtatt cactgctttg gcgagcgcgc tgccgaaatt attcatatcg gtcaggcgat      60
tatggaacag aaaggtggcg gcaacactat tgagtacttc gtcaacacca cctttaacta     120
cccgacgatg gcggaagcct atcgggtagc tgcgttaaac ggtttaaacc gcctgtttgc     180
ggccaacgat gaaaactatt ctgaaaacta tgcggatgcg tcttaatagt tgacaattaa     240
tcatcggcat agtatatcgg catagtataa tacgactcac tataggaggg ccatcatgaa     300 gacccttcaac atctctcagc aggatctgga gctggtggag gtcgccactg agaagatcac     360
catgctctat gaggacaaca agcaccatgt cgggggcggcc atcaggacca agactgggga     420
```

-continued

```
gatcatctct gctgtccaca ttgaggccta cattggcagg gtcactgtct gtgctgaagc 480
cattgccatt gggtctgctg tgagcaacgg gcagaaggac tttgacacca ttgtggctgt 540
caggcacccc tactctgatg aggtggacag atccatcagg gtggtcagcc cctgtggcat 600
gtgcagagag ctcatctctg actatgctcc tgactgcttt gtgctcattg agatgaatgg 660
caagctggtc aaaaccacca ttgaggaact catccccctc aagtacacca ggaactaaag 720
```

```
taaaacttta tcgaaatggc catccattct tgcgcggatg gcctctgcca gctgctcata 780
gcggctgcgc agcggtgagc caggacgata aaccaggcca atagtgcggc gtggttccgg 840
cttaatgcac gg 852
```

<210> SEQ ID NO 11
<211> LENGTH: 898
<212> TYPE: DNA
<213> ORGANISM: Artificial Sequence
<220> FEATURE:
<223> OTHER INFORMATION: zwf-DAS+4:bsdR

<400> SEQUENCE: 11

```
gaagtggaag aagcctggaa atgggtagac tccattactg aggcgtgggc gatggacaat 60
gatgcgccga aaccgtatca ggccggaacc tggggacccg ttgcctcggt ggcgatgatt 120
acccgtgatg gtcgttcctg gaatgagttt gaggcggcca acgatgaaaa ctattctgaa 180
aactatgcgg atgcgtctta atagttgaca attaatcatc ggcatagtat atcggcatag 240
tataatacga ctcactatag gagggccatc atgaagacct tcaacatctc tcagcaggat 300
```

```
ctggagctgg tggaggtcgc cactgagaag atcaccatgc tctatgagga caacaagcac 360
catgtcgggg cggccatcag gaccaagact ggggagatca tctctgctgt ccacattgag 420
gcctacattg gcagggtcac tgtctgtgct gaagccattg ccattgggtc tgctgtgagc 480
aacgggcaga aggactttga caccattgtg gctgtcaggc acccctactc tgatgaggtg 540
gacagatcca tcagggtggt cagcccctgt ggcatgtgca gagagctcat ctctgactat 600
gctcctgact gctttgtgct cattgagatg aatggcaagc tggtcaaaac caccattgag 660
gaactcatcc ccctcaagta caccaggaac taaagtaata tctgcgctta tcctttatgg 720
ttattttacc ggtaacatga tcttgcgcag attgtagaac aatttttaca ctttcaggcc 780
tcgtgcggat tcacccacga ggcttttttt attacactga ctgaaacgtt tttgccctat 840
gagctccggt tacaggcgtt tcagtcataa atcctctgaa tgaaacgcgt tgtgaatc 898
```

<210> SEQ ID NO 12
<211> LENGTH: 3037
<212> TYPE: DNA
<213> ORGANISM: Artificial Sequence
<220> FEATURE:
<223> OTHER INFORMATION: Plasmid pSMART-waaHp-GFPuv

<400> SEQUENCE: 12

```
tgcccaggca tcaaataaaa cgaaaggctc agtcgaaaga ctgggccttt cgttttatct 60
gttgtttgtc ggtgaacgct ctctactaga gtcacactgg ctcaccttcg ggtgggcctt 120
tctgcgttta tacacagcta acaccacgtc gtccctatct gctgccctag gtctatgagt 180
ggttgctgga taacgtgcgt aattgtgctg atctcttata tagctgctct cattatctct 240
ctaccctgaa gtgactctct cacctgtaaa aataatatct cacaggctta atagtttctt 300
aatacaaagc ctgtaaaacg tcaggataac ttctatattc agggagacca caacggtttc 360
cctctacaaa taattttgtt taactttcgt gtgtaggagg ataatctatg gctagcaaag 420
```

-continued

```
gagaagaact tttcactgga gttgtcccaa ttcttgttga attagatggt gatgttaatg    480
ggcacaaatt ttctgtcagt ggagagggtg aaggtgatgc tacatacgga aagcttaccc    540
ttaaatttat ttgcactact ggaaaactac ctgttccatg ccaacactt gtcactactt     600 tctcttatgg tgttcaatgc ttttcccgtt atccggatca tatgaaacgg catgactttt    660
tcaagagtgc catgcccgaa ggttatgtac aggaacgcac tatatctttc aaagatgacg    720
ggaactacaa gacgcgtgct gaagtcaagt ttgaaggtga taccccttgtt aatcgtatcg   780 agttaaaagg tattgatttt aagaagatg gaaacattct cggacacaaa ctcgagtaca     840
actataactc acacaatgta tacatcacgg cagacaaaca aaagaatgga atcaaagcta    900
acttcaaaat tcgccacaac attgaagatg gatccgttca actagcagac cattatcaac    960
aaaatactcc aattggcgat ggccctgtcc ttttaccaga caaccattac ctgtcgacac   1020
aatctgccct ttcgaaagat cccaacgaaa agcgtgacca catggtcctt cttgagtttg   1080
taactgctgc tgggattaca catggcatgg atgagctcta caaataatga ggatccccgg   1140
cttatcggtc agtttcacct gatttacgta aaaacccgct tcggcgggtt tttgcttttg   1200 gagggggcaga aagatgaatg actgtccacg acgctatacc caaagaaag acgaattctc   1260 tagatatcgc tcaatactga ccatttaaat catacctgac ctccatagca gaaagtcaaa   1320
agcctccgac cggaggcttt tgacttgatc ggcacgtaag aggttccaac tttcaccata   1380
atgaaataag atcactaccg ggcgtatttt ttgagttatc gagattttca ggagctaagg   1440
aagctaaaat gagccatatt caacgggaaa cgtcttgctc gaggccgcga ttaaattcca   1500
acatggatgc tgatttatat gggtataaat gggctcgcga taatgtcggg caatcaggtg   1560
cgacaatcta tcgattgtat gggaagcccg atgcgccaga gttgtttctg aaacatggca   1620
aaggtagcgt tgccaatgat gttacagatg agatggtcag gctaaactgg ctgacggaat   1680
ttatgcctct tccgaccatc aagcatttta tccgtactcc tgatgatgca tggttactca   1740
ccactgcgat cccagggaaa acagcattcc aggtattaga agaatatcct gattcaggtg   1800
aaaatattgt tgatgcgctg gcagtgttcc tgcgccggtt gcattcgatt cctgtttgta   1860
attgtccttt taacggcgat cgcgtatttc gtctcgctca ggcgcaatca cgaatgaata   1920
acggtttggt tggtgcgagt gattttgatg acgagcgtaa tggctggcct gttgaacaag   1980
tctggaaaga aatgcataag cttttgccat tctcaccgga ttcagtcgtc actcatggtg   2040
atttctcact tgataacctt attttttgacg aggggaaatt aataggttgt attgatgttg   2100
gacgagtcgg aatcgcagac cgataccagg atcttgccat cctatggaac tgcctcggtg   2160
agttttctcc ttcattacag aaacggcttt ttcaaaaata tggtattgat aatcctgata   2220
tgaataaatt gcagtttcac ttgatgctcg atgagttttt ctaatgaggg cccaaatgta   2280
atcacctggc tcaccttcgg gtgggccttt ctgcgttgct ggcgtttttc cataggctcc   2340 gccccctga cgagcatcac aaaaatcgat gctcaagtca gaggtggcga aacccgacag   2400
gactataaag ataccaggcg tttccccctg gaagctccct cgtgcgctct cctgttccga   2460
ccctgccgct taccggatac ctgtccgcct ttctcccttc gggaagcgtg gcgctttctc   2520
atagctcacg ctgtaggtat ctcagttcgg tgtaggtcgt tcgctccaag ctgggctgtg   2580
tgcacgaacc cccgttcag cccgaccgct gcgccttatc cggtaactat cgtcttgagt    2640
ccaacccggt aagacacgac ttatcgccac tggcagcagc cactggtaac aggattagca   2700
gagcgaggta tgtaggcggt gctacagagt tcttgaagtg gtggcctaac tacggctaca   2760
```

| | |
|---|---:|
| ctagaagaac agtatttggt atctgcgctc tgctgaagcc agttacctcg gaaaaagagt | 2820 |
| tggtagctct tgatccggca acaaaccac cgctggtagc ggtggttttt ttgtttgcaa | 2880 |
| gcagcagatt acgcgcagaa aaaaggatc tcaagaagat cctttgattt tctaccgaag | 2940 |
| aaaggcccac ccgtgaaggt gagccagtga gttgattgca gtccagttac gctggagtct | 3000 |
| gaggctcgtc ctgaatgata tcaagcttga attcgtt | 3037 |

<210> SEQ ID NO 13
<211> LENGTH: 2780
<212> TYPE: DNA
<213> ORGANISM: Artificial Sequence
<220> FEATURE:
<223> OTHER INFORMATION: pCASCADE-Control Plasmid

<400> SEQUENCE: 13

| | |
|---|---:|
| gacgtcttaa gacccacttt cacatttaag ttgttttttct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttccctt tcttctttag cgacttgatg | 180 |
| ctcttgatct tccaatacgc aacctaaagt aaaatgcccc acagcgctga gtgcatataa | 240 |
| tgcattctct agtgaaaaac cttgttggca taaaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttcccctc | 420 |
| taaagggcaa aagtgagtat ggtgcctatc taacatctca atggctaagg cgtcgagcaa | 480 |
| agcccgctta ttttttacat gccaatacaa tgtaggctgc tctacaccta gcttctgggc | 540 |
| gagtttacgg gttgttaaac cttcgattcc gacctcatta agcagctcta atgcgctgtt | 600 |
| aatcacttta ctttttatcta atctagacat catccaggca tcaaataaaa cgaaaggctc | 660 |
| agtcgaaaga ctgggccttt cgttttatct gttgtttgtc ggtgaacgct ctctactaga | 720 |
| gtcacactgg ctcaccttcg ggtgggcctt tctgcgttta tacacagcta acaccacgtc | 780 |
| gtccctatct gctgccctag gtctatgagt ggttgctgga taactctttc tgacaccta | 840 |
| ctatcttaca aatgtaacaa aaagttatt tttctgtaat tcgagcatgt catgttaccc | 900 |
| cgcgagcata aaacgcgtat attcagggag accacaacgg tttccctcta caaataattt | 960 |
| tgtttaactt tgaattcaaa agatctggta ccacctcgag ttccccgcgc cagcggggat | 1020 |
| aaaccgaaaa aaaaccccg cccctgacag ggcggggttt ttttttcctag ggatatattc | 1080 |
| cgcttcctcg ctcactgact cgctacgctc ggtcgttcga ctgcggcgag cggaaatggc | 1140 |
| ttacgaacgg ggcggagatt tcctggaaga tgccaggaag atacttaaca gggaagtgag | 1200 |
| agggccgcgg caaagccgtt tttccatagg ctccgccccc ctgacaagca tcacgaaatc | 1260 |
| tgacgctcaa atcagtggtg gcgaaacccg acaggactat aaagatacca ggcgtttccc | 1320 |
| cctggcggct ccctcgtgcg ctctcctgtt cctgcctttc ggtttaccgg tgtcattccg | 1380 |
| ctgttatggc cgcgtttgtc tcattccacg cctgacactc agttccgggt aggcagttcg | 1440 |
| ctccaagctg gactgtatgc acgaaccccc cgttcagtcc gaccgctgcg ccttatccgg | 1500 |
| taactatcgt cttgagtcca acccggaaag acatgcaaaa gcaccactgg cagcagccac | 1560 |
| tggtaattga tttagaggag ttagtcttga agtcatgcgc cggttaaggc taaactgaaa | 1620 |
| ggacaagttt tggtgactgc gctcctccaa gccagttacc tcggttcaaa gagttggtag | 1680 |
| ctcagagaac cttcgaaaaa ccgccctgca aggcggtttt tcgttttca gagcaagaga | 1740 |
| ttacgcgcag accaaaacga tctcaagaag atcatcttat taatcagata aaatatttct | 1800 |

```
agatttcagt gcaatttatc tcttcaaatg tagcacctga agtcagcccc atacgatata    1860
agttgttact agtgcttgga ttctcaccaa taaaaaacgc ccggcggcaa ccgagcgttc    1920
tgaacaaatc cagatggagt tctgaggtca ttactggatc tatcaacagg agtccaagcg    1980
agctcgatat caaattacgc cccgccctgc cactcatcgc agtactgttg taattcatta    2040
agcattctgc cgacatggaa gccatcacaa acggcatgat gaacctgaat cgccagcggc    2100
atcagcacct tgtcgccttg cgtataatat ttgcccatgg tgaaaacggg ggcgaagaag    2160
ttgtccatat tggccacgtt taaatcaaaa ctggtgaaac tcacccaggg attggctgag    2220
acgaaaaaca tattctcaat aaacccttta gggaaatagg ccaggttttc accgtaacac    2280
gccacatctt gcgaatatat gtgtagaaac tgccggaaat cgtcgtggta ttcactccag    2340
agcgatgaaa acgtttcagt ttgctcatgg aaaacggtgt aacaagggtg aacactatcc    2400
catatcacca gctcaccgtc tttcattgcc atacgaaatt ccggatgagc attcatcagg    2460
cgggcaagaa tgtgaataaa ggccggataa aacttgtgct tattttttct tacggtcttt    2520
aaaaaggccg taatatccag ctgaacggtc tggttatagg tacattgagc aactgactga    2580
aatgcctcaa aatgttcttt acgatgccat gggatatat caacggtggt atatccagtg    2640
atttttttct ccatttagc ttccttagct cctgaaaatc tcgataactc aaaaaatacg    2700
cccggtagtg atcttatttc attatggtga agttggaac ctcttacgtg ccgatcaacg    2760
tctcattttc gccagatatc                                               2780

<210> SEQ ID NO 14
<211> LENGTH: 2843
<212> TYPE: DNA
<213> ORGANISM: Artificial Sequence
<220> FEATURE:
<223> OTHER INFORMATION: pCASCADE-gltA2 Plasmid

<400> SEQUENCE: 14
gacgtcttaa gacccacttt cacatttaag ttgttttttct aatccgcata tgatcaattc     60
aaggccgaat aagaaggctg gctctgcacc ttggtgatca ataattcga tagcttgtcg    120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta cacagcta acaccacgtc    780 gtccctatct gctgccctag gtctatgagt ggttgctgga taactctttc tgacacctta    840
ctatcttaca aatgtaacaa aaaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat   1020
```

| | |
|---|---|
| aaaccgtatt gaccaattca ttcgggacag ttattagttc gagttccccg cgccagcggg | 1080 |
| gataaaccga aaaaaaaacc ccgcccctga cagggcgggg ttttttttcc tagggatata | 1140 |
| ttccgcttcc tcgctcactg actcgctacg ctcggtcgtt cgactgcggc gagcggaaat | 1200 |
| ggcttacgaa cggggcggag atttcctgga agatgccagg aagatactta acagggaagt | 1260 |
| gagagggccg cggcaaagcc gttttccat aggctccgcc ccctgacaa gcatcacgaa | 1320 |
| atctgacgct caaatcagtg gtggcgaaac ccgacaggac tataaagata ccaggcgttt | 1380 |
| ccccctggcg gctccctcgt gcgctctcct gttcctgcct ttcggtttac cggtgtcatt | 1440 |
| ccgctgttat ggccgcgttt gtctcattcc acgcctgaca ctcagttccg ggtaggcagt | 1500 |
| tcgctccaag ctggactgta tgcacgaacc ccccgttcag tccgaccgct gcgccttatc | 1560 |
| cggtaactat cgtcttgagt ccaacccgga agacatgca aaagcaccac tggcagcagc | 1620 |
| cactggtaat tgatttagag gagttagtct tgaagtcatg cgccggttaa ggctaaactg | 1680 |
| aaaggacaag ttttggtgac tgcgctcctc caagccagtt acctcggttc aaagagttgg | 1740 |
| tagctcagag aaccttcgaa aaaccgccct gcaaggcggt ttttcgttt tcagagcaag | 1800 |
| agattacgcg cagaccaaaa cgatctcaag aagatcatct tattaatcag ataaaatatt | 1860 |
| tctagatttc agtgcaattt atctcttcaa atgtagcacc tgaagtcagc cccatacgat | 1920 |
| ataagttgtt actagtgctt ggattctcac caataaaaaa cgcccggcgg caaccgagcg | 1980 |
| ttctgaacaa atccagatgg agttctgagg tcattactgg atctatcaac aggagtccaa | 2040 |
| gcgagctcga tatcaaatta cgccccgccc tgccactcat cgcagtactg ttgtaattca | 2100 |
| ttaagcattc tgccgacatg gaagccatca caaacggcat gatgaacctg aatcgccagc | 2160 |
| ggcatcagca ccttgtcgcc ttgcgtataa tatttgccca tggtgaaaac ggggggcgaag | 2220 |
| aagttgtcca tattggccac gtttaaatca aaactggtga actcaccca gggattggct | 2280 |
| gagacgaaaa acatattctc aataaaccct ttagggaaat aggccaggtt ttcaccgtaa | 2340 |
| cacgccacat cttgcgaata tatgtgtaga actgccgga atcgtcgtg gtattcactc | 2400 |
| cagagcgatg aaaacgtttc agtttgctca tggaaaacgg tgtaacaagg gtgaacacta | 2460 |
| tcccatatca ccagctcacc gtctttcatt gccatacgaa attccggatg agcattcatc | 2520 |
| aggcgggcaa gaatgtgaat aaaggccgga taaaacttgt gcttatttt ctttacggtc | 2580 |
| tttaaaaagg ccgtaatatc cagctgaacg gtctggttat aggtacattg agcaactgac | 2640 |
| tgaaatgcct caaaatgttc tttacgatgc cattgggata tatcaacggt ggtatatcca | 2700 |
| gtgattttt tctccatttt agcttcctta gctcctgaaa atctcgataa ctcaaaaaat | 2760 |
| acgcccggta gtgatcttat ttcattatgg tgaaagttgg aaccctcttac gtgccgatca | 2820 |
| acgtctcatt ttcgccagat atc | 2843 |

<210> SEQ ID NO 15
<211> LENGTH: 2841
<212> TYPE: DNA
<213> ORGANISM: Artificial Sequence
<220> FEATURE:
<223> OTHER INFORMATION: pCASCADE-fabI Plasmid

<400> SEQUENCE: 15

| | |
|---|---|
| gacgtcttaa gacccacttt cacatttaag ttgttttct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttccctt tcttctttag cgacttgatg | 180 |
| ctcttgatct tccaatacgc aacctaaagt aaaatgcccc acagcgctga gtgcatataa | 240 |

```
tgcattctct agtgaaaaac cttgttggca taaaaaggct aattgatttt cgagagtttc      300
atactgtttt tctgtaggcc gtgtacctaa atgtacttt gctccatcgc gatgacttag      360
taaagcacat ctaaaactt tagcgttatt acgtaaaaaa tcttgccagc tttcccttc       420 taaagggcaa aagtgagtat ggtgcctatc taacatctca atggctaagg cgtcgagcaa     480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacaccta    840 ctatcttaca aatgtaacaa aaaagttatt tttctgtaat tcgagcatgt catgttaccc    900
cgcgagcata aaacgcgtat attcagggag accacaacgg tttccctcta caataattt     960 tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgaaa aaaaaccccc gccctgaca gggcggggtt ttttttccta gggatatatt    1140
ccgcttcctc gctcactgac tcgctacgct cggtcgttcg actgcggcga gcggaaatgg    1200
cttacgaacg gggcggagat ttcctggaag atgccaggaa gatacttaac agggaagtga   1260
gagggccgcg gcaaagccgt ttttccatag gctccgcccc cctgacaagc atcacgaaat   1320
ctgacgctca aatcagtggt ggcgaaaccc gacaggacta taaagatacc aggcgtttcc   1380
ccctggcggc tccctcgtgc gctctcctgt tcctgccttt cggtttaccg gtgtcattcc   1440
gctgttatgg ccgcgtttgt ctcattccac gcctgacact cagttccggg taggcagttc   1500
gctccaagct ggactgtatg cacgaaccc ccgttcagtc cgaccgctgc gccttatccg    1560
gtaactatcg tcttgagtcc aacccggaaa gacatgcaaa agcaccactg gcagcagcca   1620
ctggtaattg atttagagga gttagtcttg aagtcatgcg ccggttaagg ctaaactgaa    1680
aggacaagtt ttggtgactg cgctcctcca agccagttac ctcggttcaa agagttggta   1740
gctcagagaa ccttcgaaaa accgccctgc aaggcggttt tttcgttttc agagcaagag   1800
attacgcgca gaccaaaacg atctcaagaa gatcatctta ttaatcagat aaaatatttc    1860
tagatttcag tgcaatttat ctcttcaaat gtagcacctg aagtcagccc catacgatat   1920
aagttgttac tagtgcttgg attctcacca ataaaaaacg cccggcggca accgagcgtt   1980
ctgaacaaat ccagatggag ttctgaggtc attactggat ctatcaacag gagtccaagc   2040
gagctcgata tcaaattacg ccccgccctg ccactcatcg cagtactgtt gtaattcatt   2100
aagcattctg ccgacatgga agccatcaca acggcatga tgaacctgaa tcgccagcgg    2160
catcagcacc ttgtcgcctt gcgtataata tttgcccatg gtgaaaacgg ggcgaagaa    2220 gttgtccata ttggccacgt ttaaatcaaa actggtgaaa ctcacccagg gattggctga   2280
gacgaaaaac atattctcaa taaacccttt agggaaatag gccaggtttt caccgtaaca   2340
cgccacatct tgcgaatata tgtgtagaaa ctgccgaaa tcgtcgtggt attcactcca    2400
gagcgatgaa aacgtttcag tttgctcatg gaaaacggtg taacaagggt gaacactatc   2460
ccatatcacc agctcaccgt cttcattgc catacgaaat tccggatgag cattcatcag   2520
gcgggcaaga atgtgaataa aggccggata aaacttgtgc ttattttttct ttacggtctt   2580
```

| | | |
|---|---|---|
| taaaaaggcc gtaatatcca gctgaacggt ctggttatag gtacattgag caactgactg | 2640 | |
| aaatgcctca aaatgttctt tacgatgcca ttgggatata tcaacggtgg tatatccagt | 2700 | |
| gattttttc tccattttag cttccttagc tcctgaaaat ctcgataact caaaaaatac | 2760 | |
| gcccggtagt gatcttattt cattatggtg aaagttggaa cctcttacgt gccgatcaac | 2820 | |
| gtctcatttt cgccagatat c | 2841 | |

<210> SEQ ID NO 16
<211> LENGTH: 2841
<212> TYPE: DNA
<213> ORGANISM: Artificial Sequence
<220> FEATURE:
<223> OTHER INFORMATION: pCASCADE-udhA Plasmid

<400> SEQUENCE: 16

| | | |
|---|---|---|
| gacgtcttaa gacccacttt cacatttaag ttgttttct aatccgcata tgatcaattc | 60 | |
| aaggccgaat aagaaggctg gctctgcacc ttggtgatca ataattcga tagcttgtcg | 120 | |
| taataatggc ggcatactat cagtagtagg tgtttccctt tcttctttag cgacttgatg | 180 | |
| ctcttgatct tccaatacgc aacctaaagt aaaatgcccc acagcgctga gtgcatataa | 240 | |
| tgcattctct agtgaaaaac cttgttggca taaaaaggct aattgatttt cgagagtttc | 300 | |
| atactgtttt tctgtaggcc gtgtacctaa atgtactttt gctccatcgc gatgacttag | 360 | |
| taaagcacat ctaaaacttt tagcgttatt acgtaaaaaa tcttgccagc tttcccttc | 420 | |
| taaagggcaa aagtgagtat ggtgcctatc taacatctca atggctaagg cgtcgagcaa | 480 | |
| agcccgctta ttttttacat gccaatacaa tgtaggctgc tctacaccta gcttctgggc | 540 | |
| gagtttacgg gttgttaaac cttcgattcc gacctcatta agcagctcta atgcgctgtt | 600 | |
| aatcacttta cttttatcta atctagacat catccaggca tcaaataaaa cgaaaggctc | 660 | |
| agtcgaaaga ctgggccttt cgttttatct gttgtttgtc ggtgaacgct ctctactaga | 720 | |
| gtcacactgg ctcaccttcg ggtgggcctt tctgcgttta tacacagcta acaccacgtc | 780 | |
| gtccctatct gctgccctag gtctatgagt ggttgctgga taactctttc tgacacctta | 840 | |
| ctatcttaca aatgtaacaa aaagttatt tttctgtaat tcgagcatgt catgttaccc | 900 | |
| cgcgagcata aaacgcgtat attcagggag accacaacgg tttccctcta caaataattt | 960 | |
| tgtttaactt tgaattcaaa agatctggta ccacctcgag ttccccgcgc cagcggggat | 1020 | |
| aaaccgttac cattctgttg cttttatgta taagaatcga gttccccgcg ccagcgggga | 1080 | |
| taaaccgaaa aaaaacccc gcccctgaca gggcggggtt ttttttccta gggatatatt | 1140 | |
| ccgcttcctc gctcactgac tcgctacgct cggtcgttcg actgcggcga gcggaaatgg | 1200 | |
| cttacgaacg gggcggagat tcctggaag atgccaggaa gatacttaac agggaagtga | 1260 | |
| gagggccgcg gcaaagccgt ttttccatag gctccgcccc cctgacaagc atcacgaaat | 1320 | |
| ctgacgctca aatcagtggt ggcgaaaccc gacaggacta taagatacc aggcgtttcc | 1380 | |
| ccctggcggc tccctcgtgc gctctcctgt tcctgccttt cggtttaccg gtgtcattcc | 1440 | |
| gctgttatgg ccgcgtttgt ctcattccac gcctgacact cagttccggg taggcagttc | 1500 | |
| gctccaagct ggactgtatg cacgaacccc ccgttcagtc cgaccgctgc gccttatccg | 1560 | |
| gtaactatcg tcttgagtcc aacccggaaa gacatgcaaa agcaccactg gcagcagcca | 1620 | |
| ctggtaattg atttagagga gttagtcttg aagtcatgcg ccggttaagg ctaaactgaa | 1680 | |
| aggacaagtt ttggtgactg cgctcctcca agccagttac ctcggttcaa agagttgta | 1740 | |
| gctcagagaa ccttcgaaaa accgccctgc aaggcggttt tttcgttttc agagcaagag | 1800 | |

```
attacgcgca gaccaaaacg atctcaagaa gatcatctta ttaatcagat aaaatatttc   1860
tagatttcag tgcaatttat ctcttcaaat gtagcacctg aagtcagccc catacgatat   1920
aagttgttac tagtgcttgg attctcacca ataaaaaacg cccggcggca accgagcgtt   1980
ctgaacaaat ccagatggag ttctgaggtc attactggat ctatcaacag gagtccaagc   2040
gagctcgata tcaaattacg ccccgccctg ccactcatcg cagtactgtt gtaattcatt   2100
aagcattctg ccgacatgga agccatcaca acggcatga tgaacctgaa tcgccagcgg    2160
catcagcacc ttgtcgcctt gcgtataata tttgcccatg gtgaaaacgg gggcgaagaa   2220
gttgtccata ttggccacgt ttaaatcaaa actggtgaaa ctcacccagg gattggctga   2280
gacgaaaaac atattctcaa taaacccttt agggaaatag gccaggtttt caccgtaaca   2340
cgccacatct tgcgaatata tgtgtagaaa ctgccggaaa tcgtcgtggt attcactcca   2400
gagcgatgaa aacgtttcag tttgctcatg gaaaacggtg taacaagggt gaacactatc   2460
ccatatcacc agctcaccgt ctttcattgc catacgaaat tccggatgag cattcatcag   2520
gcgggcaaga atgtgaataa aggccggata aaacttgtgc ttatttttct ttacggtctt   2580
taaaaaggcc gtaatatcca gctgaacggt ctggttatag gtacattgag caactgactg   2640
aaatgcctca aaatgttctt tacgatgcca ttgggatata tcaacggtgg tatatccagt   2700 gattttttc tccatttag cttccttagc tcctgaaaat ctcgataact caaaaaatac     2760
gcccggtagt gatcttattt cattatggtg aaagttggaa cctcttacgt gccgatcaac   2820
gtctcatttt cgccagatat c                                             2841

<210> SEQ ID NO 17
<211> LENGTH: 2841
<212> TYPE: DNA
<213> ORGANISM: Artificial Sequence
<220> FEATURE:
<223> OTHER INFORMATION: pCASCADE-zwf Plasmid

<400> SEQUENCE: 17
gacgtcttaa gacccacttt cacatttaag ttgttttttct aatccgcata tgatcaattc    60
aaggccgaat aagaaggctg gctctgcacc ttggtgatca ataattcga tagcttgtcg     120 taataatggc ggcatactat cagtagtagg tgtttccctt tcttctttag cgacttgatg    180
ctcttgatct tccaatacgc aacctaaagt aaaatgcccc acagcgctga gtgcatataa   240
tgcattctct agtgaaaaac cttgttggca taaaaggct aattgatttt cgagagtttc    300
atactgtttt tctgtaggcc gtgtacctaa atgtactttt gctccatcgc gatgacttag   360
taaagcacat ctaaaacttt tagcgttatt acgtaaaaaa tcttgccagc tttccccttc   420
taaagggcaa aagtgagtat ggtgcctatc taacatctca atggctaagg cgtcgagcaa   480
agcccgctta tttttacat gccaatacaa tgtaggctgc tctacaccta gcttctgggc    540
gagtttacgg gttgttaaac cttcgattcc gacctcatta agcagctcta atgcgctgtt   600
aatcacttta cttttatcta atctagacat catccaggca tcaaataaaa cgaaaggctc   660
agtcgaaaga ctgggccttt cgttttatct gttgtttgtc ggtgaacgct ctctactaga   720
gtcacactgg ctcaccttcg ggtgggcctt tctgcgttta tacacagcta acaccacgtc   780
gtccctatct gctgccctag gtctatgagt ggttgctgga taactctttc tgacaccta    840 ctatcttaca aatgtaacaa aaaagttatt tttctgtaat tcgagcatgt catgttaccc    900
cgcgagcata aaacgcgtat attcagggag accacaacgg tttccctcta caaataattt   960
```

```
tgtttaacttt tgaattcaaa agatctggta ccacctcgag ttccccgcgc cagcggggat    1020
aaaccgctcg taaaagcagt acagtgcacc gtaagatcga gttccccgcg ccagcgggga    1080
taaaccgaaa aaaaaacccc gccccctgaca gggcggggtt ttttttccta gggatatatt   1140
ccgcttcctc gctcactgac tcgctacgct cggtcgttcg actgcggcga gcggaaatgg    1200
cttacgaacg gggcggagat ttcctggaag atgccaggaa gatacttaac agggaagtga    1260
gagggccgcg gcaaagccgt ttttccatag gctccgcccc cctgacaagc atcacgaaat    1320
ctgacgctca aatcagtggt ggcgaaaccc gacaggacta taaagatacc aggcgtttcc    1380
ccctggcggc tccctcgtgc gctctcctgt tcctgccttt cggtttaccg gtgtcattcc    1440
gctgttatgg ccgcgtttgt ctcattccac gcctgacact cagttccggg taggcagttc    1500
gctccaagct ggactgtatg cacgaacccc ccgttcagtc cgaccgctgc gccttatccg    1560
gtaactatcg tcttgagtcc aacccggaaa gacatgcaaa agcaccactg gcagcagcca    1620
ctggtaattg atttagagga gttagtcttg aagtcatgcg ccggttaagg ctaaactgaa    1680
aggacaagtt ttggtgactg cgctcctcca agccagttac ctcggttcaa agagttggta    1740
gctcagagaa ccttcgaaaa accgccctgc aaggcggttt tttcgttttc agagcaagag    1800
attacgcgca gaccaaaacg atctcaagaa gatcatctta ttaatcagat aaaatatttc    1860
tagatttcag tgcaatttat ctcttcaaat gtagcacctg aagtcagccc catacgatat    1920
aagttgttac tagtgcttgg attctcacca ataaaaaacg cccggcggca accgagcgtt    1980
ctgaacaaat ccagatggag ttctgaggtc attactggat ctatcaacag gagtccaagc    2040
gagctcgata tcaaattacg ccccgccctg ccactcatcg cagtactgtt gtaattcatt    2100
aagcattctg ccgacatgga agccatcaca acggcatga tgaacctgaa tcgccagcgg     2160
catcagcacc ttgtcgcctt gcgtataata tttgcccatg gtgaaaacgg gggcgaagaa    2220
gttgtccata ttggccacgt ttaaatcaaa actggtgaaa ctcacccagg gattggctga    2280
gacgaaaaac atattctcaa taaacccttt agggaaatag gccaggtttt caccgtaaca    2340
cgccacatct gcgaatata tgtgtagaaa ctgccggaaa tcgtcgtggt attcactcca     2400
gagcgatgaa aacgtttcag tttgctcatg gaaaacggtg taacaagggt gaacactatc    2460
ccatatcacc agctcaccgt ctttcattgc catacgaaat tccggatgag cattcatcag    2520 gcggcaaga atgtgaataa aggccggata aaacttgtgc ttattttct ttacggtctt      2580 taaaaaggcc gtaatatcca gctgaacggt ctggttatag gtacattgag caactgactg    2640
aaatgcctca aatgttctt tacgatgcca ttgggatata tcaacggtgg tatatccagt     2700
gatttttttc tccattttag cttccttagc tcctgaaaat ctcgataact caaaaaatac    2760
gcccggtagt gatcttattt cattatggtg aaagttggaa cctcttacgt gccgatcaac    2820
gtctcatttt cgccagatat c                                              2841
```

<210> SEQ ID NO 18
<211> LENGTH: 2842
<212> TYPE: DNA
<213> ORGANISM: Artificial Sequence
<220> FEATURE:
<223> OTHER INFORMATION: pCASCADE-gltA1 Plasmid

<400> SEQUENCE: 18

```
gacgtcttaa gacccacttt cacatttaag ttgttttct aatccgcata tgatcaattc       60
aaggccgaat aagaaggctg gctctgcacc ttggtgatca aataattcga tagcttgtcg     120
taataatggc ggcatactat cagtagtagg tgtttccctt tcttctttag cgacttgatg    180
```

```
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacacctta    840
ctatcttaca aatgtaacaa aaagttatt tttctgtaat tcgagcatgt catgttaccc    900
cgcgagcata aaacgcgtat attcagggag accacaacgg tttccctcta caaataattt    960
tgtttaactt tgaattcaaa agatctggta ccacctcgag ttccccgcgc cagcggggat    1020
aaaccgaaaa gcatataatg cgtaaaagtt atgaagttcg agttccccgc gccagcgggg    1080
ataaaccgaa aaaaaacccc gcccctgaca gggcgggt ttttttttcct agggatatat    1140 tccgcttcct cgctcactga ctcgctacgc tcggtcgttc gactgcggcg agcggaaatg    1200
gcttacgaac ggggcggaga tttcctggaa gatgccagga agatacttaa cagggaagtg    1260
agagggccgc ggcaaagccg ttttttccata ggctccgccc ccctgacaag catcacgaaa    1320
tctgacgctc aaatcagtgg tggcgaaacc cgacaggact ataaagatac caggcgtttc    1380
cccctggcgg ctccctcgtg cgctctcctg ttcctgcctt tcggtttacc ggtgtcattc    1440
cgctgttatg gccgcgtttg tctcattcca cgcctgacac tcagttccgg gtaggcagtt    1500
cgctccaagc tggactgtat gcacgaaccc cccgttcagt ccgaccgctg cgccttatcc    1560
ggtaactatc gtcttgagtc caacccggaa agacatgcaa aagcaccact ggcagcagcc    1620
actggtaatt gatttagagg agttagtctt gaagtcatgc gccggttaag gctaaactga    1680
aaggacaagt tttggtgact gcgctcctcc aagccagtta cctcggttca aagagttggt    1740
agctcagaga accttcgaaa aaccgccctg caaggcggtt ttttcgtttt cagagcaaga    1800
gattacgcgc agaccaaaac gatctcaaga agatcatctt attaatcaga taaaatattt    1860
ctagatttca gtgcaatta tctcttcaaa tgtagcacct gaagtcagcc ccatacgata    1920
taagttgtta ctagtgcttg gattctcacc aataaaaaac gcccggcggc aaccgagcgt    1980
tctgaacaaa tccagatgga gttctgaggt cattactgga tctatcaaca ggagtccaag    2040
cgagctcgat atcaaattac gccccgccct gccactcatc gcagtactgt tgtaattcat    2100
taagcattct gccgacatgg aagccatcac aaacggcatg atgaacctga atcgccagcg    2160
gcatcagcac cttgtcgcct tgcgtataat atttgcccat ggtgaaaacg ggggcgaaga    2220
agttgtccat attggccacg tttaaatcaa aactggtgaa actcacccag ggattggctg    2280
agacgaaaaa catattctca ataaacccett tagggaaata ggccaggttt tcaccgtaac    2340
acgccacatc ttgcgaatat atgtgtagaa actgccggaa atcgtcgtgg tattcactcc    2400
agagcgatga aaacgtttca gtttgctcat ggaaaacggt gtaacaaggg tgaacactat    2460
cccatatcac cagctcaccg tctttcattg ccatacgaaa ttccggatga gcattcatca    2520
```

-continued

| ggcgggcaag aatgtgaata aaggccggat aaaacttgtg cttattttc tttacggtct | 2580 |
| --- | --- |
| ttaaaaaggc cgtaatatcc agctgaacgg tctggttata ggtacattga gcaactgact | 2640 |
| gaaatgcctc aaaatgttct ttacgatgcc attgggatat atcaacggtg gtatatccag | 2700 |
| tgatttttt ctccatttta gcttccttag ctcctgaaaa tctcgataac tcaaaaaata | 2760 |
| cgcccggtag tgatcttatt tcattatggt gaaagttgga acctcttacg tgccgatcaa | 2820 |
| cgtctcattt tcgccagata tc | 2842 |

```
<210> SEQ ID NO 19
<211> LENGTH: 2903
<212> TYPE: DNA
<213> ORGANISM: Artificial Sequence
<220> FEATURE:
<223> OTHER INFORMATION: pCASCADE-gltA2-udhA Plasmid

<400> SEQUENCE: 19
```

| gacgtcttaa gacccacttt cacatttaag ttgttttct aatccgcata tgatcaattc | 60 |
| --- | --- |
| aaggccgaat aagaaggctg gctctgcacc ttggtgatca ataattcga tagcttgtcg | 120 |
| taataatggc ggcatactat cagtagtagg tgtttcctt tcttctttag cgacttgatg | 180 |
| ctcttgatct tccaatacgc aacctaaagt aaaatgcccc acagcgctga gtgcatataa | 240 |
| tgcattctct agtgaaaaac cttgttggca taaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttcccttc | 420 |
| taaagggcaa aagtgagtat ggtgcctatc taacatctca atggctaagg cgtcgagcaa | 480 |
| agcccgctta ttttttacat gccaataaat gtaggctgct ctacacctag cttctgggcg | 540 |
| agtttacggg ttgttaaacc ttcgattccg acctcattaa gcagctctaa tgcgctgtta | 600 |
| atcactttac ttttatctaa tctagacatc atccaggcat caaataaaac gaaaggctca | 660 |
| gtcgaaagac tgggcctttc gttttatctg ttgtttgtcg gtgaacgctc tctactagag | 720 |
| tcacactggc tcaccttcgg gtgggccttt ctgcgtttat acacagctaa caccacgtcg | 780 |
| tccctatctg ctgccctagg tctatgagtg gttgctggat aactcttct gacaccttac | 840 |
| tatcttacaa atgtaacaaa aaagttattt ttctgtaatt cgagcatgtc atgttacccc | 900 |
| gcgagcataa aacgcgtata ttcagggaga ccacaacggt ttccctctac aaataatttt | 960 |
| gtttaacttt gaattcaaaa gatctggtac cacctcgagt tccccgcgcc agcggggata | 1020 |
| aaccgtattg accaattcat tcgggacagt tattagttcg agttccccgc gccagcgggg | 1080 |
| ataaaccgtt accattctgt tgcttttatg tataagaatc gagttccccg cgccagcggg | 1140 |
| gataaaccga aaaaaaaacc ccgccctga caggcgggg ttttttttcc tagggatata | 1200 |
| ttccgcttcc tcgctcactg actcgctacg ctcggtcgtt cgactgcggc gagcggaaat | 1260 |
| ggcttacgaa cggggcggag atttcctgga agatgccagg aagatactta acagggaagt | 1320 |
| gagagggccg cggcaaagcc gttttttccat aggctccgcc cccctgacaa gcatcacgaa | 1380 |
| atctgacgct caaatcagtg gtggcgaaac ccgacaggac tataaagata ccaggcgttt | 1440 |
| cccctggcg ctccctcgt gcgctctcct gttcctgcct ttcggtttac cggtgtcatt | 1500 |
| ccgctgttat ggccgcgttt gtctcattcc acgcctgaca ctcagttccg ggtaggcagt | 1560 |
| tcgctccaag ctggactgta tgcacgaacc cccgttcag tccgaccgct gcgccttatc | 1620 |
| cggtaactat cgtcttgagt ccaacccgga agacatgca aaagcaccac tggcagcagc | 1680 |
| cactggtaat tgatttagag gagttagtct tgaagtcatg cgccggttaa ggctaaactg | 1740 |

```
aaaggacaag ttttggtgac tgcgctcctc caagccagtt acctcggttc aaagagttgg    1800
tagctcagag aaccttcgaa aaaccgccct gcaaggcggt tttttcgttt tcagagcaag    1860
agattacgcg cagaccaaaa cgatctcaag aagatcatct tattaatcag ataaaatatt    1920
tctagatttc agtgcaattt atctcttcaa atgtagcacc tgaagtcagc cccatacgat    1980
ataagttgtt actagtgctt ggattctcac caataaaaaa cgcccggcgg caaccgagcg    2040
ttctgaacaa atccagatgg agttctgagg tcattactgg atctatcaac aggagtccaa    2100
gcgagctcga tatcaaatta cgccccgccc tgccactcat cgcagtactg ttgtaattca    2160
ttaagcattc tgccgacatg gaagccatca caaacggcat gatgaacctg aatcgccagc    2220
ggcatcagca ccttgtcgcc ttgcgtataa tatttgccca tggtgaaaac ggggggcgaag    2280 aagttgtcca tattgccac gtttaaatca aaactggtga aactcaccca gggattggct    2340
gagacgaaaa acatattctc aataaaccct ttagggaaat aggccaggtt ttcaccgtaa    2400
cacgccacat cttgcgaata tatgtgtaga actgccgga atcgtcgtg gtattcactc    2460 cagagcgatg aaaacgtttc agtttgctca tggaaaacgg tgtaacaagg gtgaacacta    2520
tcccatatca ccagctcacc gtctttcatt gccatacgaa attccggatg agcattcatc    2580
aggcgggcaa gaatgtgaat aaaggccgga taaaacttgt gcttattttt ctttacggtc    2640
tttaaaaagg ccgtaatatc cagctgaacg gtctggttat aggtacattg agcaactgac    2700
tgaaatgcct caaaatgttc tttacgatgc cattgggata tatcaacggt ggtatatcca    2760
gtgatttttt tctccatttt agcttcctta gctcctgaaa atctcgataa ctcaaaaaat    2820
acgcccggta gtgatcttat ttcattatgg tgaaagttgg aacctcttac gtgccgatca    2880
acgtctcatt ttcgccagat atc                                           2903

<210> SEQ ID NO 20
<211> LENGTH: 2902
<212> TYPE: DNA
<213> ORGANISM: Artificial Sequence
<220> FEATURE:
<223> OTHER INFORMATION: pCASCADE-fabI-udhA Plasmid

<400> SEQUENCE: 20
gacgtcttaa gacccacttt cacatttaag ttgttttttct aatccgcata tgatcaattc      60
aaggccgaat aagaaggctg gctctgcacc ttggtgatca aataattcga tagcttgtcg     120
taataatggc ggcatactat cagtagtagg tgtttccctt tcttctttag cgacttgatg     180
ctcttgatct tccaatacgc aacctaaagt aaaatgcccc acagcgctga gtgcatataa     240
tgcattctct agtgaaaaac cttgttggca taaaaggct aattgatttt cgagagtttc     300
atactgtttt tctgtaggcc gtgtacctaa atgtactttt gctccatcgc gatgacttag     360
taaagcacat ctaaaacttt tagcgttatt acgtaaaaaa tcttgccagc tttcccttc     420 taaagggcaa aagtgagtat ggtgcctatc taacatctca atggctaagg cgtcgagcaa     480
agcccgctta ttttttacat gccaatacaa tgtaggctgc tctacaccta gcttctgggc     540
gagtttacgg gttgttaaac cttcgattcc gacctcatta agcagctcta atgcgctgtt     600
aatcacttta cttttatcta atctagacat catccaggca tcaaataaaa cgaaaggctc     660
agtcgaaaga ctgggccttt cgttttatct gttgtttgtc ggtgaacgct ctctactaga     720
gtcacactgg ctcaccttcg ggtgggcctt tctgcgttta cacagcta acaccacgtc      780 gtccctatct gctgccctag gtctatgagt ggttgctgga taactctttc tgacacctta     840
```

```
ctatcttaca aatgtaacaa aaaagttatt tttctgtaat tcgagcatgt catgttaccc      900
cgcgagcata aaacgcgtat attcagggag accacaacgg tttccctcta caaataattt      960 tgtttaacttt tgaattcaaa agatctggta ccacctcgag ttccccgcgc cagcggggat    1020
aaaccgttga ttataataac cgtttatctg ttcgtatcga gttccccgcg ccagcgggga    1080
taaaccgtta ccattctgtt gcttttatgt ataagaatcg agttccccgc gccagcgggg    1140
ataaaccgaa aaaaaaccc cgcccctgac agggcgggt tttttttcct agggatatat      1200
tccgcttcct cgctcactga ctcgctacgc tcggtcgttc gactgcggcg agcggaaatg    1260
gcttacgaac ggggcggaga tttcctggaa gatgccagga agatacttaa cagggaagtg    1320
agagggccgc ggcaaagccg ttttttccata ggctccgccc ccctgacaag catcacgaaa   1380
tctgacgctc aaatcagtgg tggcgaaacc cgacaggact ataaagatac caggcgtttc    1440
cccctggcgg ctccctcgtg cgctctcctg ttcctgcctt tcggtttacc ggtgtcattc     1500
cgctgttatg gccgcgtttg tctcattcca cgcctgacac tcagttccgg gtaggcagtt    1560
cgctccaagc tggactgtat gcacgaaccc cccgttcagt ccgaccgctg cgccttatcc    1620
ggtaactatc gtcttgagtc aacccggaa agacatgcaa aagcaccact ggcagcagcc     1680
actggtaatt gatttagagg agttagtctt gaagtcatgc gccggttaag gctaaactga    1740
aaggacaagt tttggtgact gcgctcctcc aagccagtta cctcggttca aagagttggt    1800
agctcagaga accttcgaaa aaccgccctg caaggcggtt ttttcgtttt cagagcaaga    1860
gattacgcgc agaccaaaac gatctcaaga agatcatctt attaatcaga taaaatattt    1920
ctagatttca gtgcaatta tctcttcaaa tgtagcacct gaagtcagcc ccatacgata    1980
taagttgtta ctagtgcttg gattctcacc aataaaaaac gcccggcggc aaccgagcgt    2040
tctgaacaaa tccagatgga gttctgaggt cattactgga tctatcaaca ggagtccaag    2100
cgagctcgat atcaaattac gccccgccct gccactcatc gcagtactgt tgtaattcat    2160
taagcattct gccgacatgg aagccatcac aaacggcatg atgaacctga atcgccagcg    2220
gcatcagcac cttgtcgcct tgcgtataat atttgcccat ggtgaaaacg ggggcgaaga    2280
agttgtccat attggccacg tttaaatcaa aactggtgaa actcacccag ggattggctg    2340
agacgaaaaa catattctca ataaaccctt tagggaaata ggccaggttt tcaccgtaac    2400
acgccacatc ttgcgaatat atgtgtagaa actgccggaa atcgtcgtgg tattcactcc    2460
agagcgatga aaacgtttca gtttgctcat ggaaaacggt gtaacaaggg tgaacactat    2520
cccatatcac cagctcaccg tctttcattg ccatacgaaa ttccggatga gcattcatca    2580
ggcgggcaag aatgtgaata aaggccggat aaaacttgtg cttattttc tttacggtct    2640 ttaaaaaggc cgtaatatcc agctgaacgg tctggttata ggtacattga gcaactgact    2700
gaaatgcctc aaaatgttct ttacgatgcc attgggatat atcaacggtg gtatatccag    2760 tgatttttt ctccatttta gcttccttag ctcctgaaaa tctcgataac tcaaaaaata    2820
cgcccggtag tgatcttatt tcattatggt gaaagttgga acctcttacg tgccgatcaa    2880
cgtctcattt tcgccagata tc                                            2902
```

<210> SEQ ID NO 21
<211> LENGTH: 2903
<212> TYPE: DNA
<213> ORGANISM: Artificial Sequence
<220> FEATURE:
<223> OTHER INFORMATION: pCASCADE-fabI-gltA1 Plasmid

<400> SEQUENCE: 21

```
gacgtcttaa gacccacttt cacatttaag ttgtttttct aatccgcata tgatcaattc    60
aaggccgaat aagaaggctg gctctgcacc ttggtgatca ataattcga tagcttgtcg   120 taataatggc ggcatactat cagtagtagg tgtttccctt tcttctttag cgacttgatg   180
ctcttgatct tccaatacgc aacctaaagt aaaatgcccc acagcgctga gtgcatataa   240
tgcattctct agtgaaaaac cttgttggca taaaaggct aattgatttt cgagagtttc    300
atactgtttt tctgtaggcc gtgtacctaa atgtactttt gctccatcgc gatgacttag   360
taaagcacat ctaaaacttt tagcgttatt acgtaaaaaa tcttgccagc tttccccttc   420
taaagggcaa aagtgagtat ggtgcctatc taacatctca atggctaagg cgtcgagcaa   480
agcccgctta ttttttacat gccaatacaa tgtaggctgc tctacaccta gcttctgggc   540
gagtttacgg gttgttaaac cttcgattcc gacctcatta agcagctcta atgcgctgtt   600
aatcacttta cttttatcta atctagacat catccaggca tcaaataaaa cgaaaggctc   660
agtcgaaaga ctgggccttt cgttttatct gttgtttgtc ggtgaacgct ctctactaga   720
gtcacactgg ctcaccttcg ggtgggcctt tctgcgttta tacacagcta acaccacgtc   780
gtccctatct gctgccctag gtctatgagt ggttgctgga taactctttc tgacacctta   840
ctatcttaca aatgtaacaa aaaagttatt tttctgtaat tcgagcatgt catgttaccc   900
cgcgagcata aaacgcgtat attcagggag accaacggg tttccctcta caaataattt     960
tgtttaactt tgaattcaaa agatctggta ccacctcgag ttccccgcgc cagcggggat  1020
aaaccgttga ttataataac cgtttatctg ttcgtatcga gttccccgcg ccagcgggga  1080
taaaccgaaa agcatataat gcgtaaaagt tatgaagttc gagttccccg cgccagcggg  1140
gataaaccga aaaaaaaacc ccgccctga cagggcgggg ttttttttcc tagggatata  1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gttttttccat aggctccgcc ccctgacaa gcatcacgaa   1380 atctgacgct caaatcagtg gtggcgaaac ccgacaggac tataaagata ccaggcgttt   1440 cccccctggcg gctccctcgt gcgctctcct gttcctgcct ttcggtttac cggtgtcatt   1500
ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga agacatgca aaagcaccac tggcagcagc     1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgccct gcaaggcggt ttttttcgttt tcagagcaag  1860 agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca cctgtcgcc ttgcgtataa tatttgccca tggtgaaaac gggggcgaag   2280
aagttgtcca tattggccac gtttaaatca aaactggtga aactcaccca gggattggct   2340
```

-continued

```
gagacgaaaa acatattctc aataaaccct ttagggaaat aggccaggtt ttcaccgtaa    2400
cacgccacat cttgcgaata tatgtgtaga aactgccgga aatcgtcgtg gtattcactc    2460
cagagcgatg aaaacgtttc agtttgctca tggaaaacgg tgtaacaagg gtgaacacta    2520
tcccatatca ccagctcacc gtctttcatt gccatacgaa attccggatg agcattcatc    2580
aggcgggcaa gaatgtgaat aaaggccgga taaaacttgt gcttattttt ctttacggtc    2640
tttaaaaagg ccgtaatatc cagctgaacg gtctggttat aggtacattg agcaactgac    2700
tgaaatgcct caaaatgttc tttacgatgc cattgggata tatcaacggt ggtatatcca    2760
gtgatttttt tctccatttt agcttcctta gctcctgaaa atctcgataa ctcaaaaaat    2820
acgcccggta gtgatcttat ttcattatgg tgaaagttgg aacctcttac gtgccgatca    2880
acgtctcatt ttcgccagat atc                                           2903
```

<210> SEQ ID NO 22
<211> LENGTH: 2904
<212> TYPE: DNA
<213> ORGANISM: Artificial Sequence
<220> FEATURE:
<223> OTHER INFORMATION: pCASCADE-fabI-gltA2 Plasmid

<400> SEQUENCE: 22

```
gacgtcttaa gacccacttt cacatttaag ttgttttttct aatccgcata tgatcaattc     60
aaggccgaat aagaaggctg gctctgcacc ttggtgatca ataattcga tagcttgtcg    120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaggct aattgatttt cgagagtttc    300
atactgtttt tctgtaggcc gtgtacctaa atgtacttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgccctag gtctatgagt ggttgctgga taactctttc tgacaccttta    840 ctatcttaca aatgtaacaa aaaagttatt tttctgtaat tcgagcatgt catgttaccc    900
cgcgagcata aaacgcgtat attcagggag accacaacgg tttccctcta caataatttt    960
tgtttaactt tgaattcaaa agatctggta ccacctcgag ttccccgcgc cagcggggat   1020
aaaccgttga ttataataac cgtttatctg ttcgtatcga gttccccgcg ccagcgggga   1080
taaaccgtat tgaccaattc attcgggaca gttattagtt cgagttcccc gcgccagcgg   1140
ggataaaccg aaaaaaaaac cccgcccctg acagggcggg gttttttttc ctagggatat   1200
attccgcttc ctcgctcact gactcgctac gctcggtcgt tcgactgcgg cgagcggaaa   1260
tggcttacga acggggcgga gatttcctgg aagatgccag gaagatactt aacagggaag   1320
tgagagggcc gcggcaaagc cgttttttcca taggctccgc cccctgaca agcatcacga   1380 aatctgacgc tcaaatcagt ggtggcgaaa cccgacagga ctataaagat accaggcgtt   1440
tccccctggc ggctccctcg tgcgctctcc tgttcctgcc tttcggttta ccggtgtcat   1500
```

```
tccgctgtta tggccgcgtt tgtctcattc cacgcctgac actcagttcc gggtaggcag    1560
ttcgctccaa gctggactgt atgcacgaac cccccgttca gtccgaccgc tgcgccttat    1620
ccggtaacta tcgtcttgag tccaacccgg aaagacatgc aaaagcacca ctggcagcag    1680
ccactggtaa ttgatttaga ggagttagtc ttgaagtcat gcgccggtta aggctaaact    1740
gaaaggacaa gttttggtga ctgcgctcct ccaagccagt tacctcggtt caaagagttg    1800
gtagctcaga gaaccttcga aaaccgccc tgcaaggcgg ttttttcgtt ttcagagcaa     1860
gagattacgc gcagaccaaa acgatctcaa gaagatcatc ttattaatca gataaaatat    1920
ttctagattt cagtgcaatt tatctcttca aatgtagcac ctgaagtcag ccccatacga    1980
tataagttgt tactagtgct tggattctca ccaataaaaa acgcccggcg caaccgagc     2040 gttctgaaca atccagatg gagttctgag gtcattactg gatctatcaa caggagtcca    2100
agcgagctcg atatcaaatt acgccccgcc ctgccactca tcgcagtact gttgtaattc    2160
attaagcatt ctgccgacat ggaagccatc acaaacggca tgatgaacct gaatcgccag    2220
cggcatcagc accttgtcgc cttgcgtata atatttgccc atggtgaaaa cggggggcgaa   2280 gaagttgtcc atattggcca cgtttaaatc aaaactggtg aaactcaccc agggattggc    2340
tgagacgaaa aacatattct caataaaccc tttagggaaa taggccaggt tttcaccgta    2400
acacgccaca tcttgcgaat atatgtgtag aaactgccgg aaatcgtcgt ggtattcact    2460
ccagagcgat gaaaacgttt cagtttgctc atggaaaacg gtgtaacaag ggtgaacact    2520
atcccatatc accagctcac cgtctttcat tgccatacga aattccggat gagcattcat    2580
caggcgggca agaatgtgaa taaaggccgg ataaaacttg tgcttatttt tctttacggt    2640
ctttaaaaag gccgtaatat ccagctgaac ggtctggtta taggtacatt gagcaactga    2700
ctgaaatgcc tcaaaatgtt ctttacgatg ccattgggat atatcaacgg tggtatatcc    2760
agtgattttt ttctccattt tagcttcctt agctcctgaa atctcgata actcaaaaaa     2820 tacgcccggt agtgatctta tttcattatg gtgaaagttg gaacctctta cgtgccgatc    2880
aacgtctcat tttcgccaga tatc                                           2904
```

<210> SEQ ID NO 23
<211> LENGTH: 2902
<212> TYPE: DNA
<213> ORGANISM: Artificial Sequence
<220> FEATURE:
<223> OTHER INFORMATION: pCASCADE-fabI-zwf Plasmid

<400> SEQUENCE: 23

```
gacgtcttaa gacccacttt cacatttaag ttgttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
taaagcacat ctaaaacttt tagcgttatt acgtaaaaaa tcttgccagc tttcccttc    420 taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
```

```
aatcacttta  cttttatcta  atctagacat  catccaggca  tcaaataaaa  cgaaaggctc      660
agtcgaaaga  ctgggccttt  cgttttatct  gttgtttgtc  ggtgaacgct  ctctactaga      720
gtcacactgg  ctcaccttcg  ggtgggcctt  tctgcgttta  tacacagcta  acaccacgtc      780
gtccctatct  gctgccctag  gtctatgagt  ggttgctgga  taactctttc  tgacacctta      840
ctatcttaca  aatgtaacaa  aaaagttatt  tttctgtaat  tcgagcatgt  catgttaccc      900
cgcgagcata  aaacgcgtat  attcagggag  accacaacgg  tttccctcta  caaataattt      960
tgtttaactt  tgaattcaaa  agatctggta  ccacctcgag  ttccccgcgc  cagcggggat     1020
aaaccgttga  ttataataac  cgtttatctg  ttcgtatcga  gttccccgcg  ccagcgggga     1080
taaaccgctc  gtaaaagcag  tacagtgcac  cgtaagatcg  agttcccccgc  gccagcgggg    1140 ataaaccgaa  aaaaaaaccc  cgcccctgac  agggcgggt   ttttttttcct  agggatatat     1200 tccgcttcct  cgctcactga  ctcgctacgc  tcggtcgttc  gactgcggcg  agcggaaatg     1260
gcttacgaac  ggggcggaga  tttcctggaa  gatgccagga  agatacttaa  cagggaagtg     1320
agagggccgc  ggcaaagccg  tttttccata  ggctccgccc  ccctgacaag  catcacgaaa     1380
tctgacgctc  aaatcagtgg  tggcgaaacc  cgacaggact  ataaagatac  caggcgtttc     1440
cccctggcgg  ctccctcgtg  cgctctcctg  ttcctgcctt  tcggtttacc  ggtgtcattc     1500
cgctgttatg  gccgcgtttg  tctcattcca  cgcctgacac  tcagttccgg  gtaggcagtt     1560
cgctccaagc  tggactgtat  gcacgaaccc  cccgttcagt  ccgaccgctg  cgccttatcc     1620
ggtaactatc  gtcttgagtc  caacccggaa  agacatgcaa  aagcaccact  ggcagcagcc     1680
actggtaatt  gatttagagg  agttagtctt  gaagtcatgc  gccggttaag  gctaaactga     1740
aaggacaagt  tttggtgact  gcgctcctcc  aagccagtta  cctcggttca  agagttggt      1800 agctcagaga  accttcgaaa  aaccgccctg  caaggcggtt  ttttcgtttt  cagagcaaga     1860
gattacgcgc  agaccaaaac  gatctcaaga  agatcatctt  attaatcaga  taaaatattt     1920
ctagatttca  gtgcaattta  tctcttcaaa  tgtagcacct  gaagtcagcc  ccatacgata     1980
taagttgtta  ctagtgcttg  gattctcacc  aataaaaaac  gcccggcggc  aaccgagcgt     2040
tctgaacaaa  tccagatgga  gttctgaggt  cattactgga  tctatcaaca  ggagtccaag     2100
cgagctcgat  atcaaattac  gccccgccct  gccactcatc  gcagtactgt  tgtaattcat     2160
taagcattct  gccgacatgg  aagccatcac  aaacggcatg  atgaacctga  atcgccagcg     2220
gcatcagcac  cttgtcgcct  tgcgtataat  atttgcccat  ggtgaaaacg  ggggcgaaga     2280
agttgtccat  attggccacg  tttaaatcaa  aactggtgaa  actcacccag  ggattggctg     2340
agacgaaaaa  catattctca  ataaacccctt  tagggaaata  ggccaggttt  tcaccgtaac     2400
acgccacatc  ttgcgaatat  atgtgtagaa  actgccggaa  atcgtcgtgg  tattcactcc     2460
agagcgatga  aaacgtttca  gtttgctcat  ggaaaacggt  gtaacaaggg  tgaacactat     2520
cccatatcac  cagctcaccg  tctttcattg  ccatacgaaa  ttccggatga  gcattcatca     2580
ggcgggcaag  aatgtgaata  aaggccggat  aaaacttgtg  cttattttttc  tttacggtct     2640 ttaaaaaggc  cgtaatatcc  agctgaacgg  tctggttata  ggtacattga  gcaactgact     2700
gaaatgcctc  aaaatgttct  ttacgatgcc  attgggatat  atcaacgtg   gtatatccag     2760 tgatttttttt  ctccatttta  gcttccttag  ctcctgaaaa  tctcgataac  tcaaaaaata     2820
cgcccggtag  tgatcttatt  tcattatggt  gaaagttgga  acctcttacg  tgccgatcaa     2880
cgtctcattt  tcgccagata  tc                                                 2902
```

<210> SEQ ID NO 24
<211> LENGTH: 2903
<212> TYPE: DNA
<213> ORGANISM: Artificial Sequence
<220> FEATURE:
<223> OTHER INFORMATION: pCASCADE-gltA1-udhA Plasmid

<400> SEQUENCE: 24

| | | | | | |
|---|---|---|---|---|---|
| gacgtcttaa | gacccacttt | cacatttaag | ttgttttttct | aatccgcata | tgatcaattc | 60 |
| aaggccgaat | aagaaggctg | gctctgcacc | ttggtgatca | aataattcga | tagcttgtcg | 120 |
| taataatggc | ggcatactat | cagtagtagg | tgtttccctt | tcttctttag | cgacttgatg | 180 |
| ctcttgatct | tccaatacgc | aacctaaagt | aaaatgcccc | acagcgctga | gtgcatataa | 240 |
| tgcattctct | agtgaaaaac | cttgttggca | taaaaggct | aattgatttt | cgagagtttc | 300 |
| atactgtttt | tctgtaggcc | gtgtacctaa | atgtacttt | gctccatcgc | gatgacttag | 360 |
| taaagcacat | ctaaaacttt | tagcgttatt | acgtaaaaaa | tcttgccagc | tttcccttc | 420 |
| taaagggcaa | aagtgagtat | ggtgcctatc | taacatctca | atggctaagg | cgtcgagcaa | 480 |
| agcccgctta | ttttttacat | gccaatacaa | tgtaggctgc | tctacaccta | gcttctgggc | 540 |
| gagtttacgg | gttgttaaac | cttcgattcc | gacctcatta | agcagctcta | atgcgctgtt | 600 |
| aatcacttta | cttttatcta | atctagacat | catccaggca | tcaaataaaa | cgaaaggctc | 660 |
| agtcgaaaga | ctgggccttt | cgttttatct | gttgtttgtc | ggtgaacgct | ctctactaga | 720 |
| gtcacactgg | ctcaccttcg | ggtgggcctt | tctgcgttta | tacacagcta | acaccacgtc | 780 |
| gtccctatct | gctgccctag | gtctatgagt | ggttgctgga | taactctttc | tgacaccta | 840 |
| ctatcttaca | aatgtaacaa | aaaagttatt | tttctgtaat | tcgagcatgt | catgttaccc | 900 |
| cgcgagcata | aaacgcgtat | attcagggag | accacaacgg | tttccctcta | caaataattt | 960 |
| tgtttaactt | tgaattcaaa | agatctggta | ccacctcgag | ttccccgcgc | cagcggggat | 1020 |
| aaaccgaaaa | gcatataatg | cgtaaaagtt | atgaagttcg | agttcccgc | gccagcgggg | 1080 |
| ataaaccgtt | accattctgt | tgcttttatg | tataagaatc | gagttccccg | cgccagcggg | 1140 |
| gataaaccga | aaaaaaaacc | ccgcccctga | cagggcgggg | ttttttttcc | tagggatata | 1200 |
| ttccgcttcc | tcgctcactg | actcgctacg | ctcggtcgtt | cgactgcggc | gagcggaaat | 1260 |
| ggcttacgaa | cggggcggag | atttcctgga | agatgccagg | aagatactta | acagggaagt | 1320 |
| gagagggccg | cggcaaagcc | gttttccat | aggctccgcc | cccctgacaa | gcatcacgaa | 1380 |
| atctgacgct | caaatcagtg | gtggcgaaac | ccgacaggac | tataaagata | ccaggcgttt | 1440 |
| ccccctggcg | gctccctcgt | gcgctctcct | gttcctgcct | ttcggtttac | cggtgtcatt | 1500 |
| ccgctgttat | ggccgcgttt | gtctcattcc | acgcctgaca | ctcagttccg | ggtaggcagt | 1560 |
| tcgctccaag | ctggactgta | tgcacgaacc | ccccgttcag | tccgaccgct | gcgccttatc | 1620 |
| cggtaactat | cgtcttgagt | ccaacccgga | agacatgca | aaagcaccac | tggcagcagc | 1680 |
| cactggtaat | tgatttagag | gagttagtct | tgaagtcatg | cgccggttaa | ggctaaactg | 1740 |
| aaaggacaag | ttttggtgac | tgcgctcctc | caagccagtt | acctcggttc | aaagagttgg | 1800 |
| tagctcagag | aaccttcgaa | aaaccgccct | gcaaggcggt | tttttcgttt | tcagagcaag | 1860 |
| agattacgcg | cagaccaaaa | cgatctcaag | aagatcatct | tattaatcag | ataaaatatt | 1920 |
| tctagatttc | agtgcaattt | atctcttcaa | atgtagcacc | tgaagtcagc | cccatacgat | 1980 |
| ataagttgtt | actagtgctt | ggattctcac | caataaaaaa | cgcccggcgg | caaccgagcg | 2040 |
| ttctgaacaa | atccagatgg | agttctgagg | tcattactgg | atctatcaac | aggagtccaa | 2100 |

-continued

```
gcgagctcga tatcaaatta cgccccgccc tgccactcat cgcagtactg ttgtaattca    2160
ttaagcattc tgccgacatg gaagccatca caaacggcat gatgaacctg aatcgccagc    2220
ggcatcagca ccttgtcgcc ttgcgtataa tatttgccca tggtgaaaac gggggcgaag    2280
aagttgtcca tattggccac gtttaaatca aaactggtga aactcaccca gggattggct    2340
gagacgaaaa acatattctc aataaaccct ttagggaaat aggccaggtt ttcaccgtaa    2400
cacgccacat cttgcgaata tatgtgtaga aactgccgga atcgtcgtg gtattcactc     2460
cagagcgatg aaaacgtttc agtttgctca tggaaaacgg tgtaacaagg gtgaacacta    2520
tcccatatca ccagctcacc gtctttcatt gccatacgaa attccggatg agcattcatc    2580
aggcgggcaa gaatgtgaat aaaggccgga taaaacttgt gcttattttt ctttacggtc    2640
tttaaaaagg ccgtaatatc cagctgaacg gtctggttat aggtacattg agcaactgac    2700
tgaaatgcct caaaatgttc tttacgatgc cattgggata tatcaacggt ggtatatcca    2760
gtgatttttt tctccatttt agcttcctta gctcctgaaa atctcgataa ctcaaaaaat    2820
acgcccggta gtgatcttat ttcattatgg tgaaagttgg aaccttcttac gtgccgatca    2880
acgtctcatt ttcgccagat atc                                            2903
```

<210> SEQ ID NO 25
<211> LENGTH: 2904
<212> TYPE: DNA
<213> ORGANISM: Artificial Sequence
<220> FEATURE:
<223> OTHER INFORMATION: pCASCADE-gltA2-udhA Plasmid

<400> SEQUENCE: 25

```
gacgtcttaa gacccacttt cacatttaag ttgttttttct aatccgcata tgatcaattc     60
aaggccgaat aagaaggctg gctctgcacc ttggtgatca ataattcga tagcttgtcg     120
taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaggct aattgatttt cgagagtttc     300
atactgtttt tctgtaggcc gtgtacctaa atgtactttt gctccatcgc gatgacttag    360
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcactttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc     780
gtccctatct gctgccctag gtctatgagt ggttgctgga taactctttc tgacaccttta    840
ctatcttaca aatgtaacaa aaaagttatt tttctgtaat tcgagcatgt catgttaccc     900
cgcgagcata aaacgcgtat attcagggag accacaacgg tttccctcta caaataattt    960
tgtttaactt tgaattcaaa agatctggta ccacctcgag ttccccgcgc cagcggggat   1020
aaaccgtatt gaccaattca ttcgggacag ttattagttc gagttccccg cgccagcggg    1080
gataaaccgt taccattctg ttgcttttat gtataagaat cgagttcccc gcgccagcgg    1140
ggataaaccg aaaaaaaaac cccgccctg acagggcggg gttttttttc ctagggtatat    1200
attccgcttc ctcgctcact gactcgctac gctcggtcgt tcgactgcgg cgagcggaaa    1260
```

```
tggcttacga acggggcgga gatttcctgg aagatgccag gaagatactt aacagggaag    1320
tgagagggcc gcggcaaagc cgttttcca taggctccgc ccccctgaca agcatcacga    1380
aatctgacgc tcaaatcagt ggtggcgaaa cccgacagga ctataaagat accaggcgtt    1440
tccccctggc ggctccctcg tgcgctctcc tgttcctgcc tttcggttta ccggtgtcat    1500
tccgctgtta tggccgcgtt tgtctcattc cacgcctgac actcagttcc gggtaggcag    1560
ttcgctccaa gctggactgt atgcacgaac ccccgttca gtccgaccgc tgcgccttat    1620
ccggtaacta tcgtcttgag tccaacccgg aaagacatgc aaaagcacca ctggcagcag    1680
ccactggtaa ttgatttaga ggagttagtc ttgaagtcat gcgccggtta aggctaaact    1740
gaaaggacaa gttttggtga ctgcgctcct ccaagccagt tacctcggtt caaagagttg    1800
gtagctcaga gaaccttcga aaaaccgccc tgcaaggcgg ttttttcgtt ttcagagcaa    1860
gagattacgc gcagaccaaa acgatctcaa gaagatcatc ttattaatca gataaaatat    1920
ttctagattt cagtgcaatt tatctcttca aatgtagcac ctgaagtcag ccccatacga    1980
tataagttgt tactagtgct tggattctca ccaataaaaa acgcccggcg gcaaccgagc    2040
gttctgaaca atccagatg gagttctgag gtcattactg gatctatcaa caggagtcca    2100
agcgagctcg atatcaaatt acgccccgcc ctgccactca tcgcagtact gttgtaattc    2160
attaagcatt ctgccgacat ggaagccatc acaaacggca tgatgaacct gaatcgccag    2220
cggcatcagc accttgtcgc cttgcgtata atatttgccc atggtgaaaa cggggggcgaa    2280 gaagttgtcc atattggcca cgtttaaatc aaaactggtg aaactcaccc agggattggc    2340
tgagacgaaa aacatattct caataaaccc tttagggaaa taggccaggt tttcaccgta    2400
acacgccaca tcttgcgaat atatgtgtag aaactgccgg aaatcgtcgt ggtattcact    2460
ccagagcgat gaaaacgttt cagtttgctc atggaaaacg gtgtaacaag ggtgaacact    2520
atcccatatc accagctcac cgtctttcat tgccatacga aattccggat gagcattcat    2580
caggcgggca agaatgtgaa taaaggccgg ataaaacttg tgcttatttt tctttacggt    2640
ctttaaaaag gccgtaatat ccagctgaac ggtctggtta taggtacatt gagcaactga    2700
ctgaaatgcc tcaaaatgtt ctttacgatg ccattgggat atatcaacgg tggtatatcc    2760
agtgattttt ttctccattt tagcttcctt agctcctgaa aatctcgata actcaaaaaa    2820
tacgcccggt agtgatctta tttcattatg gtgaaagttg gaacctctta cgtgccgatc    2880
aacgtctcat tttcgccaga tatc                                           2904
```

<210> SEQ ID NO 26
<211> LENGTH: 2903
<212> TYPE: DNA
<213> ORGANISM: Artificial Sequence
<220> FEATURE:
<223> OTHER INFORMATION: pCASCADE-gltA1-zwf Plasmid

<400> SEQUENCE: 26

```
gacgtcttaa gacccacttt cacatttaag ttgttttct aatccgcata tgatcaattc      60
aaggccgaat aagaaggctg gctctgcacc ttggtgatca ataattcga tagcttgtcg     120 taataatggc ggcatactat cagtagtagg tgtttccctt tcttctttag cgacttgatg    180
ctcttgatct tccaatacgc aacctaaagt aaaatgcccc acagcgctga gtgcatataa    240
tgcattctct agtgaaaaac cttgttggca taaaaaggct aattgatttt cgagagtttc    300
atactgtttt tctgtaggcc gtgtacctaa atgtactttt gctccatcgc gatgacttag    360
```

```
taaagcacat ctaaaacttt tagcgttatt acgtaaaaaa tcttgccagc tttccccttc    420
taaagggcaa aagtgagtat ggtgcctatc taacatctca atggctaagg cgtcgagcaa    480
agcccgctta ttttttacat gccaatacaa tgtaggctgc tctacaccta gcttctgggc    540
gagtttacgg gttgttaaac cttcgattcc gacctcatta agcagctcta atgcgctgtt    600
aatcacttta cttttatcta atctagacat catccaggca tcaaataaaa cgaaaggctc    660
agtcgaaaga ctgggccttt cgttttatct gttgtttgtc ggtgaacgct ctctactaga    720
gtcacactgg ctcaccttcg ggtgggcctt tctgcgttta tacacagcta acaccacgtc    780
gtccctatct gctgcsctag gtctatgagt ggttgctgga taactctttc tgacaccttg    840
ctatcttaca aatgtaacaa aaaagttatt tttctgtaat tcgagcatgt catgttaccc    900
cgcgagcata aaacgcgtat attcagggag accacaacgg tttccctcta caataatttg    960
tgtttaactt tgaattcaaa agatctggta ccacctcgag ttccccgcgc cagcggggat   1020
aaaccgaaaa gcataatatg cgtaaaagtt atgaagttcg agttcccgc gccagcgggg   1080 ataaaccgct cgtaaaagca gtacagtgca ccgtaagatc gagttcccg cgccagcggg   1140 gataaaccga aaaaaaaacc ccgcccctga cagggcgggg ttttttttcc tagggatata   1200
ttccgcttcc tcgctcactg actcgctacg ctcggtcgtt cgactgcggc gagcggaaat   1260
ggcttacgaa cggggcggag atttcctgga agatgccagg aagatactta acagggaagt   1320
gagagggccg cggcaaagcc gttttttccat aggctccgcc cccctgacaa gcatcacgaa   1380
atctgacgct caaatcagtg gtggcgaaac ccgacaggac tataaagata ccaggcgttt   1440 cccccctggcg gctccctcgt gcgctctcct gttcctgcct tcggtttac cggtgtcatt   1500 ccgctgttat ggccgcgttt gtctcattcc acgcctgaca ctcagttccg ggtaggcagt   1560
tcgctccaag ctggactgta tgcacgaacc ccccgttcag tccgaccgct gcgccttatc   1620
cggtaactat cgtcttgagt ccaacccgga agacatgca aaagcaccac tggcagcagc   1680
cactggtaat tgatttagag gagttagtct tgaagtcatg cgccggttaa ggctaaactg   1740
aaaggacaag ttttggtgac tgcgctcctc caagccagtt acctcggttc aaagagttgg   1800
tagctcagag aaccttcgaa aaaccgcccc gcaaggcggt tttttcgttt tcagagcaag   1860
agattacgcg cagaccaaaa cgatctcaag aagatcatct tattaatcag ataaaatatt   1920
tctagatttc agtgcaattt atctcttcaa atgtagcacc tgaagtcagc cccatacgat   1980
ataagttgtt actagtgctt ggattctcac caataaaaaa cgcccggcgg caaccgagcg   2040
ttctgaacaa atccagatgg agttctgagg tcattactgg atctatcaac aggagtccaa   2100
gcgagctcga tatcaaatta cgccccgccc tgccactcat cgcagtactg ttgtaattca   2160
ttaagcattc tgccgacatg gaagccatca caaacggcat gatgaacctg aatcgccagc   2220
ggcatcagca ccttgtcgcc ttgcgtataa tatttgccca tggtgaaaac ggggcgaag   2280 aagttgtcca tattggccac gtttaaatca aaactggtga actcaccca gggattggct   2340 gagacgaaaa acatattctc aataaaccct ttagggaaat aggccaggtt ttcaccgtaa   2400
cacgccacat cttgcgaata tatgtgtaga aactgccgga atcgtcgtg gtattcactc   2460 cagagcgatg aaaacgtttc agtttgctca tggaaaacgg tgtaacaagg gtgaacacta   2520
tcccatatca ccagctcacc gtctttcatt gccatacgaa attccggatg agcattcatc   2580
aggcgggcaa gaatgtgaat aaaggccgga taaaacttgt gcttattttt ctttacggtc   2640
tttaaaaagg ccgtaatatc cagctgaacg gtctggttat aggtacattg agcaactgac   2700
tgaaatgcct caaaatgttc tttacgatgc cattgggata tatcaacggt ggtatatcca   2760
```

```
gtgattttt  tctccatttt  agcttcctta  gctcctgaaa  atctcgataa  ctcaaaaaat    2820
acgcccggta  gtgatcttat  ttcattatgg  tgaaagttgg  aacctcttac  gtgccgatca    2880
acgtctcatt  ttcgccagat  atc                                              2903
```

<210> SEQ ID NO 27
<211> LENGTH: 2904
<212> TYPE: DNA
<213> ORGANISM: Artificial Sequence
<220> FEATURE:
<223> OTHER INFORMATION: pCASCADE-gltA2-zwf Plasmid

<400> SEQUENCE: 27

```
gacgtcttaa  gacccacttt  cacatttaag  ttgttttct   aatccgcata  tgatcaattc     60
aaggccgaat  aagaaggctg  gctctgcacc  ttggtgatca  aataattcga  tagcttgtcg    120
taataatggc  ggcatactat  cagtagtagg  tgtttccctt  tcttctttag  cgacttgatg    180
ctcttgatct  tccaatacgc  aacctaaagt  aaaatgcccc  acagcgctga  gtgcatataa    240
tgcattctct  agtgaaaaac  cttgttggca  taaaaaggct  aattgatttt  cgagagtttc    300
atactgtttt  tctgtaggcc  gtgtacctaa  atgtactttt  gctccatcgc  gatgacttag    360
taaagcacat  ctaaaacttt  tagcgttatt  acgtaaaaaa  tcttgccagc  tttccccttc    420
taaagggcaa  aagtgagtat  ggtgcctatc  taacatctca  atggctaagg  cgtcgagcaa    480
agcccgctta  ttttttacat  gccaatacaa  tgtaggctgc  tctacaccta  gcttctgggc    540
gagtttacgg  gttgttaaac  cttcgattcc  gacctcatta  agcagctcta  atgcgctgtt    600
aatcacttta  cttttatcta  atctagacat  catccaggca  tcaaataaaa  cgaaaggctc    660
agtcgaaaga  ctgggccttt  cgttttatct  gttgtttgtc  ggtgaacgct  ctctactaga    720
gtcacactgg  ctcaccttcg  ggtgggcctt  tctgcgttta  tacacagcta  acaccacgtc    780
gtccctatct  gctgccctag  gtctatgagt  ggttgctgga  taactctttc  tgacaccttt    840
ctatcttaca  aatgtaacaa  aaaagttatt  tttctgtaat  tcgagcatgt  catgttaccc    900
cgcgagcata  aaacgcgtat  attcagggag  accacaacgg  tttccctcta  caaataattt    960
tgtttaactt  tgaattcaaa  agatctggta  ccacctcgag  ttccccgcgc  cagcggggat   1020
aaaccgtatt  gaccaattca  ttcgggacag  ttattagttc  gagttccccg  cgccagcggg   1080
gataaaccgc  tcgtaaaagc  agtacagtgc  accgtaagat  cgagttcccc  gcgccagcgg   1140
ggataaaccg  aaaaaaaaac  cccgcccctg  acagggcggg  gtttttttttc  ctagggatat   1200 attccgcttc  ctcgctcact  gactcgctac  gctcggtcgt  tcgactgcgg  cgagcggaaa   1260
tggcttacga  acggggcgga  gatttcctgg  aagatgccag  gaagatactt  aacagggaag   1320
tgagagggcc  gcggcaaagc  cgttttttcca  taggctccgc  ccccctgaca  agcatcacga   1380
aatctgacgc  tcaaatcagt  ggtggcgaaa  cccgacagga  ctataaagat  accaggcgtt   1440
tccccctggc  ggctccctcg  tgcgctctcc  tgttcctgcc  tttcggttta  ccggtgtcat   1500
tccgctgtta  tggccgcgtt  tgtctcattc  cacgcctgac  actcagttcc  gggtaggcag   1560
ttcgctccaa  gctggactgt  atgcacgaac  ccccgttca   gtccgaccgc  tgcgccttat   1620
ccggtaacta  tcgtcttgag  tccaacccgg  aaagacatg   aaaagcacca  ctggcagcag   1680
ccactggtaa  ttgatttaga  ggagttagtc  ttgaagtcat  gcgccggtta  aggctaaact   1740
gaaaggacaa  gttttggtga  ctgcgctcct  ccaagccagt  tacctcggtt  caaagagttg   1800
gtagctcaga  gaaccttcga  aaaaccgccc  tgcaaggcgg  ttttttcgtt  ttcagagcaa   1860
```

```
gagattacgc gcagaccaaa acgatctcaa gaagatcatc ttattaatca gataaaatat    1920
ttctagattt cagtgcaatt tatctcttca aatgtagcac ctgaagtcag ccccatacga    1980
tataagttgt tactagtgct tggattctca ccaataaaaa acgcccggcg gcaaccgagc    2040
gttctgaaca atccagatg gagttctgag gtcattactg gatctatcaa caggagtcca     2100
agcgagctcg atatcaaatt acgccccgcc ctgccactca tcgcagtact gttgtaattc    2160
attaagcatt ctgccgacat ggaagccatc acaaacggca tgatgaacct gaatcgccag    2220
cggcatcagc accttgtcgc cttgcgtata atatttgccc atggtgaaaa cggggggcgaa   2280 gaagttgtcc atattggcca cgtttaaatc aaaactggtg aaactcaccc agggattggc    2340
tgagacgaaa aacatattct caataaaccc tttagggaaa taggccaggt tttcaccgta    2400
acacgccaca tcttgcgaat atatgtgtag aaactgccgg aaatcgtcgt ggtattcact    2460
ccagagcgat gaaaacgttt cagtttgctc atggaaaacg gtgtaacaag ggtgaacact    2520
atcccatatc accagctcac cgtctttcat tgccatacga aattccggat gagcattcat    2580
caggcgggca agaatgtgaa taaaggccgg ataaaacttg tgcttatttt tctttacggt    2640
ctttaaaaag gccgtaatat ccagctgaac ggtctggtta taggtacatt gagcaactga    2700
ctgaaatgcc tcaaaatgtt ctttacgatg ccattgggat atatcaacgg tggtatatcc    2760
agtgattttt ttctccattt tagcttcctt agctcctgaa atctcgata actcaaaaaa     2820 tacgcccggt agtgatctta tttcattatg gtgaaagttg gaacctctta cgtgccgatc    2880
aacgtctcat tttcgccaga tatc                                           2904

<210> SEQ ID NO 28
<211> LENGTH: 3505
<212> TYPE: DNA
<213> ORGANISM: Artificial Sequence
<220> FEATURE:
<223> OTHER INFORMATION: pBT1-mCherry-DAS+4 Vector

<400> SEQUENCE: 28
cgcaaaaaac cccgcttcgg cggggttttt tcgcacgtct ccatcgcttg cccaagttgt     60
gaagcacagc taacaccacg tcgtccctat ctgctgccct aggtctatga gtggttgctg    120 gataaccttta cgggcatgca taaggctcgt ataatatatt cagggagacc acaacggttt    180
ccctctacaa ataattttgt ttaactttga tcgcatggtt gctactagag aaagaggaga    240
aatactagat ggtgagcaag ggcgaggagg ataacatggc catcatcaag gagttcatgc    300
gcttcaaggt gcacatggag ggctccgtga acggccacga gttcgagatc gagggcgagg    360
gcgagggccg cccctacgag ggcacccaga ccgccaagct gaaggtgacc aagggtggcc    420
ccctgccctt cgcctgggac atcctgtccc ctcagttcat gtacggctcc aaggcctacg    480
tgaagcaccc cgccgacatc cccgactact tgaagctgtc cttccccgag ggcttcaagt    540
gggagcgcgt gatgaacttc gaggacggcg gcgtggtgac cgtgacccag gactcctccc    600
tgcaggacgg cgagttcatc tacaaggtga agctgcgcgg caccaacttc ccctccgacg    660
gccccgtaat gcagaagaag accatgggct gggaggcctc ctccgagcgg atgtaccccg    720 aggacgcgc cctgaagggc gagatcaagc agaggctgaa gctgaaggac ggcggccact    780
acgacgctga ggtcaagacc acctacaagg ccaagaagcc cgtgcagctg cccggcgcct    840
acaacgtcaa catcaagttg gacatcacct cccacaacga ggactacacc atcgtggaac    900
agtacgaacg cgccgagggc cgccactcca ccggcggcat ggacgaactg tacaaggcgg    960
ccaacgatga aaactattct gaaaactatg cggatgcgtc ttaataagga cgagcctcag   1020
```

```
actccagcgt aactggactg aaaacaaact aaagcgccct tgtggcgctt tagttttgtt    1080
ccgcggccac cggctggctc gcttcgctcg gcccgtggac aaccctgctg acaagctga    1140
tggacaggct gcgcctgccc acgagcttga ccacagggat tgcccaccgg ctacccagcc    1200
ttcgaccaca tacccaccgg ctccaactgc gcggcctgcg gccttgcccc atcaattttt    1260
ttaattttct ctggggaaaa gcctccggcc tgcggcctgc gcgcttcgct tgccggttgg    1320
acaccaagtg gaaggcgggt caaggctcgc gcagcgaccg cgcagcggct tggccttgac    1380
gcgcctggaa cgacccaagc ctatgcgagt gggggcagtc gaaggcgaag cccgcccgcc    1440
tgccccccga gcctcacggc ggcgagtgcg ggggttccaa gggggcagcg ccaccttggg    1500
caaggccgaa ggccgcgcag tcgatcaaca agccccggag gggccacttt tgccggagg    1560
gggagccgcg ccgaaggcgt gggggaaccc cgcaggggtg ccttctttg ggcaccaaag    1620
aactagatat agggcgaaat gcgaaagact taaaaatcaa caacttaaaa aagggggta    1680
cgcaacagct cattgcggca ccccccgcaa tagctcattg cgtaggttaa agaaaatctg    1740
taattgactg ccacttttac gcaacgcata attgttgtcg cgctgccgaa aagttgcagc    1800
tgattgcgca tggtgccgca accgtgcggc accctaccgc atggagataa gcatggccac    1860
gcagtccaga gaaatcggca ttcaagccaa gaacaagccc ggtcactggg tgcaaacgga    1920
acgcaaagcg catgaggcgt gggccgggct tattgcgagg aaacccacgg cggcaatgct    1980
gctgcatcac ctcgtggcgc agatgggcca ccagaacgcc gtggtggtca gccagaagac    2040
actttccaag ctcatcggac gttctttgcg gacggtccaa tacgcagtca aggacttggt    2100
ggccgagcgc tggatctccg tcgtgaagct caacggcccc ggcaccgtgt cggcctacgt    2160
ggtcaatgac cgcgtggcgt ggggccagcc ccgcgaccag ttgcgcctgt cggtgttcag    2220
tgccgccgtg gtggttgatc acgacgacca ggacgaatcg ctgttggggc atggcgacct    2280
gcgccgcatc ccgaccctgt atccgggcga gcagcaacta ccgaccggcc ccggcgagga    2340
gccgccagc cagcccggca ttccgggcat ggaaccagac ctgccagcct tgaccgaaac    2400
ggaggaatgg gaacgcgcg ggcagcagcg cctgccgatg cccgatgagc cgtgttttct    2460
ggacgatggc gagccgttgg agccgccgac acgggtcacg ctgccgcgcc ggtagtacgt    2520
aagaggttcc aactttcacc ataatgaaat aagatcacta ccgggcgtat tttttgagtt    2580
atcgagattt tcaggagcta aggaagctaa aatgagtatt caacatttcc gtgtcgccct    2640
tattcccttt tttgcggcat tttgccttcc tgttttgct cacccagaaa cgctggtgaa    2700
agtaaaagat gctgaagatc agttgggtgc acgagtgggt tacatcgaac tggatctcaa    2760
cagcggtaag atccttgaga gtttacgccc cgaagaacgt tttccaatga tgagcacttt    2820
taaagttctg ctatgtggcg cggtattatc ccgtattgac gccgggcaag agcaactcgg    2880
tcgccgcata cactattctc agaatgactt ggttgagtac tcaccagtca cagaaaagca    2940
tctcacggat ggcatgacag taagagaatt atgcagtgct gccataacca tgagtgataa    3000
cactgcggcc aacttacttc tgcaacgat cggaggaccg aaggagctaa ccgcttttttt    3060
gcacaacatg gggatcatg taactcgcct tgatcgttgg gaaccggagc tgaatgaagc    3120
cataccaaac gacgagcgtg acaccacgat gcctgtagca atggcaacaa cgttgcgcaa    3180
actattaact ggcgaactac ttactctagc ttcccggcaa caattaatag actggatgga    3240
ggcggataaa gttgcaggat cacttctgcg ctcggccctc ccggctggct ggtttattgc    3300
tgataaatct ggagccggtg agcgtgggtc tcgcggtatc attgcagcac tggggccaga    3360
```

| | |
|---|---|
| tggtaagccc tcccgcatcg tagttatcta cacgacgggg agtcaggcaa ctatggatga | 3420 |
| acgaaataga cagatcgctg agataggtgc ctcactgatt aagcattggt aatgaggatc | 3480 |
| cccctcaagt caaaagcctc cggtc | 3505 |

<210> SEQ ID NO 29
<211> LENGTH: 2841
<212> TYPE: DNA
<213> ORGANISM: Artificial Sequence
<220> FEATURE:
<223> OTHER INFORMATION: pCASCADE-proD Plasmid

<400> SEQUENCE: 29

| | |
|---|---|
| gacgtcttaa gacccacttt cacatttaag ttgttttttct aatccgcata tgatcaattc | 60 |
| aaggccgaat aagaaggctg gctctgcacc ttggtgatca ataattcga tagcttgtcg | 120 |
| taataatggc ggcatactat cagtagtagg tgtttccctt tcttctttag cgacttgatg | 180 |
| ctcttgatct tccaatacgc aacctaaagt aaaatgcccc acagcgctga gtgcatataa | 240 |
| tgcattctct agtgaaaaac cttgttggca taaaaaggct aattgatttt cgagagtttc | 300 |
| atactgtttt tctgtaggcc gtgtacctaa atgtactttt gctccatcgc gatgacttag | 360 |
| taaagcacat ctaaaacttt tagcgttatt acgtaaaaaa tcttgccagc tttcccctc | 420 |
| taaagggcaa aagtgagtat ggtgcctatc taacatctca atggctaagg cgtcgagcaa | 480 |
| agcccgctta tttttacat gccaatacaa tgtaggctgc tctacaccta gcttctgggc | 540 |
| gagtttacgg gttgttaaac cttcgattcc gacctcatta agcagctcta atgcgctgtt | 600 |
| aatcacttta cttttatcta atctagacat catccaggca tcaaataaaa cgaaaggctc | 660 |
| agtcgaaaga ctgggccttt cgttttatct gttgtttgtc ggtgaacgct ctctactaga | 720 |
| gtcacactgg ctcaccttcg ggtgggcctt tctgcgttta tacacagcta acaccacgtc | 780 |
| gtccctatct gctgccctag gtctatgagt ggttgctgga taactctttc tgacacctta | 840 |
| ctatcttaca aatgtaacaa aaagttatt tttctgtaat tcgagcatgt catgttaccc | 900 |
| cgcgagcata aaacgcgtat attcagggag accacaacgg tttccctcta caaataattt | 960 |
| tgtttaactt tgaattcaaa agatctggta ccacctcgag ttccccgcgc cagcggggat | 1020 |
| aaaccgagtg gttgctggat aactttacgg gcatgctcga gttccccgcg ccagcgggga | 1080 |
| taaaccgaaa aaaaaccccc gcccctgaca gggcggggtt ttttttccta gggatatatt | 1140 |
| ccgcttcctc gctcactgac tcgctacgct cggtcgttcg actgcggcga gcggaaatgg | 1200 |
| cttacgaacg gggcggagat ttcctggaag atgccaggaa gatacttaac agggaagtga | 1260 |
| gagggccgcg gcaaagccgt ttttccatag gctccgcccc cctgacaagc atcacgaaat | 1320 |
| ctgacgctca aatcagtggt ggcgaaaccc gacaggacta taaagatacc aggcgtttcc | 1380 |
| ccctggcggc tccctcgtgc gctctcctgt tcctgccttt cggtttaccg gtgtcattcc | 1440 |
| gctgttatgg ccgcgtttgt ctcattccac gcctgacact cagttccggg taggcagttc | 1500 |
| gctccaagct ggactgtatg cacgaacccc ccgttcagtc cgaccgctgc gccttatccg | 1560 |
| gtaactatcg tcttgagtcc aacccggaaa gacatgcaaa agcaccactg gcagcagcca | 1620 |
| ctggtaattg atttagagga gttagtcttg aagtcatgcg ccggttaagg ctaaactgaa | 1680 |
| aggacaagtt ttggtgactg cgctcctcca agccagttac ctcggttcaa agagttggta | 1740 |
| gctcagagaa ccttcgaaaa accgccctgc aaggcggttt tttcgttttc agagcaagag | 1800 |
| attacgcgca gaccaaaacg atctcaagaa gatcatctta ttaatcagat aaaatatttc | 1860 |
| tagatttcag tgcaatttat ctcttcaaat gtagcacctg aagtcagccc catacgatat | 1920 |

| | | |
|---|---|---|
| aagttgttac tagtgcttgg attctcacca ataaaaaacg cccggcggca accgagcgtt | 1980 |
| ctgaacaaat ccagatggag ttctgaggtc attactggat ctatcaacag gagtccaagc | 2040 |
| gagctcgata tcaaattacg ccccgccctg ccactcatcg cagtactgtt gtaattcatt | 2100 |
| aagcattctg ccgacatgga agccatcaca aacggcatga tgaacctgaa tcgccagcgg | 2160 |
| catcagcacc ttgtcgcctt gcgtataata tttgcccatg gtgaaaacgg gggcgaagaa | 2220 |
| gttgtccata ttggccacgt ttaaatcaaa actggtgaaa ctcacccagg gattggctga | 2280 |
| gacgaaaaac atattctcaa taaacccttt agggaaatag gccaggtttt caccgtaaca | 2340 |
| cgccacatct tgcgaatata tgtgtagaaa ctgccggaaa tcgtcgtggt attcactcca | 2400 |
| gagcgatgaa aacgtttcag tttgctcatg gaaaacggtg taacaagggt gaacactatc | 2460 |
| ccatatcacc agctcaccgt ctttcattgc catacgaaat tccggatgag cattcatcag | 2520 |
| gcgggcaaga atgtgaataa aggccggata aaacttgtgc ttattttttct ttacggtctt | 2580 |
| taaaaaggcc gtaatatcca gctgaacggt ctggttatag gtacattgag caactgactg | 2640 |
| aaatgcctca aaatgttctt tacgatgcca ttgggatata tcaacggtgg tatatccagt | 2700 |
| gatttttttc tccattttag cttccttagc tcctgaaaat ctcgataact caaaaaatac | 2760 |
| gcccggtagt gatcttattt cattatggtg aaagttggaa cctcttacgt gccgatcaac | 2820 |
| gtctcatttt cgccagatat c | 2841 |

<210> SEQ ID NO 30
<211> LENGTH: 4866
<212> TYPE: DNA
<213> ORGANISM: Artificial Sequence
<220> FEATURE:
<223> OTHER INFORMATION: pSMART-3HP1 Plasmid

<400> SEQUENCE: 30

| | | |
|---|---|---|
| gtgcgtaatt gtgctgatct cttatatagc tgctctcatt atctctctac cctgaagtga | 60 |
| ctctctcacc tgtaaaaata atatctcaca ggcttaatag tttcttaata caaagcctgt | 120 |
| aaaacgtcag gataacttct tttctggaaa aaggagatat accatggcga cgacggggc | 180 |
| acgtagcgct agtgttggtt gggccgagag cctgatcggt ctgcatttgg gaaaagtggc | 240 |
| cttaatcacc ggaggctcag ccggcatcgg cgggcagatc ggccgccttt tagcgctgtc | 300 |
| tggcgcgcgt gttatgctgg ccgctcgcga ccgtcacaaa ctcgaacaaa tgcaggccat | 360 |
| gattcaatcc gaactggcgg aagttggtta taccgatgtc gaagaccgcg tgcacatcgc | 420 |
| gccggggtgt gacgtttcct ctgaagcgca gctggcagat ctggttgaac gcactctgtc | 480 |
| agcattcggt accgtggatt atctgatcaa taacgcgggt attgcgggtg tcgaagagat | 540 |
| ggttatcgac atgccggtgg aaggctggcg tcatacgtta tttgccaacc ttatctcaaa | 600 |
| ttatagcctg atgcgcaaac tggcccctct gatgaagaaa caggggagtg gctatatctt | 660 |
| gaacgtctcg tcgtactttg gtggcgaaaa agatgcggct atcccatacc aaatcgtgc | 720 |
| cgattatgcg gtttcaaaag ccggtcaacg tgcaatggct gaagtgttcg cccgtttcct | 780 |
| cggcccggag atccagatta acgctatcgc cccaggcccg gtggaaggtg accgcctccg | 840 |
| cggcacgggc gaacgtcccg gcttgttgc gcgccgcgcg cgtttgattt tagaaaataa | 900 |
| gcgtttaaac gagctgcatg ctgcccttat tgcggctgcg cgtacagatg agcgctccat | 960 |
| gcacgaactg gtggaattac tgctgccgaa tgatgtagcg gcactcgagc agaatcccgc | 1020 |
| agccccaacg gcgttgcgcg aactcgcgcg ccgttttcgc agcgaaggcg acccggccgc | 1080 |

-continued

| | | | | | |
|---|---|---|---|---|---|
| gtcaagctcc | agtgctctgc | tcaaccgcag | cattgcggcg | aagttactgg | cccgcctgca | 1140 |
| caacggcggc | tatgttctgc | cggcggatat | cttcgccaac | ctgccgaacc | ctccagaccc | 1200 |
| gttcttcacg | cgcgcgcaga | ttgatcgcga | agcccgtaaa | gtgcgcgacg | ggattatggg | 1260 |
| aatgctgtat | ctgcagcgca | tgcctaccga | gtttgacgta | gcaatggcta | ccgtttacta | 1320 |
| tctggcggat | cgcaatgtga | gtggagagac | cttccatccg | agtgggggc | tgcgttacga | 1380 |
| gcgcacacct | accggcggtg | agttatttgg | cctgccgtct | cccgagcgcc | tggcggagtt | 1440 |
| agttggaagc | accgtatatt | tgatcggtga | acacttaacc | gaacatctga | acttgctcgc | 1500 |
| acgtgcgtat | cttgaacgtt | acggtgcgcg | tcaggttgtt | atgatcgtgg | aaacggagac | 1560 |
| aggcgcggaa | accatgcgcc | gcttacttca | cgaccatgtc | gaagcaggtc | gccttatgac | 1620 |
| cattgtggcg | ggtgaccaaa | tcgaagccgc | catcgaccag | gcgattacgc | gctacgccg | 1680 |
| tcctggtccg | gttgtgtgca | cccccttccg | cccccttccg | accgtcccgt | tagttggccg | 1740 |
| caaggactcc | gattggagca | ccgtactgag | tgaagccgaa | tttgccgaac | tgtgtgaaca | 1800 |
| tcaactgaca | catcattttc | gcgtagcgcg | caaaatcgca | ctttcggatg | gtgcctcact | 1860 |
| ggctctggtt | accccgaaa | ccacagcgac | aagtaccact | gaacagttcg | ccctggccaa | 1920 |
| ctttattaag | acaaccctgc | acgcttttac | ggccactatc | ggagttgaaa | gtgagcgcac | 1980 |
| ggcgcagcgt | atcctgatta | atcaggtaga | cctcacccgt | cgtgctcgtg | cggaagaacc | 2040 |
| acgcgatccg | catgaacgtc | agcaggaact | ggaacgtttc | atcgaggcgg | tactgctggt | 2100 |
| tacggcccca | ttaccgccgg | aagcagatac | ccgctacgct | ggccgcatcc | accgtgggcg | 2160 |
| tgccattact | gtctagtaag | ctcttcttct | ggaaaaagga | gatataccat | gatcgttta | 2220 |
| gtaactggag | caacggcagg | ttttggtgaa | tgcattactc | gtcgttttat | tcaacaaggg | 2280 |
| cataaagtta | tcgccactgg | ccgtcgccag | gaacggttgc | aggagttaaa | agacgaactg | 2340 |
| ggagataatc | tgtatatcgc | ccaactggac | gttcgcaacc | gcgccgctat | tgaagagatg | 2400 |
| ctggcatcgc | ttcctgccga | gtggtgcaat | attgatatcc | tggtaaataa | tgccggcctg | 2460 |
| gcgttgggca | tggagcctgc | gcataaagcc | agcgttgaag | actgggaaac | gatgattgat | 2520 |
| accaacaaca | aaggcctggt | atatatgacg | cgcgccgtct | taccgggtat | ggttgaacgt | 2580 |
| aatcatggtc | atattattaa | cattggctca | acggcaggta | gctggccgta | tgccggtggt | 2640 |
| aacgtttacg | gtgcgacgaa | agcgtttgtt | cgtcagttta | gcctgaatct | gcgtacggat | 2700 |
| ctgcatggta | cggcggtgcg | cgtcaccgac | atcgaaccgg | gtctggtggg | tggtaccgag | 2760 |
| ttttccaatg | tccgctttaa | aggcgatgac | ggtaaagcag | aaaaaaccta | tcaaaatacc | 2820 |
| gttgcattga | cgccagaaga | tgtcagcgaa | gccgtctggt | gggtgtcaac | gctgcctgct | 2880 |
| cacgtcaata | tcaatacccct | ggaaatgatg | ccggttaccc | aaagctatgc | cggactgaat | 2940 |
| gtccaccgtc | agtaatagga | tcgtcccggc | ttatcggtca | gtttcacctg | atttacgtaa | 3000 |
| aaacccgctt | cggcgggttt | ttgcttttgg | aggggcagaa | agatgaatga | ctgtccacga | 3060 |
| cgctatacccc | aaaagaaaga | cgaattctct | agatatcgct | caatactgac | catttaaatc | 3120 |
| atacctgacc | tccatagcag | aaagtcaaaa | gcctccgacc | ggaggctttt | gacttgatcg | 3180 |
| gcacgtaaga | ggttccaact | ttcaccataa | tgaaataaga | tcactaccgg | gcgtattttt | 3240 |
| tgagttatcg | agattttcag | gagctaagga | agctaaaatg | agccatattc | aacgggaaac | 3300 |
| gtcttgctcg | aggccgcgat | taaattccaa | catggatgct | gatttatatg | ggtataaatg | 3360 |
| ggctcgcgat | aatgtcgggc | aatcaggtgc | gacaatctat | cgattgtatg | ggaagcccga | 3420 |
| tgcgccagag | ttgtttctga | aacatggcaa | aggtagcgtt | gccaatgatg | ttacagatga | 3480 |

```
gatggtcagg ctaaactggc tgacggaatt tatgcctctt ccgaccatca agcattttat    3540
ccgtactcct gatgatgcat ggttactcac cactgcgatc caagggaaaa cagcattcca    3600
ggtattagaa gaatatcctg attcaggtga aaatattgtt gatgcgctgg cagtgttcct    3660
gcgccggttg cattcgattc ctgtttgtaa ttgtcctttt aacggcgatc gcgtatttcg    3720
tctcgctcag gcgcaatcac gaatgaataa cggtttggtt ggtgcgagtg attttgatga    3780
cgagcgtaat ggctggcctg ttgaacaagt ctggaaagaa atgcataagc ttttgccatt    3840
ctcaccggat tcagtcgtca ctcatggtga tttctcactt gataaccta ttttgacga    3900 ggggaaatta ataggttgta ttgatgttgg acgagtcgga atcgcagacc gataccagga    3960
tcttgccatc ctatggaact gcctcggtga gttttctcct tcattacaga acggcttt     4020 tcaaaaatat ggtattgata atcctgatat gaataaattg cagtttcact tgatgctcga    4080 tgagttttc taatgagggc ccaaatgtaa tcacctggct caccttcggg tgggcctttc    4140
tgcgttgctg gcgtttttcc ataggctccg cccccctgac gagcatcaca aaaatcgatg    4200
ctcaagtcag aggtggcgaa acccgacagg actataaaga taccaggcgt ttcccctgg     4260 aagctccctc gtgcgctctc ctgttccgac cctgccgctt accggatacc tgtccgcctt    4320
tctcccttcg ggaagcgtgg cgctttctca tagctcacgc tgtaggtatc tcagttcggt    4380
gtaggtcgtt cgctccaagc tgggctgtgt gcacgaaccc cccgttcagc ccgaccgctg    4440
cgccttatcc ggtaactatc gtcttgagtc aacccggta agacacgact tatcgccact    4500
ggcagcagcc actggtaaca ggattagcag agcgaggtat gtaggcggtg ctacagagtt    4560
cttgaagtgg tggcctaact acggctacac tagaagaaca gtatttggta tctgcgctct    4620
gctgaagcca gttaccctcgg aaaaagagtt ggtagctctt gatccggcaa acaaaccacc    4680
gctggtagcg gtggtttttt tgtttgcaag cagcagatta cgcgcagaaa aaaaggatct    4740
caagaagatc ctttgatttt ctaccgaaga aaggcccacc cgtgaaggtg agccagtgag    4800
ttgattgcag tccagttacg ctggagtctg aggctcgtcc tgaatgatat caagcttgaa    4860
ttcgtt                                                               4866
```

<210> SEQ ID NO 31
<211> LENGTH: 3353
<212> TYPE: DNA
<213> ORGANISM: Artificial Sequence
<220> FEATURE:
<223> OTHER INFORMATION: Plasmid pSMART-F6AA82M

<400> SEQUENCE: 31

```
ccatggttga atgactccta taacgaagtt cacagctaac accacgtcgt ccctatctgc      60
tgccctaggt ctatgagtgg ttgctggata acgtgcgtaa ttgtgctgat ctcttatata     120
gctgctctca ttatctctct accctgaagt gactctctca cctgtaaaaa taatatctca     180
caggcttaat agtttcttaa tacaaagcct gtaaaacgtc aggataactt ctatattcag     240
ggagaccaca acggtttccc tctacaaata attttgttta actttcgaca tggcaaaatc     300 ccccccctcgc gacttgctct tcagcttct ggaaaaagga gatataccat gaatgttacg     360
tttgaagaac gtgcgagtct gcacggttac cgtatcggca ttgcaagctt ggatgccccg     420
gcttccttaa acgccttgag cctgcctatg atcgatgcgc tccaagatcg tttgcgcgct     480
tgggcggaag atgccgatat cgcttgcgtt ctgttacgtg gtaatggcag caaggcgttt     540
tgcgctggtg gcgatgtagt tcaattggcc aaaaatgct tagcaagccc aggtgaagcc     600
```

```
ccggaactgg ccgagcgttt tttcgcccgt agctatcgct tggatcatta tttgcacacc    660 tacccaaac cgttgatctg ttgggcccat ggtcacgtgc tgggtggtgg aatgggactt    720
ttacagggcg ccggcatccg tattgtgaca ccatcgtctc gcttagctat gccggaaatt    780
tctatcgggc tgttccctga cgtgggtggc tcccatttcc tgagtcgcct cccgggaaaa    840
ctggggttgt ttttcggtct taccgcgtct ccccttaacg cacgcgacgc gctggactta    900
aatctggctg accgtttcct gcttgacacg cagcaggatg cgctgatcga tggtctgatt    960
cagttaaatt ggcgcgagca acctgatctg cagctgcact ctcttctgaa agctctggaa   1020
cagcaggctc gtagtgagct gccggccgct cagtggttgc ctcgtcgtga acgccttgat   1080
gccctcctgg accaagccac gttaccattg tcctggcagg cgctggcgtc gctcgaaaat   1140
gatgaggatg ctctgttagc taaggcagct aaaacgatgc tgggcggtag cccgctcacc   1200
ggccatctcg tgtggggtca aattcgtcgt gcacgccacc tgtccttggc gcaggtgttt   1260
cagatggaat acggtatgtc attgaactgc tgccgccatc cggagttcgc ggaaggcgtc   1320
cgcgcccgtt tgattgacaa ggatcacgcc ccccattggc actggccgga cgttaaccag   1380
gttccggaac aggtaattgc agcgcatttc gcgccattgg atgatcaccc tttagccgat   1440
ctggcatagt aaccggctta tcggtcagtt tcacctgatt tacgtaaaaa cccgcttcgg   1500 cgggttttg cttttggagg ggcagaaaga tgaatgactg tccacgacgc tatcccaaa   1560 agaaagacga attctctaga tatcgctcaa tactgaccat ttaaatcata cctgacctcc   1620
atagcagaaa gtcaaaagcc tccgaccgga ggcttttgac ttgatcggca cgtaagaggt   1680
tccaactttc accataatga aataagatca ctaccgggcg tattttttga gttatcgaga   1740
ttttcaggag ctaaggaagc taaaatgagc catattcaac gggaaacgtc ttgctcgagg   1800
ccgcgattaa attccaacat ggatgctgat ttatatgggt ataaatgggc tcgcgataat   1860
gtcgggcaat caggtgcgac aatctatcga ttgtatggga agcccgatgc gccagagttg   1920
tttctgaaac atggcaaagg tagcgttgcc aatgatgtta cagatgagat ggtcaggcta   1980
aactggctga cggaatttat gcctcttccg accatcaagc attttatccg tactcctgat   2040
gatgcatggt tactcaccac tgcgatccca gggaaaacag cattccaggt attagaagaa   2100
tatcctgatt caggtgaaaa tattgttgat gcgctggcag tgttcctgcg ccggttgcat   2160
tcgattcctg tttgtaattg tccttttaac ggcgatcgcg tatttcgtct cgctcaggcg   2220
caatcacgaa tgaataacgg tttggttggt gcgagtgatt ttgatgacga gcgtaatggc   2280
tggcctgttg aacaagtctg gaaagaaatg cataagcttt tgccattctc accggattca   2340
gtcgtcactc atggtgattt ctcacttgat aaccttattt ttgacgaggg gaaattaata   2400
ggttgtattg atgttggacg agtcggaatc gcagaccgat accaggatct tgccatccta   2460
tggaactgcc tcggtgagtt ttctccttca ttacagaaac ggctttttca aaaatatggt   2520
attgataatc ctgatatgaa taaattgcag tttcacttga tgctcgatga gttttttctaa   2580 tgagggccca aatgtaatca cctggctcac cttcgggtgg gcctttctgc gttgctggcg   2640 ttttccata ggctccgccc cctgacgag catcacaaaa atcgatgctc aagtcagagg   2700
tggcgaaacc cgacaggact ataaagatac caggcgtttc cccctggaag ctccctcgtg   2760
cgctctcctg ttccgaccct gccgcttacc ggatacctgt ccgcctttct cccttcggga   2820
agcgtggcgc tttctcatag ctcacgctgt aggtatctca gttcggtgta ggtcgttcgc   2880
tccaagctgg gctgtgtgca cgaaccccc gttcagcccg accgctgcgc cttatccggt   2940
aactatcgtc ttgagtccaa cccggtaaga cacgacttat cgccactggc agcagccact   3000
```

-continued

```
ggtaacagga ttagcagagc gaggtatgta ggcggtgcta cagagttctt gaagtggtgg   3060
cctaactacg gctacactag aagaacagta tttggtatct gcgctctgct gaagccagtt   3120
acctcggaaa aagagttggt agctcttgat ccggcaaaca aaccaccgct ggtagcggtg   3180 gttttttgt ttgcaagcag cagattacgc gcagaaaaaa aggatctcaa gaagatcctt    3240 tgatttctcta ccgaagaaag gcccacccgt gaaggtgagc cagtgagttg attgcagtcc  3300
agttacgctg gagtctgagg ctcgtcctga atgatatcaa gcttgaattc gtt           3353
```

<210> SEQ ID NO 32
<211> LENGTH: 3424
<212> TYPE: DNA
<213> ORGANISM: Artificial Sequence
<220> FEATURE:
<223> OTHER INFORMATION: Plasmid pSMART-Ala1

<400> SEQUENCE: 32

```
ccaggcatca ataaaaacga aaggctcagt cgaaagactg ggcctttcgt tttatctgtt     60
gtttgtcggt gaacgctctc tactagagtc acactggctc accttcgggt gggcctttct   120
gcgtttatac acagctaaca ccacgtcgtc cctatctgct gccctaggtc tatgagtggt   180
tgctggataa ctcttctga caccttacta tcttacaaat gtaacaaaaa agttattttt    240
ctgtaattcg agcatgtcat gttaccccgc gagcataaaa cgcgtatatt cagggagacc   300
acaacggttt ccctctacaa ataattttgt ttaactttgg aaaaggaga tataccatga    360 tcattgggt gccgaaggag atcaaaaata atgagaaccg cgtcgcgttg accccgggag    420
gtgtcagcca gctgatctct aatggccatc gtgtcttagt tgaaacaggc gctggcctgg   480
gttctggctt cgaaaacgag gcctacgaat ctgcaggtgc ggaaattatt gctgatccaa   540
aacaggtctg ggatgcagag atggtcatga agtgaaaga accgctcccg gaagaatatg   600 tctatttcg taaggtctg gtgctgttta catatctgca tctggcagct gaaccggagc    660
tcgcacaagc ccttaaagat aaaggtgtca cggccatcgc atacgaaact gtcagcgaag   720
ggcgcacgct gccattactg accccgatgt cagaagtggc aggccgtatg gctgcgcaga   780
tcggcgcaca gtttcttgaa aaaccaaagg gcgggaaggg tattctctta gcaggagtgc   840
cgggcgtcag tcgtgggaaa gtaactatta ttggtggcgg cgtggtagga acaaatgctg   900
ccaaaatggc cgtcggtttg ggggccgacg taacaatcat tgcgcgtaat gccgatcgcc   960
ttcgtcaatt agacgatatc tttggccacc aaatcaaaac cctgatttcg aacccagtca  1020
atatcgcgga tgcggtggcg gaagctgatt tgttgatctg cgccgtgtta attccgggag  1080
cgaaagcacc tacattggtg acggaagaaa tggtgaaaca aatgaaaccg ggttcagtca  1140
ttgttgatgt ggctattgat cagggtgca tcgtggaaac ggtggaccat attaccactc   1200
acgaccagcc gacgtatgaa aaacatggtg tcgtacacta tgcggtggcg aatatgcctg   1260
gtgcggtccc acgtacgagt acaatcgcac tgacaaatgt caccgtgccg tatgcgttgc   1320
aaatcgcgaa caaaggtgcc gtgaaagcgc tggccgacaa tacggcgtta cgtgccggtc   1380
tgaacaccgc taacggtcac gtgacatatg aagcggtcgc gcgtgatttg gggtacgaat   1440
atgtaccggc ggaaaaagcc ttacaagacg aatcgagtgt cgctggtgca tagtaagctc   1500
ttctaatacg actcactata gggccggctt atcggtcagt ttcacctgat ttacgtaaaa   1560
acccgcttcg gcgggttttt gcttttggag gggcagaaag atgaatgact gtccacgacg   1620
ctatacccaa aagaaagacg aattctctag atatcgctca atactgacca tttaaatcat  1680
```

| | |
|---|---|
| acctgacctc catagcagaa agtcaaaagc ctccgaccgg aggcttttga cttgatcggc | 1740 |
| acgtaagagg ttccaacttt caccataatg aaataagatc actaccgggc gtattttttg | 1800 |
| agttatcgag attttcagga gctaaggaag ctaaaatgag ccatattcaa cgggaaacgt | 1860 |
| cttgctcgag gccgcgatta aattccaaca tggatgctga tttatatggg tataaatggg | 1920 |
| ctcgcgataa tgtcgggcaa tcaggtgcga caatctatcg attgtatggg aagcccgatg | 1980 |
| cgccagagtt gtttctgaaa catggcaaag gtagcgttgc caatgatgtt acagatgaga | 2040 |
| tggtcaggct aaactggctg acggaattta tgcctcttcc gaccatcaag catttatcc | 2100 |
| gtactcctga tgatgcatgg ttactcacca ctgcgatccc agggaaaaca gcattccagg | 2160 |
| tattagaaga atatcctgat tcaggtgaaa atattgttga tgcgctggca gtgttcctgc | 2220 |
| gccggttgca ttcgattcct gtttgtaatt gtccttttaa cggcgatcgc gtatttcgtc | 2280 |
| tcgctcaggc gcaatcacga atgaataacg gtttggttgg tgcgagtgat tttgatgacg | 2340 |
| agcgtaatgg ctggcctgtt gaacaagtct ggaaagaaat gcataagctt ttgccattct | 2400 |
| caccggattc agtcgtcact catggtgatt tctcacttga taaccttatt tttgacgagg | 2460 |
| ggaaattaat aggttgtatt gatgttggac gagtcggaat cgcagaccga taccaggatc | 2520 |
| ttgccatcct atggaactgc ctcggtgagt tttctccttc attacagaaa cggctttttc | 2580 |
| aaaaatatgg tattgataat cctgatatga taaattgca gtttcacttg atgctcgatg | 2640 |
| agttttcta atgagggccc aaatgtaatc acctggctca ccttcgggtg gcctttctg | 2700 |
| cgttgctggc gtttttccat aggctccgcc cccctgacga gcatcacaaa aatcgatgct | 2760 |
| caagtcagag gtggcgaaac ccgacaggac tataaagata ccaggcgttt ccccctggaa | 2820 |
| gctccctcgt gcgctctcct gttccgaccc tgccgcttac cggatacctg tccgcctttc | 2880 |
| tcccttcggg aagcgtggcg ctttctcata gctcacgctg taggtatctc agttcggtgt | 2940 |
| aggtcgttcg ctccaagctg ggctgtgtgc acgaaccccc cgttcagccc gaccgctgcg | 3000 |
| ccttatccgg taactatcgt cttgagtcca acccggtaag acacgactta tcgccactgg | 3060 |
| cagcagccac tggtaacagg attagcagag cgaggtatgt aggcggtgct acagagttct | 3120 |
| tgaagtggtg gcctaactac ggctacacta agaacagt attggtatc tgcgctctgc | 3180 |
| tgaagccagt tacctcggaa aaagagttgg tagctcttga tccggcaaac aaaccaccgc | 3240 |
| tggtagcggt ggtttttttg tttgcaagca gcagattacg cgcagaaaaa aaggatctca | 3300 |
| agaagatcct ttgatttct accgaagaaa ggcccacccg tgaaggtgag ccagtgagtt | 3360 |
| gattgcagtc cagttacgct ggagtctgag gctcgtcctg aatgatatca gcttgaatt | 3420 |
| cgtt | 3424 |

<210> SEQ ID NO 33
<211> LENGTH: 6275
<212> TYPE: DNA
<213> ORGANISM: Artificial Sequence
<220> FEATURE:
<223> OTHER INFORMATION: Plasmid pSMART-Mev1

<400> SEQUENCE: 33

| | |
|---|---|
| tgcccaggca tcaaataaaa cgaaaggctc agtcgaaaga ctgggccttt cgttttatct | 60 |
| gttgtttgtc ggtgaacgct ctctactaga gtcacactgg ctcaccttcg ggtgggcctt | 120 |
| tctgcgttta tacacagcta acaccacgtc gtccctatct gctgccctag gtctatgagt | 180 |
| ggttgctgga taacgtgcgt aattgtgctg atctcttata tagctgctct cattatctctc | 240 |
| ctaccctgaa gtgactctct cacctgtaaa aataatatct cacaggctta atagtttctt | 300 |

```
aatacaaagc ctgtaaaacg tcaggataac ttctatattc agggagacca caacggtttc    360
cctctacaaa taattttgtt taactttcgt ggaaaaagga gatataccat gaagacggta    420
gttattatcg acgcactgcg taccccatt ggaaaataca aaggaagtct gagccaggta     480
agcgccgtcg acctgggcac acatgtgacc acgcagttgt tgaagcgtca cagcactatc    540
agcgaggaaa ttgatcaggt cattttggt aatgttctgc aggcgggcaa tgggcagaac     600
cctgcacgtc agattgcaat caactcaggt ttaagccatg aaattccagc gatgacggtc    660
aatgaggtct gtggcagtgg gatgaaagcg gtaatcctgg ccaaacagtt aatccagctg    720
ggtgaggcgg aggtacttat cgcaggtggt attgaaaaca tgtcacaggc cccgaaactg    780
caacgcttta actacgaaac agaaagctac gatgcgcctt tttcgtccat gatgtatgat    840
ggtcttaccg acgcattcag tggtcaggcg atgggtctga cggccgagaa tgttgctgaa    900
aaataccacg ttacccgtga ggaacaagac caattctctg tccatagcca actcaaagcg    960
gcacaggctc aggcagaagg cattttgcc gatgagattg caccactgga gtttccggc     1020 accctggtgg aaaaggacga gggcattcgt ccgaatagca gtgttgaaaa actcggtact    1080
ttgaaaaccg tattcaaaga ggacggcacg gtgactgccg gtaatgcctc aactatcaac    1140
gacggtgcct cggcactgat tattgcgtct caagaatacg cggaagcgca cggcttgccg    1200
tatctcgcga ttatccgcga ttcagtggag gtcggcatcg atcccgcgta catgggcatt    1260
tcgccgatca aagcaattca gaagcttctg gcacgcaacc agttgacgac cgaagagatt    1320
gatttatacg aaatcaatga agcgttcgcg gcgacctcga ttgtggttca gcgtgaactt    1380
gccctcccgg aagaaaaggt caacatctat ggcggaggca tcagtttggg ccatgccatc    1440
ggagcgaccg tgcccgtct gctcaccagc ttatcatatc agttgaacca gaaagaaaaa     1500
aagtacggcg ttgcatctct gtgtattggc ggaggtctgg gcctcgccat gttgttagaa    1560
cgtccgcagc aaaaaaaaaa ctcccgcttt tatcagatgt cgccggagga acgtctggcg    1620
agcttgttga acgaagggca gatctctgcc gacactaaaa aggaattcga aaacacggca    1680
ctgagcagtc agattgcgaa ccatatgatt gaaaatcaga tcagcgagac cgaggtgccc    1740
atgggcgtgg gccttcatct cacggtggac gaaacggatt atctggtacc aatggccaca    1800
gaagaaccgt cggtaatcgc cgcgttgtca atggcgcga aaatcgcgca agggttcaaa     1860
acggtcaacc agcagcgtct catgcgcggc cagatcgtgt tctatgatgt agcagatgca    1920
gagagtctga ttgacgagtt acaggttcgt gagacggaga ttttttcagca agccgagctg    1980 tcgtacccga gcattgttaa acgtggcggt ggccttcgtg acttgcagta tcgcgccttc    2040
gacgaatcgt tcgtgagtgt cgactttctg gtagacgtga aggacgccat gggggccaat    2100
atcgttaatg ccatgctgga aggggttgca gagctgtttc gtgagtggtt cgccgaacaa    2160
aaaatcctgt ttagcatctt aagcaattac gcaacggaaa gcgtcgtgac catgaaaacc    2220
gcgatccctg ttagccgcct ttcaaagggc agtaacggtc gtgaaatcgc tgaaaaaatt    2280
gttctcgcgt cccgctatgc atcgttggat ccttatcgcg cggtgacaca caacaaaggc    2340
attatgaatg gtatcgaagc ggtcgttctg cgcaccggca acgatactcg cgccgtgagc    2400
gcgtcctgcc atgcttttgc tgtgaaagag ggccgttatc agggcttgac gtcctggacc    2460
ctggacggtg aacagctgat cggcgaaatc tcggtgcccc tcgccctggc cactgtgggc    2520
ggcgccacaa aagtgttgcc aaaaagccaa gcggcggcgg atctgctggc cgtaactgat    2580
gctaaggaac tgagtcgcgt ggttgccgca gtgggcctgg cccaaaacct ggcagcactg    2640
```

```
cgcgcgctgg tttctgaagg catccagaaa ggtcatatgg ccctgcaagc gcgctctctg   2700
gccatgaccg tagggggcgac cggcaaggaa gtcgaagcgg tagctcaaca gttaaaacgc   2760
cagaaaacta tgaatcagga tcgtgcgctg gccatcctca atgacctgcg caaacagtaa   2820
tagtcgcgcc gaaaaccccg cttcggcggg gttttgccgc acgtctccat cgcttgccca   2880
agttgtgaag cacagctaac accacgtcgt ccctatctgc tgccctaggt ctatgagtgg   2940
ttgctggata accatccata aattttgcat aattaatgta aagaccaggc tcgccagtaa   3000
cgctaaattc atttggctgt aagcgcggtg tcatccgcgt caggaaaatt aaacagttac   3060
tttaaaaaat gaaaacgtaa aaaggttggg tttcgatgta ttgacgggta aactttgtcg   3120
cccgctaaac atttgtttat attcagggag accacaacgg tttccctcta caaataattt   3180
tgtttaactt tgctggaaaa aggagatata ccatgaccat tgggattgat aaaatctcgt   3240
ttttcgtgcc tccttattat atcgacatga cggccctggc cgaggctcgc aatgtggatc   3300
ccggcaaatt tcacatcggt atcggccagg accaaatggc ggtgaatccc atctcgcagg   3360
acattgtcac cttcgccgca aacgcagcag aagctatctt gactaaagaa gataaagagg   3420
ccatcgacat ggtgatcgtg ggtacggaaa gctctattga cgaaagtaaa gccgcggcgg   3480
tggtattaca ccgcctgatg ggtatccagc cgtttgcgcg ctccttttgaa atcaaagagg   3540 cctgctacgg cgcaacggct ggactgcaac tcgcgaagaa ccatgttgca ttacatccgg   3600
ataaaaaagt cctggttgtc gcggcggaca tcgcgaaata cggcctgaac tccggcgggg   3660
aaccaacgca gggtgccggc gcagtggcga tgcttgtcgc aagcgagcct cgtatcctgg   3720 cttttaaagga ggacaacgtg atgctgacac aggatattta cgattttggg cgtcccaccg   3780 gtcatcccata tccgatggtt gatggtcctc tgtccaatga aacttatatt cagagcttcg   3840
cgcaagtttg ggatgaacat aagaaacgta ccggtctgga ttttgcggat tacgacgctc   3900
tggcttttca cattccatac acgaaaatgg gcaaaaaagc cctcttagct aaaatctcag   3960
accagaccga ggcagaacag gaacgcattt tagcgcgtta cgaagagtca attatctaca   4020
gccgccgtgt aggtaattta tatacgggggt cgctttatct gggattgatt tccttactcg   4080
aaaacgccac aaccctgacg gcgggtaacc aaatcggttt attctcttac ggtagcggtg   4140
ccgttgccga attcttcacg ggtgagctgg ttgccggtta ccagaaccac ttacagaaag   4200
aaacccacct cgccctgctg acaaccgta ctgaactcag catcgcagaa tatgaggcca   4260
tgttcgccga aacactcgac acggatatcg atcaaacctt agaggatgaa ctcaaatatt   4320
ccatttcagc gattaataac accgtccgct cctatcgcaa ttagtaagat cgtcccggct   4380
tatcggtcag tttcacctga tttacgtaaa aacccgcttc ggcgggtttt tgcttttgga   4440
ggggcagaaa gatgaatgac tgtccacgac gctatcccca aaagaaagac gaattctcta   4500
gatatcgctc aatactgacc atttaaatca tacctgacct ccatagcaga aagtcaaaag   4560
cctccgaccg gaggcttttg acttgatcgg cacgtaagag gttccaactt tcaccataat   4620
gaaataagat cactaccggg cgtatttttt gagttatcga gattttcagg agctaaggaa   4680
gctaaaatga ccatattca acgggaaacg tcttgctcga ggccgcgatt aaattccaac   4740
atggatgctg atttatatgg gtataaatgg gctcgcgata atgtcgggca atcaggtgcg   4800
acaatctatc gattgtatgg gaagcccgat gcgccagagt tgtttctgaa acatggcaaa   4860
ggtagcgttg ccaatgatgt tacagatgag atggtcaggc taaactggct gacggaattt   4920
atgcctcttc cgaccatcaa gcattttatc cgtactcctg atgatgcatg ttactcacc   4980 actgcgatcc cagggaaaac agcattccag gtattagaag aatatcctga ttcaggtgaa   5040
```

```
aatattgttg atgcgctggc agtgttcctg cgccggttgc attcgattcc tgtttgtaat    5100 tgtccttta  acggcgatcg cgtatttcgt ctcgctcagg cgcaatcacg aatgaataac    5160
ggtttggttg gtgcgagtga ttttgatgac gagcgtaatg ctggcctgt  tgaacaagtc    5220 tggaaagaaa tgcataagct tttgccattc tcaccggatt cagtcgtcac tcatggtgat    5280
ttctcacttg ataaccttat ttttgacgag gggaaattaa taggttgtat tgatgttgga    5340
cgagtcggaa tcgcagaccg ataccaggat cttgccatcc tatggaactg cctcggtgag    5400
ttttctcctt cattacagaa acggcttttt caaaaatatg gtattgataa tcctgatatg    5460
aataaattgc agtttcactt gatgctcgat gagttttct  aatgagggcc caaatgtaat    5520
cacctggctc accttcgggt gggcctttct gcgttgctgg cgttttcca  taggctccgc    5580 cccctgacg  agcatcacaa aaatcgatgc tcaagtcaga ggtggcgaaa cccgacagga    5640
ctataaagat accaggcgtt tccccctgga agctccctcg tgcgctctcc tgttccgacc    5700
ctgccgctta ccggatacct gtccgccttt ctcccttcgg gaagcgtggc gctttctcat    5760
agctcacgct gtaggtatct cagttcggtg taggtcgttc gctccaagct gggctgtgtg    5820
cacgaacccc ccgttcagcc cgaccgctgc gccttatccg gtaactatcg tcttgagtcc    5880
aacccggtaa gacacgactt atcgccactg gcagcagcca ctggtaacag gattagcaga    5940
gcgaggtatg taggcggtgc tacagagttc ttgaagtggt ggcctaacta cggctacact    6000
agaagaacag tatttggtat ctgcgctctg ctgaagccag ttacctcgga aaaagagttg    6060
gtagctcttg atccggcaaa caaccaccg  ctggtagcgg tggttttttt gtttgcaagc    6120
agcagattac gcgcagaaaa aaaggatctc aagaagatcc tttgattttc taccgaagaa    6180
aggcccaccc gtgaaggtga gccagtgagt tgattgcagt ccagttacgc tggagtctga    6240
ggctcgtcct gaatgatatc aagcttgaat tcgtt                               6275
```

<210> SEQ ID NO 34
<211> LENGTH: 5364
<212> TYPE: DNA
<213> ORGANISM: Artificial Sequence
<220> FEATURE:
<223> OTHER INFORMATION: Plasmid pSMART-2,3-BDO1

<400> SEQUENCE: 34

```
gtgcgtaatt gtgctgatct cttatatagc tgctctcatt atctctctac cctgaagtga     60
ctctctcacc tgtaaaaata atatctcaca ggcttaatag tttcttaata caaagcctgt    120
aaaacgtcag gataacttct tggaaaaagg agatatacca tgatgcacag cagcgcatgt    180
gattgtgaag cgagtttgtg cgagacactc cgtggttttt ccgcaaaaca cccggattcc    240
gtaatctacc agacatcact gatgtccgcc ttctgtcag  gcgtatatga aggggacacg    300
actattgcgg atcttctggc ccacggcgat tttggcctgg gtacgttcaa tgaactcgac    360
ggcgaaatga tcgcgttttc ttcgcaagtt tatcagctcc gtgcggatgg gagcgcccgc    420
gccgcgaagc cagaacaaaa aacaccgttt gcagtaatga catggttcca accgcagtat    480
cgtaaaactt tcgatgcccc ggtgagtcgt cagcagatcc acgatgtaat cgatcaacag    540
attccttcag acaacctgtt ttgcgcgctg cgtattgacg ggaatttccg tcatgctcac    600
acacgtaccg ttccgcgcca gaccccaccc tatcgcgcga tgaccgatgt gctggatgat    660
caaccggtct ttcgttttaa ccagcgcgaa ggagttctgg tgggttttcg taccccgcaa    720
catatgcagg gtattaacgt ggcgggctac catgagcatt tcattacaga tgatcgccaa    780
```

```
ggcggtggtc acctgttgga ttaccagctg gaatctggcg tcctgacttt cggcgagatt     840
cacaaactga tgattgacct gccggcggat tctgcattcc tgcaggcaaa tttgcacccc     900
agcaaccttg atgccgccat ccgctccgtc gagaactaat aggctcttca cttctggaaa     960
aaggagatat accatgaatt ccgaaaaaca atcgcgtcag tgggcacatg gtgctgatat    1020
ggttgtgggc cagctggagg cgcagggggt taaacaggtc tttggtattc cgggtgctaa    1080
gatcgacaaa gtgtttgatt ctttactgga tagctcaatc gagattatcc cggtgcgtca    1140
tgaagcaaac gcagcgttca tggccgcggc agttggtcgc cttacgggta agctggcgt    1200
agccctggtc acaagcggcc ccgggtgctc gaatctcatt accggcattg caaccgcaaa    1260
ttctgaggga gatcctgtag tggcactggg gggcgcggta aaacgtgctg ataaagcgaa    1320
attagttcac cagagtatgg acaccgtcgc gatgttctct ccagtaacca aatatgcgt    1380
tgaagtttct tccccagatg caattgcaga ggtagtatca aacgcttttc gtgccgcgga    1440
acatggccgc ccaggtgggg cgttcgtttc gctgccgcag gatattgtag accaaccggc    1500
gacaggcgcc atcctgcctg catctggccc ggcactgatg gcccagcgc cagagtcggc    1560
gattaacgat gtggcaaaac ttatcgacaa cgccaaaaac cctgtgattc tgttgggctt    1620
aatggcatca cagccggcta attcggctgc attgcgtaag ctgctggaga gagtcgcat    1680
cccggtgact tccacctacc aagccgccgg agctgtgaac caagaacatt tcacccgctt    1740
cgccggtcgt gttggccttt tcaataacca agcgggagc gtctgctgc atttggccga    1800
tctcattatc tgtattggat actctccagt cgagtatgaa ccgagcatgt ggaactcggg    1860
tgacgcaacc ctcgttcata ttgacgtgct gccagcttat gaagaacgca actatgtacc    1920
cgatatcgag ttggtaggcg acattgcggc gacactgaac ctgctcgctt cccgcattga    1980
tcataaactg gagctctcgc agcgtgcctc cgagatctta gtcgatcgcc aacaccagcg    2040
cgatctgctg gatcgccgtg gcgcaagctt aaatcaattt gcgctgcatc cattacgtat    2100
cgtccgtgcc atgcaggaca tcgtaaacaa tgacgtaacg ctgaccgtgg acatgggctc    2160
atttcatatt tggatcgcac gctatctcta ttcatttcgc gcacgtcagg tcatgattag    2220
taatgggcaa caaactatgg gcgtggctct gccttgggct atcggtgcgt ggctggtgaa    2280
ccccggccgc aaagtggtga gcgttagcgg tgacggagga tttctgcaga gtagcatgga    2340
gttagaaacc gctgtccgcc tgaacgctaa tgtgttacac atcatttggg tggataatgg    2400
ttataatatg gttgcaatcc aggaggagaa aaagtatcag cgtttaagcg gtgtggcgtt    2460
tggaccggta gatttcaaag cctacgccga tgcattcggc gcccgtggct cgcggtcga    2520
aagcgcggat gccttagaga gcaccttacg tgcggcaatg gatgtgaatg gtccggccgt    2580
cgtggcgatt ccggtggatt attcggataa tccgctgctg atgggacaac tgcacctttc    2640
gcagatcctg tagtaagctc ttctggaaaa aggagatata ccatgcagaa ggtggcgctc    2700
gttaccggat ctggccaagg cattggcaaa gcgattgcgc ttcgtctggt caaagacgga    2760
ttcgccgttg caattgctga ttacaacgac gaaacggcgc gtgctgtcgc cgatgaaatc    2820
atccgtaatg gtggcaacgc tgtcgcagtg aaagtggacg tctctgatcg cgaccaagta    2880
tttgcagcgg tcgagaaagc acgtaccgct ctgggcggtt caacgttat cgtgaacaac    2940
gcgggcattg cgccgtcgac gcctatcgaa agcatcaccc cggagattgt agataaggtg    3000
tacaacatca acgtaaaagg agtaatctgg ggtatgcaag ctgccatcga tgcgttccgc    3060
aaagaggggc acgcggtaa aatcattaac gcgtgttcgc aggctggtca tactggtaac    3120
ccggaactgg cggtttatag cagcagcaaa ttcgccgtgc gtggcctgac ccagaccgct    3180
```

```
gcacgcgatc tggcgccgct ggggatcacc gtcaatgcat attgtccggg tatcgtaaaa    3240
accccgatgt gggcggaaat tgatcgccag gtatcagagg ccgctggcaa accgctgggc    3300
tatggcacgg aaacgtttgc caagcgcatc acgttaggcc gtctgtcgga accggaggat    3360
gttgcagcat gcgtctctta cctggcgggc ccggattctg attatatgac gggtcagtcc    3420
ctgctgattg atggtggcat ggtctttaac tagtaagatc gtcccggctt atcggtcagt    3480
ttcacctgat ttacgtaaaa acccgcttcg gcgggttttt gcttttggag gggcagaaag    3540
atgaatgact gtccacgacg ctatacccaa aagaaagacg aattctctag atatcgctca    3600
atactgacca tttaaatcat acctgacctc catagcagaa agtcaaaagc ctccgaccgg    3660
aggcttttga cttgatcggc acgtaagagg ttccaacttt caccataatg aaataagatc    3720
actaccgggc gtattttttg agttatcgag attttcagga gctaaggaag ctaaaatgag    3780
ccatattcaa cgggaaacgt cttgctcgag gccgcgatta aattccaaca tggatgctga    3840
tttatatggg tataaatggg ctcgcgataa tgtcgggcaa tcaggtgcga caatctatcg    3900
attgtatggg aagcccgatg cgccagagtt gtttctgaaa catggcaaag gtagcgttgc    3960
caatgatgtt acagatgaga tggtcaggct aaactggctg acggaattta tgcctcttcc    4020
gaccatcaag cattttatcc gtactcctga tgatgcatgg ttactcacca ctgcgatccc    4080
agggaaaaca gcattccagg tattagaaga atatcctgat tcaggtgaaa atattgttga    4140
tgcgctggca gtgttcctgc gccggttgca ttcgattcct gtttgtaatt gtccttttaa    4200
cggcgatcgc gtatttcgtc tcgctcaggc gcaatcacga tgaataacg gtttggttgg    4260 tgcgagtgat tttgatgacg agcgtaatgg ctggcctgtt aacaagtct  ggaaagaaat    4320 gcataagctt ttgccattct caccggattc agtcgtcact catggtgatt tctcacttga    4380
taaccttatt tttgacgagg ggaaattaat aggttgtatt gatgttggac gagtcggaat    4440
cgcagaccga taccaggatc ttgccatcct atggaactgc ctcggtgagt tttctccttc    4500
attacagaaa cggctttttc aaaaatatgg tattgataat cctgatatga ataaattgca    4560
gtttcacttg atgctcgatg agtttttcta atgagggccc aaatgtaatc acctggctca    4620
ccttcgggtg ggcctttctg cgttgctggc gttttttccat aggctccgcc ccctgacga    4680 gcatcacaaa aatcgatgct caagtcagag gtggcgaaac ccgacaggac tataaagata    4740
ccaggcgttt ccccctggaa gctccctcgt gcgctctcct gttccgaccc tgccgcttac    4800
cggatacctg tccgcctttc tcccttcggg aagcgtggcg ctttctcata gctcacgctg    4860
taggtatctc agttcggtgt aggtcgttcg ctccaagctg ggctgtgtgc acgaaccccc    4920
cgttcagccc gaccgctgcg ccttatccgg taactatcgt cttgagtcca acccggtaag    4980
acacgactta tcgccactgg cagcagccac tggtaacagg attagcagag cgaggtatgt    5040
aggcggtgct acagagttct tgaagtggtg gcctaactac ggctacacta agaacagt    5100 atttggtatc tgcgctctgc tgaagccagt taccttcggaa aaagagttgg tagctcttga    5160
tccggcaaac aaaccaccgc tggtagcggt ggtttttttg tttgcaagca gcagattacg    5220
cgcagaaaaa aaggatctca agaagatcct ttgatttcct accgaagaaa ggcccacccg    5280
tgaaggtgag ccagtgagtt gattgcagtc cagttacgct ggagtctgag gctcgtcctg    5340
aatgatatca agcttgaatt cgtt                                           5364
```

<210> SEQ ID NO 35
<211> LENGTH: 5748
<212> TYPE: DNA

<213> ORGANISM: Artificial Sequence
<220> FEATURE:
<223> OTHER INFORMATION: Plasmid pSMART-2,3-BDO2

<400> SEQUENCE: 35

```
gtgcgtaatt gtgctgatct cttatatagc tgctctcatt atctctctac cctgaagtga    60
ctctctcacc tgtaaaaata atatctcaca ggcttaatag tttcttaata caaagcctgt   120
aaaacgtcag gataacttct tggaaaaagg agatatacca tgatgcacag cagcgcatgt   180
gattgtgaag cgagtttgtg cgagacactc cgtggttttt ccgcaaaaca cccggattcc   240
gtaatctacc agacatcact gatgtccgcc cttctgtcag gcgtatatga aggggacacg   300
actattgcgg atcttctggc ccacggcgat tttggcctgg gtacgttcaa tgaactcgac   360
ggcgaaatga tcgcgttttc ttcgcaagtt tatcagctcc gtgcggatgg gagcgcccgc   420
gccgcgaagc cagaacaaaa aacaccgttt gcagtaatga catggttcca accgcagtat   480
cgtaaaactt tcgatgcccc ggtgagtcgt cagcagatcc acgatgtaat cgatcaacag   540
attccttcag acaacctgtt ttgcgcgctg cgtattgacg ggaatttccg tcatgctcac   600
acacgtaccg ttccgcgcca gaccccaccc tatcgcgcga tgaccgatgt gctggatgat   660
caaccggtct ttcgttttaa ccagcgcgaa ggagttctgg tgggttttcg taccccgcaa   720
catatgcagg gtattaacgt ggcgggctac catgagcatt tcattacaga tgatcgccaa   780
ggcggtggtc acctgttgga ttaccagctg aatctggcg tcctgacttt cggcgagatt   840
cacaaactga tgattgacct gccggcggat tctgcattcc tgcaggcaaa tttgcacccc   900
agcaaccttg atgccgccat ccgctccgtc gagaactaat aggctcttca cttctggaaa   960
aaggagatat accatgaatt ccgaaaaaca atcgcgtcag tgggcacatg gtgctgatat  1020
ggttgtgggc cagctggagg cgcagggggt taaacaggtc tttggtattc cgggtgctaa  1080
gatcgacaaa gtgtttgatt ctttactgga tagctcaatc gagattatcc cggtgcgtca  1140
tgaagcaaac gcagcgttca tggccgcggc agttggtcgc cttacgggta aagctggcgt  1200
agccctggtc acaagcggcc ccgggtgctc gaatctcatt accggcattg caaccgcaaa  1260
ttctgaggga gatcctgtag tggcactggg gggcgcggta aaacgtgctg ataaagcgaa  1320
attagttcac cagagtatgg acaccgtcgc gatgttctct ccagtaacca aatatgcggt  1380
tgaagttttct tccccagatg caattgcaga ggtagtatca aacgcttttc gtgccgcgga  1440
acatggccgc ccaggtgggg cgttcgtttc gctgccgcag gatattgtag accaaccggc  1500
gacaggcgcc atcctgcctg catctggccc ggcactgatg ggcccagcgc cagagtcggc  1560
gattaacgat gtggcaaaac ttatcgacaa cgccaaaaac cctgtgattc tgttgggctt  1620
aatggcatca cagccggcta attcggctgc attgcgtaag ctgctggaga agagtcgcat  1680
cccggtgact tccacctacc aagccgccgg agctgtgaac caagaacatt tcacccgctt  1740
cgccggtcgt gttggccttt tcaataacca agcgggagac cgtctgctgc atttggccga  1800
tctcattatc tgtattggat actctccagt cgagtatgaa ccgagcatgt ggaactcggg  1860
tgacgcaacc ctcgttcata ttgacgtgct gccagcttat gaagaacgca actatgtacc  1920
cgatatcgag ttggtaggcg acattgcggc gacactgaac ctgctcgctt cccgcattga  1980
tcataaactg gagctctcgc agcgtgcctc cgagatctta gtcgatcgcc aacaccagcg  2040
cgatctgctg gatcgccgtg gcgcaagctt aaatcaattt gcgctgcatc cattacgtat  2100
cgtccgtgcc atgcaggaca tcgtaaacaa tgacgtaacg ctgaccgtgg acatgggctc  2160
atttcatatt tggatcgcac gctatctcta ttcatttcgc gcacgtcagg tcatgattag  2220
```

```
taatgggcaa caaactatgg gcgtggctct gccttgggct atcggtgcgt ggctggtgaa    2280
ccccggccgc aaagtggtga gcgttagcgg tgacggagga tttctgcaga gtagcatgga    2340
gttagaaacc gctgtccgcc tgaacgctaa tgtgttacac atcatttggg tggataatgg    2400
ttataatatg gttgcaatcc aggaggagaa aaagtatcag cgtttaagcg gtgtggcgtt    2460
tggaccggta gatttcaaag cctacgccga tgcattcggc gcccgtggct cgcggtcga    2520 aagcgcggat gccttagaga gcaccttacg tgcggcaatg gatgtgaatg gtccggccgt    2580
cgtggcgatt ccggtggatt attcggataa tccgctgctg atgggacaac tgcacctttc    2640
gcagatcctg tagtaagctc ttctggaaaa aggagatata ccatgcgtgc gttggcatat    2700
ttcaaaaaag gagacatcca ctttaccaac gatattccgc gtccggagat ccagacggat    2760
gatgaagtga ttattgatgt gagctggtgt gggatttgcg gttcggattt gcatgaatat    2820
ctggatggtc caattttat gccgaaggat ggcgaatgtc acaaactgag taacgcggcg    2880
ctgcccctgg caatgggaca cgagatgtcg ggaattgtca gtaaagtcgg cccgaaagtg    2940
accaaggtca aagtgggcga tcatgttgtt gttgatgctg catcgtcctg tgccgatctc    3000
cattgctggc cccacagcaa attctataac tctaaaccct tgtgacgcgtg tcaacgcgga    3060 tcggagaacc tgtgcacgca tgccggtttt gtcgggcttg gggttatctc tggcggtttt    3120
gcggaacaag tggtggtatc tcaacatcac attattcccg tgccgaagga aatccctctg    3180
gacgtagcag cactggtgga accgctctcg gtaacctggc acgcagtaaa aatttcgggc    3240
tttaagaaag gctcgagtgc actggtgttg ggggccggcc caatcggtct gtgtacgatt    3300
ctggtgctga aaggtatggg tgcgagcaaa atcgtagtta gttcgcgttc cgagcgtcgc    3360
atcgaaatgg caaaaaaact cggcgtcgaa gtgtttaatc catcgaaaca cggccataag    3420
agtattgaaa ttctgcgtgg tctgaccaaa tcacatgacg gtttcgatta tagctatgac    3480
tgcagtggaa ttcaggttac cttcgaaacc agccttaaag cccttacttt taaaggcacc    3540
gccaccaata tcgctgtttg gggtcccaaa cccgtaccct tccagcctat ggatgtgaca    3600
cttcaggaaa aagttatgac gggatccatc ggctacgtgg tggaggactt cgaagaagtg    3660
gtccgtgcca ttcacaacgg agatatcgcg atggaagatt gtaagcagct gattaccggc    3720
aaacagcgca ttgaggatgg gtgggaaaaa ggcttccagg aattaatgga ccacaaagag    3780
tctaatgtaa aaattctgct gaccccgaat aatcatggag aaatgaaata gtaatagtaa    3840
gatcgtcccg gcttatcggt cagtttcacc tgatttacgt aaaaacccgc ttcggcgggt    3900
ttttgctttt ggaggggcag aaagatgaat gactgtccac gacgctatac ccaaaagaaa    3960
gacgaattct ctagatatcg ctcaatactg accatttaaa tcatacctga cctccatagc    4020
agaaagtcaa aagcctccga ccggaggctt ttgacttgat cggcacgtaa gaggttccaa    4080 cttttcaccat aatgaaataa gatcactacc gggcgtattt tttgagttat cgagattttc    4140
aggagctaag gaagctaaaa tgagccatat tcaacgggaa acgtcttgct cgaggccgcg    4200
attaaattcc aacatggatg ctgatttata tgggtataaa tgggctcgcg ataatgtcgg    4260
gcaatcaggt gcgacaatct atcgattgta tgggaagccc gatgcgccag agttgtttct    4320
gaaacatggc aaaggtagcg ttgccaatga tgttacagat gagatggtca ggctaaactg    4380
gctgacggaa tttatgcctc ttccgaccat caagcatttt atccgtactc ctgatgatgc    4440
atggttactc accactgcga tccccaggaa aacagcattc caggtattag aagaatatcc    4500
tgattcaggt gaaaatattg ttgatgcgct ggcagtgttc ctgcgccggt tgcattcgat    4560
```

```
tcctgtttgt aattgtcctt ttaacggcga tcgcgtattt cgtctcgctc aggcgcaatc    4620
acgaatgaat aacggtttgg ttggtgcgag tgattttgat gacgagcgta atggctggcc    4680
tgttgaacaa gtctggaaag aaatgcataa gcttttgcca ttctcaccgg attcagtcgt    4740
cactcatggt gatttctcac ttgataacct tattttgac gaggggaaat taataggttg    4800
tattgatgtt ggacgagtcg gaatcgcaga ccgataccag gatcttgcca tcctatggaa    4860
ctgcctcggt gagttttctc cttcattaca gaaacggctt tttcaaaaat atggtattga    4920
taatcctgat atgaataaat tgcagtttca cttgatgctc gatgagtttt tctaatgagg    4980
gcccaaatgt aatcacctgg ctcaccttcg ggtgggcctt tctgcgttgc tggcgttttt    5040
ccataggctc cgcccccctg acgagcatca caaaaatcga tgctcaagtc agaggtggcg    5100
aaacccgaca ggactataaa gataccaggc gtttccccct ggaagctccc tcgtgcgctc    5160
tcctgttccg accctgccgc ttaccggata cctgtccgcc tttctccctt cgggaagcgt    5220
ggcgctttct catagctcac gctgtaggta tctcagttcg gtgtaggtcg ttcgctccaa    5280
gctgggctgt gtgcacgaac cccccgttca gcccgaccgc tgcgccttat ccggtaacta    5340
tcgtcttgag tccaacccgg taagacacga cttatcgcca ctggcagcag ccactggtaa    5400
caggattagc agagcgaggt atgtaggcgg tgctacagag ttcttgaagt ggtggcctaa    5460
ctacggctac actagaagaa cagtatttgg tatctgcgct ctgctgaagc cagttacctc    5520
ggaaaaagag ttggtagctc ttgatccggc aaacaaacca ccgctggtag cggtggtttt    5580
tttgtttgca agcagcagat tacgcgcaga aaaaaggat ctcaagaaga tcctttgatt    5640
ttctaccgaa gaaaggccca cccgtgaagg tgagccagtg agttgattgc agtccagtta    5700
cgctggagtc tgaggctcgt cctgaatgat atcaagcttg aattcgtt                5748
```

<210> SEQ ID NO 36
<211> LENGTH: 2818
<212> TYPE: DNA
<213> ORGANISM: Artificial Sequence
<220> FEATURE:
<223> OTHER INFORMATION: Plasmid pSMART-amnp-GFPuv

<400> SEQUENCE: 36

```
tgaggctcgt cctgaatgat atcaagcttg aattcgttag acagtcaacg cgcttgatag      60
cctggcgaag atcatccgat cttcgcctta cacttttgtt tcacatttct gtgacatact     120
atcggatgtg cggtaattgt atgtgtagga ggataatcta tggctagcaa aggagaagaa     180
cttttcacat ggctagcaaa ggagaagaac ttttcactgg agttgtccca attcttgttg     240
aattagatgg tgatgttaat gggcacaaat tttctgtcag tggagagggt gaaggtgatg     300
ctacatacgg aaagcttacc cttaaattta tttgcactac tggaaaacta cctgttccat     360
ggccaacact tgtcactact ttctcttatg gtgttcaatg cttttcccgt tatccggatc     420
atatgaaacg gcatgacttt ttcaagagtg ccatgcccga aggttatgta caggaacgca     480
ctatatcttt caaagatgac gggaactaca agacgcgtgc tgaagtcaag tttgaaggtg     540
atacccttgt taatcgtatc gagttaaaag gtattgattt taaagaagat ggaaacattc     600
tcggacacaa actcgagtac aactataact cacacaatgt atacatcacg gcagacaaac     660
aaaagaatgg aatcaaagct aacttcaaaa ttcgccacaa cattgaagat ggatccgttc     720
aactagcaga ccattatcaa caaaatactc caattggcga tggccctgtc cttttaccag     780
acaaccatta cctgtcgaca caatctgccc tttcgaaaga tcccaacgaa aagcgtgacc     840
acatggtcct tcttgagttt gtaactgctg ctgggattac acatggcatg gatgagctct     900
```

```
acaaataatg aggatcccg gcttatcggt cagtttcacc tgatttacgt aaaaacccgc      960
ttcggcgggt ttttgctttt ggaggggcag aaagatgaat gactgtccac gacgctatac   1020
ccaaaagaaa gacgaattct ctagatatcg ctcaatactg accatttaaa tcatacctga   1080
cctccatagc agaaagtcaa aagcctccga ccggaggctt tgacttgat cggcacgtaa    1140
gaggttccaa cttttcaccat aatgaaataa gatcactacc gggcgtattt tttgagttat  1200
cgagattttc aggagctaag gaagctaaaa tgagccatat tcaacgggaa acgtcttgct   1260
cgaggccgcg attaaattcc aacatggatg ctgatttata tgggtataaa tgggctcgcg   1320
ataatgtcgg gcaatcaggt gcgacaatct atcgattgta tgggaagccc gatgcgccag   1380
agttgtttct gaaacatggc aaaggtagcg ttgccaatga tgttacagat gagatggtca   1440
ggctaaactg gctgacggaa tttatgcctc ttccgaccat caagcatttt atccgtactc   1500
ctgatgatgc atggttactc accactgcga tcccagggaa aacagcattc caggtattag   1560
aagaatatcc tgattcaggt gaaaatattg ttgatgcgct ggcagtgttc ctgcgccggt   1620
tgcattcgat tcctgtttgt aattgtcctt ttaacggcga tcgcgtattt cgtctcgctc   1680
aggcgcaatc acgaatgaat aacggtttgg ttggtgcgag tgattttgat gacgagcgta   1740
atggctggcc tgttgaacaa gtctggaaag aaatgcataa gcttttgcca ttctcaccgg   1800
attcagtcgt cactcatggt gatttctcac ttgataacct tattttgac gaggggaaat   1860
taataggttg tattgatgtt ggacgagtcg gaatcgcaga ccgataccag gatcttgcca   1920
tcctatggaa ctgcctcggt gagttttctc cttcattaca gaaacggctt tttcaaaaat   1980
atggtattga taatcctgat atgaataaat tgcagtttca cttgatgctc gatgagtttt   2040
tctaatgagg gccaaatgt aatcacctgg ctcaccttcg ggtgggcctt tctgcgttgc   2100
tggcgttttt ccataggctc cgcccccctg acgagcatca caaaaatcga tgctcaagtc   2160
agaggtggcg aaacccgaca ggactataaa gataccaggc gtttccccct ggaagctccc   2220
tcgtgcgctc tcctgttccg accctgccgc ttaccggata cctgtccgcc tttctccctt   2280
cgggaagcgt ggcgctttct catagctcac gctgtaggta tctcagttcg gtgtaggtcg   2340
ttcgctccaa gctgggctgt gtgcacgaac cccccgttca gcccgaccgc tgcgccttat   2400
ccggtaacta tcgtcttgag tccaacccgg taagacacga cttatcgcca ctggcagcag   2460
ccactggtaa caggattagc agagcgaggt atgtaggcgg tgctacagag ttcttgaagt   2520
ggtggcctaa ctacggctac actagaagaa cagtatttgg tatctgcgct ctgctgaagc   2580
cagttacctc ggaaaagagt tggtagctct tgatccggc aaacaaacca ccgctggtag   2640
cggtggtttt tttgtttgca agcagcagat tacgcgcaga aaaaaggat ctcaagaaga   2700
tcctttgatt ttctaccgaa gaaaggccca ccgtgaagg tgagccagtg agttgattgc   2760
agtccagtta cgctggagtc tgaggctcgt cctgaatgat atcaagcttg aattcgtt    2818
```

<210> SEQ ID NO 37
<211> LENGTH: 2839
<212> TYPE: DNA
<213> ORGANISM: Artificial Sequence
<220> FEATURE:
<223> OTHER INFORMATION: Plasmid pSMART-phoAp-GFPuv

<400> SEQUENCE: 37

```
tgaggctcgt cctgaatgat atcaagcttg aattcgttcg attacgtaaa gaagttattg     60
aagcatcctc gtcagtaaaa agttaatctt ttcaacagct gtcataaagt tgtcacggcc    120
```

```
gagacttata gtcgctttgt ttttattttt taatgtattt gtagtgtagg aggataatct    180
atggctagca aaggagaaga acttttcaca tggctagcaa aggagaagaa cttttcactg    240
gagttgtccc aattcttgtt gaattagatg gtgatgttaa tgggcacaaa ttttctgtca    300
gtggagaggg tgaaggtgat gctacatacg gaaagcttac ccttaaattt atttgcacta    360
ctggaaaact acctgttcca tggccaacac ttgtcactac tttctcttat ggtgttcaat    420
gcttttcccg ttatccggat catatgaaac ggcatgactt tttcaagagt gccatgcccg    480
aaggttatgt acaggaacgc actatatctt tcaaagatga cgggaactac aagacgcgtg    540
ctgaagtcaa gtttgaaggt gatacccttg ttaatcgtat cgagttaaaa ggtattgatt    600
ttaaagaaga tggaaacatt ctcggacaca aactcgagta caactataac tcacacaatg    660
tatacatcac ggcagacaaa caaaagaatg gaatcaaagc taacttcaaa attcgccaca    720
acattgaaga tggatccgtt caactagcag accattatca acaaaatact ccaattggcg    780
atggccctgt ccttttacca gacaaccatt acctgtcgac acaatctgcc ctttcgaaag    840
atcccaacga aaagcgtgac cacatggtcc ttcttgagtt tgtaactgct gctgggatta    900
cacatggcat ggatgagctc tacaaataat gaggatcccc ggcttatcgg tcagtttcac    960
ctgatttacg taaaaacccg cttcggcggg ttttgctttt tggagggggca gaaagatgaa   1020 tgactgtcca cgacgctata cccaaaagaa agacgaattc tctagatatc gctcaatact   1080
gaccatttaa atcatacctg acctccatag cagaaagtca aaagcctccg accggaggct   1140
tttgacttga tcggcacgta agaggttcca actttcacca taatgaaata agatcactac   1200
cgggcgtatt ttttgagtta tcgagatttt caggagctaa ggaagctaaa atgagccata   1260
ttcaacggga aacgtcttgc tcgaggccgc gattaaattc caacatggat gctgatttat   1320
atgggtataa atgggctcgc gataatgtcg ggcaatcagg tgcgacaatc tatcgattgt   1380
atgggaagcc cgatgcgcca gagttgtttc tgaaacatgg caaaggtagc gttgccaatg   1440
atgttacaga tgagatggtc aggctaaaact ggctgacgga atttatgcct cttccgacca   1500
tcaagcattt tatccgtact cctgatgatg catggttact caccactgcg atcccaggga   1560
aaacagcatt ccaggtatta gaagaatatc ctgattcagg tgaaaatatt gttgatgcgc   1620
tggcagtgtt cctgcgccgg ttgcattcga ttcctgtttg taattgtcct tttaacggcg   1680
atcgcgtatt tcgtctcgct caggcgcaat cacgaatgaa taacggtttg gttggtgcga   1740
gtgattttga tgacgagcgt aatggctggc ctgttgaaca agtctggaaa gaaatgcata   1800
agcttttgcc attctcaccg gattcagtcg tcactcatgg tgatttctca cttgataacc   1860
ttatttttga cgaggggaaa ttaataggtt gtattgatgt tggacgagtc ggaatcgcag   1920
accgatacca ggatcttgcc atcctatgga actgcctcgg tgagttttct ccttcattac   1980
agaaacggct ttttcaaaaa tatggtattg ataatcctga tatgaataaa ttgcagtttc   2040
acttgatgct cgatgagttt ttctaatgag gcccaaatgt aatcacctg gctcaccttc    2100 gggtgggcct ttctgcgttg ctggcgtttt tccataggct ccgcccccct gacgagcatc   2160
acaaaaatcg atgctcaagt cagaggtggc gaaacccgac aggactataa agataccagg   2220
cgtttccccc tggaagctcc ctcgtgcgct ctcctgttcc gaccctgccg cttaccggat   2280
acctgtccgc ctttctccct tcgggaagcg tggcgctttc tcatagctca cgctgtaggt   2340
atctcagttc ggtgtaggtc gttcgctcca agctgggctg tgtgcacgaa ccccccgttc   2400
agcccgaccg ctgcgcctta tccggtaact atcgtcttga gtccaacccg gtaagacacg   2460
acttatcgcc actggcagca gccactggta acaggattag cagagcgagg tatgtaggcg   2520
```

```
gtgctacaga gttcttgaag tggtggccta actacggcta cactagaaga acagtatttg    2580
gtatctgcgc tctgctgaag ccagttacct cggaaaaaga gttggtagct cttgatccgg    2640
caaacaaacc accgctggta gcggtggttt ttttgtttgc aagcagcaga ttacgcgcag    2700
aaaaaaagga tctcaagaag atcctttgat tttctaccga agaaaggccc acccgtgaag    2760
gtgagccagt gagttgattg cagtccagtt acgctggagt ctgaggctcg tcctgaatga    2820
tatcaagctt gaattcgtt                                                 2839

<210> SEQ ID NO 38
<211> LENGTH: 2819
<212> TYPE: DNA
<213> ORGANISM: Artificial Sequence
<220> FEATURE:
<223> OTHER INFORMATION: Plasmid pSMART-phoBp-GFPuv

<400> SEQUENCE: 38
tgaggctcgt cctgaatgat atcaagcttg aattcgttgc cacggaaatc aataacctga      60
agatatgtgc gacgagcttt tcataaatct gtcataaatc tgacgcataa tgacgtcgca     120
ttaatgatcg caacctattt attgtgtagg aggataatct atggctagca aggagaagaa     180
acttttcaca tggctagcaa aggagaagaa cttttcactg gagttgtccc aattcttgtt     240
gaattagatg gtgatgttaa tgggcacaaa ttttctgtca gtggagaggg tgaaggtgat     300
gctacatacg gaaagcttac ccttaaattt atttgcacta ctggaaaact acctgttcca     360
tggccaacac ttgtcactac tttctcttat ggtgttcaat gcttttcccg ttatccggat     420
catatgaaac ggcatgactt tttcaagagt gccatgcccg aaggttatgt acaggaacgc     480
actatatctt tcaaagatga cgggaactac aagacgcgtg ctgaagtcaa gtttgaaggt     540
gatacccttg ttaatcgtat cgagttaaaa ggtattgatt taaagaaga tggaaacatt     600 ctcggacaca aactcgagta caactataac tcacacaatg tatacatcac ggcagacaaa     660
caaaagaatg gaatcaaagc taacttcaaa attcgccaca cattgaaga tggatccgtt     720 caactagcag accattatca acaaaatact ccaattggcg atggccctgt ccttttacca     780
gacaaccatt acctgtcgac acaatctgcc ctttcgaaag atcccaacga aaagcgtgac     840
cacatggtcc ttcttgagtt tgtaactgct gctgggatta cacatggcat ggatgagctc     900
tacaaataat gaggatcccc ggcttatcgg tcagtttcac ctgatttacg taaaaacccg     960
cttcggcggg ttttgctttt tggaggggca gaaagatgaa tgactgtcca cgacgctata    1020
cccaaaagaa agacgaattc tctagatatc gctcaatact gaccatttaa atcatacctg    1080
acctccatag cagaaagtca aaagcctccg accggaggct tttgacttga tcggcacgta    1140
agaggttcca actttcacca taatgaaata agatcactac cgggcgtatt ttttgagtta    1200
tcgagatttt caggagctaa ggaagctaaa atgagccata ttcaacggga acgtcttgc    1260 tcgaggccgc gattaaattc caacatggat gctgatttat atgggtataa atgggctcgc    1320
gataatgtcg ggcaatcagg tgcgacaatc tatcgattgt atgggaagcc cgatgcgcca    1380
gagttgtttc tgaaacatgg caaaggtagc gttgccaatg atgttacaga tgagatggtc    1440
aggctaaact ggctgacgga atttatgcct cttccgacca tcaagcattt tatccgtact    1500
cctgatgatg catggttact caccactgcg atcccaggga aaacagcatt ccaggtatta    1560
gaagaatatc ctgattcagg tgaaaatatt gttgatgcgc tggcagtgtt cctgcgccgg    1620
ttgcattcga ttcctgtttg taattgtcct tttaacggcg atcgcgtatt tcgtctcgct    1680
```

-continued

```
caggcgcaat cacgaatgaa taacggtttg gttggtgcga gtgattttga tgacgagcgt      1740
aatggctggc ctgttgaaca agtctggaaa gaaatgcata agcttttgcc attctcaccg      1800
gattcagtcg tcactcatgg tgatttctca cttgataacc ttattttga cgaggggaaa      1860 ttaataggtt gtattgatgt tggacgagtc ggaatcgcag accgatacca ggatcttgcc      1920
atcctatgga actgcctcgg tgagttttct ccttcattac agaaacggct ttttcaaaaa      1980
tatggtattg ataatcctga tatgaataaa ttgcagtttc acttgatgct cgatgagttt      2040
ttctaatgag ggcccaaatg taatcacctg gctcaccttc gggtgggcct ttctgcgttg      2100
ctggcgtttt tccataggct ccgcccccct gacgagcatc acaaaaatcg atgctcaagt      2160
cagaggtggc gaaacccgac aggactataa agataccagg cgtttccccc tggaagctcc      2220
ctcgtgcgct ctcctgttcc gaccctgccg cttaccggat acctgtccgc ctttctccct      2280
tcgggaagcg tggcgctttc tcatagctca cgctgtaggt atctcagttc ggtgtaggtc      2340
gttcgctcca agctgggctg tgtgcacgaa ccccccgttc agcccgaccg ctgcgcctta      2400
tccggtaact atcgtcttga gtccaacccg gtaagacacg acttatcgcc actggcagca      2460
gccactggta acaggattag cagagcgagg tatgtaggcg gtgctacaga gttcttgaag      2520
tggtggccta actacggcta cactagaaga acagtatttg gtatctgcgc tctgctgaag      2580
ccagttacct cggaaaaaga gttggtagct cttgatccgg caaacaaacc accgctggta      2640
gcggtggttt ttttgtttgc aagcagcaga ttacgcgcag aaaaaaagga tctcaagaag      2700
atcctttgat tttctaccga gaaaggccc accgtgaag gtgagccagt gagttgattg      2760
cagtccagtt acgctggagt ctgaggctcg tcctgaatga tatcaagctt gaattcgtt      2819
```

<210> SEQ ID NO 39
<211> LENGTH: 2880
<212> TYPE: DNA
<213> ORGANISM: Artificial Sequence
<220> FEATURE:
<223> OTHER INFORMATION: Plasmid pSMART-phoEp-GFPuv

<400> SEQUENCE: 39

```
tgaggctcgt cctgaatgat atcaagcttg aattcgttag catggcgttt tgttgcgcgg       60
gatcagcaag cctagcggca gttgtttacg ctttattac agatttaata aattaccaca      120
ttttaagaat attattaatc tgtaatatat ctttaacaat ctcaggttaa aaactttcct      180
gttttcaacg ggactctccc gctggtgtag gaggataatc tatggctagc aaaggagaag      240
aacttttcac atggctagca aaggagaaga acttttcact ggagttgtcc caattcttgt      300
tgaattagat ggtgatgtta atgggcacaa attttctgtc agtggagagg gtgaaggtga      360
tgctacatac ggaaagctta cccttaaatt tatttgcact actggaaaac tacctgttcc      420
atggccaaca cttgtcacta ctttctctta tggtgttcaa tgcttttccc gttatccgga      480
tcatatgaaa cggcatgact ttttcaagag tgccatgccc gaaggttatg tacaggaacg      540
cactatatct ttcaaagatg acgggaacta caagacgcgt gctgaagtca gtttgaagg      600 tgatacccct gttaatcgta tcgagttaaa aggtattgat tttaagaag atggaaacat      660 tctcggacac aaactcgagt acaactataa ctcacacaat gtatacatca cggcagacaa      720
acaaaagaat ggaatcaaag ctaacttcaa aattcgccac aacattgaag atggatccgt      780
tcaactagca gaccattatc aacaaaatac tccaattggc gatggccctg tccttttacc      840
agacaaccat tacctgtcga cacaatctgc cctttcgaaa gatcccaacg aaaagcgtga      900
ccacatggtc cttcttgagt ttgtaactgc tgctgggatt acacatggca tggatgagct      960
```

-continued

| | |
|---|---|
| ctacaaataa tgaggatccc cggcttatcg gtcagtttca cctgatttac gtaaaaaccc | 1020 |
| gcttcggcgg ttttttgctt ttggagggc agaaagatga atgactgtcc acgacgctat | 1080 |
| acccaaaaga aagacgaatt ctctagatat cgctcaatac tgaccattta aatcatacct | 1140 |
| gacctccata gcagaaagtc aaaagcctcc gaccggaggc ttttgacttg atcggcacgt | 1200 |
| aagaggttcc aactttcacc ataatgaaat aagatcacta ccgggcgtat ttttttgagtt | 1260 |
| atcgagattt tcaggagcta aggaagctaa atgagccat attcaacggg aaacgtcttg | 1320 |
| ctcgaggccg cgattaaatt ccaacatgga tgctgattta tatgggtata atgggctcg | 1380 |
| cgataatgtc gggcaatcag gtgcgacaat ctatcgattg tatgggaagc ccgatgcgcc | 1440 |
| agagttgttt ctgaaacatg gcaaaggtag cgttgccaat gatgttacag atgagatggt | 1500 |
| caggctaaac tggctgacgg aatttatgcc tcttccgacc atcaagcatt ttatccgtac | 1560 |
| tcctgatgat gcatggttac tcaccactgc gatcccaggg aaaacagcat tccaggtatt | 1620 |
| agaagaatat cctgattcag gtgaaaatat tgttgatgcg ctggcagtgt tcctgcgccg | 1680 |
| gttgcattcg attcctgttt gtaattgtcc ttttaacggc gatcgcgtat tcgtctcgc | 1740 |
| tcaggcgcaa tcacgaatga ataacggttt ggttggtgcg agtgattttg atgacgagcg | 1800 |
| taatggctgg cctgttgaac aagtctggaa agaaatgcat aagcttttgc cattctcacc | 1860 |
| ggattcagtc gtcactcatg gtgatttctc acttgataac cttatttttg acgaggggaa | 1920 |
| attaataggt tgtattgatg ttggacgagt cggaatcgca gaccgatacc aggatcttgc | 1980 |
| catcctatgg aactgcctcg gtgagttttc tccttcatta cagaaacggc ttttttcaaaa | 2040 |
| atatggtatt gataatcctg atatgaataa attgcagttt cacttgatgc tcgatgagtt | 2100 |
| tttctaatga gggcccaaat gtaatcacct ggctcacctt cgggtgggcc tttctgcgtt | 2160 |
| gctggcgttt ttccataggc tccgcccccc tgacgagcat cacaaaaatc gatgctcaag | 2220 |
| tcagaggtgg cgaaacccga caggactata aagataccag gcgtttcccc ctggaagctc | 2280 |
| cctcgtgcgc tctcctgttc cgacccgcc gcttaccgga tacctgtccg cctttctccc | 2340 |
| ttcgggaagc gtggcgcttt tcatagctc acgctgtagg tatctcagtt cggtgtaggt | 2400 |
| cgttcgctcc aagctgggct gtgtgcacga accccccgtt cagcccgacc gctgcgcctt | 2460 |
| atccggtaac tatcgtcttg agtccaaccc ggtaagacac gacttatcgc cactggcagc | 2520 |
| agccactggt aacaggatta gcagagcgag gtatgtaggc ggtgctacag agttcttgaa | 2580 |
| gtggtggcct aactacggct acactagaag aacagtattt ggtatctgcg ctctgctgaa | 2640 |
| gccagttacc tcgaaaaag agttggtagc tcttgatccg gcaaacaaac caccgctggt | 2700 |
| agcggtggtt ttttttgtttg caagcagcag attacgcgca gaaaaaaagg atctcaagaa | 2760 |
| gatcctttga ttttctaccg aagaaaggcc caccccgtgaa ggtgagccag tgagttgatt | 2820 |
| gcagtccagt tacgctggag tctgaggctc gtcctgaatg atatcaagct tgaattcgtt | 2880 |

<210> SEQ ID NO 40
<211> LENGTH: 2879
<212> TYPE: DNA
<213> ORGANISM: Artificial Sequence
<220> FEATURE:
<223> OTHER INFORMATION: Plasmid pSMART-phoHp-GFPuv

<400> SEQUENCE: 40

| | |
|---|---|
| tgaggctcgt cctgaatgat atcaagcttg aattcgttaa tctgctgaa agcacacagc | 60 |
| tttttttcatc actgtcatca ctctgtcatc tttccagtag aaactaatgt cactgaaatg | 120 |

```
gtgttttata gttaaatata agtaaatata ttgttgcaat aaatgcgaga tctgttgtac    180
ttattaagta gcagcggaag ttcgtgtagg aggataatct atggctagca aaggagaaga    240
acttttcaca tggctagcaa aggagaagaa cttttcactg gagttgtccc aattcttgtt    300
gaattagatg gtgatgttaa tgggcacaaa ttttctgtca gtggagaggg tgaaggtgat    360
gctacatacg gaaagcttac ccttaaattt atttgcacta ctggaaaact acctgttcca    420
tggccaacac ttgtcactac tttctcttat ggtgttcaat gcttttcccg ttatccggat    480
catatgaaac ggcatgactt tttcaagagt gccatgcccg aaggttatgt acaggaacgc    540
actatatctt tcaaagatga cgggaactac aagacgcgtg ctgaagtcaa gtttgaaggt    600
gatacccttg ttaatcgtat cgagttaaaa ggtattgatt ttaaagaaga tggaaacatt    660
ctcggacaca aactcgagta caactataac tcacacaatg tatacatcac ggcagacaaa    720
caaaagaatg gaatcaaagc taacttcaaa attcgccaca acattgaaga tggatccgtt    780
caactagcag accattatca acaaaatact ccaattggcg atggccctgt ccttttacca    840
gacaaccatt acctgtcgac acaatctgcc ctttcgaaag atcccaacga aaagcgtgac    900
cacatggtcc ttcttgagtt tgtaactgct gctgggatta cacatggcat ggatgagctc    960
tacaaataat gaggatcccc ggcttatcgg tcagtttcac ctgatttacg taaaaacccg    1020
cttcggcggg ttttgctt tggaggggca gaaagatgaa tgactgtcca cgacgctata    1080
cccaaaagaa agacgaattc tctagatatc gctcaatact gaccatttaa atcatacctg    1140
acctccatag cagaaagtca aaagcctccg accggaggct tttgacttga tcggcacgta    1200
agaggttcca actttcacca taatgaaata agatcactac cggcgtatt ttttgagtta    1260 tcgagatttt caggagctaa ggaagctaaa atgagccata ttcaacggga aacgtcttgc    1320
tcgaggccgc gattaaattc caacatggat gctgatttat atgggtataa atgggctcgc    1380
gataatgtcg gcaatcagg tgcgacaatc tatcgattgt atgggaagcc cgatgcgcca    1440
gagttgtttc tgaaacatgg caaaggtagc gttgccaatg atgttacaga tgagatggtc    1500 aggctaaaact ggctgacgga atttatgcct cttccgacca tcaagcattt tatccgtact    1560
cctgatgatg catggttact caccactgcg atcccaggga aaacagcatt ccaggtatta    1620
gaagaatatc ctgattcagg tgaaaatatt gttgatgcgc tggcagtgtt cctgcgccgg    1680
ttgcattcga ttcctgtttg taattgtcct tttaacggcg atcgcgtatt tcgtctcgct    1740
caggcgcaat cacgaatgaa taacggtttg gttggtgcga gtgattttga tgacgagcgt    1800
aatggctggc ctgttgaaca agtctggaaa gaaatgcata gcttttgcc attctcaccg    1860 gattcagtcg tcactcatgg tgatttctca cttgataacc ttattttga cgaggggaaa    1920 ttaataggtt gtattgatgt tggacgagtc ggaatcgcag accgatacca ggatcttgcc    1980
atcctatgga actgcctcgg tgagttttct ccttcattac agaaacggct ttttcaaaaa    2040
tatggtattg ataatcctga tatgaataaa ttgcagtttc acttgatgct cgatgagttt    2100
ttctaatgag ggcccaaatg taatcacctg gctcaccttc gggtgggcct ttctgcgttg    2160
ctggcgtttt tccataggct ccgcccccct gacgagcatc acaaaaatcg atgctcaagt    2220
cagaggtggc gaaacccgac aggactataa agataccagg cgtttccccc tggaagctcc    2280
ctcgtgcgct ctcctgttcc gaccctgccg cttaccggat acctgtccgc ctttctccct    2340
tcgggaagcg tggcgctttc tcatagctca cgctgtaggt atctcagttc ggtgtaggtc    2400
gttcgctcca agctgggctg tgtgcacgaa ccccccgttc agcccgaccg ctgcgcctta    2460
tccggtaact atcgtcttga gtccaacccg gtaagacacg acttatcgcc actggcagca    2520
```

```
gccactggta acaggattag cagagcgagg tatgtaggcg gtgctacaga gttcttgaag    2580
tggtggccta actacggcta cactagaaga acagtatttg gtatctgcgc tctgctgaag    2640
ccagttacct cggaaaaaga gttggtagct cttgatccgg caaacaaacc accgctggta    2700
gcggtggttt ttttgtttgc aagcagcaga ttacgcgcag aaaaaaagga tctcaagaag    2760
atcctttgat tttctaccga gaaaggccc acccgtgaag gtgagccagt gagttgattg    2820
cagtccagtt acgctggagt ctgaggctcg tcctgaatga tatcaagctt gaattcgtt    2879
```

<210> SEQ ID NO 41
<211> LENGTH: 2850
<212> TYPE: DNA
<213> ORGANISM: Artificial Sequence
<220> FEATURE:
<223> OTHER INFORMATION: Plasmid pSMART-phoUp-GFPuv

<400> SEQUENCE: 41

```
tgaggctcgt cctgaatgat atcaagcttg aattcgttac cgaactgaag caggattaca      60
ccgtggtgat cgtcacccac aacatgcagc aggctgcgcg ttgttccgac cacacggcgt     120
ttatgtacct gggcgaattg attgagttca gcaacacgga cgatctgttc accagtgtag     180
gaggataatc tatggctagc aaaggagaag aacttttcac atggctagca aaggagaaga     240
acttttcact ggagttgtcc caattcttgt tgaattagat ggtgatgtta atgggcacaa     300
attttctgtc agtggagagg gtgaaggtga tgctacatac ggaaagctta cccttaaatt     360
tatttgcact actggaaaac tacctgttcc atggccaaca cttgtcacta ctttctctta     420
tggtgttcaa tgcttttccc gttatccgga tcatatgaaa cggcatgact ttttcaagag     480
tgccatgccc gaaggttatg tacaggaacg cactatatct ttcaaagatg acgggaacta     540
caagacgcgt gctgaagtca gtttgaagg tgataccctt gttaatcgta tcgagttaaa     600
aggtattgat tttaaagaag atggaaacat tctcggacac aaactcgagt acaactataa     660
ctcacacaat gtatacatca cggcagacaa acaaaagaat ggaatcaaag ctaacttcaa     720
aattcgccac aacattgaag atggatccgt tcaactagca gaccattatc aacaaaatac     780
tccaattggc gatggccctg tccttttacc agacaaccat tacctgtcga cacaatctgc     840
cctttcgaaa gatcccaacg aaaagcgtga ccacatggtc cttcttgagt ttgtaactgc     900
tgctgggatt acacatggca tggatgagct ctacaaataa tgaggatccc cggcttatcg     960
gtcagtttca cctgatttac gtaaaaaccc gcttcggcgg gttttttgctt ttggaggggc    1020 agaaagatga atgactgtcc acgacgctat acccaaaaga aagacgaatt ctctagatat    1080
cgctcaatac tgaccatta aatcatacct gacctccata gcagaaagtc aaaagcctcc    1140
gaccggaggc ttttgacttg atcggcacgt aagaggttcc aactttcacc ataatgaaat    1200
aagatcacta ccgggcgtat tttttgagtt atcgagattt tcaggagcta aggaagctaa    1260
aatgagccat attcaacggg aaacgtcttg ctcgaggccg cgattaaatt ccaacatgga    1320
tgctgattta tatgggtata aatgggctcg cgataatgtc gggcaatcag gtgcgacaat    1380
ctatcgattg tatgggaagc ccgatgcgcc agagttgttt ctgaaacatg gcaaaggtag    1440
cgttgccaat gatgttacag atgagatggt caggctaaac tggctgacgg aatttatgcc    1500
tcttccgacc atcaagcatt ttatccgtac tcctgatgat gcatggttac tcaccactgc    1560
gatcccaggg aaaacagcat tccaggtatt agaagaatat cctgattcag gtgaaaatat    1620
tgttgatgcg ctggcagtgt tcctgcgccg gttgcattcg attcctgttt gtaattgtcc    1680
```

| | |
|---|---|
| ttttaacggc gatcgcgtat ttcgtctcgc tcaggcgcaa tcacgaatga ataacggttt | 1740 |
| ggttggtgcg agtgattttg atgacgagcg taatggctgg cctgttgaac aagtctggaa | 1800 |
| agaaatgcat aagcttttgc cattctcacc ggattcagtc gtcactcatg gtgatttctc | 1860 |
| acttgataac cttattttg acgaggggaa attaataggt tgtattgatg ttggacgagt | 1920 |
| cggaatcgca gaccgatacc aggatcttgc catcctatgg aactgcctcg gtgagttttc | 1980 |
| tccttcatta cagaaacggc ttttcaaaa atatggtatt gataatcctg atatgaataa | 2040 |
| attgcagttt cacttgatgc tcgatgagtt tttctaatga gggcccaaat gtaatcacct | 2100 |
| ggctcacctt cgggtgggcc tttctgcgtt gctggcgttt ttccataggc tccgcccccc | 2160 |
| tgacgagcat cacaaaaatc gatgctcaag tcagaggtgg cgaaacccga caggactata | 2220 |
| aagataccag gcgtttcccc ctggaagctc cctcgtgcgc tctcctgttc cgaccctgcc | 2280 |
| gcttaccgga tacctgtccg cctttctccc ttcgggaagc gtggcgcttt ctcatagctc | 2340 |
| acgctgtagg tatctcagtt cggtgtaggt cgttcgctcc aagctgggct gtgtgcacga | 2400 |
| accccccgtt cagcccgacc gctgcgcctt atccggtaac tatcgtcttg agtccaaccc | 2460 |
| ggtaagacac gacttatcgc cactggcagc agccactggt aacaggatta gcagagcgag | 2520 |
| gtatgtaggc ggtgctacag agttcttgaa gtggtggcct aactacggct acactagaag | 2580 |
| aacagtattt ggtatctgcg ctctgctgaa gccagttacc tcggaaaaag agttggtagc | 2640 |
| tcttgatccg gcaaacaaac caccgctggt agcggtggtt ttttgtttg caagcagcag | 2700 |
| attacgcgca gaaaaaagg atctcaagaa gatcctttga ttttctaccg aagaaaggcc | 2760 |
| cacccgtgaa ggtgagccag tgagttgatt gcagtccagt tacgctggag tctgaggctc | 2820 |
| gtcctgaatg atatcaagct tgaattcgtt | 2850 |

<210> SEQ ID NO 42
<211> LENGTH: 2900
<212> TYPE: DNA
<213> ORGANISM: Artificial Sequence
<220> FEATURE:
<223> OTHER INFORMATION: Plasmid pSMART-mipAp-GFPuv

<400> SEQUENCE: 42

| | |
|---|---|
| tgaggctcgt cctgaatgat atcaagcttg aattcgttca tccataaatt ttgcataatt | 60 |
| aatgtaaaga ccaggctcgc cagtaacgct aaattcattt ggctgtaagc gcggtgtcat | 120 |
| ccgcgtcagg aaaattaaac agttacttta aaaatgaaa acgtaaaaag gttgggtttc | 180 |
| gatgtattga cgggtaaact ttgtcgcccg ctaaacattt gtttgtgtag gaggataatc | 240 |
| tatggctagc aaaggagaag aacttttcac atggctagca aaggagaaga acttttcact | 300 |
| ggagttgtcc caattcttgt tgaattagat ggtgatgtta atgggcacaa attttctgtc | 360 |
| agtggagagg gtgaaggtga tgctacatac ggaaagctta cccttaaatt tatttgcact | 420 |
| actggaaaac tacctgttcc atggccaaca cttgtcacta ctttctctta tggtgttcaa | 480 |
| tgcttttccc gttatccgga tcatatgaaa cggcatgact ttttcaagag tgccatgccc | 540 |
| gaaggttatg tacaggaacg cactatatct ttcaagatg acgggaacta caagacgcgt | 600 |
| gctgaagtca gtttgaagg tgatacccct gttaatcgta tcgagttaaa aggtattgat | 660 |
| tttaagaag atggaaacat tctcggacac aaactcgagt acaactataa ctcacacaat | 720 |
| gtatacatca cggcagacaa acaaaagaat ggaatcaaag ctaacttcaa aattcgccac | 780 |
| aacattgaag atggatccgt tcaactagca gaccattatc aacaaaatac tccaattggc | 840 |
| gatggccctg tccttttacc agacaaccat tacctgtcga cacaatctgc cctttcgaaa | 900 |

```
gatcccaacg aaaagcgtga ccacatggtc cttcttgagt ttgtaactgc tgctgggatt    960
acacatggca tggatgagct ctacaaataa tgaggatccc cggcttatcg gtcagtttca   1020
cctgatttac gtaaaaaccc gcttcggcgg ttttttgctt ttggaggggc agaaagatga   1080
atgactgtcc acgacgctat acccaaaaga aagacgaatt ctctagatat cgctcaatac   1140
tgaccattta aatcatacct gacctccata gcagaaagtc aaaagcctcc gaccggaggc   1200
ttttgacttg atcggcacgt aagaggttcc aactttcacc ataatgaaat aagatcacta   1260
ccgggcgtat ttttgagtt atcgagattt caggagcta aggaagctaa aatgagccat   1320
attcaacggg aaacgtcttg ctcgaggccg cgattaaatt ccaacatgga tgctgattta   1380
tatgggtata atgggctcg cgataatgtc gggcaatcag gtgcgacaat ctatcgattg   1440
tatgggaagc ccgatgcgcc agagttgttt ctgaaacatg gcaaaggtag cgttgccaat   1500
gatgttacag atgagatggt caggctaaac tggctgacgg aatttatgcc tcttccgacc   1560
atcaagcatt tatccgtac tcctgatgat gcatggttac tcaccactgc gatcccaggg   1620
aaaacagcat tccaggtatt agaagaatat cctgattcag gtgaaaatat tgttgatgcg   1680
ctggcagtgt tcctgcgccg gttgcattcg attcctgttt gtaattgtcc ttttaacggc   1740
gatcgcgtat ttcgtctcgc tcaggcgcaa tcacgaatga ataacggttt ggttggtgcg   1800
agtgattttg atgacgagcg taatggctgg cctgttgaac aagtctggaa agaaatgcat   1860
aagcttttgc cattctcacc ggattcagtc gtcactcatg gtgatttctc acttgataac   1920 cttattttg acgagggaa attaataggt tgtattgatg ttggacgagt cggaatcgca   1980
gaccgatacc aggatcttgc catcctatgg aactgcctcg gtgagttttc tccttcatta   2040
cagaaacggc ttttcaaaa atatggtatt gataatcctg atatgaataa attgcagttt   2100
cacttgatgc tcgatgagtt tttctaatga gggcccaaat gtaatcacct ggctcacctt   2160
cgggtgggcc tttctgcgtt gctggcgttt ttccataggc tccgcccccc tgacgagcat   2220
cacaaaaatc gatgctcaag tcagaggtgg cgaaacccga caggactata aagataccag   2280
gcgtttcccc ctggaagctc cctcgtgcgc tctcctgttc cgaccctgcc gcttaccgga   2340
tacctgtccg cctttctccc ttcgggaagc gtggcgcttt ctcatagctc acgctgtagg   2400
tatctcagtt cggtgtaggt cgttcgctcc aagctgggct gtgtgcacga accccccgtt   2460
cagcccgacc gctgcgcctt atccggtaac tatcgtcttg agtccaaccc ggtaagacac   2520
gacttatcgc cactggcagc agccactggt aacaggatta gcagagcgag gtatgtaggc   2580
ggtgctacag agttcttgaa gtggtggcct aactacggct acactagaag aacagtattt   2640
ggtatctgcg ctctgctgaa gccagttacc tcggaaaaag agttggtagc tcttgatccg   2700
gcaaacaaac caccgctggt agcggtggtt ttttgtttg caagcagcag attacgcgca   2760 gaaaaaagg atctcaagaa gatcctttga ttttctaccg aagaaggcc cacccgtgaa   2820 ggtgagccag tgagttgatt gcagtccagt tacgctggag tctgaggctc gtcctgaatg   2880
atatcaagct tgaattcgtt                                               2900
```

<210> SEQ ID NO 43
<211> LENGTH: 2816
<212> TYPE: DNA
<213> ORGANISM: Artificial Sequence
<220> FEATURE:
<223> OTHER INFORMATION: Plasmid pSMART-pstSp-GFPuv

<400> SEQUENCE: 43

```
tgaggctcgt cctgaatgat atcaagcttg aattcgttaa gactttatct ctctgtcata    60
aaactgtcat attccttaca tataactgtc acctgtttgt cctatttgc ttctcgtagc    120 caacaaacaa tgctttatga gtgtaggagg ataatctatg gctagcaaag gagaagaact   180
tttcacatgg ctagcaaagg agaagaactt ttcactggag ttgtcccaat tcttgttgaa   240
ttagatggtg atgttaatgg gcacaaattt tctgtcagtg gagagggtga aggtgatgct   300
acatacggaa agcttaccct taaatttatt tgcactactg gaaaactacc tgttccatgg   360
ccaacacttg tcactacttt ctcttatggt gttcaatgct tttcccgtta ccggatcat    420 atgaaacggc atgactttt caagagtgcc atgcccgaag gttatgtaca ggaacgcact    480
atatctttca aagatgacgg aactacaag acgcgtgctg aagtcaagtt tgaaggtgat    540
acccttgtta atcgtatcga gttaaaaggt attgatttta agaagatggg aaacattctc   600
ggacacaaac tcgagtacaa ctataactca cacaatgtat acatcacggc agacaaacaa   660
aagaatggaa tcaaagctaa cttcaaaatt cgccacaaca ttgaagatgg atccgttcaa   720
ctagcagacc attatcaaca aaatactcca attggcgatg ccctgtcct tttaccagac    780 aaccattacc tgtcgacaca atctgcccctt tcgaaagatc ccaacgaaaa gcgtgaccac   840
atggtccttc ttgagtttgt aactgctgct gggattacac atggcatgga tgagctctac   900
aaataatgag atccccggc ttatcggtca gtttcacctg atttacgtaa aaacccgctt    960
cggcgggttt ttgcttttgg aggggcagaa agatgaatga ctgtccacga cgctataccc   1020
aaaagaaaga cgaattctct agatatcgct caatactgac catttaaatc atacctgacc   1080
tccatagcag aaagtcaaaa gcctccgacc ggaggctttt gacttgatcg cgcgtaaga    1140 ggttccaact ttcaccataa tgaaataaga tcactaccgg gcgtattttt tgagttatcg   1200
agattttcag gagctaagga agctaaaatg agccatattc aacgggaaac gtcttgctcg   1260
aggccgcgat taaattccaa catggatgct gatttatatg ggtataaatg gctcgcgat    1320 aatgtcgggc aatcaggtgc gacaatctat cgattgtatg ggaagcccga tgcgccagag   1380
ttgtttctga acatggcaa aggtagcgtt gccaatgatg ttacagatga gatggtcagg    1440
ctaaactggc tgacggaatt tatgcctctt ccgaccatca agcatttat ccgtactcct    1500 gatgatgcat ggttactcac cactgcgatc ccagggaaaa cagcattcca ggtattagaa   1560
gaatatcctg attcaggtga aaatattgtt gatgcgctgg cagtgttcct gcgccggttg   1620
cattcgattc ctgtttgtaa ttgtccttt aacggcgatc gcgtatttcg tctcgctcag    1680
gcgcaatcac gaatgaataa cggtttggtt ggtgcgagtg attttgatga cgagcgtaat   1740
ggctggcctg ttgaacaagt ctggaaagaa atgcataagc ttttgccatt ctcaccggat   1800
tcagtcgtca ctcatggtga tttctcactt gataaccta ttttttgacga ggggaaatta   1860 ataggttgta ttgatgttgg acgagtcgga atcgcagacc gataccagga tcttgccatc   1920
ctatggaact gcctcggtga gttttctcct tcattacaga aacggctttt tcaaaaatat   1980
ggtattgata atcctgatat gaataaattg cagtttcact tgatgctcga tgagtttttc   2040
taatgagggc ccaaatgtaa tcacctggct caccttcggg tgggcctttc tgcgttgctg   2100
gcgtttttcc ataggctccg cccccctgac gagcatcaca aaaatcgatg ctcaagtcag   2160
aggtggcgaa acccgacagg actataaaga taccaggcgt ttccccctgg aagctccctc   2220
gtgcgctctc ctgttccgac cctgccgctt accggatacc tgtccgcctt tctcccttcg   2280
ggaagcgtgg cgctttctca tagctcacgc tgtaggtatc tcagttcggt gtaggtcgtt   2340
cgctccaagc tgggctgtgt gcacgaaccc cccgttcagc ccgaccgctg cgccttatcc   2400
```

```
ggtaactatc gtcttgagtc caacccggta agacacgact tatcgccact ggcagcagcc    2460
actggtaaca ggattagcag agcgaggtat gtaggcggtg ctacagagtt cttgaagtgg    2520
tggcctaact acggctacac tagaagaaca gtatttggta tctgcgctct gctgaagcca    2580
gttacctcgg aaaagagtt ggtagctctt gatccggcaa acaaaccacc gctggtagcg    2640
gtggtttttt tgtttgcaag cagcagatta cgcgcagaaa aaaggatctc aagaagatc    2700 ctttgatttt ctaccgaaga aggcccacc cgtgaaggtg agccagtgag ttgattgcag     2760
tccagttacg ctggagtctg aggctcgtcc tgaatgatat caagcttgaa ttcgtt        2816
```

<210> SEQ ID NO 44
<211> LENGTH: 2808
<212> TYPE: DNA
<213> ORGANISM: Artificial Sequence
<220> FEATURE:
<223> OTHER INFORMATION: Plasmid pSMART-ugpBp-GFPuv

<400> SEQUENCE: 44

```
tgaggctcgt cctgaatgat atcaagcttg aattcgtttc tttctgacac cttactatct    60
tacaaatgta acaaaaaagt tattttttctg taattcgagc atgtcatgtt accccgcgag   120
cataaaacgc gtgtgtagga ggataatcta tggctagcaa aggagaagaa cttttcacat    180
ggctagcaaa ggagaagaac ttttcactgg agttgtccca attcttgttg aattagatgg    240
tgatgttaat gggcacaaat tttctgtcag tggagagggt gaaggtgatg ctacatacgg    300
aaagcttacc cttaaattta tttgcactac tggaaaacta cctgttccat ggccaacact    360
tgtcactact ttctcttatg gtgttcaatg cttttcccgt tatccggatc atatgaaacg    420
gcatgacttt ttcaagagtg ccatgcccga aggttatgta caggaacgca ctatatcttt    480
caaagatgac gggaactaca agacgcgtgc tgaagtcaag tttgaaggtg atacccttgt    540
taatcgtatc gagttaaaag gtattgattt taaagaagat ggaaacattc tcggacacaa    600
actcgagtac aactataact cacacaatgt atacatcacg gcagacaaac aaaagaatgg    660
aatcaaagct aacttcaaaa ttcgccacaa cattgaagat ggatccgttc aactagcaga    720
ccattatcaa caaaatactc caattggcga tggccctgtc cttttaccag acaaccatta    780
cctgtcgaca caatctgccc tttcgaaaga tcccaacgaa aagcgtgacc acatggtcct    840
tcttgagttt gtaactgctg ctgggattac acatggcatg gatgagctct acaaataatg    900
aggatccccg gcttatcggt cagtttcacc tgatttacgt aaaaacccgc ttcggcgggt    960
ttttgctttt ggaggggcag aaagatgaat gactgtccac gacgctatac ccaaaagaaa    1020
gacgaattct ctagatatcg ctcaatactg accatttaaa tcatacctga cctccatagc    1080
agaaagtcaa aagcctccga ccggaggctt ttgacttgat cggcacgtaa gaggttccaa    1140
ctttcaccat aatgaaataa gatcactacc gggcgtattt tttgagttat cgagattttc    1200
aggagctaag gaagctaaaa tgagccatat tcaacgggaa acgtcttgct cgaggccgcg    1260
attaaattcc aacatggatg ctgatttata tgggtataaa tgggctcgcg ataatgtcgg    1320
gcaatcaggt gcgacaatct atcgattgta tgggaagccc gatgcgccag agttgtttct    1380
gaaacatggc aaaggtagcg ttgccaatga tgttacagat gagatggtca ggctaaactg    1440
gctgacggaa tttatgcctc ttccgaccat caagcatttt atccgtactc ctgatgatgc    1500
atggttactc accactgcga tcccagggaa aacagcattc caggtattag aagaatatcc    1560
tgattcaggt gaaaatattg ttgatgcgct ggcagtgttc ctgcgccggt tgcattcgat    1620
```

```
tcctgtttgt aattgtcctt ttaacggcga tcgcgtattt cgtctcgctc aggcgcaatc    1680
acgaatgaat aacggtttgg ttggtgcgag tgattttgat gacgagcgta atggctggcc    1740
tgttgaacaa gtctggaaag aaatgcataa gcttttgcca ttctcaccgg attcagtcgt    1800
cactcatggt gatttctcac ttgataacct tattttgac gaggggaaat taataggttg      1860
tattgatgtt ggacgagtcg gaatcgcaga ccgataccag gatcttgcca tcctatggaa    1920 ctgcctcgt gagttttctc cttcattaca gaaacggctt tttcaaaaat atggtattga      1980
taatcctgat atgaataaat tgcagtttca cttgatgctc gatgagtttt tctaatgagg    2040
gcccaaatgt aatcacctgg ctcaccttcg ggtgggcctt tctgcgttgc tggcgttttt    2100
ccataggctc cgcccccctg acgagcatca caaaaatcga tgctcaagtc agaggtggcg    2160
aaacccgaca ggactataaa gataccaggc gtttccccct ggaagctccc tcgtgcgctc    2220
tcctgttccg accctgccgc ttaccggata cctgtccgcc tttctccctt cgggaagcgt    2280
ggcgctttct catagctcac gctgtaggta tctcagttcg gtgtaggtcg ttcgctccaa    2340
gctgggctgt gtgcacgaac cccccgttca gcccgaccgc tgcgccttat ccggtaacta    2400
tcgtcttgag tccaacccgg taagacacga cttatcgcca ctggcagcag ccactggtaa    2460
caggattagc agagcgaggt atgtaggcgg tgctacagag ttcttgaagt ggtggcctaa    2520
ctacggctac actagaagaa cagtatttgg tatctgcgct ctgctgaagc cagttacctc    2580
ggaaaaagag ttggtagctc ttgatccggc aaacaaacca ccgctggtag cggtggtttt    2640
tttgtttgca agcagcagat tacgcgcaga aaaaaggat ctcaagaaga tcctttgatt     2700
ttctaccgaa gaaaggccca cccgtgaagg tgagccagtg agttgattgc agtccagtta    2760
cgctggagtc tgaggctcgt cctgaatgat atcaagcttg aattcgtt                 2808
```

<210> SEQ ID NO 45
<211> LENGTH: 2819
<212> TYPE: DNA
<213> ORGANISM: Artificial Sequence
<220> FEATURE:
<223> OTHER INFORMATION: Plasmid pSMART-ydfHp-GFPuv

<400> SEQUENCE: 45

```
tgaggctcgt cctgaatgat atcaagcttg aattcgttgc tatgccggac tgaatgtcca      60
ccgtcagtaa ttttataccc ggcgtaact gccgggttat tgcttgtcac aaaaaagtgg     120
tagactcatg cagttaactc actgtgtagg aggataatct atggctagca aggagaaga    180 acttttcaca tggctagcaa aggagaagaa cttttcactg gagttgtccc aattcttgtt    240
gaattagatg gtgatgttaa tgggcacaaa ttttctgtca gtggagaggg tgaaggtgat    300
gctacatacg gaaagcttac ccttaaattt atttgcacta ctggaaaact acctgttcca    360
tggccaacac ttgtcactac tttctcttat ggtgttcaat gcttttcccg ttatccggat    420
catatgaaac ggcatgactt tttcaagagt gccatgcccg aaggttatgt acaggaacgc    480
actatatctt tcaaagatga cgggaactac aagacgcgtg ctgaagtcaa gtttgaaggt    540
gatacccttg ttaatcgtat cgagttaaaa ggtattgatt ttaaagaaga tggaaacatt    600
ctcggacaca aactcgagta caactataac tcacacaatg tatacatcac ggcagacaaa    660
caaaagaatg gaatcaaagc taacttcaaa attcgccaca cattgaaga tggatccgtt      720 caactagcag accattatca acaaaatact ccaattggcg atggccctgt ccttttacca    780
gacaaccatt acctgtcgac acaatctgcc ctttcgaaag atcccaacga aaagcgtgac    840
cacatggtcc ttcttgagtt tgtaactgct gctgggatta cacatggcat ggatgagctc    900
```

```
tacaaataat gaggatcccc ggcttatcgg tcagtttcac ctgatttacg taaaaacccg      960
cttcggcggg ttttgctttt tggaggggca gaaagatgaa tgactgtcca cgacgctata     1020
cccaaaagaa agacgaattc tctagatatc gctcaatact gaccatttaa atcatacctg     1080
acctccatag cagaaagtca aaagcctccg accggaggct tttgacttga tcggcacgta     1140
agaggttcca actttcacca taatgaaata agatcactac cgggcgtatt ttttgagtta     1200
tcgagatttt caggagctaa ggaagctaaa atgagccata ttcaacggga aacgtcttgc     1260
tcgaggccgc gattaaattc caacatggat gctgatttat atgggtataa atgggctcgc     1320
gataatgtcg ggcaatcagg tgcgacaatc tatcgattgt atgggaagcc cgatgcgcca     1380
gagttgtttc tgaaacatgg caaaggtagc gttgccaatg atgttacaga tgagatggtc     1440
aggctaaact ggctgacgga atttatgcct cttccgacca tcaagcattt tatccgtact     1500
cctgatgatg catggttact caccactgcg atcccaggga aaacagcatt ccaggtatta     1560
gaagaatatc ctgattcagg tgaaaatatt gttgatgcgc tggcagtgtt cctgcgccgg     1620
ttgcattcga ttcctgtttg taattgtcct tttaacggcg atcgcgtatt tcgtctcgct     1680
caggcgcaat cacgaatgaa taacggtttg gttggtgcga gtgattttga tgacgagcgt     1740
aatggctggc ctgttgaaca agtctggaaa gaaatgcata agcttttgcc attctcaccg     1800
gattcagtcg tcactcatgg tgatttctca cttgataacc ttattttga cgaggggaaa      1860 ttaataggtt gtattgatgt tggacgagtc ggaatcgcag accgatacca ggatcttgcc     1920
atcctatgga actgcctcgg tgagttttct ccttcattac agaaacggct ttttcaaaaa     1980
tatggtattg ataatcctga tatgaataaa ttgcagtttc acttgatgct cgatgagttt     2040
ttctaatgag ggcccaaatg taatcacctg gctcaccttc gggtgggcct ttctgcgttg     2100
ctggcgtttt tccataggct ccgcccccct gacgagcatc acaaaaatcg atgctcaagt     2160
cagaggtggc gaaacccgac aggactataa agataccagg cgtttccccc tggaagctcc     2220
ctcgtgcgct ctcctgttcc gaccctgccg cttaccggat acctgtccgc ctttctccct     2280
tcgggaagcg tggcgctttc tcatagctca cgctgtaggt atctcagttc ggtgtaggtc     2340
gttcgctcca agctgggctg tgtgcacgaa ccccccgttc agcccgaccg ctgcgcctta     2400
tccggtaact atcgtcttga gtccaacccg gtaagacacg acttatcgcc actggcagca     2460
gccactggta acaggattag cagagcgagg tatgtaggcg gtgctacaga gttcttgaag     2520
tggtggccta actacggcta cactagaaga acagtatttg gtatctgcgc tctgctgaag     2580
ccagttacct cggaaaaaga gttggtagct cttgatccgg caaacaaacc accgctggta     2640
gcggtggttt tttgtttgc aagcagcaga ttacgcgcag aaaaaaagga tctcaagaag     2700
atcctttgat ttctaccga agaaaggccc accgtgaag gtgagccagt gagttgattg      2760
cagtccagtt acgctggagt ctgaggctcg tcctgaatga tatcaagctt gaattcgtt      2819
```

<210> SEQ ID NO 46
<211> LENGTH: 3424
<212> TYPE: DNA
<213> ORGANISM: Artificial Sequence
<220> FEATURE:
<223> OTHER INFORMATION: Plasmid pSMART-Ala2

<400> SEQUENCE: 46

```
ccaggcatca aataaaacga aaggctcagt cgaaagactg ggcctttcgt tttatctgtt      60
gtttgtcggt gaacgctctc tactagagtc acactggctc accttcgggt gggcctttct     120
```

```
gcgtttatac acagctaaca ccacgtcgtc cctatctgct gccctaggtc tatgagtggt     180
tgctggataa ctcttctga caccttacta tcttacaaat gtaacaaaaa agttatttt     240 ctgtaattcg agcatgtcat gttaccccgc gagcataaaa cgcgtatatt cagggagacc    300
acaacggttt ccctctacaa ataattttgt ttaactttgg aaaaggaga tataccatga     360 tcattggggt gccgaaggag atcaaaaata atgagaaccg cgtcgcgttg accccgggag    420
gtgtcagcca gctgatctct aatggccatc gtgtcttagt tgaaacaggc gctggcctgg    480
gttctggctt cgaaaacgag gcctacgaat ctgcaggtgc ggaaattatt gctgatccaa    540
aacaggtctg ggatgcagag atggtcatga aagtgaaaga accgctcccg gaagaatatg    600 tctatttcg taaggtctg gtgctgttta catatctgca tctggcagct gaaccggagc     660
tcgcacaagc ccttaaagat aaaggtgtca cggccatcgc atacgaaact gtcagcgaag    720
ggcgcacgct gccattactg accccgatgt cagaagtggc aggccgtatg gctgcgcaga    780
tcggcgcaca gtttcttgaa aaccaaaagg gcgggaaggg tattctctta gcaggagtgc    840
cgggcgtcag tcgtgggaaa gtaactatta ttggtggcgg cgtggtagga acaaatgctg    900
ccaaaatggc cgtcggtttg ggggccgacg taacaatcat tgcgcgtaat gccgatcgcc    960
ttcgtcaatt agacgatatc tttggccacc aaatcaaaac cctgatttcg aacccagtca    1020
atatcgcgga tgcggtggcg gaagctgatt tgttgatctg cgccgtgtta attccgggag    1080
cgaaagcacc tacattggtg acggaagaaa tggtgaaaca aatgaaaccg ggttcagtca    1140
ttgttgatgt ggctattgat cagggtggca tcgtggaaac ggtggaccat attaccactc    1200
acgaccagcc gacgtatgaa aaacatggtg tcgtacacta tgcggtggcg aatatgcctg    1260
gtgcggtccc acgtacgagt acaatcgcac tgacaaatgt caccgtgccg tatgcgttgc    1320
aaatcgcgaa caaggtgcc gtgaaagcgc tggccgacaa tacggcgtta cgtgccggtc    1380
tgaacaccgc taacggtcac gtgacatatg aagcggtcgc gcgtgatttg gggtacgaat    1440
atgtaccggc ggaaaaagcc ttacaagacg aatcgagtgt cgctggtgca tagtaagctc    1500
ttctaatacg actcactata gggccggctt atcggtcagt ttcacctgat ttacgtaaaa    1560
acccgcttcg gcgggttttt gcttttggag gggcagaaag atgaatgact gtccacgacg    1620
ctatacccaa aagaaagacg aattctctag atatcgctca atactgacca tttaaatcat    1680
acctgacctc catagcagaa agtcaaaagc ctccgaccgg aggcttttga cttgatcggc    1740
acgtaagagg ttccaacttt caccataatg aaataagatc actaccgggc gtatttttg    1800 agttatcgag attttcagga gctaaggaag ctaaaatgag ccatattcaa cgggaaacgt    1860
cttgctcgag gccgcgatta aattccaaca tggatgctga tttatatggg tataaatggg    1920
ctcgcgataa tgtcgggcaa tcaggtgcga caatctatcg attgtatggg aagcccgatg    1980
cgccagagtt gtttctgaaa catggcaaag gtagcgttgc caatgatgtt acagatgaga    2040
tggtcaggct aaactggctg acggaattta tgcctcttcc gaccatcaag cattttatcc    2100
gtactcctga tgatgcatgg ttactcacca ctgcgatccc agggaaaaca gcattccagg    2160
tattagaaga atatcctgat tcaggtgaaa atattgttga tgcgctggca gtgttcctgc    2220
gccggttgca ttcgattcct gtttgtaatt gtccttttaa cggcgatcgc gtatttcgtc    2280
tcgctcaggc gcaatcacga atgaataacg gtttggttgg tgcgagtgat tttgatgacg    2340
agcgtaatgg ctggcctgtt gaacaagtct ggaaagaaat gcataagctt ttgccattct    2400
caccggattc agtcgtcact catggtgatt tctcacttga taaccttatt tttgacgagg    2460
ggaaattaat aggttgtatt gatgttggac gagtcggaat cgcagaccga taccaggatc    2520
```

```
ttgccatcct atggaactgc ctcggtgagt tttctccttc attacagaaa cggcttttc      2580 aaaaatatgg tattgataat cctgatatga ataaattgca gtttcacttg atgctcgatg      2640
agttttctta atgagggccc aaatgtaatc acctggctca ccttcgggtg ggcctttctg      2700
cgttgctggc gttttccat aggctccgcc ccctgacga gcatcacaaa aatcgatgct        2760
caagtcagag gtggcgaaac ccgacaggac tataaagata ccaggcgttt ccccctggaa      2820 gctcccttcgt gcgctctcct gttccgaccc tgccgcttac cggatacctg tccgcctttc    2880
tcccttcggg aagcgtggcg ctttctcata gctcacgctg taggtatctc agttcggtgt     2940
aggtcgttcg ctccaagctg gctgtgtgc acgaacccc cgttcagccc gaccgctgcg       3000
ccttatccgg taactatcgt cttgagtcca acccggtaag acacgactta cgccactgg      3060 cagcagccac tggtaacagg attagcagag cgaggtatgt aggcggtgct acagagttct     3120
tgaagtggtg gcctaactac ggctacacta gaagaacagt atttggtatc tgcgctctgc     3180
tgaagccagt tacctcggaa aaagagttgg tagctcttga tccggcaaac aaaccaccgc     3240
tggtagcggt ggtttttttg tttgcaagca gcagattacg cgcagaaaaa aaggatctca     3300
agaagatcct ttgatttct accgaagaaa ggcccacccg tgaaggtgag ccagtgagtt      3360
gattgcagtc cagttacgct ggagtctgag gctcgtcctg aatgatatca gcttgaatt      3420 cgtt                                                                   3424

<210> SEQ ID NO 47
<211> LENGTH: 21
<212> TYPE: DNA
<213> ORGANISM: Artificial Sequence
<220> FEATURE:
<223> OTHER INFORMATION: fabI T2 targeting sequence

<400> SEQUENCE: 47
cagcctgctc cggtcggacc g                                                21

<210> SEQ ID NO 48
<211> LENGTH: 45
<212> TYPE: DNA
<213> ORGANISM: Artificial Sequence
<220> FEATURE:
<223> OTHER INFORMATION: C-terminal DAS+4 tag

<400> SEQUENCE: 48
gcggccaacg atgaaaacta ttctgaaaac tatgcggatg cgtct                      45

<210> SEQ ID NO 49
<211> LENGTH: 59
<212> TYPE: DNA
<213> ORGANISM: Artificial Sequence
<220> FEATURE:
<223> OTHER INFORMATION: Primer gltA2-FOR

<400> SEQUENCE: 49
gggacagtta ttagttcgag ttccccgcgc cagcggggat aaaccgaaaa aaaaacccc       59

<210> SEQ ID NO 50
<211> LENGTH: 63
<212> TYPE: DNA
<213> ORGANISM: Artificial Sequence
<220> FEATURE:
<223> OTHER INFORMATION: Primer gltA2-REV

<400> SEQUENCE: 50
```

```
gaatgaattg gtcaatacgg tttatccccg ctggcgcggg gaactcgagg tggtaccaga    60
tct                                                                  63

<210> SEQ ID NO 51
<211> LENGTH: 28
<212> TYPE: DNA
<213> ORGANISM: Artificial Sequence
<220> FEATURE:
<223> OTHER INFORMATION: Primer G2U-FOR1

<400> SEQUENCE: 51
ccggatgagc attcatcagg cgggcaag                                       28

<210> SEQ ID NO 52
<211> LENGTH: 47
<212> TYPE: DNA
<213> ORGANISM: Artificial Sequence
<220> FEATURE:
<223> OTHER INFORMATION: Primer G2U-REV1

<400> SEQUENCE: 52
cggtttatcc ccgctggcgc ggggaactcg aacttcataa cttttac                  47

<210> SEQ ID NO 53
<211> LENGTH: 34
<212> TYPE: DNA
<213> ORGANISM: Artificial Sequence
<220> FEATURE:
<223> OTHER INFORMATION: Primer G2U-FOR2

<400> SEQUENCE: 53
gcgccagcgg ggataaaccg ttaccattct gttg                                34

<210> SEQ ID NO 54
<211> LENGTH: 28
<212> TYPE: DNA
<213> ORGANISM: Artificial Sequence
<220> FEATURE:
<223> OTHER INFORMATION: Primer G2U-REV2

<400> SEQUENCE: 54
cttgcccgcc tgatgaatgc tcatccgg                                       28
```